United States Patent
Callahan et al.

(10) Patent No.: US 12,247,071 B2
(45) Date of Patent: Mar. 11, 2025

(54) ANTI-TNF ALPHA ANTIBODY FORMULATIONS

(71) Applicant: Amgen Inc., Thousand Oaks, CA (US)

(72) Inventors: William J. Callahan, Thousand Oaks, CA (US); Rahul Rajan Kaushik, Newbury Park, CA (US); Joy Brennan, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 63 days.

(21) Appl. No.: 17/820,958

(22) Filed: Aug. 19, 2022

(65) Prior Publication Data

US 2023/0151086 A1    May 18, 2023

Related U.S. Application Data

(63) Continuation of application No. 16/471,492, filed as application No. PCT/US2017/067723 on Dec. 20, 2017, now abandoned.

(60) Provisional application No. 62/437,640, filed on Dec. 21, 2016.

(51) Int. Cl.
```
C07K 16/24    (2006.01)
A61K 9/00     (2006.01)
A61K 9/08     (2006.01)
A61K 47/10    (2017.01)
A61K 47/18    (2017.01)
```

(52) U.S. Cl.
CPC ............ *C07K 16/241* (2013.01); *A61K 47/10* (2013.01); *A61K 47/183* (2013.01); *A61K 9/0019* (2013.01); *A61K 9/08* (2013.01)

(58) Field of Classification Search
CPC ..... C07K 16/241; A61K 47/183; A61K 47/10
See application file for complete search history.

(56) References Cited

U.S. PATENT DOCUMENTS

| | | | |
|---|---|---|---|
| 5,656,272 A | 8/1997 | Le |
| 5,698,195 A | 12/1997 | Le |
| 5,919,452 A | 7/1999 | Le |
| 5,945,098 A | 8/1999 | Sarno |
| 6,090,382 A | 7/2000 | Salfeld |
| 6,171,586 B1 | 1/2001 | Lam |
| 6,238,664 B1 | 5/2001 | Hellerbrand |
| 6,252,055 B1 | 6/2001 | Relton |
| 6,277,969 B1 | 8/2001 | Le |
| 6,281,336 B1 | 8/2001 | Laursen |
| 6,284,471 B1 | 9/2001 | Le |
| 6,328,979 B1 | 12/2001 | Yamashita |
| 6,359,145 B1 | 3/2002 | Terasaka |
| 6,368,629 B1 | 4/2002 | Watanabe |
| 6,369,065 B1 | 4/2002 | Chatelain |
| 6,506,407 B2 | 1/2003 | Watanabe |
| 6,610,700 B2 | 8/2003 | Norman |
| 6,670,326 B1 | 12/2003 | Nagai |
| 6,716,613 B1 | 4/2004 | Yamaji |
| 6,780,874 B2 | 8/2004 | John |
| 6,790,444 B2 | 9/2004 | Le |
| 6,805,686 B1 | 10/2004 | Fathallah |
| 6,835,823 B2 | 12/2004 | Le |
| 6,991,791 B2 | 1/2006 | Le |
| 7,012,135 B2 | 3/2006 | Athwal |
| 7,070,775 B2 | 7/2006 | Le |
| 7,094,590 B2 | 8/2006 | Yamajii |
| 7,098,024 B2 | 8/2006 | Nagai |
| 7,101,674 B2 | 9/2006 | Le |
| 7,105,160 B1 | 9/2006 | Smith |
| 7,128,907 B2 | 10/2006 | Le |
| 7,128,908 B2 | 10/2006 | Le |
| 7,135,178 B2 | 11/2006 | Le |
| 7,135,179 B2 | 11/2006 | Le |
| 7,138,118 B2 | 11/2006 | Le |
| 7,141,590 B2 | 11/2006 | Cutshall |
| 7,153,854 B2 | 12/2006 | Abe |
| 7,160,542 B2 | 1/2007 | Le |
| 7,160,543 B2 | 1/2007 | Le |
| 7,160,995 B2 | 1/2007 | Le |
| 7,166,284 B2 | 1/2007 | Le |
| 7,169,386 B1 | 1/2007 | Le |
| 7,169,388 B2 | 1/2007 | Le |
| 7,179,466 B2 | 2/2007 | Le |
| 7,179,893 B2 | 2/2007 | Le |
| 7,186,511 B2 | 3/2007 | Kawakami |
| 7,186,820 B2 | 3/2007 | Athwal |
| 7,192,584 B2 | 3/2007 | Le |
| 7,193,073 B2 | 3/2007 | Yamaji |
| 7,196,080 B2 | 3/2007 | Iwata |
| 7,204,985 B2 | 4/2007 | Le |
| 7,214,376 B2 | 5/2007 | Le |
| 7,223,396 B2 | 5/2007 | Le |

(Continued)

FOREIGN PATENT DOCUMENTS

| | | |
|---|---|---|
| EP | 1593393 B1 | 11/2011 |
| EP | 1528933 B1 | 5/2012 |

(Continued)

OTHER PUBLICATIONS

US 7,521,050 B2, 02/2006, Salfeld (withdrawn)
Adalimumab (Humira®)Package Insert (Dec. 2002).
Baselga, et al., Phase II Study of Weekly Intravenous Trastuzumab (Herceptin) in Patients With HER2/neu-Overexpressing Metastatic Breast Cancer, Semin. Oncol., 26(4)(suppl 12):78-83 (1999).
Baughman, Ph.D., PK/PD Study Strategies for Biopharmaceuticals: Is Bigger Better?, presented to the New Jersey American Chemical Society Drug Metabolism Discussion Group (Oct. 14, 2009).
Bingham & Ruffing, Rheumatoid Arthritis Treatment.

(Continued)

*Primary Examiner* — Vanessa L. Ford
*Assistant Examiner* — Sandra Carter
(74) *Attorney, Agent, or Firm* — Carlos Garcia

(57) ABSTRACT

Stable adalimumab formulations are disclosed.

1 Claim, 90 Drawing Sheets
Specification includes a Sequence Listing.

(56) References Cited

U.S. PATENT DOCUMENTS

| | | |
|---|---|---|
| 7,226,593 B2 | 6/2007 | Le |
| 7,227,003 B2 | 6/2007 | Le |
| 7,241,873 B2 | 7/2007 | Uede |
| 7,250,165 B2 | 7/2007 | Heavner |
| 7,252,823 B2 | 8/2007 | Le |
| 7,261,892 B2 | 8/2007 | Terrett |
| 7,273,744 B2 | 9/2007 | McKenzie |
| 7,276,239 B2 | 10/2007 | Le |
| 7,300,765 B2 | 11/2007 | Patel |
| 7,317,009 B2 | 1/2008 | Abe |
| 7,335,358 B2 | 2/2008 | Le |
| 7,374,761 B2 | 5/2008 | Le |
| 7,402,662 B2 | 7/2008 | Athwal |
| 7,404,955 B2 | 7/2008 | Le |
| 7,416,729 B2 | 8/2008 | Le |
| 7,423,047 B2 | 9/2008 | Brookings |
| 7,425,330 B2 | 9/2008 | Le |
| 7,456,286 B2 | 11/2008 | Brookings |
| 7,459,451 B2 | 12/2008 | Abe |
| 7,521,206 B2 | 4/2009 | Heavner |
| 7,521,460 B2 | 4/2009 | Brookings |
| 7,592,455 B2 | 9/2009 | Brookings |
| 7,601,817 B2 | 10/2009 | Mozier |
| 7,638,630 B2 | 12/2009 | Lassoie |
| 7,655,426 B2 | 2/2010 | Boyd |
| 7,670,624 B2 | 3/2010 | Tsutsumi |
| 7,678,785 B2 | 3/2010 | Carr |
| 7,691,378 B2 | 4/2010 | Heavner |
| 7,732,614 B2 | 6/2010 | Perry |
| 7,744,885 B2 | 6/2010 | Le |
| 7,745,156 B2 | 6/2010 | Terrett |
| 7,763,729 B2 | 7/2010 | Brookings |
| 7,790,414 B2 | 9/2010 | Lawson |
| 7,795,256 B2 | 9/2010 | Alexander |
| 7,807,161 B2 | 10/2010 | Yamamoto |
| 7,815,909 B2 | 10/2010 | Heavner |
| 7,820,169 B2 | 10/2010 | Heavner |
| 7,858,095 B2 | 12/2010 | Vaishnaw |
| 7,863,426 B2 | 1/2011 | Wan |
| 7,910,618 B2 | 3/2011 | Eaton |
| 7,919,264 B2 | 4/2011 | Maksymowych |
| 7,931,900 B2 | 4/2011 | Christie |
| 7,935,808 B2 | 5/2011 | Gion |
| 7,938,802 B2 | 5/2011 | Bicknell |
| 7,947,495 B2 | 5/2011 | Dubridge |
| 7,977,464 B2 | 7/2011 | Athwal |
| 7,989,594 B2 | 8/2011 | Humphreys |
| 8,003,331 B2 | 8/2011 | Endoh |
| 8,003,596 B2 | 8/2011 | Appeldoorn |
| 8,017,393 B2 | 9/2011 | Lanza |
| 8,034,906 B2 | 10/2011 | Borhani |
| 8,053,562 B2 | 11/2011 | Humphreys |
| 8,053,564 B2 | 11/2011 | Baker |
| 8,057,794 B2 | 11/2011 | Rapecki |
| 8,062,865 B2 | 11/2011 | Humphreys |
| 8,067,005 B1 | 11/2011 | Chapman |
| 8,071,095 B2 | 12/2011 | Karrer |
| 8,071,582 B2 | 12/2011 | Carr |
| 8,075,889 B2 | 12/2011 | Gelinas |
| 8,092,998 B2 | 1/2012 | Stuhlmüller |
| 8,093,045 B2 | 1/2012 | Pla |
| 8,129,505 B2 | 3/2012 | Norman |
| 8,162,887 B2 | 4/2012 | Bicknell |
| 8,168,427 B2 | 5/2012 | Sahin |
| 8,173,684 B2 | 5/2012 | Kasahara |
| 8,187,836 B2 | 5/2012 | Hsieh |
| 8,216,583 B2 | 7/2012 | Kruase |
| 8,231,875 B2 | 7/2012 | Adams |
| 8,231,876 B2 | 7/2012 | Wan |
| 8,241,899 B2 | 8/2012 | Heavner |
| 8,268,587 B2 | 9/2012 | Karrer |
| 8,283,170 B2 | 10/2012 | Dubridge |
| 8,283,447 B2 | 10/2012 | Karrer |
| 8,293,237 B2 | 10/2012 | Burkly |
| 8,303,953 B2 | 11/2012 | Adams |
| 8,318,176 B2 | 11/2012 | Karrer |
| 8,329,431 B2 | 12/2012 | Adams |
| 8,378,073 B2 | 2/2013 | Heywood |
| 8,410,259 B2 | 4/2013 | Gion |
| 8,420,081 B2 | 4/2013 | Fraunhofer |
| 8,425,902 B2 | 4/2013 | Sahin |
| 8,435,761 B2 | 5/2013 | Rapecki |
| 8,436,149 B2 | 5/2013 | Borhani |
| 8,445,230 B2 | 5/2013 | Karrer |
| 8,455,219 B2 | 6/2013 | Hsieh |
| 8,486,662 B2 | 7/2013 | Gelinas |
| 8,491,899 B2 | 7/2013 | Karrer |
| 8,496,935 B2 | 7/2013 | Karrer |
| 8,507,654 B2 | 8/2013 | Baker |
| 8,540,992 B2 | 9/2013 | Naso |
| 8,580,265 B2 | 11/2013 | Adams |
| 8,598,355 B2 | 12/2013 | Nozawa |
| 8,603,778 B2 | 12/2013 | Heavner |
| 8,617,847 B2 | 12/2013 | Adams |
| 8,624,022 B2 | 1/2014 | Carr |
| 8,629,246 B2 | 1/2014 | Humphreys |
| 8,636,704 B2 | 1/2014 | Shang |
| 8,663,945 B2 | 3/2014 | Pla |
| 8,668,670 B2 | 3/2014 | Bicknell |
| 8,679,061 B2 | 3/2014 | Julian |
| 8,679,494 B2 | 3/2014 | Ceska |
| 8,691,233 B2 | 4/2014 | Gozzard |
| 8,691,918 B2 | 4/2014 | Jaber |
| 8,715,664 B2 | 5/2014 | Hoffman |
| 8,722,353 B2 | 5/2014 | Smith |
| 8,722,860 B2 | 5/2014 | Harding |
| 8,747,845 B2 | 6/2014 | Wong |
| 8,753,839 B2 | 6/2014 | Fraunhofer |
| 8,758,301 B2 | 6/2014 | Shang |
| 8,772,458 B2 | 7/2014 | Koenigsdorfer |
| 8,784,823 B2 | 7/2014 | Burkly |
| 8,795,632 B2 | 8/2014 | Nagakura |
| 8,795,670 B2 | 8/2014 | Krause |
| 8,796,021 B2 | 8/2014 | Lanza |
| 8,802,100 B2 | 8/2014 | Krause |
| 8,802,101 B2 | 8/2014 | Krause |
| 8,808,700 B1 | 8/2014 | Hoffman |
| 8,821,865 B2 | 9/2014 | Neu |
| 8,846,046 B2 | 9/2014 | Kaymakcalan |
| 8,852,889 B2 | 10/2014 | Prentice |
| 8,865,167 B2 | 10/2014 | Adams |
| 8,877,194 B2 | 11/2014 | Hsieh |
| 8,883,146 B2 | 11/2014 | Fraunhofer |
| 8,883,156 B2 | 11/2014 | Wan |
| 8,889,135 B2 | 11/2014 | Fischkoff |
| 8,889,136 B2 | 11/2014 | Hoffman |
| 8,895,009 B2 | 11/2014 | Wan |
| 8,906,372 B2 | 12/2014 | Wan |
| 8,906,373 B2 | 12/2014 | Banerjee |
| 8,906,646 B2 | 12/2014 | Pla |
| 8,911,737 B2 | 12/2014 | Fischkoff |
| 8,911,741 B2 | 12/2014 | Krause |
| 8,911,964 B2 | 12/2014 | Pla |
| 8,916,153 B2 | 12/2014 | Wan |
| 8,916,157 B2 | 12/2014 | Krause |
| 8,916,158 B2 | 12/2014 | Krause |
| 8,921,526 B2 | 12/2014 | Chumsae |
| 8,926,975 B2 | 1/2015 | Wong |
| 8,932,591 B2 | 1/2015 | Krause |
| 8,940,305 B2 | 1/2015 | Krause |
| 8,945,067 B2 | 2/2015 | McLoughlin |
| 8,946,388 B2 | 2/2015 | Sahin |
| 8,946,395 B1 | 2/2015 | Herigstad |
| 8,961,956 B2 | 2/2015 | Kimbrel |
| 8,961,973 B2 | 2/2015 | Hoffman |
| 8,961,974 B2 | 2/2015 | Hoffman |
| 8,962,321 B2 | 2/2015 | Kimbrel |
| 8,969,024 B2 | 3/2015 | Kaymakcalan |
| 8,969,037 B2 | 3/2015 | Ellis |
| 8,969,038 B2 | 3/2015 | Ellis |
| 8,969,039 B2 | 3/2015 | Ellis |
| 8,974,790 B2 | 3/2015 | Fischkoff |
| 8,975,040 B2 | 3/2015 | Naso |
| 8,986,693 B1 | 3/2015 | Hoffman |

(56) References Cited

U.S. PATENT DOCUMENTS

| | | |
|---|---|---|
| 8,992,476 B2 | 3/2015 | Shang |
| 8,992,926 B2 | 3/2015 | Fischkoff |
| 8,993,731 B2 | 3/2015 | Tyson |
| 8,999,337 B2 | 4/2015 | Medich |
| 9,017,287 B2 | 4/2015 | Bicknell |
| 9,017,680 B2 | 4/2015 | Fischkoff |
| 9,017,687 B1 | 4/2015 | Wang |
| 9,018,361 B2 | 4/2015 | Hickman |
| 9,034,600 B2 | 5/2015 | Adams |
| 9,040,048 B2 | 5/2015 | Adams |
| 9,045,529 B2 | 6/2015 | Humphreys |
| 9,045,537 B2 | 6/2015 | Ceska |
| 9,061,005 B2 | 6/2015 | Hoffman |
| 9,062,106 B2 | 6/2015 | Bengea |
| 9,067,990 B2 | 6/2015 | Wang |
| 9,067,992 B2 | 6/2015 | Hoffman |
| 9,073,987 B2 | 7/2015 | Fischkoff |
| 9,073,988 B2 | 7/2015 | Pla |
| 9,085,618 B2 | 7/2015 | Ramasubramanyan |
| 9,085,619 B2 | 7/2015 | Fraunhofer |
| 9,085,620 B1 | 7/2015 | Hoffman |
| 9,086,418 B2 | 7/2015 | Maksymowych |
| 9,090,688 B2 | 7/2015 | Bengea |
| 9,090,689 B1 | 7/2015 | Hoffman |
| 9,090,867 B2 | 7/2015 | Pla |
| 9,096,666 B2 | 8/2015 | Wan |
| 9,096,668 B2 | 8/2015 | Gelinas |
| 9,096,879 B2 | 8/2015 | Khetan |
| 9,096,887 B2 | 8/2015 | Smith |
| 9,102,723 B2 | 8/2015 | Wan |
| 9,102,728 B2 | 8/2015 | Tyson |
| 9,109,010 B2 | 8/2015 | Hickman |
| 9,109,216 B2 | 8/2015 | Ellis |
| 9,114,166 B2 | 8/2015 | Krause |
| 9,135,573 B1 | 9/2015 | Rodriguez |
| 9,150,645 B2 | 10/2015 | Subramanian |
| 9,170,249 B2 | 10/2015 | Washburn |
| 9,180,244 B2 | 11/2015 | Anderson |
| 9,181,337 B2 | 11/2015 | Subramanian |
| 9,181,572 B2 | 11/2015 | Subramanian |
| 9,187,559 B2 | 11/2015 | Hoffman |
| 9,193,787 B2 | 11/2015 | Chumsae |
| 9,200,069 B2 | 12/2015 | Ramasubramanyan |
| 9,200,070 B2 | 12/2015 | Ramasubramanyan |
| 9,206,390 B2 | 12/2015 | Rives |
| 9,212,228 B2 | 12/2015 | Sahin |
| 9,216,218 B2 | 12/2015 | Sahin |
| 9,217,048 B2 | 12/2015 | Jaber |
| 9,217,168 B2 | 12/2015 | Prentice |
| 9,220,781 B2 | 12/2015 | Krause |
| 9,226,983 B2 | 1/2016 | Benatuil |
| 9,234,032 B2 | 1/2016 | Pla |
| 9,234,033 B2 | 1/2016 | Rives |
| 9,249,182 B2 | 2/2016 | Herigstad |
| 9,249,232 B2 | 2/2016 | Adams |
| 9,255,143 B2 | 2/2016 | Bengea |
| 9,265,887 B2 | 2/2016 | Julian |
| 9,266,949 B2 | 2/2016 | Ramasubramanyan |
| 9,272,041 B2 | 3/2016 | Krause |
| 9,272,042 B2 | 3/2016 | Krause |
| 9,273,132 B2 | 3/2016 | Wan |
| 9,279,015 B2 | 3/2016 | Wong |
| 9,279,016 B2 | 3/2016 | Harding |
| 9,284,370 B1 | 3/2016 | Medich |
| 9,284,371 B2 | 3/2016 | Pla |
| 9,289,497 B2 | 3/2016 | Krause |
| 9,290,568 B2 | 3/2016 | Rives |
| 9,295,725 B2 | 3/2016 | Krause |
| 9,302,011 B2 | 4/2016 | Krause |
| 9,309,243 B2 | 4/2016 | Bentley |
| 9,309,280 B2 | 4/2016 | Spitali |
| 9,309,327 B2 | 4/2016 | Humphreys |
| 9,315,574 B2 | 4/2016 | Ramasubramanyan |
| 9,315,770 B2 | 4/2016 | Ellis |
| 9,321,836 B2 | 4/2016 | Heavner |
| 9,321,840 B2 | 4/2016 | Burkly |
| 9,321,846 B2 | 4/2016 | Kaymakcalan |
| 9,327,032 B2 | 5/2016 | Krause |
| 9,328,165 B2 | 5/2016 | Wan |
| 9,333,305 B2 | 5/2016 | McLoughlin |
| 9,334,319 B2 | 5/2016 | Ramasubramanyan |
| 9,334,320 B2 | 5/2016 | Okun |
| 9,334,478 B2 | 5/2016 | West |
| 9,340,611 B2 | 5/2016 | Manning |
| 9,340,612 B2 | 5/2016 | Manning |
| 9,346,879 B2 | 5/2016 | Ramasubramanyan |
| 9,346,880 B2 | 5/2016 | Manning |
| 9,365,645 B1 | 6/2016 | Bengea |
| 9,371,391 B2 | 6/2016 | Yonezawa |
| 9,382,317 B2 | 7/2016 | Manning |
| 9,394,357 B2 | 7/2016 | Lawson |
| 9,394,361 B2 | 7/2016 | Gozzard |
| 9,399,061 B2 | 7/2016 | Kupper |
| 9,408,973 B2 | 8/2016 | Shang |
| 9,410,123 B2 | 8/2016 | Lanza |
| 9,416,181 B2 | 8/2016 | Wang |
| 9,428,570 B2 | 8/2016 | Lawson |
| 9,443,445 B2 | 9/2016 | Laurusonis |
| 9,452,138 B2 | 9/2016 | Trollsas |
| 9,475,820 B2 | 10/2016 | Bentley |
| 9,475,858 B2 | 10/2016 | Prentice |
| 9,493,558 B2 | 11/2016 | Ellis |
| 9,493,559 B2 | 11/2016 | Ellis |
| 9,499,603 B2 | 11/2016 | Tyson |
| 9,499,609 B2 | 11/2016 | Ugur |
| 9,499,614 B2 | 11/2016 | Hossler |
| 9,499,615 B2 | 11/2016 | Hoffman |
| 9,499,616 B2 | 11/2016 | Subramanian |
| 9,505,833 B2 | 11/2016 | Chumsae |
| 9,505,834 B2 | 11/2016 | Bengea |
| 9,512,214 B2 | 12/2016 | Rives |
| 9,512,216 B2 | 12/2016 | Hoffman |
| 9,522,953 B2 | 12/2016 | Ramasubramanyan |
| 9,528,998 B2 | 12/2016 | Yoshimura |
| 9,546,212 B2 | 1/2017 | Fischkoff |
| 9,550,737 B2 | 1/2017 | Brookings |
| 9,550,826 B2 | 1/2017 | Labkovsky |
| 9,550,973 B2 | 1/2017 | Ellis |
| 9,556,276 B2 | 1/2017 | Ohori |
| 9,572,938 B2 | 2/2017 | Julian |
| 9,587,227 B2 | 3/2017 | Ellis |
| 9,605,064 B2 | 3/2017 | Okun |
| 9,624,295 B2 | 4/2017 | Medich |
| 9,629,834 B2 | 4/2017 | Aoki |
| 9,631,015 B2 | 4/2017 | Gelinas |
| 9,663,810 B2 | 5/2017 | Prentice |
| 9,669,093 B2 | 6/2017 | Medich |
| 9,682,145 B2 | 6/2017 | Manning |
| 9,683,033 B2 | 6/2017 | Subramanian |
| 9,688,752 B2 | 6/2017 | Wang |
| 9,707,293 B2 | 7/2017 | Manning |
| 9,708,399 B2 | 7/2017 | Wang |
| 9,708,400 B2 | 7/2017 | Subramanian |
| 9,714,251 B2 | 7/2017 | Brookings |
| 9,724,414 B2 | 8/2017 | Manning |
| 9,724,415 B2 | 8/2017 | Manning |
| 9,731,008 B2 | 8/2017 | Manning |
| 9,731,009 B2 | 8/2017 | Manning |
| 9,731,288 B2 | 8/2017 | Jaber |
| 9,732,152 B2 | 8/2017 | Krause |
| 9,737,600 B2 | 8/2017 | Manning |
| 9,738,714 B2 | 8/2017 | Krause |
| 9,750,808 B2 | 9/2017 | Krause |
| 9,751,930 B2 | 9/2017 | Wild |
| 9,751,934 B2 | 9/2017 | Sahin |
| 9,757,454 B2 | 9/2017 | Manning |
| 9,770,487 B2 | 9/2017 | Sahin |
| 9,770,507 B2 | 9/2017 | Manning |
| 9,771,420 B2 | 9/2017 | Ceska |
| 9,782,479 B2 | 10/2017 | Manning |
| 9,782,480 B2 | 10/2017 | Manning |
| 9,789,185 B2 | 10/2017 | Manning |
| 9,803,004 B2 | 10/2017 | Adams |
| 9,803,009 B2 | 10/2017 | Hsieh |

(56) References Cited

U.S. PATENT DOCUMENTS

| | | |
|---|---|---|
| 9,808,525 B2 | 11/2017 | Manning |
| 9,815,797 B2 | 11/2017 | Alexander |
| 9,821,117 B2 | 11/2017 | Anderson |
| 9,828,424 B2 | 11/2017 | Heavner |
| 9,828,438 B2 | 11/2017 | Humphreys |
| 9,834,553 B2 | 12/2017 | Jackson |
| 9,840,556 B2 | 12/2017 | Brown |
| 9,850,240 B2 | 12/2017 | Brookings |
| 9,856,502 B2 | 1/2018 | Nair |
| 9,861,695 B2 | 1/2018 | Manning |
| 9,868,749 B2 | 1/2018 | Alexander |
| 9,873,703 B2 | 1/2018 | Ali |
| 9,873,735 B2 | 1/2018 | Adams |
| 9,890,154 B2 | 2/2018 | Jackson |
| 9,890,174 B2 | 2/2018 | Alexander |
| 9,890,219 B2 | 2/2018 | Adams |
| 9,890,410 B2 | 2/2018 | Washburn |
| 9,902,720 B2 | 2/2018 | Brookings |
| 9,902,768 B2 | 2/2018 | Humphreys |
| 9,908,941 B2 | 3/2018 | Sato |
| 9,914,951 B2 | 3/2018 | Prentice |
| 9,920,052 B2 | 3/2018 | Jackson |
| 9,926,313 B2 | 3/2018 | Deligny |
| 9,932,334 B2 | 4/2018 | Jackson |
| 9,932,342 B2 | 4/2018 | Ali |
| 9,932,343 B2 | 4/2018 | Alexander |
| 9,944,968 B2 | 4/2018 | Yang |
| 9,951,365 B2 | 4/2018 | Bassett |
| 9,957,255 B2 | 5/2018 | Brookings |
| 9,957,318 B2 | 5/2018 | Ramasubramanyan |
| 9,957,320 B2 | 5/2018 | Gozzard |
| 9,969,728 B2 | 5/2018 | Defays |
| 9,969,729 B2 | 5/2018 | Jackson |
| 9,988,383 B2 | 6/2018 | Jackson |
| 9,988,446 B2 | 6/2018 | Adams |
| 9,994,609 B2 | 6/2018 | Ghose |
| 10,004,737 B2 | 6/2018 | Brown |
| 10,023,631 B2 | 7/2018 | Adams |
| 10,053,464 B2 | 8/2018 | Brookings |
| 10,087,179 B2 | 10/2018 | Alexander |
| 10,093,652 B2 | 10/2018 | Heer |
| 10,093,728 B2 | 10/2018 | Mendiratta |
| 10,100,130 B2 | 10/2018 | Humphreys |
| 10,106,523 B2 | 10/2018 | Okuda |
| 10,155,039 B2 | 12/2018 | Manning |
| 10,159,732 B2 | 12/2018 | Manning |
| 10,159,733 B2 | 12/2018 | Manning |
| 10,160,798 B2 | 12/2018 | Hotamisligil |
| 10,179,811 B2 | 1/2019 | Moodie |
| 10,189,897 B2 | 1/2019 | Spitali |
| 10,195,275 B2 | 2/2019 | Manning |
| 10,196,402 B2 | 2/2019 | Ebel |
| 10,196,429 B2 | 2/2019 | Anderson |
| 10,196,452 B2 | 2/2019 | Min |
| 10,202,405 B2 | 2/2019 | De Haro Garcia |
| 10,202,448 B2 | 2/2019 | Barrett |
| 10,202,449 B2 | 2/2019 | Simard |
| 10,202,451 B2 | 2/2019 | Konopitzky |
| 10,202,456 B2 | 2/2019 | Park |
| 10,207,000 B2 | 2/2019 | Manning |
| 10,208,024 B2 | 2/2019 | Andrews |
| 10,208,113 B2 | 2/2019 | Chi |
| 10,208,349 B2 | 2/2019 | Platt |
| 10,213,452 B2 | 2/2019 | Aguilera Peralta |
| 10,213,508 B2 | 2/2019 | Manning |
| 10,220,165 B2 | 3/2019 | Dunne |
| 10,221,210 B2 | 3/2019 | Bolton |
| 10,221,242 B2 | 3/2019 | Wong |
| 10,221,251 B2 | 3/2019 | Humphreys |
| 10,226,525 B2 | 3/2019 | Anderson |
| 10,227,346 B2 | 3/2019 | Schnute |
| 10,233,243 B2 | 3/2019 | Finney |
| 10,238,633 B2 | 3/2019 | Anderskewitz |
| 10,238,658 B2 | 3/2019 | Ito |
| 10,238,697 B2 | 3/2019 | Langella |
| 10,238,736 B2 | 3/2019 | Dominowski |
| 10,246,433 B2 | 4/2019 | Edwards |
| 10,251,844 B2 | 4/2019 | Müller |
| 10,253,105 B2 | 4/2019 | Takeuchi |
| 10,258,689 B2 | 4/2019 | Choi |
| 10,258,740 B2 | 4/2019 | McLoughlin |
| 10,259,867 B2 | 4/2019 | Giles-Komar |
| 10,259,872 B2 | 4/2019 | Pullen |
| 10,259,876 B2 | 4/2019 | Wong |
| 10,260,071 B2 | 4/2019 | Debelak |
| 10,266,513 B2 | 4/2019 | Springer |
| 10,266,519 B2 | 4/2019 | Ito |
| 10,272,152 B2 | 4/2019 | Benson |
| 10,273,247 B2 | 4/2019 | Alexander |
| 10,273,301 B2 | 4/2019 | Snyder |
| 10,273,302 B2 | 4/2019 | Atherfold |
| 10,273,307 B2 | 4/2019 | Simons |
| 10,278,931 B2 | 5/2019 | Kang |
| 10,280,219 B2 | 5/2019 | Bedian |
| 10,280,231 B2 | 5/2019 | Singh |
| 10,286,071 B2 | 5/2019 | Manning |
| 10,286,072 B2 | 5/2019 | Manning |
| 10,287,299 B2 | 5/2019 | Brace |
| 10,287,343 B2 | 5/2019 | Knight |
| 10,287,346 B2 | 5/2019 | Hashimoto |
| 10,293,049 B2 | 5/2019 | Manning |
| 10,294,216 B2 | 5/2019 | Longshaw |
| 10,294,301 B2 | 5/2019 | Nakao |
| 10,294,304 B2 | 5/2019 | Kuo |
| 10,301,286 B2 | 5/2019 | Sugane |
| 10,301,392 B2 | 5/2019 | Chen |
| 10,301,663 B2 | 5/2019 | Sun |
| 10,307,444 B2 | 6/2019 | Lanza |
| 10,308,615 B2 | 6/2019 | Casimiro-Garcia |
| 10,308,723 B2 | 6/2019 | Adams |
| 10,314,890 B2 | 6/2019 | Sahin |
| 10,316,018 B2 | 6/2019 | Lee |
| 10,316,086 B2 | 6/2019 | Yamajuku |
| 10,316,097 B2 | 6/2019 | Godard |
| 10,322,093 B2 | 6/2019 | Mueller |
| 10,322,997 B2 | 6/2019 | Nakajima |
| 10,323,042 B2 | 6/2019 | Chappie |
| 10,323,086 B2 | 6/2019 | Rosenthal |
| 10,323,095 B2 | 6/2019 | Newman |
| 10,328,082 B2 | 6/2019 | Chekler et al. |
| 10,329,302 B2 | 6/2019 | Trzupek |
| RE47,493 E | 7/2019 | Gnamm |
| 10,336,748 B2 | 7/2019 | Schnute |
| 10,336,828 B2 | 7/2019 | Hwang |
| 10,342,925 B2 | 7/2019 | McLoughlin |
| 10,344,081 B2 | 7/2019 | Tyson |
| 10,350,174 B2 | 7/2019 | Wolff |
| 10,350,286 B2 | 7/2019 | Bublot |
| 10,350,287 B2 | 7/2019 | Audonnet |
| 10,351,575 B2 | 7/2019 | Allen |
| 10,357,519 B2 | 7/2019 | Herrera Sanchez |
| 10,358,443 B2 | 7/2019 | Wrasidlo |
| 10,358,445 B2 | 7/2019 | Murray |
| 10,358,460 B2 | 7/2019 | Bassett |
| 10,358,491 B2 | 7/2019 | Chi |
| 10,358,493 B2 | 7/2019 | Finney |
| 10,363,300 B2 | 7/2019 | Audonnet |
| 10,364,255 B2 | 7/2019 | Bosanac |
| 10,364,289 B2 | 7/2019 | Nam |
| 10,364,419 B2 | 7/2019 | Buller |
| 10,370,355 B2 | 8/2019 | Ates |
| 10,370,447 B2 | 8/2019 | Finney |
| 10,376,372 B2 | 8/2019 | Serhan |
| 10,376,588 B2 | 8/2019 | Manning |
| 10,377,804 B2 | 8/2019 | Brodeur |
| 10,385,036 B2 | 8/2019 | Schnute |
| 10,391,097 B2 | 8/2019 | Mjalli |
| 10,392,419 B2 | 8/2019 | Oost |
| 10,392,420 B2 | 8/2019 | Han |
| 10,392,438 B2 | 8/2019 | Bennett |
| 10,405,986 B2 | 9/2019 | Kelly |
| 10,406,220 B2 | 9/2019 | Siber |
| 10,407,475 B2 | 9/2019 | Kim |
| 10,407,513 B2 | 9/2019 | Adams |

(56) References Cited

U.S. PATENT DOCUMENTS

| | | |
|---|---|---|
| 10,413,536 B2 | 9/2019 | Reiser |
| 10,420,651 B2 | 9/2019 | Serhan |
| 10,421,717 B2 | 9/2019 | Defrance |
| 10,421,814 B2 | 9/2019 | Craggs |
| 10,421,815 B2 | 9/2019 | Liu |
| 10,421,816 B2 | 9/2019 | Adams |
| RE47,636 E | 10/2019 | Vintonyak |
| 10,426,135 B2 | 10/2019 | Schnute |
| 10,426,763 B2 | 10/2019 | Kahrs |
| 10,426,784 B2 | 10/2019 | Kawakami |
| 10,426,799 B2 | 10/2019 | Feng |
| 10,426,832 B2 | 10/2019 | Rinaldi |
| 10,426,833 B2 | 10/2019 | Rinaldi |
| 10,433,971 B2 | 10/2019 | Dimauro |
| 10,435,464 B1 | 10/2019 | Puchacz |
| 10,435,472 B2 | 10/2019 | Straub |
| 10,435,670 B2 | 10/2019 | Coffman |
| 10,456,425 B2 | 10/2019 | Herrera Sanchez |
| 10,456,432 B2 | 10/2019 | Mohr |
| 10,456,463 B2 | 10/2019 | Davis |
| 10,457,748 B2 | 10/2019 | Dave |
| 10,463,675 B2 | 11/2019 | Fensome |
| 10,464,932 B2 | 11/2019 | De Haro Garcia |
| 10,465,003 B2 | 11/2019 | Hedrick |
| 10,472,362 B2 | 11/2019 | Jackson |
| 10,472,410 B2 | 11/2019 | Barelle |
| 10,472,426 B2 | 11/2019 | Heywood |
| 10,479,824 B2 | 11/2019 | Lawson et al. |
| 10,485,829 B2 | 11/2019 | Malcuit |
| 10,485,857 B2 | 11/2019 | Fischer |
| 10,485,869 B2 | 11/2019 | Manning |
| 10,487,136 B2 | 11/2019 | Bilgischer |
| 10,492,918 B2 | 12/2019 | Dimauro |
| 10,493,074 B2 | 12/2019 | Allen |
| 10,493,104 B2 | 12/2019 | Chang |
| 10,493,144 B2 | 12/2019 | Widener |
| 10,493,151 B2 | 12/2019 | Manning |
| 10,493,152 B2 | 12/2019 | Rinaldi |
| 10,494,604 B2 | 12/2019 | Hans-Moore |
| 10,500,341 B2 | 12/2019 | McLoughlin |
| 10,501,723 B2 | 12/2019 | West |
| 10,507,241 B2 | 12/2019 | Visvanathan |
| 10,507,251 B2 | 12/2019 | Morinaka |
| 10,512,681 B2 | 12/2019 | Anderson |
| 10,517,966 B2 | 12/2019 | Morinaka |
| 10,519,231 B2 | 12/2019 | Giles-Komar |
| 10,519,479 B1 | 12/2019 | Solacroup |
| 10,526,631 B1 | 1/2020 | Solacroup |
| 10,537,590 B2 | 1/2020 | Oost |
| 10,537,632 B2 | 1/2020 | David |
| 10,537,887 B2 | 1/2020 | Hahn |
| 10,538,786 B2 | 1/2020 | Kamrud |
| 10,544,212 B2 | 1/2020 | Bloom |
| 10,544,229 B2 | 1/2020 | Fransson |
| 10,548,912 B2 | 2/2020 | Karas |
| 10,550,159 B2 | 2/2020 | Anderson |
| 10,555,958 B2 | 2/2020 | Reiche |
| 10,556,906 B2 | 2/2020 | Kuramoto |
| 10,561,722 B2 | 2/2020 | Volkmann |
| 10,562,948 B2 | 2/2020 | Rutkoski |
| 10,562,966 B2 | 2/2020 | Humphreys |
| 10,568,888 B2 | 2/2020 | Mjalli |
| 10,570,118 B2 | 2/2020 | Bosanac |
| 10,570,121 B2 | 2/2020 | Collins |
| 10,570,125 B2 | 2/2020 | Riether |
| 10,576,150 B2 | 3/2020 | Benson |
| 10,577,336 B2 | 3/2020 | Mazzaferro |
| 10,583,087 B2 | 3/2020 | Suda |
| 10,584,313 B2 | 3/2020 | Lanza |
| 10,590,427 B2 | 3/2020 | Gasser |
| 10,729,769 B2 | 8/2020 | Rinaldi |
| 11,447,559 B2 | 9/2022 | Choi |
| 11,534,402 B2 | 12/2022 | Badiali |
| 11,613,581 B2 | 3/2023 | Charati |
| 11,707,524 B2 | 7/2023 | Rinaldi |
| 11,712,471 B2 | 8/2023 | Rinaldi |
| 2003/0138417 A1 | 7/2003 | Kaisheva |
| 2004/0033535 A1 | 2/2004 | Boyle |
| 2004/0126372 A1 | 7/2004 | Banerjee |
| 2004/0166517 A1 | 8/2004 | Terrett |
| 2006/0173009 A1 | 8/2006 | Kanoh |
| 2007/0167450 A1 | 7/2007 | Kobayashi |
| 2007/0265289 A1 | 11/2007 | Okamoto |
| 2008/0233562 A1 | 9/2008 | Sasakawa |
| 2010/0179137 A1 | 7/2010 | Kamikubo |
| 2010/0303813 A1 | 12/2010 | Carulli |
| 2011/0082133 A1 | 4/2011 | Kamikubo |
| 2012/0253036 A1 | 10/2012 | Nagakura |
| 2014/0186361 A1 | 7/2014 | Manning |
| 2014/0273092 A1 | 9/2014 | Flikweert |
| 2014/0288278 A1 | 9/2014 | Nti-Gyabaah |
| 2015/0036833 A1 | 2/2015 | Lukasczyk |
| 2015/0071936 A1 | 3/2015 | Mendiratta |
| 2015/0110799 A1 | 4/2015 | Ramasubramanyan |
| 2015/0111251 A1 | 4/2015 | Hsieh |
| 2015/0150979 A1 | 6/2015 | Yates |
| 2015/0150982 A1 | 6/2015 | Michael |
| 2015/0291946 A1 | 10/2015 | Naso |
| 2015/0329589 A1 | 11/2015 | Bauer |
| 2015/0329628 A1 | 11/2015 | Antochshuk |
| 2016/0129112 A1 | 5/2016 | Neelon |
| 2016/0192626 A1 | 7/2016 | Kajitani |
| 2016/0215319 A1 | 7/2016 | Mendiratta |
| 2016/0235845 A1 | 8/2016 | Cini |
| 2016/0237149 A1 | 8/2016 | Flikweert |
| 2016/0237399 A1 | 8/2016 | Yang |
| 2016/0319011 A1 | 11/2016 | Gokarn |
| 2016/0347787 A1 | 12/2016 | Ng |
| 2016/0347788 A1 | 12/2016 | Bolton |
| 2017/0037381 A1 | 2/2017 | Coffman |
| 2017/0106090 A1 | 4/2017 | Gadgil |
| 2017/0189528 A1 | 7/2017 | Kaya |
| 2017/0226553 A1 | 8/2017 | Prentice |
| 2017/0312361 A1 | 11/2017 | Manning |
| 2017/0348225 A1 | 12/2017 | Freitag |
| 2018/0009876 A1 | 1/2018 | Yonan |
| 2018/0021433 A1 | 1/2018 | Manning |
| 2018/0028655 A1 | 2/2018 | Manning |
| 2018/0028656 A1 | 2/2018 | Manning |
| 2018/0028657 A1 | 2/2018 | Manning |
| 2018/0055929 A1 | 3/2018 | Manning |
| 2018/0079796 A1 | 3/2018 | Ghil |
| 2018/0087080 A1 | 3/2018 | Nair |
| 2018/0140701 A1 | 5/2018 | Manning |
| 2018/0187230 A1 | 7/2018 | Prentice |
| 2018/0291091 A1 | 10/2018 | Moodie |
| 2018/0291092 A1 | 10/2018 | Moodie |
| 2018/0291329 A1 | 10/2018 | Moretto |
| 2018/0296674 A1 | 10/2018 | Rinaldi |
| 2018/0311349 A1 | 11/2018 | Manning |
| 2018/0311350 A1 | 11/2018 | Manning |
| 2018/0311351 A1 | 11/2018 | Manning |
| 2018/0311352 A1 | 11/2018 | Manning |
| 2018/0346881 A1 | 12/2018 | Clemens |
| 2019/0358330 A9 | 1/2019 | Gay |
| 2019/0038728 A1 | 2/2019 | Binder |
| 2019/0038752 A1 | 2/2019 | Bang |
| 2019/0046717 A1 | 2/2019 | Laubrock |
| 2019/0046969 A1 | 2/2019 | Hahn |
| 2019/0048000 A1 | 2/2019 | Liu |
| 2019/0048073 A1 | 2/2019 | Miyara |
| 2019/0048089 A1 | 2/2019 | Babbe |
| 2019/0054009 A1 | 2/2019 | Cawello |
| 2019/0060455 A1 | 2/2019 | Manning |
| 2019/0062420 A1 | 2/2019 | Chiu |
| 2019/0062698 A1 | 2/2019 | Chung |
| 2019/0062703 A1 | 2/2019 | Malcuit |
| 2019/0070117 A1 | 3/2019 | Genin |
| 2019/0070223 A1 | 3/2019 | Chang |
| 2019/0070282 A1 | 3/2019 | Watson |
| 2019/0070283 A1 | 3/2019 | Han |
| 2019/0070292 A1 | 3/2019 | Manning |
| 2019/0070293 A1 | 3/2019 | Manning |
| 2019/0070294 A1 | 3/2019 | Manning |

(56) References Cited

U.S. PATENT DOCUMENTS

| | | |
|---|---|---|
| 2019/0071396 A1 | 3/2019 | Deodhar |
| 2019/0071448 A1 | 3/2019 | Brown |
| 2019/0071496 A1 | 3/2019 | Mendiratta |
| 2019/0071647 A1 | 3/2019 | Fiadeiro |
| 2019/0076365 A1 | 3/2019 | Hattori |
| 2019/0084908 A1 | 3/2019 | Dasseux |
| 2019/0085069 A1 | 3/2019 | Giles-Komar |
| 2019/0085369 A1 | 3/2019 | Yang |
| 2019/0092759 A1 | 3/2019 | Bosanac |
| 2019/0092849 A1 | 3/2019 | Hedrick |
| 2019/0092853 A1 | 3/2019 | Rose |
| 2019/0092856 A1 | 3/2019 | Almagro |
| 2019/0099499 A1 | 4/2019 | Katragadda |
| 2019/0100525 A1 | 4/2019 | Deligny |
| 2019/0100526 A1 | 4/2019 | De Haro Garcia |
| 2019/0100587 A1 | 4/2019 | Brack |
| 2019/0108505 A1 | 4/2019 | Perlman |
| 2019/0111129 A1 | 4/2019 | Ikeda |
| 2019/0111164 A1 | 4/2019 | Rainey |
| 2019/0112302 A1 | 4/2019 | Bentzien |
| 2019/0112314 A1 | 4/2019 | Heer |
| 2019/0112584 A1 | 4/2019 | Lotvin |
| 2019/0117649 A1 | 4/2019 | Bahceci |
| 2019/0119302 A1 | 4/2019 | Deligny |
| 2019/0127422 A1 | 5/2019 | Yang |
| 2019/0127489 A1 | 5/2019 | Humphreys |
| 2019/0135909 A1 | 5/2019 | Spitali |
| 2019/0135910 A1 | 5/2019 | Hsia |
| 2019/0135932 A1 | 5/2019 | Min |
| 2019/0142759 A1 | 5/2019 | Fanara |
| 2019/0142918 A1 | 5/2019 | Binder |
| 2019/0142922 A1 | 5/2019 | Anderson |
| 2019/0144429 A1 | 5/2019 | Schnute |
| 2019/0144529 A1 | 5/2019 | Adams |
| 2019/0144534 A1 | 5/2019 | Barrett |
| 2019/0144550 A1 | 5/2019 | Wong |
| 2019/0144557 A1 | 5/2019 | Ahmadi |
| 2019/0144565 A1 | 5/2019 | Adams |
| 2019/0144945 A1 | 5/2019 | Platt |
| 2019/0151434 A1 | 5/2019 | Barouch |
| 2019/0153096 A1 | 5/2019 | Brack |
| 2019/0153497 A1 | 5/2019 | Jordan |
| 2019/0160105 A1 | 5/2019 | Chang |
| 2019/0161536 A1 | 5/2019 | Hotamisligil |
| 2019/0167636 A1 | 6/2019 | Anderskewitz |
| 2019/0167801 A1 | 6/2019 | Houston |
| 2019/0169283 A1 | 6/2019 | Groth |
| 2019/0169291 A1 | 6/2019 | Anderson |
| 2019/0169301 A1 | 6/2019 | Barrett |
| 2019/0175656 A1 | 6/2019 | Kimbrel |
| 2019/0177420 A1 | 6/2019 | Brodeur |
| 2019/0184011 A1 | 6/2019 | Boden |
| 2019/0184017 A1 | 6/2019 | Manning |
| 2019/0185458 A1 | 6/2019 | Ito |
| 2019/0194335 A1 | 6/2019 | Wong |
| 2019/0202798 A1 | 7/2019 | Springer |
| 2019/0202815 A1 | 7/2019 | Sugane |
| 2019/0202859 A1 | 7/2019 | Rose |
| 2019/0202928 A1 | 7/2019 | Simons |
| 2019/0209567 A1 | 7/2019 | Allen |
| 2019/0216920 A1 | 7/2019 | Pritchard |
| 2019/0216930 A1 | 7/2019 | Manning |
| 2019/0217531 A1 | 7/2019 | Ikeda |
| 2019/0218300 A1 | 7/2019 | Del Rio |
| 2019/0218620 A1 | 7/2019 | Sasaki |
| 2019/0224301 A1 | 7/2019 | Callendret |
| 2019/0233528 A1 | 8/2019 | Srivatsa Srinivasan |
| 2019/0233529 A1 | 8/2019 | Panowski |
| 2019/0241669 A1 | 8/2019 | Kuo |
| 2019/0241678 A1 | 8/2019 | Singh |
| 2019/0247303 A1 | 8/2019 | Morgan |
| 2019/0248890 A1 | 8/2019 | Finney |
| 2019/0248910 A1 | 8/2019 | Chen |
| 2019/0256593 A1 | 8/2019 | Konopitzky |
| 2019/0262450 A1 | 8/2019 | Jezek |
| 2019/0262468 A1 | 8/2019 | Van Berkel |
| 2019/0263742 A1 | 8/2019 | Dasseux |
| 2019/0263816 A1 | 8/2019 | Chappie |
| 2019/0263828 A1 | 8/2019 | Bosanac |
| 2019/0263877 A1 | 8/2019 | Yeung |
| 2019/0269655 A1 | 9/2019 | Bell |
| 2019/0269757 A1 | 9/2019 | Adedokun |
| 2019/0269791 A1 | 9/2019 | Hooper |
| 2019/0269896 A1 | 9/2019 | Kim |
| 2019/0270751 A1 | 9/2019 | Trzupek |
| 2019/0270778 A1 | 9/2019 | Che |
| 2019/0270799 A1 | 9/2019 | Hashimoto |
| 2019/0270811 A1 | 9/2019 | Atherfold |
| 2019/0270826 A1 | 9/2019 | Heidrich |
| 2019/0275126 A1 | 9/2019 | Wraith |
| 2019/0282569 A1 | 9/2019 | Sakurai |
| 2019/0282577 A1 | 9/2019 | Gupta |
| 2019/0282622 A1 | 9/2019 | Klimanskaya |
| 2019/0284170 A1 | 9/2019 | Heer |
| 2019/0284267 A1 | 9/2019 | Knight |
| 2019/0284273 A1 | 9/2019 | Boecher |
| 2019/0284285 A1 | 9/2019 | Thoma |
| 2019/0290650 A1 | 9/2019 | Gupta |
| 2019/0290765 A1 | 9/2019 | Manning |
| 2019/0290766 A1 | 9/2019 | Manning |
| 2019/0290767 A1 | 9/2019 | Manning |
| 2019/0290768 A1 | 9/2019 | Manning |
| 2019/0292157 A1 | 9/2019 | Casimiro-Garcia |
| 2019/0292255 A1 | 9/2019 | Glatt |
| 2019/0292265 A1 | 9/2019 | Brodmerkel |
| 2019/0292533 A1 | 9/2019 | Nager |
| 2019/0298803 A1 | 10/2019 | Sahin |
| 2019/0298837 A1 | 10/2019 | Manning |
| 2019/0298859 A1 | 10/2019 | Baker |
| 2019/0300541 A1 | 10/2019 | Ebel |
| 2019/0300546 A1 | 10/2019 | Chappie |
| 2019/0300598 A1 | 10/2019 | Schenk |
| 2019/0300600 A1 | 10/2019 | Arakawa |
| 2019/0300601 A1 | 10/2019 | Arakawa |
| 2019/0300602 A1 | 10/2019 | Arakawa |
| 2019/0300605 A1 | 10/2019 | Pullen |
| 2019/0308965 A1 | 10/2019 | Wrasidlo |
| 2019/0309016 A1 | 10/2019 | Garidel |
| 2019/0309034 A1 | 10/2019 | Brodeur |
| 2019/0314294 A1 | 10/2019 | Wolff |
| 2019/0314498 A1 | 10/2019 | Manning |
| 2019/0314499 A1 | 10/2019 | Manning |
| 2019/0314500 A1 | 10/2019 | Manning |
| 2019/0315715 A1 | 10/2019 | Casimiro-Garcia |
| 2019/0321414 A1 | 10/2019 | Lanza |
| 2019/0322674 A1 | 10/2019 | Chappie |
| 2019/0322736 A1 | 10/2019 | Randolph |
| 2019/0322739 A1 | 10/2019 | Finney |
| 2019/0324000 A1 | 10/2019 | Randolph |
| 2019/0328783 A1 | 10/2019 | Valton |
| 2019/0328875 A1 | 10/2019 | Manning |
| 2019/0330265 A1 | 10/2019 | Han |
| 2019/0330321 A1 | 10/2019 | Bon |
| 2019/0330325 A1 | 10/2019 | Arakawa |
| 2019/0330329 A1 | 10/2019 | Fujino |
| 2019/0330349 A1 | 10/2019 | Molloy |
| 2019/0331694 A1 | 10/2019 | Arch |
| 2019/0336552 A1 | 11/2019 | Nakamura |
| 2019/0336601 A1 | 11/2019 | Manning |
| 2019/0338022 A1 | 11/2019 | Harrison |
| 2019/0343946 A1 | 11/2019 | Cooper |
| 2019/0343955 A1 | 11/2019 | Manning |
| 2019/0345104 A1 | 11/2019 | Mueller |
| 2019/0345186 A1 | 11/2019 | Ahmad |
| 2019/0345244 A1 | 11/2019 | Harrison |
| 2019/0345245 A1 | 11/2019 | Drevets |
| 2019/0352388 A1 | 11/2019 | Cesaroni |
| 2019/0352391 A1 | 11/2019 | Simard |
| 2019/0352420 A1 | 11/2019 | Hofmann |
| 2019/0352421 A1 | 11/2019 | Adams |
| 2019/0353643 A1 | 11/2019 | Yoo |
| 2019/0358218 A1 | 11/2019 | Reiser |
| 2019/0359620 A1 | 11/2019 | Dahmann |
| 2019/0359701 A1 | 11/2019 | Arndt-Schmitz |

(56) References Cited

U.S. PATENT DOCUMENTS

| | | |
|---|---|---|
| 2019/0359705 A1 | 11/2019 | Chi |
| 2019/0359713 A1 | 11/2019 | Finney |
| 2019/0365886 A1 | 12/2019 | Ahmed |
| 2019/0367502 A1 | 12/2019 | Hall |
| 2019/0367513 A1 | 12/2019 | Hall |
| 2019/0367535 A1 | 12/2019 | De Haro Garcia |
| 2019/0370970 A1 | 12/2019 | Kim |
| 2019/0374610 A1 | 12/2019 | Johnson |
| 2019/0375829 A1 | 12/2019 | Tyson |
| 2019/0375836 A1 | 12/2019 | Hedrick |
| 2019/0375849 A1 | 12/2019 | Hipp |
| 2019/0381012 A1 | 12/2019 | Lu |
| 2019/0381023 A1 | 12/2019 | Kahrs |
| 2019/0382481 A1 | 12/2019 | Diem |
| 2019/0382486 A1 | 12/2019 | Apgar |
| 2019/0387710 A1 | 12/2019 | Schnute |
| 2019/0389946 A1 | 12/2019 | Giamarellos-Bourboulis |
| 2019/0389957 A1 | 12/2019 | Cook |
| 2019/0390170 A1 | 12/2019 | Bielser |
| 2020/0001626 A1 | 1/2020 | Rinaldi |
| 2020/0002727 A1 | 1/2020 | Feary |
| 2020/0010566 A1 | 1/2020 | Chang |
| 2020/0010571 A1 | 1/2020 | Chiu |
| 2020/0016074 A1 | 1/2020 | Badiali |
| 2020/0016075 A1 | 1/2020 | Badiali |
| 2020/0016154 A1 | 1/2020 | Andries et al. |
| 2020/0016268 A1 | 1/2020 | Rinaldi |
| 2020/0017589 A1 | 1/2020 | Snyder |
| 2020/0022988 A1 | 1/2020 | Brown |
| 2020/0023011 A1 | 1/2020 | Feng |
| 2020/0024346 A1 | 1/2020 | Finney |
| 2020/0024360 A1 | 1/2020 | Anderson |
| 2020/0025776 A1 | 1/2020 | Munoz |
| 2020/0031918 A1 | 1/2020 | Cook |
| 2020/0038409 A1 | 2/2020 | Fensome |
| 2020/0039960 A1 | 2/2020 | Schnute |
| 2020/0039977 A1 | 2/2020 | Chappie |
| 2020/0040302 A1 | 2/2020 | Yoo |
| 2020/0046684 A1 | 2/2020 | Impagnatiello |
| 2020/0046723 A1 | 2/2020 | Brookings |
| 2020/0048242 A1 | 2/2020 | Deng |
| 2020/0048278 A1 | 2/2020 | Pouzet |
| 2020/0048346 A1 | 2/2020 | Yates |
| 2020/0048349 A1 | 2/2020 | Gaudet |
| 2020/0048372 A1 | 2/2020 | Adams |
| 2020/0048686 A1 | 2/2020 | Cohen |
| 2020/0055843 A1 | 2/2020 | Bosanac |
| 2020/0055930 A1 | 2/2020 | Beaumont |
| 2020/0055959 A1 | 2/2020 | Dave |
| 2020/0061015 A1 | 2/2020 | Labrenz |
| 2020/0061177 A1 | 2/2020 | Donald |
| 2020/0062822 A1 | 2/2020 | Ghil |
| 2020/0062841 A1 | 2/2020 | Giles-Komar |
| 2020/0069663 A1 | 3/2020 | Godbout |
| 2020/0069764 A1 | 3/2020 | Ma |
| 2020/0071387 A1 | 3/2020 | Bilgischer |
| 2020/0071404 A1 | 3/2020 | Sato |
| 2020/0079855 A1 | 3/2020 | Niessen |
| 2020/0085944 A1 | 3/2020 | Heidenreich |
| 2020/0085948 A1 | 3/2020 | Rinaldi |
| 2020/0087632 A1 | 3/2020 | Coffman |
| 2022/0372130 A1 | 11/2022 | Yoshimoto |

FOREIGN PATENT DOCUMENTS

| | | |
|---|---|---|
| EP | 2571903 B1 | 3/2013 |
| EP | 2773439 A1 | 9/2014 |
| EP | 2946766 A1 | 11/2015 |
| EP | 3036320 B1 | 6/2016 |
| EP | 2946765 B1 | 8/2016 |
| EP | 3050557 A1 | 8/2016 |
| EP | 3053572 A1 | 8/2016 |
| EP | 3053573 A1 | 8/2016 |
| EP | 2946767 B1 | 10/2016 |
| EP | 3013849 B1 | 9/2017 |
| EP | 2822591 B1 | 5/2018 |
| EP | 3148510 B1 | 6/2018 |
| EP | 3145487 B1 | 8/2018 |
| EP | 2971040 B1 | 9/2018 |
| EP | 3372241 | 9/2018 |
| EP | 3372242 A1 | 9/2018 |
| EP | 3403646 A1 | 11/2018 |
| EP | 3412310 A1 | 12/2018 |
| EP | 2935309 B1 | 1/2019 |
| EP | 3659582 A1 | 6/2020 |
| EP | 3145488 B1 | 7/2020 |
| EP | 3236990 B1 | 9/2020 |
| EP | 3701968 A1 | 9/2020 |
| EP | 3741358 A1 | 11/2020 |
| EP | 2970378 B1 | 5/2021 |
| EP | 3085385 B1 | 8/2021 |
| EP | 3247718 B1 | 9/2021 |
| EP | 3597670 B1 | 9/2021 |
| EP | 3912639 A1 | 11/2021 |
| EP | 3916081 A2 | 12/2021 |
| EP | 3936515 A1 | 1/2022 |
| EP | 3592383 B2 | 5/2022 |
| EP | 3592385 B1 | 5/2022 |
| EP | 3597671 B1 | 9/2022 |
| EP | 3476386 B1 | 1/2024 |
| WO | 1997029131 A1 | 8/1997 |
| WO | 98004281 | 2/1998 |
| WO | 1999064460 A1 | 12/1999 |
| WO | 2000005217 A1 | 2/2000 |
| WO | 2000027435 A1 | 5/2000 |
| WO | 2000056772 A1 | 9/2000 |
| WO | 2001046392 A2 | 6/2001 |
| WO | 2001062784 A2 | 8/2001 |
| WO | 2001079173 A2 | 10/2001 |
| WO | 2001094585 A1 | 12/2001 |
| WO | 2002053544 A1 | 7/2002 |
| WO | 2002103362 A2 | 12/2002 |
| WO | 2003018760 A2 | 3/2003 |
| WO | 2003046581 A2 | 6/2003 |
| WO | 2003048208 A2 | 6/2003 |
| WO | 2003083485 A2 | 10/2003 |
| WO | 2003087841 A2 | 10/2003 |
| WO | 2003093237 A1 | 11/2003 |
| WO | 2004000846 A1 | 12/2003 |
| WO | 2004004728 A1 | 1/2004 |
| WO | 2004014920 A1 | 2/2004 |
| WO | 2004016286 A2 | 2/2004 |
| WO | 2004031188 A1 | 4/2004 |
| WO | 2004048552 A2 | 6/2004 |
| WO | 2004063197 A1 | 7/2004 |
| WO | 2004105783 A1 | 12/2004 |
| WO | 2004106377 A1 | 12/2004 |
| WO | 2004113347 A1 | 12/2004 |
| WO | 2004113348 A1 | 12/2004 |
| WO | 2005042540 A1 | 5/2005 |
| WO | 2005046657 A2 | 5/2005 |
| WO | 2005051422 A1 | 6/2005 |
| WO | 2005068623 A1 | 7/2005 |
| WO | 2005068624 A1 | 7/2005 |
| WO | 2005072397 A2 | 8/2005 |
| WO | 2005117984 A2 | 12/2005 |
| WO | 2005123697 A1 | 12/2005 |
| WO | 2005123745 A1 | 12/2005 |
| WO | 2006004188 A1 | 1/2006 |
| WO | 2006004191 A1 | 1/2006 |
| WO | 2006038734 A1 | 4/2006 |
| WO | 2006054059 A1 | 5/2006 |
| WO | 2006085631 A2 | 8/2006 |
| WO | 2006088088 A1 | 8/2006 |
| WO | 2006106323 A1 | 10/2006 |
| WO | 2006138181 A2 | 12/2006 |
| WO | 2007003898 A1 | 1/2007 |
| WO | 2007010231 A1 | 1/2007 |
| WO | 2007019398 A1 | 2/2007 |
| WO | 2007020103 A2 | 2/2007 |
| WO | 2007020853 A1 | 2/2007 |
| WO | 2007026950 A1 | 3/2007 |
| WO | 2007031734 A1 | 3/2007 |
| WO | 2007039714 A1 | 4/2007 |

(56) References Cited

FOREIGN PATENT DOCUMENTS

| | | |
|---|---|---|
| WO | 2007059997 A1 | 5/2007 |
| WO | 2007060406 A1 | 5/2007 |
| WO | 2007060411 A1 | 5/2007 |
| WO | 2007066082 A1 | 6/2007 |
| WO | 2007141018 A1 | 12/2007 |
| WO | 2007147556 A1 | 12/2007 |
| WO | 2008001063 A1 | 1/2008 |
| WO | 2008003931 A1 | 1/2008 |
| WO | 2008012524 A1 | 1/2008 |
| WO | 2008012543 A1 | 1/2008 |
| WO | 2008026781 A1 | 3/2008 |
| WO | 2008031556 A2 | 3/2008 |
| WO | 2008038024 A1 | 4/2008 |
| WO | 2008047134 A2 | 4/2008 |
| WO | 2008064823 A1 | 6/2008 |
| WO | 2008064829 A2 | 6/2008 |
| WO | 2008064830 A1 | 6/2008 |
| WO | 2008074445 A1 | 6/2008 |
| WO | 2008103462 A2 | 8/2008 |
| WO | 2008118356 A2 | 10/2008 |
| WO | 2008122378 A1 | 10/2008 |
| WO | 2008125210 A1 | 10/2008 |
| WO | 2008125215 A1 | 10/2008 |
| WO | 2008138591 A2 | 11/2008 |
| WO | 2008138592 A1 | 11/2008 |
| WO | 2008138615 A1 | 11/2008 |
| WO | 2008140066 A2 | 11/2008 |
| WO | 2008145338 A2 | 12/2008 |
| WO | 2009047255 A1 | 4/2009 |
| WO | 2009051671 A1 | 4/2009 |
| WO | 2009130459 A2 | 10/2009 |
| WO | 2009137624 A2 | 11/2009 |
| WO | 2009137629 A2 | 11/2009 |
| WO | 2010007395 A1 | 1/2010 |
| WO | 2010031551 A2 | 3/2010 |
| WO | 2010035012 A1 | 4/2010 |
| WO | 2010096418 A2 | 8/2010 |
| WO | 2010103274 A1 | 9/2010 |
| WO | 2011013302 A1 | 2/2011 |
| WO | 2011032633 A1 | 3/2011 |
| WO | 2011036454 A1 | 3/2011 |
| WO | 2011036455 A1 | 3/2011 |
| WO | 2011036460 A1 | 3/2011 |
| WO | 2011043371 A1 | 4/2011 |
| WO | 2011061246 A2 | 5/2011 |
| WO | 2011061492 A2 | 5/2011 |
| WO | 2011063005 A2 | 5/2011 |
| WO | 2011065940 A2 | 6/2011 |
| WO | 2011086091 A1 | 7/2011 |
| WO | 2011086136 A1 | 7/2011 |
| WO | 2011086138 A1 | 7/2011 |
| WO | 2011086139 A1 | 7/2011 |
| WO | 2011086141 A1 | 7/2011 |
| WO | 2011095506 A1 | 8/2011 |
| WO | 2011110604 A1 | 9/2011 |
| WO | 2011110621 A1 | 9/2011 |
| WO | 2011116885 A1 | 9/2011 |
| WO | 2011117648 A2 | 9/2011 |
| WO | 2011117653 A1 | 9/2011 |
| WO | 2012012803 A2 | 1/2012 |
| WO | 2012013682 A2 | 2/2012 |
| WO | 2012013930 A2 | 2/2012 |
| WO | 2012013933 A1 | 2/2012 |
| WO | 2012022982 A2 | 2/2012 |
| WO | 2012036193 A1 | 3/2012 |
| WO | 2012095662 A1 | 7/2012 |
| WO | 2012125553 A2 | 9/2012 |
| WO | 2013066707 A1 | 5/2013 |
| WO | 2013068563 A2 | 5/2013 |
| WO | 2013068571 A1 | 5/2013 |
| WO | 2013074681 A1 | 5/2013 |
| WO | 2013082543 A1 | 6/2013 |
| WO | 2013124450 A1 | 8/2013 |
| WO | 2013124451 A1 | 8/2013 |
| WO | 2013174510 A1 | 11/2013 |
| WO | 2013186229 A1 | 12/2013 |
| WO | 2013186230 A1 | 12/2013 |
| WO | 2013190047 A1 | 12/2013 |
| WO | 2014009295 A1 | 1/2014 |
| WO | 2014009296 A1 | 1/2014 |
| WO | 2014020171 A1 | 2/2014 |
| WO | 2014021408 A1 | 2/2014 |
| WO | WO-2014039903 A2 * | 3/2014 ....... A61K 39/39533 |
| WO | 2014075697 A1 | 5/2014 |
| WO | 2014094957 A1 | 6/2014 |
| WO | 2014096390 A1 | 6/2014 |
| WO | 2014099636 A1 | 6/2014 |
| WO | 2014100779 A1 | 6/2014 |
| WO | 2014127785 A1 | 8/2014 |
| WO | 2014127906 A1 | 8/2014 |
| WO | 2014129270 A1 | 8/2014 |
| WO | 2014146778 A1 | 9/2014 |
| WO | 2014149935 A1 | 9/2014 |
| WO | 2014171532 A1 | 10/2014 |
| WO | 2014187863 A1 | 11/2014 |
| WO | 2014193821 A1 | 12/2014 |
| WO | 2014207763 A1 | 12/2014 |
| WO | 2015004679 A1 | 1/2015 |
| WO | 2015011660 A1 | 1/2015 |
| WO | 2015026846 A1 | 2/2015 |
| WO | 2015057910 A1 | 4/2015 |
| WO | 2015086496 A1 | 6/2015 |
| WO | 2015086498 A1 | 6/2015 |
| WO | 2015086499 A1 | 6/2015 |
| WO | 2015086500 A1 | 6/2015 |
| WO | 2015086501 A1 | 6/2015 |
| WO | 2015086502 A1 | 6/2015 |
| WO | 2015086503 A1 | 6/2015 |
| WO | 2015086504 A1 | 6/2015 |
| WO | 2015086505 A1 | 6/2015 |
| WO | 2015086506 A1 | 6/2015 |
| WO | 2015086507 A1 | 6/2015 |
| WO | 2015086508 A1 | 6/2015 |
| WO | 2015086509 A1 | 6/2015 |
| WO | 2015086511 A1 | 6/2015 |
| WO | 2015086512 A1 | 6/2015 |
| WO | 2015086513 A1 | 6/2015 |
| WO | 2015086519 A1 | 6/2015 |
| WO | 2015086520 A1 | 6/2015 |
| WO | 2015086521 A1 | 6/2015 |
| WO | 2015086523 A1 | 6/2015 |
| WO | 2015086525 A1 | 6/2015 |
| WO | 2015086526 A1 | 6/2015 |
| WO | 2015086527 A1 | 6/2015 |
| WO | 2015151115 A1 | 10/2015 |
| WO | 2015177057 A1 | 11/2015 |
| WO | 2015181282 A1 | 12/2015 |
| WO | 2016037159 A1 | 3/2016 |
| WO | 2016050975 A1 | 4/2016 |
| WO | 2016066688 A1 | 5/2016 |
| WO | 2016102378 A1 | 6/2016 |
| WO | 2016102383 A1 | 6/2016 |
| WO | WO-2016103093 A1 * | 6/2016 ........... A61K 39/395 |
| WO | 2016118707 A1 | 7/2016 |
| WO | 2016119909 A1 | 8/2016 |
| WO | 2016120413 A1 | 8/2016 |
| WO | 2016128564 A1 | 8/2016 |
| WO | 2016156476 | 10/2016 |
| WO | 2016162819 A1 | 10/2016 |
| WO | 2016165765 A1 | 10/2016 |
| WO | 2016176656 A2 | 11/2016 |
| WO | 2016189045 A1 | 12/2016 |
| WO | 2016196315 A2 | 12/2016 |
| WO | 2016198398 A1 | 12/2016 |
| WO | 2016198400 A1 | 12/2016 |
| WO | 2016198401 A1 | 12/2016 |
| WO | 2016202411 A1 | 12/2016 |
| WO | 2016202413 A1 | 12/2016 |
| WO | 2016202414 A1 | 12/2016 |
| WO | 2016202415 A1 | 12/2016 |
| WO | 2017005358 A1 | 1/2017 |
| WO | 2017060242 A1 | 4/2017 |
| WO | 2017072183 A1 | 5/2017 |
| WO | 2017093402 A1 | 6/2017 |

(56) References Cited

FOREIGN PATENT DOCUMENTS

| | | |
|---|---|---|
| WO | 2017093404 A1 | 6/2017 |
| WO | 2017093406 A1 | 6/2017 |
| WO | 2017093408 A1 | 6/2017 |
| WO | 2017093410 A1 | 6/2017 |
| WO | 2017102830 A1 | 6/2017 |
| WO | 2017140881 A1 | 8/2017 |
| WO | 2017167960 A1 | 10/2017 |
| WO | 2017167993 A1 | 10/2017 |
| WO | 2017167994 A1 | 10/2017 |
| WO | 2017167995 A1 | 10/2017 |
| WO | 2017167996 A1 | 10/2017 |
| WO | 2017191062 A1 | 11/2017 |
| WO | 2018077775 A1 | 5/2018 |
| WO | 2018104534 A1 | 6/2018 |
| WO | 2018119142 A1 | 6/2018 |
| WO | 2018197503 A1 | 11/2018 |
| WO | 2018224951 A2 | 12/2018 |
| WO | 2018229079 A1 | 12/2018 |
| WO | 2019030373 A1 | 2/2019 |
| WO | 2019034973 A1 | 2/2019 |
| WO | 2019035649 A1 | 2/2019 |
| WO | 2019038338 A1 | 2/2019 |
| WO | 2019040808 A1 | 2/2019 |
| WO | 2019043067 A1 | 3/2019 |
| WO | 2019055754 A1 | 3/2019 |
| WO | 2019058345 A2 | 3/2019 |
| WO | 2019059741 A1 | 3/2019 |
| WO | 2019068632 A1 | 4/2019 |
| WO | 2019068633 A1 | 4/2019 |
| WO | 2019072889 A1 | 4/2019 |
| WO | 2019073069 A1 | 4/2019 |
| WO | 2019075032 A1 | 4/2019 |
| WO | 2019077132 A1 | 4/2019 |
| WO | 2019090329 A1 | 5/2019 |
| WO | 2019101582 A1 | 5/2019 |
| WO | 2019108639 A1 | 6/2019 |
| WO | 2019115671 A1 | 6/2019 |
| WO | 2019115674 A1 | 6/2019 |
| WO | 2019121961 A2 | 6/2019 |
| WO | 2019123207 A1 | 6/2019 |
| WO | 2019123250 A1 | 6/2019 |
| WO | 2019126257 A1 | 6/2019 |
| WO | 2019138017 A1 | 7/2019 |
| WO | 2019140425 A1 | 7/2019 |
| WO | 2019152705 A1 | 8/2019 |
| WO | 2019152742 A1 | 8/2019 |
| WO | 2019166932 A1 | 9/2019 |
| WO | 2019166946 A1 | 9/2019 |
| WO | 2019171252 A1 | 9/2019 |
| WO | 2019171253 A1 | 9/2019 |
| WO | 2019177883 A2 | 9/2019 |
| WO | 2019177888 A1 | 9/2019 |
| WO | 2019185476 A1 | 10/2019 |
| WO | 2019185477 A1 | 10/2019 |
| WO | 2019204721 A1 | 10/2019 |
| WO | 2019204734 A1 | 10/2019 |
| WO | 2019212253 A1 | 11/2019 |
| WO | 2019214610 A1 | 11/2019 |
| WO | 2019215701 A1 | 11/2019 |
| WO | 2019220368 A1 | 11/2019 |
| WO | 2019220369 A2 | 11/2019 |
| WO | 2019220412 A2 | 11/2019 |
| WO | 2019224025 A2 | 11/2019 |
| WO | 2019224333 A1 | 11/2019 |
| WO | 2019224715 A1 | 11/2019 |
| WO | 2019224716 A2 | 11/2019 |
| WO | 2019224717 A2 | 11/2019 |
| WO | 2019231243 A1 | 12/2019 |
| WO | 2019232110 A1 | 12/2019 |
| WO | 2019234680 A1 | 12/2019 |
| WO | 2019235839 A1 | 12/2019 |
| WO | 2019241098 A1 | 12/2019 |
| WO | 2019243964 A1 | 12/2019 |
| WO | 2019243965 A1 | 12/2019 |
| WO | 2020001448 A1 | 1/2020 |
| WO | 2020002494 A1 | 1/2020 |
| WO | 2020006347 A1 | 1/2020 |
| WO | 2020016838 A2 | 1/2020 |
| WO | 2020039321 A2 | 2/2020 |
| WO | 2020039359 A2 | 2/2020 |
| WO | 2020039384 A1 | 2/2020 |
| WO | 2020043658 A1 | 3/2020 |
| WO | 2020050626 A1 | 3/2020 |
| WO | 2020051333 A1 | 3/2020 |

OTHER PUBLICATIONS

Cai, et al., Recommendations and requirements for the design of bioanalytical testing used in comparability studies for biosimilar drug development, Bioanalysis, 3(5):535-540 (2011).
Casadevall, Pure red cell aplasia and anti-erythropoietin antibodies in patients treated with epoetin, Nephrol. Dial. Transplant., 18(Suppl. 8):viii37-viii41 (2003).
Christen et al., Immune Response to a Recombinant Human TNFR55-IgG1 Fusion Protein: Auto-Antibodies in Rheumatoid Arthritis (RA) and Multiple Sclerosis (MS) Patients Have Neither Neutralizing nor Agonist Activities, Human Immunology, 60(9):774-790 (1999).
Clark, Antibody humanization: a case of the 'Emperor's new clothes'?, Immunology Today, 21(8):397-402 (2000).
Declaration of Dr. Alexander A. Vinks.
Declaration of Dr. Allan Gibofsky.
Declaration of Dr. Brian Harvey.
Declaration of Dr. Jerry A. Hausman.
Declaration of Jeffrey M. Sailstad.
Denosumab/PROLIA™ label (Jun. 2010).
Eckardt & Casadevail, Pure red-cell aplasia due to anti-erythropoietin antibodies, Nephrol. Dial. Transplant., 18:865-869 (2003).
Feldmann & Maini, Anti-TNFa Therapy of Rheumatoid Arthritis: What Have We Learned?, Annu. Rev. Immunol., 19:163-96 (2001).
Findlay, et al., Validation of immunoassays for bioanalysis: a pharmaceutical industry perspective, J. Pharm. Biomed. Anal., 21:1249-1273 (2000).
Furst, et al., Intravenous Human Recombinant Tumor Necrosis Factor Receptor p55-Fc IgG1 Fusion Protein, Ro 45-2081 (Lenercept): Results of a Dose-Finding Study in Rheumatoid Arthritis, J. Rheumatol., 30(10):2123-2126 (2003).
Furst, et al., Neutralization of TNF by Lenercept (TNFR55-IgG1, Ro 45-2081) in Patients With Rheumatoid Arthritis Treated for 3 Months: Results of an US Phase II Trial, Arthritis & Rheumatism, 39(6)(Suppl.):S243(Abstract 1295) (1996).
Furst, et al., Updated consensus statement on biological agents for the treatment of rheumatic diseases, 2008, Ann. Rheum. Dis., 67(Suppl. III):iii2-iii25 (2008).
Furst, et al., Updated consensus statement on biological agents for the treatment of rheumatoid arthritis and other immune mediated inflammatory diseases (May 2003), Ann. Rheum. Dis., 62(Suppl II):ii2-ii9 (2003).
Gibofsky, et al., Real-world utilization of DMARDs and biologics in rheumatoid arthritis: the RADIUS (Rheumatoid Arthritis Disease-Modifying Anti-Rheumatic Drug Intervention and Utilization Study) study, Current Medical Research and Opinion, 22(1):169-183 (2006).
Gibosky, Liability Issues in the Treatment of Patients With Rheumatic Diseases, Am. J.Medicine, 102(Suppl. 1A):1A-40S-1A-42S (1997).
Hanauer, Review article: safety of infliximab in clinical trials, Ailment Pharmacol. Ther., 13(Suppl. 4):16-22 (1999).
Hasler, et al., Safety and Efficacy of TNF Neutralization by Lenercept (TNFR55-IgG1, Ro 45-2081) in Patients With Rheumatoid Arthritis Exposed to a Single Dose, Am. Coll. of Rheumatology 60th Nat'l Scientific Meeting & Ass'n of Rheumatology Health Prof'ls 31st Nat'l Scientific Meeting, S243 (Abstract 1291) (1996).
Karlsson, et al., The population pharmacokinetics of recombinant- and urinary-human follicle stimulating hormone in women, Br. J. Clin. Pharmacol., 45(1):13-20 (1998).
Kavanaugh, Anti-Tumor Necrosis Factor-á Monoclonal Antibody Therapy for Rheumatoid Arthritis, Rheumatic Disease Clinics of North America, 24(3):593-614 (1998).

(56) References Cited

OTHER PUBLICATIONS

Maini & Feldmann, How does infliximab work in rheumatoid arthritis?, Arthritis Res., 4(Suppl. 2):S22-S28 (2002).
Mayo Clinic Staff, Rheumatoid arthritis.
O'Dell, Combination DMARD therapy for rheumatoid arthritis: a step closer to the goal, Ann. Rheum. Dis., 55:781-783 (1996).
O'Dell, et al., Treatment of Early Seropositive Rheumatoid Arthritis With Minocycline: Four-Year Followup of a Double-Blind, Placebo-Controlled Trial, Arthritis & Rheumatism, 42(8):1691-1695 (1999).
O'Dell, et al., Treatment of Early Seropositive Rheumatoid Arthritis: A Two-Year, Double-Blind Comparison of Minocycline and Hydroxychloroquine, Arthritis & Rheumatism, 44(10):2235-2241 (2001).
O'Dell, It Is the Best of Times; It Is the Worst of Times: Is There a Way Forward? A Plethora of Treatment Options for Rheumatoid Arthritis, but Critical Trial Design Issues, Arthritis & Rheumatism, 56(12):3884-3886 (2007).
O'Dell, M.D., et al., Treatment of Rheumatoid Arthritis With Methotrexate Alone, Sulfasalazine and Hydroxychloroquine, or a Combination of All Three Medications, New Eng. J. Med., 334(20):1287-1291 (1996).
O'Dell, MD, Combination DMARD therapy with hydroxychloroquine, sulfasalazine, and methotrexate, Clin. Exp. Rheumatol., 17(Suppl. 18):S53-S58 (1999).
O'Dell, MD, et al., Conference Summary: American College of Rheumatology Clinical Trial Priorities and Design Conference, Jul. 22-23, 2010, Arthritis & Rheumatism, 63(8):2151-2156 (2011).
O'Dell, MD, Rheumatoid Arthritis: The Crisis in Clinical Research, Current Rheumatology Reports, 2:1-2 (2000).
O'Dell, MD, TNF-a Inhibition: The Need for a Tumor Necrosis Factor Thermostat, Mayo Clin. Proc., 76:573-575 (2001).
Proudfoot, (updated by John Collett), Chapter 19: Dosage regimens, in Pharmaceutics, the Science of Dosage Form Design (Michael E. Aulton ed., 2d ed. 2002).
Ruderman & Tambar, Rheumatoid Arthritis, American Collee of Rheumatology, (last updated Aug. 2013).
Ruffing & Bingham, Rheumatoid Arthritis Signs and Symptoms.
Smolen, et al., Efficacy and safety of tabalumab, an anti-B-cell-activating factor monoclonal antibody, in patients with rheumatoid arthritis who had an inadequate response to methotrexate therapy: results from a phase III multicentre, randomised, double-blind study, Ann. Rheum. Dis., 74:1567-1570 (2015).
The Lenercept Multiple Sclerosis Study Group & the Univ. of British Columbia MS/MRI Analysis Group, TNF neutralization in MS, Neurology, 53(3):457-465 (1999).
Trastuzumab/Herceptin® label (Mar. 2016).
U.S. Department of Health and Human Services Food and Drug Administration Center for Biologics Evaluation and Research, Points to Consider in the Manufacture and Testing of Monoclonal Antibody Products for Human Use (Feb. 28, 1997).
U.S. Department of Health and Human Services Food and Drug Administration Center for Drug Evaluation and Research (CDER) Center for Biologics Evaluation and Research (CBER) ICH, Guidance for Industry: E6 Good Clinical Practice: Consolidated Guidance (Apr. 1996).
U.S. Department of Health and Human Services Food and Drug Administration Center for Drug Evaluation and Research (CDER) Center for Biologics Evaluation and Research (CBER), Guidance for Industry: Population Pharmacokinetics (Feb. 1999).
U.S. Department of Health and Human Services Public Health Service Food and Drug Administration Center for Biologics Evaluation and Research, Approval Letter, Adalimumab (Humira®) dated Dec. 31, 2002, (last visited Jul. 19, 2016).
Wolfe, et al., Evaluating Severity and Status in Rheumatoid Arthritis, J. Rheumatol., 28(6):1453-1462 (2001).
Ziminski & O'Dell, Roundtable I: Practice Patterns for Treating Rheumatoid Arthritis, Am. J. of Managed Care, 5(14)(Suppl.):S870-S879 (1999).
IPR2017-00822 Patent Owner's Preliminary Response (Jun. 11, 2017).

"Fraunhofer Substantive Motion 3," in *Fraunhofer v. Gokarn*, Patent Interference No. 106,057 (filed on Oct. 12, 2016).
Abbvie Biotechnology Ltd., "Annex A—The Humira® Story," in Opposition Proceeding for EP1406656 (filed on Dec. 22, 2014).
Adalimumab Product Approval Information, http://www.fda.gov/Drugs/DevelopmentApprovalProcess/HowDrugsareDevelopedandApproved/ApprovalApplications/TherapeuticBiologicApplications/ucm080610.htm (accessed Jan. 23, 2017).
Akers et al., "Formulation Development of Protein Dosage Forms," Ch. 2 in Development and Manufacture of Protein Pharmaceuticals, Kluwer Academic/Plenum Publishers: New York, 47-127 (Nail et al., eds., 2002).
Barn et al., J Pharm Sci. (1998) 87(12):1554-9.
Carpenter & Manning, eds., Rational Design of Stable Protein Formulations, Theory and Practice, Pharmaceutical Biotechnology 13 (Kluwer Academic/Plenum Publishers, New York) (2002).
Carpenter et al., Pharmaceutical Research (1997) 14(8):969-975.
Carpenter, et al., "Rational Design of Stable Lyophilized Protein Formulations: Some Practical Advice," Pharm. Res. 14(8), 969-975 (1997).
Chen, et al., "Aggregation Pathway of Recombinant Human Keratinocyte Growth Factor and Its Stabilization," Pharm. Res. 11(11), 1581-1587 (1994).
Chiodi et al., Electrophoresis (1985) 6:124-128.
Cleland & Langer, "Formulation and Delivery of Proteins and Peptides: Design and Development Strategies," Ch. 1 in Formulation and Delivery of Proteins and Peptides, ACS Symposium Series 567, 1-19 (1994).
Cleland et al., Crit Rev Ther Drug Carrier Syst. (1993) 10(4):307-377.
Daugherty, et al., "Formulation and Delivery Issues for Monoclonal Antibody Therapeutics," Adv. Drug Deliv. Rev. 58, 686-706 (2006).
Declaration of Mark C. Manning, Ph.D. dated May 6, 2016 from IPR2016-01018, Ex. 1002.
Declaration of Theodore W. Randolph, Ph.D.
Exposure Factors Handbook (E.P.A. 1997).
Fayos, et al., "On the Origin of the Thermostabilization of Proteins Induced by Sodium Phosphate," J. Am. Chem. Soc. 127(27), 9690-9691 (2005).
Frenken et al., "Identification of the Component Part in an Epoetin Alfa Preparation that Causes Pain after Subcutaneous Injection," American J. of Kidney Diseases, 22(4): 553-556 (1993).
Gamimune® Label (Oct. 2005); IPR 2017-000822 Exhibit 1016.
Gokarn, et al., "Self-Buffering Antibody Formulations," J. Pharm. Sci. 97(8), 3051-3066 (Aug. 2008).
Handbook of Pharmaceutical Excipients, Pharmaceutical Press (Raymond C. Rowe, Paul J. Sheskey, & Siân C. Owen eds., 5th ed. 2006).
Helms, et al., "Destabilizing Loop Swaps in the CDRs of an Immunoglobulin VL Domain," Protein Sci. 4, 2073-2081 (1995).
Humira® Label (Nov. 2016); IPR 2017-000822 Exhibit 1032.
Laursen et al., "Pain Perception after Subcutaneous Injections of Media Containing Different Buffers," Basic & Clinical Pharmacology & Toxicology, 98:218-221 (2006).
Liu, et al., "Reversible Self-Association Increases the Viscosity of a Concentrated Monoclonal Antibody in Aqueous Solution," J. Pharm. Sci. 94(9), 1928-1940 (Sep. 2005).
Mcdonnell, "Production of Antibodies in Hybridoma and Non-hybridoma Cell Lines," Ch. 3 in Animal Cell Culture, Cell Engineering vol. 9, 65-88 (M. Al-Rubeai ed., 2015).
Mezzasalma, et al., "Enhancing Recombinant Protein Quality and Yield by Protein Stability Profiling," J. Biomolecular Screening 12(3), 418-428 (2007).
Nail et al. "Development and Manufacture of Protein Pharmaceuticals," (Kluwer Academic/Plenum Publishers, New York, Jun. 30, 2002).
Nema et al., PDA J Pharm Sci and Tech (1997) 51:166-171.
Petition for Inter Partes Review of U.S. Pat. No. 8,916,157, IPR 2015-01514 (Jun. 26, 2015).
Petition for Inter Partes Review of U.S. Pat. No. 9,085,619 Pursuant to 35 U.S.C. §§ 311-319 and 37 C.F.R. § 42, IPR 2017-00822 (Jan. 31, 2017).

(56) References Cited

OTHER PUBLICATIONS

Raibekas, et al., "Anion Binding and Controlled Aggregation of Human Interleukin-1 Receptor Antagonist," Biochemistry 4(29), 9871-9879 (2005).
Rational Design of Stable Protein Formulations: Theory and Practice (Carpenter and Manning, ed., Apr. 30, 2002).
Rouet, et al., "Stability Engineering of the Human Antibody Repertoire," FEBS Letters 588, 269-277 (2014).
Ruiz, et al., "Aggregation of Recombinant Human Interferon Alpha 2b in Solution: Technical Note," AAPS Pharm. Sci. Tech. 7(4), Article 99, E1-E5 (2006).
Salinas, et al., "Understanding and Modulating Opalescence and Viscosity in a Monoclonal Antibody Formulation," J. Pharm. Sci. 99(1), 82-93 (2010).
Schwartz, "Diafiltration for Desalting of Buffer Exchange," BioProcess Int'l (May 2003).
Shire, "Formulation of Proteins and Monoclonal Antibodies (mAbs)," Monoclonal Antibodies, Meeting the Challenges in Manufacturing, Formulation, Delivery and Stability of Final Drug Product, Woodhead Publishing Series in Biomedicine 77, Chap. 4, 93-120 (Woodland Publishing, Cambridge, UK) (2015).
Stoner et al., "Protein-Solute Interactions Affect the Outcome of Ultrafiltration/Diafiltration Operations," J. Pharm. Sci., 93:2332-2342 (2004).
Thomson Reuters, "A Bioworld Special Report: Biosimilars: U.S. Market Opportunities and Critical Strategies 2016" (2016).
U.S. Prosecution History of U.S. Appl. No. 12/325,049 (U.S. Pat. No. 8,420,081).
U.S. Prosecution History of U.S. Appl. No. 13/774,735 (U.S. Pat. No. 8,883,146).
U.S. Prosecution History of U.S. Appl. No. 61/004,992.
U.S. Prosecution History of U.S. Appl. No. 14/506,576 (U.S. Pat. No. 9,085,619).
United States Pharmacopeia and National Formulary (USP 24-NF 19) Rockville, MD: United States Pharmacopeia Convention, 2000.
Wang, "Instability, Stabilization, and Formulation of Liquid Protein Pharmaceuticals," Int'l J. Pharmaceutics 185, 129-188 (1999).
Wang, et al., "Antibody Structure, Instability, and Formulation," J. Pharm. Sci. 96(1), 1-26 (Jan. 2007).
Wang, Int. J. Pharm., (1999) 185:129-188.
Zevalin® Label, Physicians' Desk Reference (Thomson PDR, Montvale, N.J., 60th ed.) (2006).
Abbott Laboratories, Abbott Receives FDA Approval for New Humira(R) Delivery Device, Press Release dated Jun. 26, 2006.
Anantharaman, Biologics for Rheumatoid Arthritis: Challenges and opportunities in tackling this crippling disorder, Frost & Sullivan, Jul. 20, 2004.
Berndt, et al., Chapter 7: The Roles of Marketing, Product Quality and Price Competition in the Growth and Composition of the U.S. Antiulcer Drug Industry, in the Economics of New Goods (Timothy f. Bresnahan & Robert J. Gordon, eds. 1997).
Center for Drug Evaluation and Research, Summary Review of sBLA 125057/110 dated Jan. 16, 2008.
Certolizumab pegol/CIMZIA® label (Nov. 18, 2009).
Chilton & Collett, BA, PhD, CBiol, Treatment choices, preferences and decision-making by patients with rheumatoid arthritis, Musculoskelet. Care, 6(1):1-14 (2008).
Curtis & Singh, The Use of Biologics in Rheumatoid Arthritis: Current and Emerging Paradigms of Care, Clin. Ther. 33(6):679-707 (2011).
Department of Health & Human Services Food and Drug Administration, Approval Letter for BL 103795/5110 dated Oct. 17, 2003.
Department of Health & Human Services Food and Drug Administration, Approval Letter for BL 12057/89 dated Feb. 27, 2007.
Department of Health & Human Services Food and Drug Administration, Approval Letter for BL 125057/110 dated Jan. 18, 2008.
Department of Health & Human Services Food and Drug Administration, Approval Letter for BL 125057/45 dated Oct. 3, 2005.
Department of Health & Human Services Food and Drug Administration, Approval Letter for sBLA 125057/114 dated Feb. 21, 2008.
Department of Health & Human Services Food and Drug Administration, Supplemental Approval Letter for BLA 125057/232 dated Sep. 28, 2012.
Department of Health & Human Services Food and Drug Administration, Supplemental Approval Letter for BLA 125057/S-363 dated Sep. 9, 2015.
Department of Health & Human Services Food and Drug Administration, Supplemental Approval Letter for BLA 125057/S-397 dated Jun. 30, 2016.
Department of Health and Human Services Office of Therapeutics Research and Review Center for Biologics Evaluation and Research Food and Drug Administration, Review of BLA submission 99-O 128 Infliximab (Remicade) for signs and symptoms of rheumatoid arthritis (Oct. 22, 1999).
GlobalData, Top 50 pharmaceutical products by global sales, PMLiVe.
Golimumab/Simponi® label (Apr. 2009).
Greenapple, MSPH, Trends in Biologic Therapies for Rheumatoid Arthritis: Results from a Survey of Payers and Providers, Am. Health Drug Benefits, 5(2_:83-95 (2012).
Liscki & Chu, What Matters to Patients and Physicians When Considering Biologic Therapy for Rheumatoid Arthritis, Postgraduate Medicine, 120(3):154-160 (2008).
Mevorach & Paget, Chapter 28: Rheumatoid Arthritis, in Manual of Rheumatology and Outpatient Orthopedic Disorders: Diagnosis and Therapy (Stephen A. Paget, et al. eds., 4th ed. 2000).
Miller, et al., Workshop on Bioanalytical Methods Validation for Macromolecules: Summary Report, Pharmaceutical Research, 18(9):1373-1383 (2001).
Mire-Sluis, et al., Recommendations for the design and optimization of immunoassays used in the detection of host antibodies against biotechnology products, J. Immunological Methods, 289(1-2):1-16 (2004).
Mordenti, et al., Efficacy and Concentration—Response of Murine Anti-VEGF Monoclonal Antibody in Tumor-Bearing Mice and Extrapolation to Humans, Toxicologic Pathology, 27(1):14-21 (1999).
Moreland, et al., Biologic Agents for Treating Rheumatoid Arthritis, Arthritis & Rheumatism, 40(3):397-409 (1997).
Moreland, et al., Phase I/II Trial of Recombinant Methionyl Human Tumor Necrosis Factor Binding Protein PEGylated Dimer in Patients with Active Refractory Rheumatoid Arthritis, J. Rheumatol., 27(3):601-609 (2000).
MW\PHARM Version 3.15, vol. 1: Installation & Quick Reference (Fourth print, Dec. 20, 1997); vol. 2: Tour de Pharm (Fourth print, Dec. 20, 1997); vol. 3: Methods (First Print, Jan. 3, 1995), Mediware.
Nestorov, Clinical Pharmacokinetics of Tumor Necrosis Factor Antagonists, J. Rheumatol., 32(Suppl. 74):13-18 (2005).
Palmer, Top 10 rheumatoid arthritis drugs 2013, FiercePharma, Sep. 16, 2013.
Prevoo, et al., Modified Disease Activity Scores That Include Twenty-Eight-Joint Counts, Arthritis & Rheumatism, 38(1):44-48 (1995).
Rankin, et al., The Therapeutic Effects of an Engineered Human Anti-Tumou Necrosis Factor Alpha Antibody (CDP571) in Rheumatoid Arthritis, Br. J. Rheumatol., 34:334-342 (1995).
Rheumatoid Arthritis: What is Rheumatoid Arthritis?.
Ross, et al, Immunogenicity of Interferon-â in Multiple Sclerosis Patients: Influence of Preparation, Dosage, Dose Frequency, and Route of Administration, Ann. Neurol., 48(5):706-712 (2000).
Rossert et al, Anti-Erythropoietin Antibodies and Pure Red Cell Aplasia, J. Am. Soc. Nephrol., 15(2):398-406 (2004).
Rowland & Tozer, Chapter 1: Why Clinical Pharmacokinetics?, Chapter 2: Basic Considerations, Chapter 5: Therapeutic Response and Toxicity, Chapter 6: Constant-Rate Regimens & Chapter 7: Multiple-Dose Regimens in Clinical Pharmacokinetics: Concepts and Applications (3d ed. 1995).
Rowland & Tozer, Chapter 11: Multiple-Dose Regimens, in Clinical Pharmacokinetics and Pharmacodynamics: Concepts and Applications (4th ed. 2011).

(56) References Cited

OTHER PUBLICATIONS

Sailstad, et al., A White Paper—Consensus and Recommendations of a Global Harmonization Team on Assessing the Impact of Immunogenicity on Pharmacokinetic Measurements, The AAPS Journal, 16(3):488-498 (2014).
Sander & Rau, Clinical trials on biologics in rheumatoid arthritis, Int'l J. Clin. Pharm. Therapeutics, 36(11):621-624 (1998).
Securities and Exchange Commission Form 10-K for Abbott Laboratories for the fiscal year ended Dec. 31, 2003.
Securities and Exchange Commission Form 10-K for Abbott Laboratories for the fiscal year ended Dec. 31, 2005.
Securities and Exchange Commission Form 10-K for AbbVie Inc. for the fiscal year ended Dec. 31, 2015.
Sedger & McDermott, TNF and TNF-receptors: From mediators of cell death and inflammation to therapeutic giants—past, present and future, Cytokine & Growth Factor Reviews, 25:453-472 (2014).
Smolen, et al., Consensus statement on blocking the effects of interleukin-6 and in particular by interleukin-6 receptor inhibition in rheumatoid arthritis and other inflammatory conditions, Ann. Rheum. Dis., 72(4):482-492 (2013).
Taylor, et al., Reduction of Chemokine Levels and Leukocyte Traffic to Joints by Tumor Necrosis Factor á Blockade in Patients With Rheumatoid Arthritis, Arthritis & Rheumatism, 43(1):38-47 (2000).
Tishler, et al., Methotrexate treatment of rheumatoid arthritis: is a fortnightly maintenance schedule enough?, Ann. Rheum. Dis., 51(12):1330-1331 (1992).
U.S. Food and Drug Administration, How Drugs are Developed and Approved, page last updated Aug. 18, 2015.
Van de Putte et al., Efficacy and safety of the fully human antitumour necrosis factor á monoclonal antibody adalimumab (D2E7) in DMARD refractory patients with rheumatoid arthritis: a 12 week, phase II study, Ann. Rheum. Dis., 62:1168-1177 (2003).
Van de Putte et al., Six Month Efficacy of the Fully Human Anti-TNF Antibody D2E7 in Rheumatoid Arthritis, Ann. Rheum. Dis., 59(Suppl. 1):Abstract OP.056 (2000).
Weaver et al., Real-world effectiveness of select biologic and DMARD monotherapy and combination therapy in the treatment of rheumatoid arthritis: results from the Radius observational registry, Current Medical Research and Opinion, 22(1):185-198 (2006).
Weinblatt, Methotrexate in Rheumatoid Arthritis: A Quarter Century of Development, Transactions of the American Clinical and Climatological Association, 124:16-25 (2013).
"Nutropin AQ®", Physicians' Desk Reference, 1420-1423 (56th ed. 2002).
2004 Express Scripts National Preferred Alpha Formulary List (1q-04) dated Dec. 29, 2003.
Abciximab/Reopro® label (Nov. 4, 1997).
Adalimumab M10-261 Clinical Study Report R&D/09/173 (Apr. 9, 2010).
Alemtuzumab/Campath® label (May 2001).
An, Monoclonal antibodies—a proven and rapidly expanding therapeutic modality for human diseases, Protein Cell, 1(4):319-330 (2010).
Basiliximab/Simulect® label (May 1998).
Bross, et al., Approval Summary: Gemtuzumab Ozogamicin in Relapsed Acute Myeloid Leukemia, Clinical Cancer Res., 7:1490-1496 (Jun. 2001).
As-filed U.S. Appl. No. 13/471,820 (issued as U.S. Pat. No. 8,932,591).
CVS Caremark Primary/Preferred Drug List dated Oct. 2010.
Daclizumab/Zenapax® label (Dec. 1997).
Declaration of Diane R. Mould Under 37 C.F.R. § 1.132 dated Jan. 29, 2014, submitted during prosecution of U.S. Appl. No. 10/163,657 (U.S. Pat. No. 8,889,135) (corresponds to Ex. 1002 at 1201-1233).
Declaration of Janet Pope Under 37 C.F.R. § 1.132 dated Jan. 31, 2014, submitted during prosecution of U.S. Appl. No. 10/163,657 (U.S. Pat. No. 8,889,135) (corresponds to Ex. 1002 at 1141-1171).
Declaration of Michael E. Weinblatt, MD Under 37 C.F.R. § 1.132 dated Feb. 3, 2014, submitted during prosecution of U.S. Appl. No. 10/163,657 (U.S. Pat. No. 8,889,135) (corresponds to Ex. 1002 at 1173-1199).
Declaration of Mr. Medgar Williams Under 37 C.F.R. § 1.132 dated Feb. 7, 2014, submitted during prosecution of U.S. Appl. No. 10/163,657 (U.S. Pat. No. 8,889,135) (corresponds to Ex. 1002 at 1240-1251).
Declaration Under 37 C.F.R. § 1.132 by Dr. Harmut Kupper dated Jun. 4, 2010, submitted during prosecution of U.S. Appl. No. 10/163,657 (U.S. Pat. No. 8,889,135) ("Kupper II Decl.") (corresponds to Ex. 1002 at 808-818).
Declaration Under 37 C.F.R. § 1.132 of Harmut Kupper dated Jul. 1, 2008, submitted during prosecution of U.S. Appl. No. 10/163,657 (U.S. Pat. No. 8,889,135) ("Kupper I Decl.") (corresponds to Ex. 1002 at 600-604).
Direct Narrative Statement of Brian C. Reisetter, Ph.D., *Novo Nordisk A/S et al. v. Caraco Pharm. Labs., Ltd. et al.*, No. 2:05-cv-40188 (E.D. Mich. Aug. 11, 2010) (D.I. 488).
Exhibit D to the Declaration of Mr. Medgar Williams Under 37 C.F.R. § 1.132 dated Feb. 7, 2014, submitted during prosecution of U.S. Appl. No. 10/163,657 (U.S. Pat. No. 8,889,135) (see Ex. 1002 at 1250).
Exhibit M to the Declaration of Mr. Medgar Williams Under 37 C.F.R. § 1.132 dated Feb. 7, 2014, submitted during prosecution of U.S. Appl. No. 10/163,657 (U.S. Pat. No. 8,889,135) (see Ex. 1002 at 1251).
File History of U.S. Pat. No. 8,916,158.
Gemtuzumab/Mylotarg® label (Aug. 2005).
Kamerzell, et al., Increasing IgG Concentration Modulates the Conformational Heterogeneity and Bonding Network that Influence Solution Properties, 113 J. Phys. Chem. B 6109 (2009).
Kress, M.D., Clinical Review: Abbott, Biologic Licensing Application STN 125057 Adalimumab—for use in the treatment of rheumatoid arthritis, Center for Biologics Evaluation and Research Office of Therapeutics Research and Review Division of Clinical Trial Design and Analysis Immunology and Infectious Diseases Branch HFM-582 (Dec. 24, 2002).
Krishnamurthy & Manning, The Stability Factor: Importance in Formulation Development, 3 Current Pharm. Biotech. 361 (2002).
Lobb, et al., Chapter 30: Pricing Issues for Biotechnology Products, in Advances in Large-Scale Biopharmaceutical Manufacturing and Scale-Up Production (Eric S. Langer ed., 2007).
Maini, et al., Therapeutic Efficacy of Multiple Intravenous Infusions of Anti-Tumor Necrosis Factor á Monoclonal Antibody Combined with Low-Dose Weekly Methotrexate in Rheumatoid Arthritis, Arthritis & Rheumatism, 41(9):1552-1563 (1998).
Nishida, et al., Characterization of novel murine anti-CD20 monoclonal antibodies and their comparison to 2B8 and c2B8 (rituximab), 31 Int'l. J. Oncology 29 (2007).
O'Dell, Chapter 10: Combination Disease-Modifying Anti-Rheumatic Drug (DMARD) Therapy, in Modern Therapeutics in Rheumatic Diseases (G.C. Tsokos, et al. ed. 2002).
Palivizumab/Synagis® label (Mar. 2014).
Patent Owner's Preliminary Response IPR2016-00172 (Feb. 18, 2018).
Petition for Inter Partes Review of U.S. Pat. No. 8,889,135 Pursuant to 35 U.S.C. §§ 311-319 and 37 C.F.R. § 42, IPR 2016-00172 (Nov. 9, 2015).
Petition for Inter Partes Review of U.S. Pat. No. 8,916,158, IPR 2015-01517 (Jun. 26, 2015).
Porter & Charman, Lymphatic Transport of Proteins After Subcutaneous Administration, J. Pharm. Sci., 89(3):297-310 (2000).
Rau et al., "Long-Term Efficacy and Tolerability of Multiple I.V. Doses of the Fully Human Anti-TNF-Antibody D2E7 in Patients with Rheumaoid [sic] Arthritis," Arthritis & Rheum., 41(Suppl.):S55, No. 137 (1998) ("Rau 1998").
Rau, Erfahrungen mit D2E7, Zettschrift Fur Rheumatologie, 58(Supplement 1):Abstract S51 (1999) (original German).
Rau, Experiences with D2E7, J. Rheumatol., 58(Supplement 1):Abstract S51 (1999) (certified English translation).
Rituximab/Rituxan® label (Nov. 1997).

(56) References Cited

OTHER PUBLICATIONS

Rowland, Ph.D. & Tozer, Ph.D., Chapter 3: Intravenous Dose, and Chapter 4: Extravascular Dose, in Clinical Pharmacokinetics Concepts and Applications (3d ed. 1995).
Securities and Exchange Commission Form 10-K for AbbVie Inc. for the fiscal year ended Dec. 31, 2013.
Trastuzumab/Herceptin® label (Sep. 1998).
U.S. Appl. No. 11/443,943, filed Jan. 29, 2008 Amendment and Response to Office Action.
U.S. Appl. No. 11/437,602 (U.S. Pat. No. 8,858,935) (Amgen), filed Jun. 25, 2009 Declaration by Dr. Grace C. Chu.
U.S. Appl. No. 14/091,888 (U.S. Pat. No. 8,802,101), filed Jan. 28, 2014 Office Action.
U.S. Appl. No. 14/147,287 (U.S. Pat. No. 8,802,102), filed Feb. 7, 2014 Office Action.
UnitedHealthcare 2013 Prescription Drug List Quick-Reference Guide.
Van de Putte, et al., Efficacy and safety of adalimumab as monotherapy in patients with rheumatoid arthritis for whom previous disease modifying antirheumatic drug treatment has failed, Ann. Rheum. Dis., 63(5):508-516 (2004).
Van Schouwenburg, et al., Immunogenicity of anti-TNF biologic therapies for rheumatoid arthritis, Nat. Rev. Rheumatol., 9:164-172 (2013).
Vincent, et al., Antidrug antibodies (ADAb) to tumor necrosis factor (TNF)-specific neutralizing agents in chronic inflammatory diseases: a real issue, a clinical perspective, Ann. Rheum. Dis., 72:165-178 (2013).
Wolfe, et al., Consensus Recommendations for the Assessment and Treatment of Rheumatoid Arthritis, J. Rheumatol., 28(6):1423-1430 (2001).
"Campath®", Physicians' Desk Reference, 992-995 (56th ed. 2002).
"Orthoclone OKT®3 Sterile Solution", Physicians' Desk Reference, 2498-2502 (56th ed. 2002).
"Reopro®", Physicians' Desk Reference, 1958-1962 (56th ed. 2002).
"Rituxan®", Physicians' Desk Reference, 1428-1430, 1750-1752 (56th ed. 2002).
"Winrho SDF™", Physicians' Desk Reference, 2297-2299 (56th ed. 2002).
Abbott Laboratories 2003 Annual Report, Abbott Laboratories (2004).
AbbVie Response to Oppositions Against EP 1 528 933 (B1) (Jan. 17, 2014) (incl. consolidated list of documents filed by all parties (D1 to D49).
Activase (alteplase) [package insert]. South San Francisco, CA: Genentech, Inc.; 2002.
Arakawa et al. Pharmaceutical Research (1991) 8(3):285-291.
Aranesp (dargbepoetin alpha) [package insert]. Thousand Oaks, CA: Amgen Inc.; 2002.
Banks, et al., (Amgen) Native-State Solubility and Transfer Free Energy as Predictive Tools for Selecting Excipients to Include in Protein Formulation Development Studies, 101 J. Pharm. Scis. 2720 (2012).
Carpenter, et al., Chapter 7: Freezing- and Drying-Induced Perturbations of Protein Structure and Mechanisms of Protein Protection by Stabilizing Additives, in Freezedrying/ Lyophilization of Pharmaceutical and Biological Products 167 (2d ed. 2004).
Carpenter, et al., Inhibition of Stress-Induced Aggregation of Protein Therapeutics, 309 Methods in Enzymology 236 (1999).
Chi, et al., Physical Stability of Proteins in Aqueous Solution: Mechanism and Driving Forces in Nonnative Protein Aggregation, 20 Pharm. Res. 1325 (2003).
Ewert et al., J. Mol. Biol. (2003) 325:531-553.
Expert Opinion of G. Winter (dated Jan. 13, 2014) AbbVie submitted during opposition of EP 1 528 933 (B1).
File History of U.S. Pat. No. 8,802,101.
Ha, et al., Peroxide Formation in Polysorbate 80 and Protein Stability, 91 J. Pharm. Scis. 2252 (2002).
Helms et al., Protein Science (1995) 4:2073-2081.

Herceptin (trastuzumab) [package insert]. South San Francisco, CA: Genentech, Inc.; 1998.
Humphreys, Top 200 Medicines—Special Report, Pharmalive (Aug. 12, 2015).
IPR2015-01514 Patent Owner's Preliminary Response Oct. 19, 2015.
Kempeni et al., Ann Rheum. Dis. (1999), 58: (Suppl. I) I70-I72.
Kineret (anakinra) [package insert]. Thousand Oaks, CA: Amgen Inc.; 2001.
King, The Best Selling Drugs of All Time; Humira Joins the Elite, Forbes (Jan. 28, 2013, 9:58 AM).
Krishnan, et al., (Amgen) Chapter 16: Development of Formulations for Therapeutic Monoclonal Antibodies and Fc Fusion Proteins, in Formulation and Process Development Strategies for Manufacturing Biopharmaceuticals 383 (2010).
Lee, et al., Toward aggregation-resistant antibodies by design, 31 Trends in Biotech. 612 (2013).
Levine, J Parenteral Sci and Tech (1991) 45(3):160-165.
Lorenz, Current Opinion in Molecular Therapeutics (2002) 4(2):185-190.
Neulasta (pegfilgrastim) [package insert]. Thousand Oaks, CA: Amgen Inc.; 2002, http://www.accessdata.fda.gov/drugsatfda_docs/nda/2002/125031_0000_NeulastaTOC.cfm (identifying biologics license approval on Jan. 31, 2002).
Neupogen (filgrastim) [package insert]. Thousand Oaks, CA: Amgen Inc.; 1998.
Ohnishi & Sagitani, The Effect of Nonionic Surfactant Structure on Hemolysis, 70 J. Am. Oil Chemists' Soc'y 679 (1993).
Pegintron (peginterferon alpha-2b) [package insert] Kenilworth, NJ: Schering Corporation; 2001.
Perchiacca et al., Annu. Rev. Chem. Biomol. (2012) 3:263-286.
Preliminary amendment (filed Feb. 16, 2005) in U.S. Appl. No. 10/525,292 (issued as U.S. Pat. No. 8,216,583).
Randolph & Carpenter, Engineering Challenges of Protein Formulations, 53 Am. Inst. Chem. Eng. J. 1902 (2007).
Remicade (infliximab) [package insert]. Malvern, PA: Centocor, Inc.; 1998.
Remington: The Science and Practice of Pharmacy (Alfonso Gennaro ed., 20th ed. 2000).
Schein, Nature Biotechnol (1990) 8:308-317.
Test Report AbbVie submitted to EPO (May 15, 2009) during prosecution of EP 1 528 933 (B1).
Timmerman, Abbott's Humira, the 3rd-in-Class Drug That Toppled Lipitor as No. 1, Xconomy (Apr. 16, 2012).
U.S. Appl. No. 11/437,602 (U.S. Pat. No. 8,858,935) (Amgen), filed Jun. 25, 2009 Office Action Response.
U.S. Appl. No. 11/784,538 (U.S. Pat. No. 7,648,702) (Amgen), filed Jul. 24, 2009 Office Action Response.
U.S. Appl. No. 13/401,496 (U.S. Pat. No. 8,828,947) (Immunex/Amgen), filed Apr. 21, 2014 Office Action Response.
U.S. Appl. No. 13/521,999 (U.S. Pat. No. 8,883,151) (Amgen), filed Dec. 3, 2013 Office Action Response.
U.S. Appl. No. 14/091,661 (U.S. Pat. No. 8,802,100), filed Jan. 27, 2014 Office Action.
U.S. Appl. No. 14/091,938 (U.S. Pat. No. 8,795,670), filed Jan. 29, 2014 Office Action.
U.S. Appl. No. 14/322,565 (U.S. Pat. No. 8,940,305), filed Sep. 26, 2014 Office Action Response.
Van De Weert & Randolph, Chapter 6: Physical Instability of Peptides and Proteins, in Pharmaceutical Formulation Development of Peptides and Proteins 107 (2012).
Zenapax (daclizumab) [package insert]. Nutley, NJ: Hoffmann-LaRoche, Inc.; 1997.
"Updated consensus statement on tumour necrosis factor blocking agents for the treatment of rheumatoid arthritis and other rheumatic diseases." (Apr. 2001).
Abbott Laboratories, Helping Your RA Patients Live More Normal Lives: Practicing Possibility: Supporting rheumatology nurses who make more normal living possible, Mar. 2004.
Abbvie Biotechnology Ltd., "Patent Owner's Preliminary Response," in *Coherus Biosciences Inc. v. AbbVie Biotechnology Ltd.*, IPR2016-01018, Paper No. 9 (PTAB Aug. 9, 2016).
Avastin Label (Feb. 2004).

(56) References Cited

OTHER PUBLICATIONS

Carnahan et al., "Epratuzumab, a Humanized Monoclonal Antibody Targeting CD22: Characterization of In Vitro Properties," Clin. Cancer Res., 9:3982s-90s (2003).
Excerpts from appeal proceedings relating to EP 1593393.
Gebhart, "Biotech Company Preparing Several Drugs for Takeoff," Drug Topics, vol. 145, No. 5, p. 50 (Mar. 5, 2001).
Huynh, et al., Preferences of patients and health professionals for route and frequency of administration of biologic agents in the treatment of rheumatoid arthritis, Patient Preferences and Adherence, 8:93-99 (2014).
Navarro-Millan, et al., Comparative Effectiveness of Etanercept and Adalimumab in Patient Reported Outcomes and Injection-Related Tolerability, PLOS One, 11(3):e0149781 (2016).
Petition for Inter Partes Review of U.S. Pat. No. 9,017,680 Pursuant to 35 U.S.C. §§ 311-319 and 37 C.F.R. § 42, IPR 2016-00188 (Dec. 7, 2015).
Petition for Inter Partes Review of U.S. Pat. No. 9,085,619 Pursuant to 35 U.S.C. §§ 311-319 and 37 C.F.R. § 42, IPR 2016-00823 (Jan. 31, 2017).
Physicians' Desk Reference, pp. 558-559, 914-931, 805-807, 2026-2028, 2295-2297, 2524-2525 (56th ed. 2002).
Sylwestrzak, et al., Considering Patient Preferences When Selecting Anti-Tumor Necrosis Factor Therapeutic Options, Am. Health Drug Benefits, 7(2):71-81 (2014).
Synagis® Label (Jul. 2004).
Tysabri® Label (Nov. 2004).
U.S. Prosecution History of Fischkoff et al., U.S. Pat. No. 8,889,135 ("the '135 patent").
U.S. Prosecution History of the '680 patent.
Williams & Edwards, Patient preferences in choosing anti-TNF therapies-R1, Rheumatology, 45:1575-1576 (2006).
U.S. Appl. No. 60/690,582, filed Jun. 14, 2005, Gokarn.
2015 Express Scripts Basic Formulary (Aug. 2014).
Adalimumab/Humira® label (Revised Jan. 2008).
Bam et al., J Pharm Sci. (1998) 87(12):1554-9.
Barrera et al. (2001) Ann Rheum. Dis. 60:660-69.
Butler & Hamilton, "Quantitation of Specific Antibodies: Methods of Express, Standards, Solid-Phase Considerations, and Specific Applications," Ch. 9 in Immunochemistry of Solid-Phase Immunoassay, CRC Press (John E. Butler ed., 1991).
Certolizumab/Cimzia® label (Revised Jul. 2010).
Christensen, "Proteins as buffers," Annals of the New York Academy of Sciences, 133:34-40 (Apr. 1966).
CVS/caremarkTM Performance Drug List (Oct. 2015).
Declaration of Dr. Brian Reisetter.
Declaration of Dr. James O'Dell.
Declaration of Dr. Sharon Baughman.
Declaration of Klaus-Peter Radtke, Ph.D., Exhibit 1002 IPR 2017-00822 (Jan. 31, 2017).
Dobrow, "DTC Report—DTC Gets Smart," Medical Marketing & Media (Apr. 1, 2014).
Dobrow, MM&M 2014 Large Pharma Marketing Team of the Year: Humira.
Dorland's Illustrated Medical Dictionary, p. 4-5 (1988).
Enbrel® Summary Basis of Approval (1998).
Etanercept/Enbrel® label (1998).
European Search Report, EP 20 21 1821, (12 pages) Issued Apr. 7, 2021.
Exhibit L to Declaration of Medgar Williams submitted during prosecution of the '135 patent.
Fransson & Espander-Jansson, "Local Tolerance of Subcutaneous Injections," J. Pharm. Pharmacol., 48:1012-1015 (1996).
Gandhi et al., "Elucidation of Degradants in Acidic Peak of Cation Exchange Chromatography in an IgG1 Monoclonal Antibody Formed on Long-Term Storage in a Liquid Formulation", Pharm Res., vol. 29, pp. 209-224 (2012).
Gokarn et al., "Excipients for Protein Drugs," Ch. 17 in Excipient Development for Pharmaceutical, Biotechnology, and Drug Delivery Systems (Ashok Katdare & Mahesh V. Chaubal eds., 2006).
Golimumab/Simponi® label (Revised Dec. 2011).
Guidance for Industry, Clinical Development Programs for Drugs, Devices and Biological Products for the Treatment of Rheumatoid Arthritis (1999).
Hamilton, The Human IgG Subclasses (2001).
Humira® Label (Jan. 2003); IPR 2017-000822 Exhibit 1005.
Humira® Label (Jan. 2008); IPR 2017-000822 Exhibit 1006.
Infliximab/Remicade® label (Nov. 1999).
Jefferis et al., "Recognition Sites on Human IgG for Fcã Receptors: The Role of Glycosylation," Immunology Letters, 44: 111-117 (1995).
Johnson et al., Nucleic Acids Research (2000) 28(1):214-218.
Manning et al., Pharm. Res. (1989) 6(11):903-918.
Methotrexate (Rheumatrex, Trexall, Otrexup, Rasuvo), American College of Rheumatology, http://www.rheumatology.org/1-Am-A/Patient-Caregiver/Treatments/Methotrexate-Rheumatrex-Trexall (Mar. 2015).
Meyer, et al, Rational Design of Stable Protein Formulations: Theory and Practice, Pharmaceutical Biotechnology, vol. 13 (Carpenter and Manning, ed., Apr. 30, 2002).
Nozaki & Tanford, "Examination of Titration Behavior," Methods Enzymol., 11:715-734 (1967).
Olthuis et al., "Characterization of Proteins by Means of their Buffer Capacity, Measured with an ISFET-based Coulometric Sensor-Actuator System," Biosensors & Bioelectronics, 9:743-751 (1994).
Parslow, "Immunoglobulins & Immunoglobulin Genes," Ch. 7 in Medical Immunology, Appleton & Lange (Daniel P. Stites, Abba I. Terr, & Tristram G. Parslow eds., 9th ed. 1997).
Pharmaceuticals, The Science of Dosage Form Design, Michael E. Aulton ed., 2d ed. 2002.
Rau et al., "Effective Combination of the Fully Human Anti-TNF Antibody D2E7 and Methotrexate in Active Rheumatoid Arthritis," Ann. Rheum. Dis., 217, No. 907 (1999) ("Rau #907").
Rau et al., "Long-term treatment with the fully human anti TNF alpha-antibody D2E7 slows radio-graphic disease progression in rheumatoid arthritis," Arthritis & Rheum., 42 (S9):S400, No. 1978, Sep. 1999 ("Rau #1978").
Remicade® Summary Basis of Approval (1999).
Schattenkirchner et al., "Efficacy and Tolerability of Weekly Subcutaneous Injections of the Fully Human Anti-TNFAntibody D2E7 in Patiens [sic] with Rheumatoid Arthritis—Results of a Phase I Study," Arthritis & Rheum., 41(S9):S57, No. 149 (1998) ("Schattenkirchner").
Tsokos, et al. Modern Therapeutics in Rheumatic Diseases. Uniformed Services University of the Health Sciences, ISBN 978-1-4684-9708-3; DOI 10.1007/978-1-59259-239-5 (2002).
U.S. Prosecution History of the U.S. Pat. No. 8,889,135 patent.
UnitedHealthcare 2015 Four-Tier Prescription Drug List (Jul. 2015).
Van de Putte et al., "A Single Dose Placebo Controlled Phase I Study of the Fully Human Anti-TNF Antibody D2E7 in Patients with Rheumatoid Arthritis," Arthritis & Rheum., 41(S9):S57, No. 148 (1998) ("van de Putte 1998").
Van de Putte et al., "Efficacy of the Fully Human Anti-TNF Antibody D2E7 in Rheumatoid Arthritis," Arthritis & Rheum. 42(S9):S400 (abstract 1977) (1999) ("van de Putte 1999").
Van de Putte et al., Arthritis & Rheum., vol. 42(9 Suppl.):S269 (2000) ("van de Putte 2000").
Van Slyke, "On the Measurement of Buffer Values and on the Relationship of Buffer Value to the Dissociation Constant of the Buffer and the Concentration and Reaction of the Buffer Solution," J. Biol. Chem., 52:525-570 (1922).
Weisman et al., "A dose escalation study designed to demonstrate the safety, tolerability and efficacy of the fully human anti-TNF antibody, D2E7, given in combination with methotrexate (MTX) in patients with active RA," Arthritis & Rheum., vol. 43 (9 Suppl. 1):S391, abstract 1948 ("Weisman 2000").

\* cited by examiner

SEQUENCE LISTING

```
Sequence total quantity: 10
SEQ ID NO: 1            moltype = AA  length = 107
FEATURE                 Location/Qualifiers
REGION                  1..107
                        note = Light chain variable region
source                  1..107
                        mol_type = protein
                        organism = synthetic construct
SEQUENCE: 1
DIQMTQSPSS LSASVGDRVT ITCRASQGIR NYLAWYQQKP GKAPKLLIYA ASTLQSGVPS   60
RFSGSGSGTD FTLTISSLQP EDVATYYCQR YNRAPYTFGQ GTKVEIK                107

SEQ ID NO: 2            moltype = AA  length = 121
FEATURE                 Location/Qualifiers
REGION                  1..121
                        note = Heavy chain variable region
source                  1..121
                        mol_type = protein
                        organism = synthetic construct
SEQUENCE: 2
EVQLVESGGG LVQPGRSLRL SCAASGFTFD DYAMHWVRQA PGKGLEWVSA ITWNSGHIDY   60
```

```
ADSVEGRFTI SRDNAKNSLY LQMNSLRAED TAVYYCAKVS YLSTASSLDY WGQGTLVTVS    120
S                                                                  121

SEQ ID NO: 3             moltype = AA  length = 214
FEATURE                  Location/Qualifiers
REGION                   1..214
                         note = Full length light chain
source                   1..214
                         mol_type = protein
                         organism = synthetic construct
SEQUENCE: 3
DIQMTQSPSS LSASVGDRVT ITCRASQGIR NYLAWYQQKP GKAPKLLIYA ASTLQSGVPS    60
RFSGSGSGTD FTLTISSLQP EDVATYYCQR YNRAPYTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                               214

SEQ ID NO: 4             moltype = AA  length = 224
FEATURE                  Location/Qualifiers
REGION                   1..224
                         note = Full length heavy chain
source                   1..224
                         mol_type = protein
                         organism = synthetic construct
SEQUENCE: 4
EVQLVESGGG LVQPGRSLRL SCAASGFTFD DYAMHWVRQA PGKGLEWVSA ITWNSGHIDY    60
ADSVEGRFTI SRDNAKNSLY LQMNSLRAED TAVYYCAKVS YLSTASSLDY WGQGTLVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKKVE PKSC                    224

SEQ ID NO: 5             moltype = AA  length = 11
FEATURE                  Location/Qualifiers
REGION                   1..11
                         note = L-CDR1
source                   1..11
                         mol_type = protein
                         organism = synthetic construct
SEQUENCE: 5
RASQGIRNYL A                                                        11

SEQ ID NO: 6             moltype = AA  length = 7
FEATURE                  Location/Qualifiers
REGION                   1..7
                         note = L-CDR2
source                   1..7
                         mol_type = protein
                         organism = synthetic construct
SEQUENCE: 6
AASTLQS                                                             7

SEQ ID NO: 7             moltype = AA  length = 9
FEATURE                  Location/Qualifiers
REGION                   1..9
                         note = L-CDR3
SITE                     9
                         note = MISC_FEATURE - Xaa is Thr or Ala
source                   1..9
                         mol_type = protein
                         organism = synthetic construct
SEQUENCE: 7
QRYNRAPYX                                                           9

SEQ ID NO: 8             moltype = AA  length = 5
FEATURE                  Location/Qualifiers
REGION                   1..5
                         note = H-CDR1
source                   1..5
                         mol_type = protein
                         organism = synthetic construct
SEQUENCE: 8
DYAMH                                                               5

SEQ ID NO: 9             moltype = AA  length = 17
FEATURE                  Location/Qualifiers
REGION                   1..17
                         note = H-CDR2
source                   1..17
                         mol_type = protein
                         organism = synthetic construct
SEQUENCE: 9
```

```
AITWNSGHID YADSVEG                                                          17

SEQ ID NO: 10           moltype = AA  length = 12
FEATURE                 Location/Qualifiers
REGION                  1..12
                        note = H-CDR3
SITE                    12
                        note = MISC_FEATURE - Xaa is Tyr or Asn
source                  1..12
                        mol_type = protein
                        organism = synthetic construct
SEQUENCE: 10
VSYLSTASSL DX                                                               12
```

ANTI-TNF ALPHA ANTIBODY FORMULATIONS

REFERENCE TO PRIOR APPLICATIONS

This application is a continuation of U.S. patent application Ser. No. 16/471,492, filed Jun. 19, 2019, which is a U.S. National Stage Application under 35 USC § 371 of PCT Application No. PCT/US2017/067723, published as PCT Publication WO 2018/119142, filed Dec. 20, 2017, which claims the benefit of U.S. Provisional Application No. 62/437,640, filed Dec. 21, 2016, all of which are hereby incorporated by reference.

The present application is being filed along with a sequence listing in electronic format. The sequence listing is provided as a file entitled A-2102-US03-CNT, created Aug. 17, 2022, which is 15 KB in size. The information in the electronic format of the sequence listing is incorporated herein by reference in its entirety.

BACKGROUND

Elevated levels of tumor necrosis factor alpha (TNFα) have been associated with a number of human disorders such as arthritis, rheumatoid arthritis, psoriatic arthritis, ankylosing spondylitis, axial spondyloarthritis, juvenile idiopathic arthritis, enthesitis related arthritis, osteoarthritis, peripheral spondyloarthritis, acute disc prolapse, inflammatory bowel disease, Crohn's disease, ulcerative colitis, intestinal Behcet's disease, chronic pouchitis, small bowel lesions, Hermansky-Pudlak syndrome, psoriasis, psoriasis vulgaris, psoriasis arthropica, plaque psoriasis, hidradenitis suppurativa, interstitial cystitis, sleep apnea, sarcoidosis, retinal vascular disorders, uveitis, choroidal neovascularization, Pyoderma Gangrenosum, giant cell arteritis, Netherton syndrome, anaplastic thyroid cancers, asthma, and refractory asthma. TNFα inhibitors are frequently used to treat these disorders. One such inhibitor is adalimumab, also known as D2E7, a recombinant human IgG1 monoclonal antibody specific for human TNFα.

SUMMARY

The present disclosure is directed to stable aqueous adalimumab formulations, to methods of making stable aqueous adalimumab formulations, to use of a formulation as disclosed herein, and to methods of treating a disease comprising administering to a patient a formulation as disclosed herein.

In one aspect, the disclosure includes a stable aqueous formulation comprising about 180 mg/mL adalimumab, about 20 mM glutamate, and about 160 mM monoethanolamine (MEA), wherein the formulation has a pH of about 5.2, and demonstrates less than about a 2.1-fold increase in acidic species as measured by cation-exchange high-performance liquid chromatography (CEX-HPLC) after storage for 28 days at 40° C.

In another aspect, the disclosure provides a stable adalimumab formulation as described in the Tables provided herein. In some aspects, the stable adalimumab formulation provided herein demonstrates one or more of the following parameters: (i) less than about a 2.1-fold increase in acidic species, as measured by cation-exchange high-performance liquid chromatography (CEX-HPLC) after storage for 28 days at 40° C.; (ii) less than about a 5-fold increase in high molecular weight species (HMWS) species, as measured by size-exclusion chromatography (SE-HPLC) after storage for 28 days at 40° C.; and/or (iii) less than about 500 nephelometric turbidity units (NTUs) after stirring at room temperature for 5 days.

BRIEF DESCRIPTION OF THE DRAWINGS

FIG. 70B is the same data presented in FIG. 70A but graphed at a different scale.

FIG. 71B is the same data presented in FIG. 71A but graphed at a different scale.

FIG. 72B is the same data presented in FIG. 72A but graphed at a different scale.

DETAILED DESCRIPTION

Figure 1:
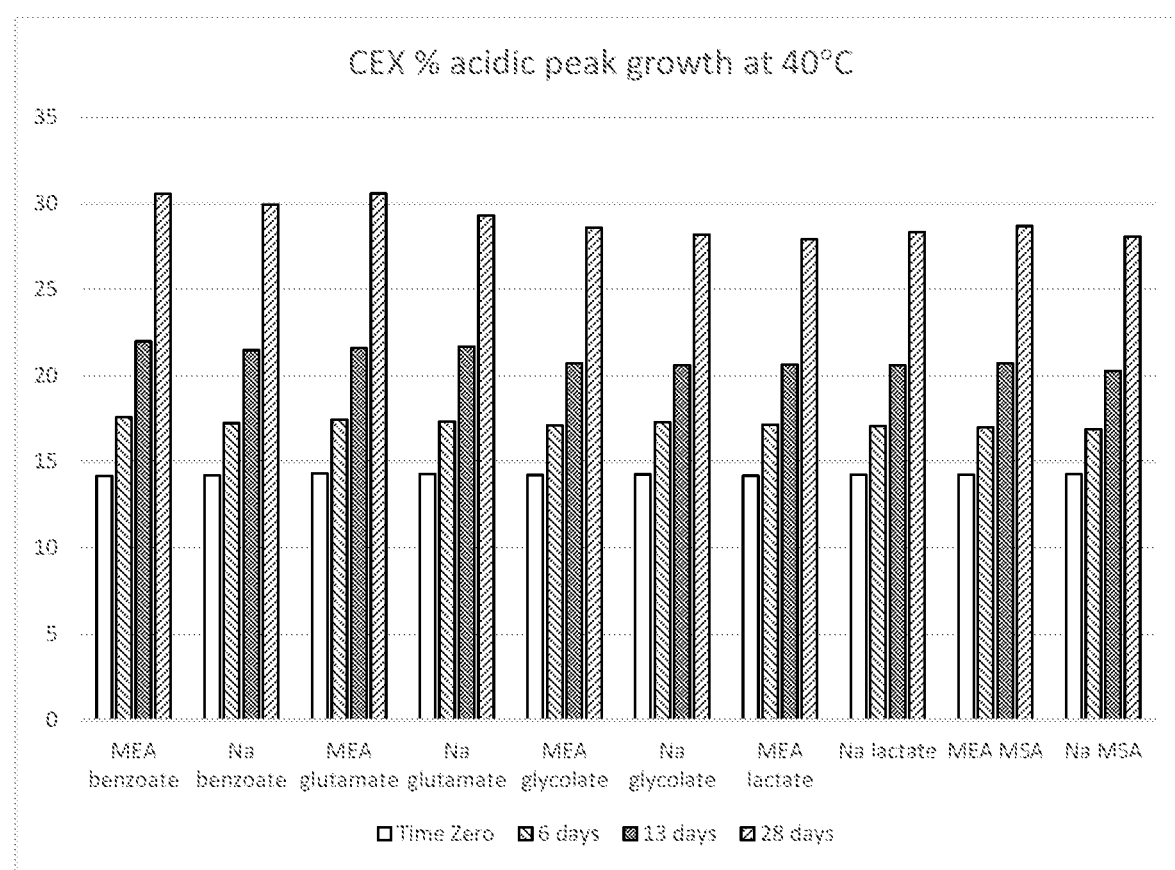
FIG. 1 is a bar graph of stability of adalimumab formulations as determined by cation-exchange high-performance liquid chromatography (CEX-HPLC).

The present disclosure provides stable aqueous adalimumab formulations and related methods of making stable aqueous adalimumab formulations. Also provided are lyophilized forms of the aqueous adalimumab formulations disclosed herein. The present disclosure also provides related uses of the formulations disclosed herein and related methods of administering these formulations to treat diseases such as arthritis, rheumatoid arthritis, psoriatic arthritis, ankylosing spondylitis, axial spondyloarthritis, juvenile idiopathic arthritis, enthesitis related arthritis, osteoarthritis, peripheral spondyloarthritis, acute disc prolapse, inflammatory bowel disease, Crohn's disease, ulcerative colitis, intestinal Behcet's disease, chronic pouchitis, small bowel lesions, Hermansky-Pudlak syndrome, psoriasis, psoriasis vulgaris, psoriasis arthropica, plaque psoriasis, hidradenitis suppurativa, interstitial cystitis, sleep apnea, sarcoidosis, retinal vascular disorders, uveitis, choroidal neovascularization, Pyoderma Gangrenosum, giant cell arteritis, Netherton syndrome, anaplastic thyroid cancers, asthma, and refractory asthma.

The stable aqueous adalimumab formulations include adalimumab and one or more excipients selected such that the formulation demonstrates characteristics suitable for use as a pharmaceutical composition. A formulation suitable for use as a pharmaceutical composition generally exhibits a low amount of high molecular weight species (HMWS), such as aggregates and dimers, and/or also exhibits a low degree of oxidation over time. For example, a suitable adalimumab formulation may exhibit minimal oxidation of residues TRP 53, MET 34, MET 256, and MET 432. A suitable formulation may also exhibit a minimal amount of sub-visible particles (e.g., particles having a diameter of ≥10 μm or ≥25 μm) and/or non-spherical particles (e.g., particles having an aspect ratio of ≥5 μm). High amounts of HMWS, oxidation, and/or particles may impact the shelf-life, safety and/or potency of a formulation. Stable aqueous adalimumab formulations are described in the embodiments set forth below.

In some cases, the stable aqueous adalimumab formulations include adalimumab, calcium chloride, and optionally one or more (typically one, two, or three) additional excipients as described herein.

In some cases, the stable aqueous adalimumab formulations include adalimumab, a buffer, and optionally one or more (typically one, two, or three) additional excipients as described herein. Suitable buffers include glutamate/glutamic acid buffers ("glutamate buffer"), adipate/adipic acid buffers ("adipate buffer"), glucuronate/glucuronic acid buffers ("glucuronate buffer"), acetate/acetic acid buffers ("acetate buffer"), benzoate/benzoic acid buffers ("benzoate buffer"), glycolate/glycolic acid buffers ("glycolate buffer"), lactate/lactic acid buffers ("lactate buffer"), and histidine buffers.

In some cases, the stable aqueous adalimumab formulations include adalimumab and do not include a buffer. Optionally, these adalimumab formulations additionally include one or more (typically one, two, or three) excipients as described herein.

In some cases, the stable aqueous adalimumab formulation includes adalimumab, a buffer (e.g., lactate buffer), calcium chloride, and optionally one or more (typically one, two, or three) additional excipients as described herein.

As used herein, a "stable" formulation demonstrates stability sufficient to permit administration to a patient. For example, a stable formulation may demonstrate long-term stability, such as stability upon storage for 6 months or 1 year. Stability of a formulation may, for example, be assessed by growth of acidic species over time, growth of high molecular weight species over time, or increase in opalescence over time. When stability is assessed by growth of acidic species over time, a stable formulation may demonstrate less than about a 4-fold increase (e.g., less than about a 3.5-fold increase, less than about a 3-fold increase, less than about a 2.5-fold increase, less than about a 2.4-fold increase, less than about a 2.3-fold increase, less than about a 2.25-fold increase, less than about a 2.2-fold increase, less than about a 2.15-fold increase, less than about a 2.1-fold increase, less than about a 2.05-fold increase, or less than about a 2-fold increase) in acidic species as measured by CEX-HPLC after storage for 28 days at 40° C. When stability is assessed by growth of high molecular weight species over time, a stable formulation may demonstrate less than about a 5-fold increase (e.g., less than about a 4.5-fold increase, less than about a 4-fold increase, less than about a 3.9-fold increase, less than about a 3.8-fold increase, less than about a 3.7-fold increase, less than about a 3.6-fold increase, less than about a 3.5-fold increase, less than about a 3.4-fold increase, less than about a 3.3-fold increase, less than about a 3.2-fold increase, less than about a 3.15-fold increase, less than about a 3.1-fold increase, less than about a 3.05-fold increase, less than about a 3-fold increase, less than about a 2.95-fold increase, or less than about a 2.9-fold increase) in HMWS species as measured by SE-HPLC after storage for 28 days at 40° C. When stability is assessed by increase in opalescence over time, a stable formulation may demonstrate less than about 500 nephelometric turbidity units (NTUs) (e.g., less than about 400 NTUs, less than about 350 NTUs, less than about 300 NTUs, less than about 250 NTUs, less than about 200 NTUs, less than about 150 NTUs, less than about 140 NTUs, less than about 130 NTUs, less than about 125 NTUs, less than about 120 NTUs, less than about 115 NTUs, less than about 110 NTUs, less than about 100 NTUs, less than about 90 NTUs, less than about 80 NTUs, or less than about 70 NTUs) after stirring at room temperature for 5 days.

As used herein, an "aqueous" formulation contains water. Aqueous formulations can be in a liquid state or a frozen state, and preferably are liquid formulations.

As used herein, an "excipient" is a component of a formulation other than water and the active agent (e.g., adalimumab or biosimilar thereof) added to the formulation. Examples of excipients include buffers; stabilizers such as amino acids and amino acid derivatives, polyethylene glycols and polyethylene glycol derivatives, polyols, acids, amines, polysaccharides or polysaccharide derivatives, salts, and surfactants; and pH-adjusting agents.

As used herein, a "biosimilar," particularly an adalimumab biosimilar, is a biological product that is highly similar to HUMIRA (also known as adalimumab or D2E7) notwithstanding minor differences in clinically inactive components; and there are no clinically meaningful differences between the biological product and HUMIRA in terms of safety, purity, and potency of the product.

As used herein, the term "about," when used to modify a particular value or range, generally means within 20 percent, e.g., within 10 percent, 5 percent, 4 percent, 3 percent, 2 percent, or 1 percent of the stated value or range.

Adalimumab is a fully human monoclonal antibody of the immunoglobulin G1 (IgG1) subclass expressed in the Chinese hamster ovary (CHO) cell line and consists of 2 heavy chains (HC), and 2 light chains (LC) of the kappa subclass. Adalimumab contains 32 total cysteine residues involved in both intrachain and interchain disulfide bonds. Each HC contains 451 amino acids with 4 intrachain disulfides. Each LC contains 214 amino acids with 2 intrachain disulfides. Each HC contains an N-linked glycan at the consensus glycosylation site on Asn301. The amino acid sequences of the adalimumab variable LC and variable HC are set out at SEQ ID NO: 1 and 2, respectively and the full length LC and HC are set out as SEQ ID NO: 3 and 4; respectively. In addition, the adalimumab LC CDRs are set out as SEQ ID NO: 5 (LC CDR1), SEQ ID NO: 6 (LC CDR2) and SEQ ID NO: 7 (LC CDR3). Adalimumab HC CDRs are set out as SEQ ID NO: 8 (HC CDR1), SEQ ID No: 9 (HC CDR2), and SEQ ID NO: 10 (HC CDR3). Adalimumab has been described and claimed in U.S. Pat. No. 6,090,382, the disclosure of which is hereby incorporated by reference in its entirety. As used herein, the term "adalimumab" includes biosimilars of adalimumab.

Formulations of Adalimumab with Calcium Chloride

In an embodiment, the stable aqueous adalimumab formulation includes adalimumab at a concentration of about 40 to about 200 mg/mL, such as about 90 to about 120 mg/mL, about 80 to about 120 mg/mL, about 90 to about 110 mg/mL, about 160 to about 190 mg/mL, about 40 to about 60 mg/mL, about 50 mg/mL, about 100 mg/mL, or about 170 mg/mL, calcium chloride at a concentration of about 1 to about 150 mM, such as about 5 to about 50 mM, about 5 to about 30 mM, about 10 to about 30 mM, about 12.5 to about 17.5 mM about 20 to about 40 mM, about 30 to about 50 mM, about 40 to about 80 mM, about 50 to about 100 mM, about 10 mM, about 15 mM, about 20 mM, about 25 mM, or about 30 mM, and one or more excipients as discussed below. The presence of calcium chloride in the formulations advantageously and unexpectedly provides improved stability over time as compared to other salts, particularly with respect to levels of acidic species at 40° C. as detected by cation-exchange high-performance liquid chromatography (CEX-HPLC). Further, the presence of calcium chloride at low concentrations (e.g., about 20 to about 25 mM, about 10 mM to about 20 mM, about 12.5 mM to about 17.5 mM, or about 15 mM) advantageously lowers the rate of growth of acidic species without significantly increasing the growth of high molecular weight species (HMWS) at 40° C. as detected by size-exclusion high-performance liquid chromatography (SE-HPLC).

Increased levels of acidic species over time are generally due to protein deamidation. It is therefore beneficial for the stable aqueous adalimumab formulations to demonstrate minimal growth of acidic species over time. Similarly, it is beneficial for the stable aqueous adalimumab formulations to demonstrate minimal growth over time of HMWS because HMWS provide a measure of soluble aggregation.

Further still, the presence of calcium chloride at low concentrations (e.g., about 10 mM to about 20 mM, about 12.5 mM to about 17.5 mM or about 15 mM) advantageously minimizes formation of sub-visible and/or non-spherical particles in a formulation, as detected by microflow imaging ("MFI") even if the formulation has been subjected to transport conditions.

Suitable excipients for combination with the calcium chloride-containing adalimumab formulations include certain buffers, and certain stabilizers such as certain amino acids and amino acid derivatives, certain polyethylene glycols and polyethylene glycol derivatives, certain polyols, certain acids, certain amines, certain polysaccharides or polysaccharide derivatives, and certain surfactants. Examples of suitable buffers include glutamate (e.g., at a concentration of about 5 mM to about 50 mM, about 10 mM to about 25 mM, about 15 mM to about 20 mM, about 15 mM, about 20 mM, and/or about 25 mM), adipate (e.g., at a concentration of about 5 mM to about 50 mM, about 10 mM to about 25 mM, about 15 mM to about 20 mM, about 10 mM, about 15 mM, about 20 mM, and/or about 25 mM), glucuronate (e.g., at a concentration of about 5 mM to about 50 mM, about 10 mM to about 30 mM, about 10 mM, about 15 mM, about 20 mM, and/or about 25 mM), acetic acid and/or acetate (e.g., at a concentration of about 0.1 mM to about 300 mM, about 2 mM to about 30 mM, about 5 mM to about 50 mM, about 5 mM to about 15 mM, about 10 mM to about 20 mM, about 10 mM to about 30 mM, about 15 mM to about 25 mM, about 30 mM to about 40 mM, about 35 mM to about 45 mM, about 40 mM to about 50 mM, about 10 mM, about 15 mM, about 20 mM, and/or about 25 mM), benzoate (e.g., at a concentration of about 5 mM to about 50 mM, about 10 mM to about 30 mM, about 10 mM, about 15 mM, about 20 mM, and/or about 25 mM), glycolate (e.g., at a concentration of about 5 mM to about 50 mM, about 10 mM to about 30 mM, about 10 mM, about 15 mM, about 20 mM, and/or about 25 mM), lactic acid and/or lactate (e.g., at a concentration of about 0.1 mM to about 300 mM, about 2 mM to about 30 mM, about 10 mM to about 30 mM, about 5 mM to about 15 mM, about 7 mM to about 12 mM, about 9 mM to about 11 mM, about 10 mM, about 15 mM, about 20 mM, and/or about 25 mM), and histidine (e.g., at a concentration of about 5 mM to about 50 mM, about 5 mM to about 15 mM, about 10 mM, about 15 mM, about 20 mM, and/or about 25 mM). Examples of suitable amino acids and amino acid derivatives include proline (e.g., at a concentration of about 0.1 to about 450 mM, about 50 to about 320 mM, and/or about 50 to about 300 mM), N-acetyl arginine (e.g., at a concentration of about 0.1 to about 450 mM or about 90 to about 150 mM), citruline (e.g., at a concentration of about 0.1 to about 450 mM or about 100 to about 150 mM), sarcosine (e.g., at a concentration of about 0.1 to about 450 mM or about 100 to about 150 mM), N-acetyl proline (e.g., at a concentration of about 0.1 to about 450 mM or about 100 to about 150 mM), N-acetyl ornithine (e.g., at a concentration of about 0.1 to about 450 mM or about 100 to about 150 mM), ornithine (e.g., at a concentration of about 0.1 to about 450 mM or about 100 to about 150 mM), beta-alanine (e.g., at a concentration of about 0.1 to about 450 mM or about 100 to about 150 mM), alanine (e.g., at a concentration of about 0.1 to about 450 mM or about 80 to about 120 mM), asparagine (e.g., at a concentration of about 0.1 to about 450 mM or about 80 to about 120 mM), isoleucine (e.g., at a concentration of about 0.1 to about 450 mM or about 80 to about 120 mM), serine (e.g., at a concentration of about 0.1 to about 450 mM or about 80 to about 120 mM), aspartic acid (e.g., at a concentration of about 0.1 to about 450 mM or about 10 to about 30 mM), creatine (e.g., at a concentration of about 0.1 to about 450 mM or about 15 to about 35 mM), glutamine (e.g., at a concentration of about 0.1 to about 450 mM or about 40 to about 60 mM), phenylalanine (e.g., at a concentration of about 0.1 to about 450 mM or about 40 to about 60 mM), tryptophan (e.g., at a concentration of about 0.1 to about 450 mM or about 15 to about 35 mM), and arginine-HCl (e.g., at a concentration of about 0.1 to about 450 mM or about 80 to about 120 mM). Examples of suitable polyethylene glycols and polyethylene glycol derivatives include PEG 15 hydroxystearate (e.g., at a concentration of about 0.1% (w/v) to about 20% (w/v) or about 3% (w/v) to about 6% (w/v)), PEG 3350 (e.g., at a concentration of about 0.1% (w/v) to about 30% (w/v) or about 1% (w/v) to about 7% (w/v)), PEG 200 (e.g., at a concentration of about 0.1% (w/v) to about 10% (w/v) or about 0.6% (w/v) to about 4.8% (w/v)), PEG 600 (e.g., at a concentration of about 0.1% (w/v) to about 30% (w/v) or about 1.2% (w/v) to about 14.5% (w/v)), and PEG 400 (e.g., at a concentration of about 0.1% (w/v) to about 20% (w/v) or about 0.3% (w/v) to about 1.5% (w/v)). Examples of suitable polyols include inositol (e.g., at a concentration of about 0.1 to about 450 mM or about 150 to about 210 mM), glycerol (also referred to as glycerin) (e.g., at a concentration of about 0.1% (w/v) to about 15% (w/v) or about 0.5% (w/v) to about 1% (w/v)), sucrose (e.g., at a concentration of about 0.1% (w/v) to about 15% (w/v), about 4% (w/v) to about 10% (w/v), about 6% (w/v) to about 8.5% (w/v), about 6.2% (w/v) to about 7.3% (w/v), about 4% (w/v) to about 9% (w/v), about 6.5% (w/v), about 6.8% (w/v), about 6.9% (w/v), about 7.4% (w/v), or about 9% (w/v)), and sorbitol (e.g., at a concentration of about 0.1% (w/v) to about 10% (w/v), about 3% (w/v) to about 5% (w/v), and/or about 4% (w/v)). Examples of suitable acids include glycolic acid (e.g., at a concentration of about 0.1 to about 300 mM or about 50 to about 70 mM), pyrollidone carboxylic acid (PCA) (e.g., at a concentration of about 0.1% (w/v) to about 15% (w/v) or about 0.05% (w/v) to about 2% (w/v)), medronic acid (e.g., at a concentration of about 0.1 to about 450 mM or about 100 to about 150 mM), benzene sulfonic acid (e.g., at a concentration of about 0.1 to about 300 mM or about 60 to about 90 mM), and methane sulfonic acid (MSA) (e.g., at a concentration of about 0.1 to about 150 mM, about 0.1 to about 50 mM, and/or about 10 to about 30 mM). Examples of suitable amines include monoethanolamine hydrochloride (MEA-HCl) (e.g., at a concentration of about 0.1 to about 150 mM or about 0.1 to about 40 mM), monoethanolamine (MEA) (e.g., at a concentration of about 0.1 to about 300 mM, about 0.1 to about 50 mM, and/or about 30 to about 160 mM), and triethanolamine (TEA) (e.g., at a concentration of about 0.1 to about 170 mM or about 30 to about 150 mM). Examples of suitable polysaccharides or polysaccharide derivatives include hyaluronic acid (e.g., at a concentration of about 0.05% (w/v) to about 2.5% (w/v) or about 0.1% (w/v) to about 0.05% (w/v)), sodium carboxymethylcellulose (NaCMC) (e.g., at a concentration of about 0.1% (w/v) to about 15% (w/v) or about 0.1% (w/v) to about 2% (w/v)), and dextran (e.g., at a concentration of about 0.1% (w/v) to about 15% (w/v) or about 8% (w/v) to about 12% (w/v)). Examples of suitable surfactants include Pluronic F68 (e.g., at a concentration of about 0.001% (w/v) to about 10% (w/v), about 0.005% (w/v) to about 1% (w/v), about 0.05% (w/v) to about 0.4% (w/v), about 0.05% (w/v) to about 0.1% (w/v), about 0.01% (w/v) to about 0.2% (w/v), about 0.03% (w/v) to about 0.06% (w/v), about 0.01% (w/v), about 0.05% (w/v), about 0.06% (w/v), and/or about 0.1% (w/v)), Polysorbate 80 (e.g., at a concentration of about 0.001% (w/v) to about 2% (w/v), about 0.005% (w/v) to about 0.1% (w/v), about 0.03% (w/v) to about 0.1% (w/v), about 0.04% (w/v) to about 0.1% (w/v), about 0.03% (w/v), about 0.04% (w/v), and/or about 0.1% (w/v)), Polysorbate 20 (e.g., at a concentration of about 0.001% (w/v) to about 2% (w/v) or about 0.005% (w/v) to about 0.1% (w/v)), Docusate sodium (e.g., at a concentration of about 0.001% (w/v) to about 1% (w/v) or about 0.005% (w/v) to about 0.05% (w/v)), benzalkonium chloride (e.g., at a concentration of about 0.001% (w/v) to about 1% (w/v) or about 0.05% (w/v) to about 0.5% (w/v)), Span 40 (sorbitan monopalmitate) (e.g., at a concentration of about 0.001% (w/v) to about 1% (w/v) or about 0.05% (w/v) to about 0.5% (w/v)), and Triton X-100 (e.g., at a concentration of about 0.001% (w/v) to about 1% (w/v) or about 0.005% (w/v) to about 0.1% (w/v)). Examples of other suitable excipients include imidazole (e.g., at a concentration of about 0.1% (w/v) to about 15% (w/v) or about 0.5% (w/v) to about 2% (w/v)), taurine (e.g., at a concentration of about 0.1 to about 450 mM or about 100 to about 150 mM), betaine (e.g., at a concentration of about 0.1 to about 450 mM or about 100 to about 150 mM), gelatin (e.g., at a concentration of about 0.1% (w/v) to about 15% (w/v) or about 0.5% (w/v) to about 2% (w/v)), niacinamide (e.g., at a concentration of about 0.1 to about 450 mM or about 100 to about 120 mM), polyvinylpyrrolidone (PVP), for example, 10K PVP, (e.g., at a concentration of about 0.001% (w/v) to about 10% (w/v) or about 0.05% (w/v) to about 2% (w/v)), guanidine hydrochloride (GnHCl) (e.g., at a concentration of about 0.1 to about 150 mM or about 10 to about 30 mM), and ethanol (e.g., at a concentration of about 0.05% (w/v) to about 2.5% (w/v) or about 0.25% (w/v) to about 1% (w/v)). Optionally, the calcium chloride-containing stable aqueous adalimumab formulation has a pH of about 4.8 to about 5.7, for example, about 4.9 to about 5.6, about 5.0 to about 5.5, about 5.1 to about 5.4, about 5.1 to about 5.3, about 5.1 to about 5.2, about 5.2 to about 5.3, and/or about 5.2. Optionally, the pH of the stable aqueous adalimumab formulation is adjusted using a strong acid and/or a strong base including, but not limited to, hydrochloric acid, sodium hydroxide, calcium hydroxide, MSA, and/or MEA.

Suitable excipients for combination with the calcium chloride-containing adalimumab formulations also include, but are not limited to, glutamate at a concentration of about 5 mM to about 50 mM (e.g., about 10 mM to about 25 mM, about 15 mM to about 20 mM, about 10 mM, about 15 mM, about 20 mM, and/or about 25 mM), adipate at a concentration of about 5 mM to about 50 mM (e.g., about 10 mM to about 25 mM, about 15 mM to about 20 mM, about 10 mM, about 15 mM, about 20 mM, and/or about 25 mM), glucuronate at a concentration of about 5 mM to about 50 mM (e.g., about 10 mM to about 30 mM, about 10 mM, about 15 mM, about 20 mM, and/or about 25 mM), acetic acid and/or acetate at a concentration of about 0.1 mM to about 300 mM (e.g., about 2 mM to about 30 mM, about 5 mM to about 50 mM, about 5 mM to about 15 mM, about 10 mM to about 20 mM, about 10 mM to about 30 mM, about 15 mM to about 25 mM, about 30 mM to about 40 mM, about 35 mM to about 45 mM, about 40 mM to about 50 mM, about 10 mM, about 15 mM, about 20 mM, and/or 25 mM), benzoate at a concentration of about 5 mM to about 50 mM (e.g., about 10 mM to about 30 mM, about 10 mM, about 15 mM, about 20 mM, and/or about 25 mM), glycolate at a concentration of about 5 mM to about 50 mM (e.g., about 10 mM to about 30 mM, about 10 mM, about 15 mM, about 20 mM, and/or about 25 mM), lactic acid and/or lactate at a concentration of about 0.1 mM to about 300 mM (e.g., about 2 mM to about 30 mM, about 10 mM to about 30 mM, about 5 mM to about 15 mM, about 10 mM, about 15 mM, about 20 mM, and/or about 25 mM), histidine at a concentration of about 5 mM to about 50 mM (e.g., about 5 mM to about 15 mM, about 10 mM, about 15 mM, about 20 mM, and/or about 25 mM), proline at a concentration of about 0.1 to about 450 mM (e.g., about 50 to about 320 mM and/or about 50 to about 300 mM), N-acetyl arginine at a concentration of about 0.1 to about 450 mM (e.g., about 90 to about 150 mM), citruline at a concentration of about 0.1 to about 450 mM (e.g., about 100 to about 150 mM), sarcosine at a concentration of about 0.1 to about 450 mM (e.g., about 100 to about 150 mM), N-acetyl proline at a concentration of about 0.1 to about 450 mM (e.g., about 100 to about 150 mM), N-acetyl ornithine at a concentration of about 0.1 to about 450 mM (e.g., about 100 to about 150 mM), ornithine at a concentration of about 0.1 to about 450 mM (e.g., about 100 to about 150 mM), beta-alanine at a concentration of about 0.1 to about 450 mM (e.g., about 100 to about 150 mM), alanine at a concentration of about 0.1 to about 450 mM (e.g., about 80 to about 120 mM), asparagine at a concentration of about 0.1 to about 450 mM (e.g., about 80 to about 120 mM), isoleucine at a concentration of about 0.1 to about 450 mM (e.g., about 80 to about 120 mM), serine at a concentration of about 0.1 to about 450 mM (e.g., about 80 to about 120 mM), aspartic acid at a concentration of about 0.1 to about 450 mM (e.g., about 10 to about 30 mM), creatine at a concentration of about 0.1 to about 450 mM (e.g., about 15 to about 35 mM), glutamine at a concentration of about 0.1 to about 450 mM (e.g., about 40 to about 60 mM), phenylalanine at a concentration of about 0.1 to about 450 mM (e.g., about 40 to about 60 mM), tryptophan at a concentration of about 0.1 to about 450 mM (e.g., about 15 to about 35 mM), arginine-HCl at a concentration of about 0.1 to about 450 mM (e.g., about 80 to about 120 mM), PEG 15 hydroxystearate at a concentration of about 0.1% (w/v) to about 20% (w/v) (e.g., about 3% (w/v) to about 6% (w/v)), PEG 3350 at a concentration of about 0.1% (w/v) to about 30% (w/v) (e.g., about 1% (w/v) to about 7% (w/v)), PEG 200 at a concentration of about 0.1% (w/v) to about 10% (w/v) (e.g., about 0.6% (w/v) to about 4.8% (w/v)), PEG 600 at a concentration of about 0.1% (w/v) to about 30% (w/v) (e.g., about 1.2% (w/v) to about 14.5% (w/v)), PEG 400 at a concentration of about 0.1% (w/v) to about 20% (w/v) (e.g., about 0.3% (w/v) to about 1.5% (w/v)), inositol at a concentration of about 0.1 to about 450 mM (e.g., about 150 to about 210 mM), glycerol (also referred to as glycerin) at a concentration of about 0.1% (w/v) to about 15% (w/v) (e.g., about 0.5% (w/v) to about 1% (w/v)), sucrose at a concentration of about 0.1% (w/v) to about 15% (w/v) (e.g., about 4% (w/v) to about 10% (w/v), about 6.2% (w/v) to about 7.3% (w/v), about 4% (w/v) to about 9% (w/v), about 6.5% (w/v), about 6.8% (w/v), about 6.9% (w/v), or about 9% (w/v)), sorbitol at a concentration of about 0.1% (w/v) to about 10% (w/v) (e.g., about 3% (w/v) to about 5% (w/v) and/or about 4% (w/v)), glycolic acid at a concentration of about 0.1 to about 300 mM (e.g., about 50 to about 70 mM), PCA at a concentration of about 0.1% (w/v) to about 15% (w/v) (e.g., about 0.05% (w/v) to about 2% (w/v)), medronic acid at a concentration of about 0.1 to about 450 mM (e.g., about 100 to about 150 mM), benzene sulfonic acid at a concentration of about 0.1 to about 300 mM (e.g., about 60 to about 90 mM), methane sulfonic acid (MSA) at a concentration of about 0.1 to about 150 mM (e.g., about 0.1 to about 50 mM and/or about 10 to about 30 mM), monoethanolamine hydrochloride (MEA-HCl) at a concentration of about 0.1 to about 150 mM (e.g., about 0.1 to about 40 mM), monoethanolamine (MEA) at a concentration of about 0.1 to about 300 mM (e.g., about 0.1 to about 50 mM and/or about 30 to about 160 mM), triethanolamine (TEA) at a concentration of about 0.1 to about 170 mM (e.g., about 30 to about 150 mM), hyaluronic acid at a concentration of about 0.05% (w/v) to about 2.5% (w/v) (e.g., about 0.1% (w/v) to about 0.05% (w/v)), sodium carboxymethylcellulose (NaCMC) at a concentration of about 0.1% (w/v) to about 15% (w/v) (e.g., about 0.1% (w/v) to about 2% (w/v)), dextran at a concentration of about 0.1% (w/v) to about 15% (w/v) (e.g., about 8% (w/v) to about 12% (w/v)), Pluronic F68 at a concentration of about 0.001% (w/v) to about 10% (w/v) (e.g., about 0.005% (w/v) to about 1% (w/v), about 0.05% (w/v) to about 0.4% (w/v), about 0.05% (w/v) to about 0.1% (w/v), about 0.01% (w/v), about 0.05% (w/v), and/or about 0.1% (w/v)), Polysorbate 80 at a concentration of about 0.001% (w/v) to about 2% (w/v) (e.g., about 0.005% (w/v) to about 0.1% (w/v), about 0.03% (w/v) to about 0.1% (w/v), about 0.04% (w/v) to about 0.1% (w/v), about 0.03% (w/v), about 0.04% (w/v), and/or about 0.1% (w/v)), Polysorbate 20 at a concentration of about 0.001% (w/v) to about 2% (w/v) (e.g., about 0.005% (w/v) to about 0.1% (w/v)), Docusate sodium at a concentration of about 0.001% (w/v) to about 1% (w/v) (e.g., about 0.005% (w/v) to about 0.05% (w/v)), benzalkonium chloride at a concentration of about 0.001% (w/v) to about 1% (w/v) (e.g., about 0.05% (w/v) to about 0.5% (w/v)), Span 40 (sorbitan monopalmitate) at a concentration of about 0.001% (w/v) to about 1% (w/v) (e.g., about 0.05% (w/v) to about 0.5% (w/v)), Triton X-100 at a concentration of about 0.001% (w/v) to about 1% (w/v) (e.g., about 0.005% (w/v) to about 0.1% (w/v)), imidazole at a concentration of about 0.1% (w/v) to about 15% (w/v) (e.g., about 0.5% (w/v) to about 2% (w/v)), taurine at a concentration of about 0.1 to about 450 mM (e.g., about 100 to about 150 mM), betaine at a concentration of about 0.1 to about 450 mM (e.g., about 100 to about 150 mM), gelatin at a concentration of about 0.1% (w/v) to about 15% (w/v) (e.g., about 0.5% (w/v) to about 2% (w/v)), niacinamide at a concentration of about 0.1 to about 450 mM (e.g., about 100 to about 120 mM), polyvinylpyrrolidone (PVP), for example, 10K PVP, at a concentration of about 0.001% (w/v) to about 10% (w/v) (e.g., about 0.05% (w/v) to about 2% (w/v)), guanidine hydrochloride (GnHCl) at a concentration of about 0.1 to about 150 mM (e.g., about 10 to about 30 mM), and ethanol at a concentration of about 0.05% (w/v) to about 2.5% (w/v) (e.g., about 0.25% (w/v) to about 1% (w/v)). Optionally, the calcium chloride-containing stable aqueous adalimumab formulation has a pH of about 4.8 to about 5.7, for example, about 4.9 to about 5.6, about 5.0 to about 5.5, about 5.1 to about 5.4, about 5.1 to about 5.3, about 5.1 to about 5.2, about 5.2 to about 5.3, and/or about 5.2. Optionally, the pH of the stable aqueous adalimumab formulation is adjusted using a strong acid and/or a strong base including, but not limited to, hydrochloric acid, sodium hydroxide, calcium hydroxide, MSA, and/or MEA.

In an embodiment, the stable aqueous adalimumab formulation includes adalimumab at a concentration of about 90 to about 120 mg/mL, glutamate at a concentration of about 10 mM to about 25 mM, PEG 3350 at a concentration of about 5% (w/v) to about 10% (w/v), calcium chloride at a concentration of about 30 to about 60 mM, and has a pH of about 5.0 to about 5.5.

In an embodiment, the stable aqueous adalimumab formulation includes adalimumab at a concentration of about 90 to about 140 mg/mL, glutamate at a concentration of about 10 mM to about 25 mM, dextran at a concentration of about 5% (w/v) to about 15% (w/v), calcium chloride at a concentration of about 30 to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PEG 200 at a concentration of about 0.5% (w/v) to about 2% (w/v), calcium chloride at a concentration of about 30 to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PEG 600 at a concentration of about 1.5% (w/v) to about 4% (w/v), calcium chloride at a concentration of about 30 to about 60 mM, and has a pH of about 5.0 to about 5.5.

In an embodiment, the stable aqueous adalimumab formulation includes adalimumab at a concentration of about 170 to about 190 mg/mL, glutamate at a concentration of about 10 mM to about 25 mM, calcium chloride at a concentration of about 50 mM to about 100 mM, proline at a concentration of about 50 mM to about 150 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, ethanol at a concentration of about 0.3% (w/v) to about 0.8% (w/v), calcium chloride at a concentration of about 30 mM to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, ethanol at a concentration of about 0.3% (w/v) to about 0.8% (w/v), PEG 3350 at a concentration of about 0.7% (w/v) to about 1.5% (w/v), calcium chloride at a concentration of about 30 mM to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, TEA at a concentration of about 100 mM to about 200 mM, calcium chloride at a concentration of about 30 mM to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, TEA at a concentration of about 20 mM to about 40 mM, calcium chloride at a concentration of about 60 mM to about 90 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, alanine at a concentration of about 80 mM to about 120 mM, calcium chloride at a concentration of about 30 mM to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, asparagine at a concentration of about 80 mM to about 120 mM, calcium chloride at a concentration of about 30 mM to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, isoleucine at a concentration of about 80 mM to about 120 mM, calcium chloride at a concentration of about 30 mM to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, serine at a concentration of about 80 mM to about 120 mM, calcium chloride at a concentration of about 30 mM to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, aspartic acid at a concentration of about 10 mM to about 30 mM, proline at a concentration of about 60 mM to about 100 mM, calcium chloride at a concentration of about 30 mM to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, creatine at a concentration of about 15 mM to about 35 mM, proline at a concentration of about 60 mM to about 90 mM, calcium chloride at a concentration of about 30 mM to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, glutamine at a concentration of about 40 mM to about 60 mM, proline at a concentration of about 40 mM to about 60 mM, calcium chloride at a concentration of about 30 mM to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, leucine at a concentration of about 40 mM to about 60 mM, proline at a concentration of about 40 mM to about 60 mM, calcium chloride at a concentration of about 30 mM to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, phenylalanine at a concentration of about 40 mM to about 60 mM, proline at a concentration of about 40 mM to about 60 mM, calcium chloride at a concentration of about 30 mM to about 60 mM, and has a pH of about 5.0 to about 5.5.

In an embodiment, the stable aqueous adalimumab formulation includes adalimumab at a concentration of about 80 to about 120 mg/mL, glutamate at a concentration of about 10 mM to about 25 mM, tryptophan at a concentration of about 10 mM to about 40 mM, proline at a concentration of about 60 mM to about 90 mM, calcium chloride at a concentration of about 30 mM to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, calcium chloride at a concentration of about 30 to about 60 mM, proline at a concentration of about 80 to about 120 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PEG 15 hydroxystearate at a concentration of about 3% (w/v) to about 8% (w/v), calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PEG 15 hydroxystearate at a concentration of about 3% (w/v) to about 8% (w/v), calcium chloride at a concentration of about 30 to about 60 mM, proline at a concentration of about 80 to about 120 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, imidazole at a concentration of about 0.7% (w/v) to about 1.5% (w/v), calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, N-acetyl arginine at a concentration of about 100 to about 150 mM, calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, inositol at a concentration of about 200 to about 300 mM, calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PEG 3350 at a concentration of about 0.7% (w/v) to about 1.5% (w/v), calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, taurine at a concentration of about 100 to about 150 mM, calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, citruline at a concentration of about 100 to about 150 mM, calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, betaine at a concentration of about 100 to about 150 mM, calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, sarcosine at a concentration of about 100 to about 150 mM, calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, glycolic acid at a concentration of about 40 to about 80 mM, calcium chloride at a concentration of about 60 to about 90 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PCA at a concentration of about 0.7% (w/v) to about 1.5% (w/v), calcium chloride at a concentration of about 60 to about 90 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, gelatin at a concentration of about 0.7% (w/v) to about 1.5% (w/v), calcium chloride at a concentration of about 60 to about 90 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, hyaluronic acid at a concentration of about 0.1% (w/v) to about 0.5% (w/v), calcium chloride at a concentration of about 60 to about 90 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, N-acetyl proline at a concentration of about 100 to about 150 mM, calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, N-acetyl ornithine at a concentration of about 100 to about 150 mM, calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, ornithine at a concentration of about 100 to about 150 mM, calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, beta-alanine at a concentration of about 100 to about 150 mM, calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, niacinamide at a concentration of about 100 to about 150 mM, calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, medronic acid at a concentration of about 100 to about 150 mM, calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PEG 200 at a concentration of about 0.7% (w/v) to about 1.5% (w/v), calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PEG 600 at a concentration of about 1.5% (w/v) to about 4% (w/v), and calcium chloride at a concentration of about 30 to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, niacinamide at a concentration of about 80 to about 120 mM, calcium chloride at a concentration of about 60 to about 100 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, benzene sulfonic acid at a concentration of about 60 to about 90 mM, calcium chloride at a concentration of about 25 to about 75 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 170 to about 190 mg/mL, glutamate at a concentration of about 10 mM to about 25 mM, PEG 400 at a concentration of about 0.25% (w/v) to about 0.75% (w/v), calcium chloride at a concentration of about 40 to about 80 mM, glycerin at a concentration of about 0.5% (w/v) to about 1% (w/v), and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 170 to about 190 mg/mL, adipate at a concentration of about 10 mM to about 25 mM, N-acetyl arginine at a concentration of about 100 to about 150 mM, calcium chloride at a concentration of about 30 to about 50 mM, and MSA at a concentration of about 10 to about 30 mM, and has a pH of about 5.0 to about 5.5.

In an embodiment, the stable aqueous adalimumab formulation includes adalimumab at a concentration of about 170 to about 190 mg/mL, adipate at a concentration of about 10 mM to about 25 mM, calcium chloride at a concentration of about 60 to about 90 mM, PEG 400 at a concentration of about 0.1% (w/v) to about 0.5% (w/v), and 10K PVP at a concentration of about 0.5% (w/v) to about 2% (w/v), and has a pH of about 5.0 to about 5.5.

In an embodiment, the stable aqueous adalimumab formulation includes adalimumab at a concentration of about 170 to about 190 mg/mL, adipate at a concentration of about 10 mM to about 25 mM, PEG 400 at a concentration of about 0.5% (w/v) to about 2% (w/v), and calcium chloride at a concentration of about 30 to about 50 mM, and has a pH of about 5.0 to about 5.5.

In an embodiment, the stable aqueous adalimumab formulation includes adalimumab at a concentration of about 170 to about 190 mg/mL, adipate at a concentration of about 10 mM to about 25 mM, PEG 3350 at a concentration of about 0.5% (w/v) to about 2% (w/v), and calcium chloride at a concentration of about 60 to about 90 mM, and has a pH of about 5.0 to about 5.5.

In an embodiment, the stable aqueous adalimumab formulation includes adalimumab at a concentration of about 170 to about 190 mg/mL, adipate at a concentration of about 10 mM to about 25 mM, PEG 3350 at a concentration of about 0.5% (w/v) to about 2% (w/v), PEG 400 at a concentration of about 1% (w/v) to about 3% (w/v), and calcium chloride at a concentration of about 10 to about 30 mM, and has a pH of about 5.0 to about 5.5.

In an embodiment, the stable aqueous adalimumab formulation includes adalimumab at a concentration of about 170 to about 190 mg/mL, adipate at a concentration of about 10 mM to about 25 mM, PEG 3350 at a concentration of about 0.5% (w/v) to about 2% (w/v), PEG 400 at a concentration of about 0.5% (w/v) to about 2% (w/v), and calcium chloride at a concentration of about 30 to about 50 mM, and has a pH of about 5.0 to about 5.5.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Polysorbate 20 at a concentration of about 0.05% (w/v) to about 0.5% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Polysorbate 80 at a concentration of about 0.05% (w/v) to about 0.5% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Pluronic F68 at a concentration of about 0.05% (w/v) to about 0.5% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Docusate sodium at a concentration of about 0.005% (w/v) to about 0.05% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and benzalkonium chloride at a concentration of about 0.05% (w/v) to about 0.5% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Span 40 at a concentration of about 0.05% (w/v) to about 0.5% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Triton X-100 at a concentration of about 0.05% (w/v) to about 0.5% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, and arginine-HCl at a concentration of about 80 to about 120 mM, and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Polysorbate 80 at a concentration of about 0.0025% (w/v) to about 0.025% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Polysorbate 80 at a concentration of about 0.005% (w/v) to about 0.05% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Polysorbate 80 at a concentration of about 0.025% (w/v) to about 0.25% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Polysorbate 20 at a concentration of about 0.0025% (w/v) to about 0.025% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Polysorbate 20 at a concentration of about 0.005% (w/v) to about 0.05% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Polysorbate 20 at a concentration of about 0.025% (w/v) to about 0.25% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Triton X-100 at a concentration of about 0.0025% (w/v) to about 0.025% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Triton X-100 at a concentration of about 0.005% (w/v) to about 0.05% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Triton X-100 at a concentration of about 0.025% (w/v) to about 0.25% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Pluronic F68 at a concentration of about 0.025% (w/v) to about 0.25% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Pluronic F68 at a concentration of about 0.05% (w/v) to about 0.5% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Pluronic F68 at a concentration of about 0.2% (w/v) to about 0.6% (w/v), and has a pH of about 5.1 to 5.3.

In an embodiment, the stable aqueous adalimumab formulation includes adalimumab at a concentration of about 40 to about 50 mg/mL, acetate at a concentration of about 5 mM to about 15 mM, sucrose at a concentration of about 6.5% (w/v) to about 7.1% (w/v), calcium chloride at a concentration of about 15 to about 35 mM, and Pluronic F68 at a concentration of about 0.05% (w/v) to about 0.5% (w/v), and has a pH of about 5.1 to 5.3.

In an embodiment, the stable aqueous adalimumab formulation includes adalimumab at a concentration of about 40 to about 50 mg/mL, acetate at a concentration of about 5 mM to about 15 mM, sucrose at a concentration of about 6.0% (w/v) to about 6.5% (w/v), calcium chloride at a concentration of about 15 to about 35 mM, and Pluronic F68 at a concentration of about 0.05% (w/v) to about 0.5% (w/v), and has a pH of about 5.1 to 5.3.

In an embodiment, the stable aqueous adalimumab formulation includes adalimumab at a concentration of about 40 to about 50 mg/mL, acetate at a concentration of about 5 mM to about 15 mM, sucrose at a concentration of about 6.7% (w/v) to about 7.3% (w/v), calcium chloride at a concentration of about 5 to about 15 mM, guanidine hydrochloride (GnHCl) at a concentration of about 10 to about 30 mM, and Pluronic F68 at a concentration of about 0.05% (w/v) to about 0.5% (w/v), and has a pH of about 5.1 to 5.3.

In an embodiment, the stable aqueous adalimumab formulation includes adalimumab at a concentration of about 40 to about 50 mg/mL, acetate at a concentration of about 5 mM to about 15 mM, sucrose at a concentration of about 6.7% (w/v) to about 7.3% (w/v), calcium chloride at a concentration of about 5 to about 15 mM, NaCMC at a concentration of about 0.2% (w/v) to about 1% (w/v), and Pluronic F68 at a concentration of about 0.05% (w/v) to about 0.5% (w/v), and has a pH of about 5.1 to 5.3.

In an embodiment, the stable aqueous adalimumab formulation includes adalimumab at a concentration of about 90 to about 120 mg/mL, acetate at a concentration of about 5 mM to about 15 mM, sucrose at a concentration of about 6.4% (w/v) to about 7.2% (w/v), calcium chloride at a concentration of about 15 to about 35 mM, and Pluronic F68 at a concentration of about 0.05% (w/v) to about 0.5% (w/v), and has a pH of about 5.1 to 5.3. Optionally, the pH of the formulation is adjusted within this range with HCl, NaOH, and/or Ca(OH)$_2$.

In an embodiment, the stable aqueous adalimumab formulation includes adalimumab at a concentration of about 90 to about 120 mg/mL, acetate at a concentration of about 5 mM to about 15 mM, proline at a concentration of about 190 to about 250 mM, calcium chloride at a concentration of about 15 to about 35 mM, and Pluronic F68 at a concentration of about 0.05% (w/v) to about 0.5% (w/v), and has a pH of about 5.1 to 5.3. Optionally, the pH of the formulation is adjusted within this range with HCl, NaOH, and/or Ca(OH)$_2$.

In an embodiment, the stable aqueous adalimumab formulation includes adalimumab at a concentration of about 90 to about 120 mg/mL, acetate at a concentration of about 5 mM to about 15 mM, sucrose at a concentration of about 6.4% (w/v) to about 7.2% (w/v), calcium chloride at a concentration of about 15 to about 35 mM, and Polysorbate 80 at a concentration of about 0.05% (w/v) to about 0.5% (w/v), and has a pH of about 5.1 to 5.3. Optionally, the pH of the formulation is adjusted within this range with HCl, NaOH, and/or Ca(OH)$_2$.

In an embodiment, the stable aqueous adalimumab formulation includes adalimumab at a concentration of about 90 to about 110 mg/mL, acetate at a concentration of about 5 mM to about 15 mM, sucrose at a concentration of about 6.6% (w/v) to about 7% (w/v), calcium chloride at a concentration of about 20 to about 30 mM, and Polysorbate 80 at a concentration of about 0.05% (w/v) to about 0.2% (w/v), and has a pH of about 5.1 to 5.3. Optionally, the pH of the formulation is adjusted within this range with HCl, NaOH, and/or Ca(OH)$_2$.

In an embodiment, the stable aqueous adalimumab formulation includes adalimumab at a concentration of about 90 to about 120 mg/mL, acetate at a concentration of about 5 mM to about 15 mM, proline at a concentration of about 190 to about 250 mM, calcium chloride at a concentration of about 15 to about 35 mM, and Polysorbate 80 at a concentration of about 0.05% (w/v) to about 0.5% (w/v), and has a pH of about 5.1 to 5.3. Optionally, the pH of the formulation is adjusted within this range with HCl, NaOH, and/or Ca(OH)$_2$.

In an embodiment, the stable aqueous adalimumab formulation includes adalimumab at a concentration of about 90 to about 120 mg/mL, acetate at a concentration of about 5 mM to about 15 mM, sucrose at a concentration of about 6.4% (w/v) to about 7.2% (w/v), calcium chloride at a concentration of about 15 to about 35 mM, and Polysorbate 80 at a concentration of about 0.01% (w/v) to about 0.1% (w/v), and has a pH of about 5.1 to 5.3. Optionally, the pH of the formulation is adjusted within this range with HCl, NaOH, and/or Ca(OH)$_2$.

In an embodiment, the stable aqueous adalimumab formulation includes adalimumab at a concentration of about 90 to about 120 mg/mL, acetate at a concentration of about 5 mM to about 15 mM, proline at a concentration of about 190 to about 250 mM, calcium chloride at a concentration of about 15 to about 35 mM, and Polysorbate 80 at a concentration of about 0.01% (w/v) to about 0.1% (w/v), and has a pH of about 5.1 to 5.3. Optionally, the pH of the formulation is adjusted within this range with HCl, NaOH, and/or Ca(OH)$_2$.

In an embodiment, the stable aqueous adalimumab formulation includes adalimumab at a concentration of about 90 to about 120 mg/mL, lactate at a concentration of about 5 mM to about 15 mM, proline at a concentration of about 190 to about 240 mM, calcium chloride at a concentration of about 15 to about 35 mM, and Pluronic F68 at a concentration of about 0.05% (w/v) to about 0.5% (w/v), and has a pH of about 5.1 to 5.3. Optionally, the pH of the formulation is adjusted within this range with MSA and/or MEA.

In an embodiment, the stable aqueous adalimumab formulation includes adalimumab at a concentration of about 160 to about 190 mg/mL, lactate at a concentration of about 5 mM to about 15 mM, proline at a concentration of about 200 to about 250 mM, calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MSA and/or MEA.

In an embodiment, the stable aqueous adalimumab formulation includes adalimumab at a concentration of about 160 to about 190 mg/mL, lactate at a concentration of about 5 mM to about 15 mM, PEG 600 at a concentration of about 11% (w/v) to about 15% (w/v), calcium chloride at a concentration of about 20 to about 40 mM, and Pluronic F68 at a concentration of about 0.05% (w/v) to about 0.5% (w/v), and has a pH of about 5.1 to 5.3. Optionally, the pH of the formulation is adjusted within this range with MSA and/or MEA.

In an embodiment, the stable aqueous adalimumab formulation includes adalimumab at a concentration of about 160 to about 190 mg/mL, lactate at a concentration of about 5 mM to about 15 mM, PEG 600 at a concentration of about 11% (w/v) to about 15% (w/v), calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MSA and/or MEA.

In an embodiment, the stable aqueous adalimumab formulation includes adalimumab at a concentration of about 160 to about 190 mg/mL, lactate at a concentration of about 5 mM to about 15 mM, PEG 600 at a concentration of about 8% (w/v) to about 9% (w/v), calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MSA and/or MEA.

In an embodiment, the stable aqueous adalimumab formulation includes adalimumab at a concentration of about 160 to about 190 mg/mL, lactate at a concentration of about 5 mM to about 15 mM, PEG 600 at a concentration of about 3% (w/v) to about 5% (w/v), PEG 200 at a concentration of about 1.2% (w/v) to about 2% (w/v), calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MSA and/or MEA.

In an embodiment, the stable aqueous adalimumab formulation includes adalimumab at a concentration of about 160 to about 190 mg/mL, lactate at a concentration of about 5 mM to about 15 mM, PEG 200 at a concentration of about 3.5% (w/v) to about 4.2% (w/v), calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MSA and/or MEA.

In an embodiment, the stable aqueous adalimumab formulation includes adalimumab at a concentration of about 160 to about 190 mg/mL, lactate at a concentration of about 5 mM to about 15 mM, PEG 600 at a concentration of about 5% (w/v) to about 5.7% (w/v), calcium chloride at a concentration of about 10 to about 30 mM, proline at a concentration of about 90 to about 130 mM, and Pluronic F68 at a concentration of about 0.05% (w/v) to about 0.5% (w/v), and has a pH of about 5.1 to 5.3. Optionally, the pH of the formulation is adjusted within this range with MSA and/or MEA.

In an embodiment, the stable aqueous adalimumab formulation includes adalimumab at a concentration of about 160 to about 190 mg/mL, lactate at a concentration of about 5 mM to about 15 mM, calcium chloride at a concentration of about 10 to about 30 mM, proline at a concentration of about 190 to about 250 mM, and Pluronic F68 at a concentration of about 0.05% (w/v) to about 0.5% (w/v), and has a pH of about 5.1 to 5.3. Optionally, the pH of the formulation is adjusted within this range with MSA and/or MEA.

In an embodiment, the stable aqueous adalimumab formulation includes adalimumab at a concentration of about 90 to about 120 mg/mL, lactate at a concentration of about 5 mM to about 15 mM, calcium chloride at a concentration of about 15 to about 35 mM, proline at a concentration of about 190 to about 250 mM, and Pluronic F68 at a concentration of about 0.05% (w/v) to about 0.5% (w/v), and has a pH of about 5.1 to 5.3. Optionally, the pH of the formulation is adjusted within this range with HCl, NaOH, and/or Ca(OH)$_2$.

In an embodiment, the stable aqueous adalimumab formulation includes adalimumab at a concentration of about 90 to about 120 mg/mL, histidine at a concentration of about 5 mM to about 15 mM, proline at a concentration of about 270 to about 370 mM, and calcium chloride at a concentration of about 10 to about 30 mM, and has a pH of about 6.7 to 6.9. Optionally, the pH of the formulation is adjusted within this range with MEA and/or MSA.

In an embodiment, the stable aqueous adalimumab formulation includes adalimumab at a concentration of about 90 to about 120 mg/mL, PEG 600 at a concentration of about 8% (w/v) to about 10% (w/v), calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, PEG 600 at a concentration of about 6.5% (w/v) to about 7.3% (w/v), PEG 200 at a concentration of about 0.3% (w/v) to about 1% (w/v), calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, PEG 600 at a concentration of about 4% (w/v) to about 5% (w/v), PEG 200 at a concentration of about 1.5% (w/v) to about 2.1% (w/v), calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, PEG 600 at a concentration of about 0.9% (w/v) to about 1.5% (w/v), PEG 200 at a concentration of about 2.5% (w/v) to about 3.5% (w/v), calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, PEG 200 at a concentration of about 3% (w/v) to about 5% (w/v), calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, PEG 600 at a concentration of about 6.9% (w/v) to about 7.7% (w/v), proline at a concentration of about 40 to about 80 mM, calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, PEG 600 at a concentration of about 5% (w/v) to about 6% (w/v), proline at a concentration of about 90 to about 150 mM, calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, PEG 600 at a concentration of about 2% (w/v) to about 3% (w/v), proline at a concentration of about 150 to about 210 mM, calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, proline at a concentration of about 200 to about 300 mM, calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, sorbitol at a concentration of about 3% (w/v) to about 5% (w/v), calcium chloride at a concentration of about 15 to about 35 mM, and Pluronic F68 at a concentration of about 0.05% (w/v) to about 0.5% (w/v), and has a pH of about 5.1 to 5.3. Optionally, the pH of the formulation is adjusted within this range with HCl and/or NaOH.

In an embodiment, the stable aqueous adalimumab formulation includes adalimumab at a concentration of about 90 to about 120 mg/mL, sucrose at a concentration of about 5% (w/v) to about 8% (w/v), calcium chloride at a concentration of about 15 to about 35 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, proline at a concentration of about 200 to about 250 mM, calcium chloride at a concentration of about 15 to about 35 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, PEG 600 at a concentration of about 11% (w/v) to about 15% (w/v), calcium chloride at a concentration of about 20 to about 40 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 160 to about 190 mg/mL, sucrose at a concentration of about 5% (w/v) to about 8% (w/v), calcium chloride at a concentration of about 15 to about 35 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, sucrose at a concentration of about 6.9% (w/v) to about 7.7% (w/v), calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, PEG 200 at a concentration of about 4.5% (w/v) to about 5.1% (w/v), calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, sorbitol at a concentration of about 3% (w/v) to about 5% (w/v), calcium chloride at a concentration of about 15 to about 35 mM, and Pluronic F68 at a concentration of about 0.05% (w/v) to about 0.5% (w/v), and has a pH of about 5.1 to 5.3. Optionally, the pH of the formulation is adjusted within this range with HCl.

In an embodiment, the stable aqueous adalimumab formulation includes adalimumab at a concentration of about 90 to about 120 mg/mL, PEG 600 at a concentration of about 13% (w/v) to about 16% (w/v), calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, PEG 600 at a concentration of about 3% (w/v) to about 3.6% (w/v), calcium chloride at a concentration of about 10 to about 30 mM, proline at a concentration of about 150 to about 210 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 40 to about 60 mg/mL, PEG 600 at a concentration of about 8% (w/v) to about 9% (w/v), and calcium chloride at a concentration of about 15 to about 35 mM, and has a pH of about 5.1 to 5.3. Optionally, the pH of the formulation is adjusted within this range with MEA and/or MSA.

In an embodiment, the stable aqueous adalimumab formulation includes adalimumab at a concentration of about 40 to about 60 mg/mL, PEG 600 at a concentration of about 6% (w/v) to about 7% (w/v), and calcium chloride at a concentration of about 40 to about 60 mM, and has a pH of about 5.1 to 5.3. Optionally, the pH of the formulation is adjusted within this range with MEA and/or MSA.

In an embodiment, the stable aqueous adalimumab formulation includes adalimumab at a concentration of about 40 to about 60 mg/mL, PEG 600 at a concentration of about 3.4% (w/v) to about 4% (w/v), and calcium chloride at a concentration of about 65 to about 85 mM, and has a pH of about 5.1 to 5.3. Optionally, the pH of the formulation is adjusted within this range with MEA and/or MSA.

In an embodiment, the stable aqueous adalimumab formulation includes adalimumab at a concentration of about 40 to about 60 mg/mL and calcium chloride at a concentration of about 80 to about 120 mM, and has a pH of about 5.1 to 5.3. Optionally, the pH of the formulation is adjusted within this range with MEA and/or MSA.

In an embodiment, the stable aqueous adalimumab formulation includes adalimumab at a concentration of about 40 to about 60 mg/mL, proline at a concentration of about 200 to about 250 mM, and calcium chloride at a concentration of about 15 to about 35 mM, and has a pH of about 5.1 to 5.3. Optionally, the pH of the formulation is adjusted within this range with MEA and/or MSA.

In an embodiment, the stable aqueous adalimumab formulation includes adalimumab at a concentration of about 40 to about 60 mg/mL, proline at a concentration of about 120 to about 180 mM, and calcium chloride at a concentration of about 40 to about 60 mM, and has a pH of about 5.1 to 5.3. Optionally, the pH of the formulation is adjusted within this range with MEA and/or MSA.

In an embodiment, the stable aqueous adalimumab formulation includes adalimumab at a concentration of about 40 to about 60 mg/mL, proline at a concentration of about 60 to about 90 mM, and calcium chloride at a concentration of about 65 to about 85 mM, and has a pH of about 5.1 to 5.3. Optionally, the pH of the formulation is adjusted within this range with MEA and/or MSA.

In an embodiment, a lyophilized form of any one of the foregoing calcium chloride-containing adalimumab formulations is provided.

In an embodiment, the stable aqueous adalimumab formulation includes adalimumab at a concentration of about 40 mg/ml to about 200 mg/ml, or about 160 mg/ml to about 190 mg/mL, or about 80 mg/ml to about 120 mg/ml, or about 90 mg/ml to about 110 mg/ml, or about 95 mg/ml to about 105 mg/ml, or about 40 mg/ml, or about 45 mg/ml, or about 50 mg/ml, or about 55 mg/ml, or about 60 mg/ml, or about 65 mg/ml, or about 70 mg/ml, or about 75 mg/ml, or about 80 mg/ml, or about 85 mg/ml, or about 90 mg/ml, or about 95 mg/ml, or about 100 mg/ml, or about 105 mg/ml, or about 110 mg/ml, or about 115 mg/ml, or about 120 mg/ml, or about 125 mg/ml, or about 130 mg/ml, or about 135 mg/ml, or about 140 mg/ml, or about 145 mg/ml, or about 150 mg/ml, or about 155 mg/ml, or about 160 mg/ml, or about 165 mg/ml, or about 170 mg/ml, or about 175 mg/ml, or about 180 mg/ml, or about 185 mg/ml, or about 190 mg/mL, with the following excipients:

(a) lactate buffer at a concentration of about 5 mM to about 15 mM, or about 7 mM to about 12 mM, or about 9 mM to about 11 mM, or about 5 mM, or about 6 mM, or about 7 mM, or about 8 mM, or about 8 mM, or about 9 mM, or about 10 mM, or about 11 mM, or about 12 mM, or about 13 mM, or about 14 mM, or about 15 mM;

(b) calcium chloride at a concentration of about 5 to about 30 mM, about 10 to about 20 mM, or about 12.5 mM to about 17.5 mM, or about 14 mM to about 16 mM, or about 10 mM, or about 10.5 mM, or about 11 mM, or about 11.5 mM, or about 12 mM, or about 12.5 mM, or about 13 mM, or about 13.5 mM, or about 14 mM, or about 14.5 mM, or about 15 mM, or about 15.5 mM, or about 16 mM, or about 16.5 mM, or about 17 mM, or about 17.5 mM, or about 18 mM, or about 18.5 mM, or about 19 mM, or about 19.5 mM, or about 20 mM;

(c) sucrose at a concentration of about 4% (w/v) to about 10% (w/v), or about 6% (w/v) to about 8.5% (w/v), or about 4% (w/v), or about 4.5% (w/v), or about 5% (w/v), or about 5.5% (w/v), or about 6% (w/v), or about 6.5% (w/v), or about 7% (w/v), or about 7.1% (w/v), or about 7.2% (w/v), or about 7.3% (w/v), or about 7.4% (w/v), or about 7.5% (w/v), or about 7.6% (w/v), or about 7.7% (w/v), or about 7.8% (w/v), or about 8% (w/v), or about 8.5% (w/v);

(d) Pluronic F68 at a concentration of about 0.03% (w/v) to about 0.09% (w/v), or about 0.03% (w/v) to about 0.06% (w/v), about 0.01% (w/v) to about 0.2% (w/v), about 0.01% (w/v) to about 0.1% (w/v), about 0.03% (w/v) to about 0.1% (w/v), or about 0.05% (w/v) to about 0.07% (w/v), or about 0.03% (w/v), or about 0.04% (w/v), or about 0.05% (w/v), or about 0.06% (w/v), or about 0.07% (w/v), or about 0.08% (w/v), about 0.09% (w/v), or about 0.1% (w/v); and (e) has a pH of about 3.5 to about 8, or about 4 to about 7, or about 4.5 to about 6, or about 5 to about 5.5, or about 3.5, or about 4, or about 4.5, or about 4.6, or about 4.7, or about 4.8, or about 4.9, or about 5.0, or about 5.1, or about 5.2, or about 5.3, or about 5.4, or about 5.5, or about 5.6, or about 5.7, or about 5.8, or about 5.9, or about 6.0, or about 6.5, or about 7.0, or about 7.5, or about 8.0.

In an embodiment, the stable aqueous adalimumab formulation includes adalimumab at a concentration or about 40 mg/ml to 200 mg/ml, lactate buffer at a concentration of about 5 mM to about 15 mM, sucrose at a concentration of about 4% (w/v) to about 10% (w/v), calcium chloride at a concentration of about 5 to about 30 mM, and Pluronic F68 at a concentration of about 0.03% (w/v) to about 0.1% (w/v), and has a pH of about 3.5 to 8.

In an embodiment, the stable aqueous adalimumab formulation includes adalimumab at a concentration or about 40 mg/ml to 200 mg/ml, lactate buffer at a concentration of about 1 mM to about 15 mM, sucrose at a concentration of about 4% (w/v) to about 10% (w/v), calcium chloride at a concentration of about 10 to about 20 mM, and Pluronic F68 at a concentration of about 0.03% (w/v) to about 0.1% (w/v), and has a pH of about 3.5 to 8.

In an embodiment, the stable aqueous adalimumab formulation includes adalimumab at a concentration of about 80 mg/ml to about 120 mg/mL, lactate buffer at a concentration of about 7 mM to about 12 mM, sucrose at a concentration of about 4% (w/v) to about 10% (w/v), calcium chloride at a concentration of about 12.5 to about 17.5 mM, and Pluronic F68 at a concentration of about 0.03% (w/v) to about 0.07% (w/v), and a pH of about 4 to about 7.

In an embodiment, the stable aqueous adalimumab formulation includes adalimumab at a concentration of about 90 mg/ml to about 110 mg/mL, lactate buffer at a concentration of about 9 mM to about 11 mM, sucrose at a concentration of about 6% (w/v) to about 8.5% (w/v), calcium chloride at a concentration of about 14 to about 16 mM, and Pluronic F68 at a concentration of about 0.03% (w/v) to about 0.07% (w/v), and a pH of about 5.0 to about 5.5.

In an embodiment, the stable aqueous adalimumab formulation includes adalimumab at a concentration of about 100 mg/mL, lactate buffer at a concentration of about 10 mM, sucrose at a concentration of about 7.4% (w/v), calcium chloride at a concentration of about 15 mM, and Pluronic F68 at a concentration of about 0.06% (w/v), and a pH of about 5.2.

In an embodiment, the stable aqueous adalimumab formulation is one of the lactate buffer formulations described in Tables G, H, I, 1, 11, 12, 13, 15, 16 or 17 provided herein.

In an embodiment, the stable aqueous adalimumab formulations described above, which include lactate buffer, calcium chloride, and Pluronic F68, are in lyophilized form. In an embodiment, the stable aqueous adalimumab formulations described above, which include lactate, calcium chloride, and Pluronic F68, are not in lyophilized form (e.g., are hydrated).

In an embodiment, the pH of the stable aqueous adalimumab formulations described above, which include lactate buffer, calcium chloride, and Pluronic F68, can be adjusted using HCl/Ca(OH)$_2$. In an embodiment, the pH of the stable aqueous adalimumab formulations described above, which include lactate buffer, calcium chloride, and Pluronic F68, is not adjusted using a pH adjusting agent.

The stable aqueous adalimumab formulations described above, which include lactate buffer, calcium chloride, and Pluronic F68, exhibit a conductivity of less than about 4 mS/cm, or less than about 3.5 mS/cm, or less than about 3 mS/cm, or less than about 2.5 mS/cm, or less than about 2 mS/cm, or less than about 1.5 mS/cm, or less than about 1 mS/cm, or less than about 0.5 mS/cm, or about 0.5 mS/cm to about 3.5 mS/cm at ambient room temperature.

The stable aqueous adalimumab formulations described above, which include lactate buffer, calcium chloride, and Pluronic F68, exhibit an osmolality of 270-330 mOsM, or about 300 mOsM.

Aqueous adalimumab formulations having the specific combination of about 5 to about 30 mM (e.g., 12.5 mM to about 17.5 mM, or about 15 mM) calcium chloride, about 5 mM to about 15 mM (e.g., about 7 mM to about 12 mM, or about 9 mM to about 11 mM, or about 10 mM) lactate buffer, and Pluronic F68 surfactant (e.g., about 0.03% (w/v) to about 0.1% (w/v); about 0.03% (w/v) or about 0.06% (w/v)), advantageously exhibit a lowered growth rate of acidic species, as detected by CEX-HPLC), a lowered growth rate of HMWS, as detected by SE-HPLC, and a minimal amount of sub-visible and/or non-spherical particles, as detected by MFI. See, e.g., Examples 15-17 below.

Formulations of Adalimumab with Glutamate Buffer

In an embodiment, the stable aqueous adalimumab formulation includes adalimumab at a concentration of about 40 to about 200 mg/mL, such as about 90 to about 120 mg/mL, about 160 to about 190 mg/mL, about 40 to about 60 mg/mL, about 50 mg/mL, about 100 mg/mL, or about 170 mg/mL, glutamate at a concentration of about 5 mM to about 50 mM (e.g., about 5 mM to about 30 mM, about 10 mM to about 25 mM, about 15 mM to about 20 mM, about 10 mM, about 15 mM, about 20 mM, and/or about 25 mM), and one or more excipients. Suitable excipients include certain stabilizers such as certain amino acids and amino acid derivatives, certain polyethylene glycols and polyethylene glycol derivatives, certain polyols, certain acids, certain amines, certain polysaccharides or polysaccharide derivatives, certain salts, and certain surfactants. Examples of suitable amino acids and amino acid derivatives include proline (e.g., at a concentration of about 0.1 to about 450 mM or about 50 to about 300 mM), arginine (e.g., at a concentration of about 0.1 to about 450 mM or about 60 to about 90 mM), N-acetyl arginine (e.g., at a concentration of about 0.1 to about 450 mM or about 90 to about 150 mM), citruline (e.g., at a concentration of about 0.1 to about 450 mM or about 100 to about 150 mM), sarcosine (e.g., at a concentration of about 0.1 to about 450 mM or about 100 to about 150 mM), N-acetyl proline (e.g., at a concentration of about 0.1 to about 450 mM or about 100 to about 150 mM), N-acetyl ornithine (e.g., at a concentration of about 0.1 to about 450 mM or about 100 to about 150 mM), ornithine (e.g., at a concentration of about 0.1 to about 450 mM or about 100 to about 150 mM), beta-alanine (e.g., at a concentration of about 0.1 to about 450 mM or about 100 to about 150 mM), alanine (e.g., at a concentration of about 0.1 to about 450 mM or about 80 to about 120 mM), asparagine (e.g., at a concentration of about 0.1 to about 450 mM or about 80 to about 120 mM), isoleucine (e.g., at a concentration of about 0.1 to about 450 mM or about 80 to about 120 mM), serine (e.g., at a concentration of about 0.1 to about 450 mM or about 80 to about 120 mM), aspartic acid (e.g., at a concentration of about 0.1 to about 450 mM or about 10 to about 30 mM), creatine (e.g., at a concentration of about 0.1 to about 450 mM or about 15 to about 35 mM), glutamine (e.g., at a concentration of about 0.1 to about 450 mM or about 40 to about 60 mM), leucine (e.g., at a concentration of about 0.1 to about 450 mM or about 40 to about 60 mM), phenylalanine (e.g., at a concentration of about 0.1 to about 450 mM or about 40 to about 60 mM), and tryptophan (e.g., at a concentration of about 0.1 to about 450 mM or about 15 to about 35 mM). Examples of suitable polyethylene glycols and polyethylene glycol derivatives include PEG 15 hydroxystearate (e.g., at a concentration of about 0.1% (w/v) to about 20% (w/v) or about 2.5% (w/v) to about 5% (w/v)), PEG 3350 (e.g., at a concentration of about 0.1% (w/v) to about 30% (w/v), about 0.5% (w/v) to about 2% (w/v), about 1% (w/v) to about 7% (w/v), about 5% (w/v) to about 10% (w/v), and/or about 6% (w/v) to about 8% (w/v)), PEG 600 (e.g., at a concentration of about 0.1% (w/v) to about 30% (w/v), about 1% (w/v) to about 4% (w/v), and/or about 1% (w/v) to about 2% (w/v)), PEG 400 (e.g., at a concentration of about 0.1% (w/v) to about 20% (w/v), about 0.5% (w/v) to about 10% (w/v), about 0.2% (w/v) to about 2% (w/v), and/or about 6% (w/v) to about 12% (w/v)), and PEG 200 (e.g., at a concentration of about 0.1% (w/v) to about 10% (w/v), about 1% (w/v) to about 4% (w/v), and/or about 0.05% (w/v) to about 5% (w/v)). Examples of suitable polyols include glycerol (also referred to as glycerin) (e.g., at a concentration of about 0.1% (w/v) to about 15% (w/v), about 0.7% (w/v) to about 2.5% (w/v), and/or about 0.5% (w/v) to about 4% (w/v)), inositol (e.g., at a concentration of about 0.1 to about 450 mM or about 180 to about 250 mM), sucrose (e.g., at a concentration of about 0.1% (w/v) to about 15% (w/v), about 4% (w/v) to about 10% (w/v), about 4% (w/v) to about 9% (w/v), about 6.5% (w/v), about 6.8% (w/v), about 6.9% (w/v), or about 9% (w/v)), and sorbitol (e.g., at a concentration of about 0.1% (w/v) to about 10% (w/v), about 3% (w/v) to about 5% (w/v), and/or about 4% (w/v)). Examples of suitable acids include glycolic acid (e.g., at a concentration of about 0.1 to about 300 mM or about 50 to about 70 mM), PCA (e.g., at a concentration of about 0.1% (w/v) to about 15% (w/v) or about 0.05% (w/v) to about 2% (w/v)), medronic acid (e.g., at a concentration of about 0.1 to about 450 mM or about 100 to about 150 mM), methane sulfonic acid (MSA) (e.g., at a concentration of about 0.1 to about 150 mM, about 0.1 to about 50 mM, and/or about 20 to about 125 mM), benzene sulfonic acid (e.g., at a concentration of about 0.1 to about 300 mM or about 75 to about 150 mM), and adipic acid (e.g., at a concentration of about 0.1 to about 300 mM or about 120 to about 180 mM). Examples of suitable amines include triethanolamine (TEA) (e.g., at a concentration of about 0.1 to about 170 mM or about 30 to about 150 mM), monoethanolamine hydrochloride (MEA-HCl) (e.g., at a concentration of about 0.1 to about 150 mM or about 0.1 to about 40 mM), monoethanolamide (MEA) (e.g., at a concentration of about 0.1 to about 300 mM, about 0.1 to about 50 mM, about 0.1 to about 170 mM, and/or about 30 to about 160 mM). Examples of suitable polysaccharides or polysaccharide derivatives include dextran (e.g., at a concentration of about 0.1% (w/v) to about 15% (w/v) or about 2% (w/v) to about 10% (w/v)) and hyaluronic acid (e.g., at a concentration of about 0.05% (w/v) to about 2.5% (w/v) or about 0.1% (w/v) to about 0.05% (w/v)). Examples of suitable salts include calcium chloride (e.g., at a concentration of about 1 to about 150 mM, about 5 to about 50 mM, about 10 to about 30 mM, about 20 to about 40 mM, about 30 to about 50 mM, about 40 to about 80 mM, about 50 to about 100 mM, or about 25 mM), sodium borate (e.g., at a concentration of about 0.1 to about 150 mM or about 60 to about 90 mM), sodium bicarbonate (e.g., at a concentration of about 0.1 to about 150 mM or about 60 to about 90 mM), sodium sulfate (e.g., at a concentration of about 0.1 to about 150 mM or about 60 to about 90 mM), calcium sulfate (e.g., at a concentration of about 0.1 to about 150 mM or about 10 to about 30 mM), ammonium sulfate (e.g., at a concentration of about 0.1 to about 150 mM or about 60 to about 90 mM), sodium chloride (e.g., at a concentration of about 10 to about 100 mM, about 60 to about 90 mM, about 15 to about 50 mM, and/or about 35 mM), and magnesium chloride (e.g., at a concentration of about 0.1 to about 150 mM or about 60 to about 90 mM). Examples of suitable surfactants include benzalkonium chloride (e.g., at a concentration of about 0.001% (w/v) to about 1% (w/v) or about 0.005% (w/v) to about 0.05% (w/v)), guanidine HCl (e.g., at a concentration of about 0.001% (w/v) to about 1% (w/v) or about 0.005% (w/v) to about 0.05% (w/v)), lecithin (e.g., at a concentration of about 0.001% (w/v) to about 1% (w/v) or about 0.005% (w/v) to about 0.05% (w/v)), oleic acid (e.g., at a concentration of about 0.001% (w/v) to about 1% (w/v) or about 0.005% (w/v) to about 0.05% (w/v)), Pluronic F68 (e.g., at a concentration of about 0.001% (w/v) to about 10% (w/v), about 0.005% (w/v) to about 1% (w/v), about 0.05% (w/v) to about 0.4% (w/v), about 0.05% (w/v) to about 0.1% (w/v), about 0.01% (w/v), about 0.05% (w/v), and/or about 0.1% (w/v)), Polysorbate 20 (e.g., at a concentration of about 0.001% (w/v) to about 2% (w/v) or about 0.005% (w/v) to about 0.1% (w/v)), Polysorbate 80 (e.g., at a concentration of about 0.001% (w/v) to about 2% (w/v), about 0.005% (w/v) to about 0.1% (w/v), about 0.005% (w/v) to about 0.05% (w/v), about 0.03% (w/v) to about 0.1% (w/v), about 0.04% (w/v) to about 0.1% (w/v), about 0.03% (w/v), about 0.04% (w/v), and/or about 0.1% (w/v)), polyvinyl alcohol, for example, 31K or 205 K polyvinyl alcohol, (e.g., at a concentration of about 0.01% (w/v) to about 10% (w/v) or about 0.05% (w/v) to about 0.5% (w/v)), polyvinylpyrrolidone (PVP), for example, 10K PVP, (e.g., at a concentration of about 0.001% (w/v) to about 10% (w/v), about 0.01% (w/v) to about 1% (w/v), and/or about 0.005% (w/v) to about 2% (w/v)), and protamine sulfate (e.g., at a concentration of about 0.001% (w/v) to about 2% (w/v) or about 0.005% (w/v) to about 0.05% (w/v)). Examples of other suitable excipients include imidazole (e.g., at a concentration of about 0.1% (w/v) to about 15% (w/v) or about 1% (w/v) to about 2% (w/v)), taurine (e.g., at a concentration of about 0.1 to about 450 mM or about 100 to about 150 mM), betaine (e.g., at a concentration of about 0.1 to about 450 mM or about 100 to about 150 mM), gelatin (e.g., at a concentration of about 0.1% (w/v) to about 15% (w/v) or about 0.5% (w/v) to about 2% (w/v)), niacinamide (e.g., at a concentration of about 0.1 to about 450 mM, about 100 to about 270 mM, and/or about 100 to about 150 mM), and ethanol (e.g., at a concentration of about 0.05% (w/v) to about 2.5% (w/v) or about 0.25% (w/v) to about 1.4% (w/v)). Optionally, the glutamate-containing stable aqueous adalimumab formulation has a pH of about 4.8 to about 5.7, for example, about 4.9 to about 5.6, about 5.0 to about 5.5, about 5.1 to about 5.4, about 5.1 to about 5.3, about 5.1 to about 5.2, about 5.2 to about 5.3, and/or about 5.2. Optionally, the pH of the stable aqueous adalimumab formulation is adjusted using a strong acid and/or a strong base including, but not limited to, hydrochloric acid, sodium hydroxide, calcium hydroxide, MSA, and/or MEA.

In an embodiment, the stable aqueous adalimumab formulation includes adalimumab at a concentration of about 40 to about 200 mg/mL, such as about 90 to about 120 mg/mL, about 160 to about 190 mg/mL, about 40 to about 60 mg/mL, about 50 mg/mL, about 100 mg/mL, or about 170 mg/mL, glutamate at a concentration of about 5 mM to about 50 mM (e.g., about 5 mM to about 30 mM, about 10 mM to about 25 mM, about 15 mM to about 20 mM, about 10 mM, about 15 mM, about 20 mM, and/or about 25 mM), and one or more excipients selected from the group consisting of PEG 3350 at a concentration of about 0.1% (w/v) to about 30% (w/v) (e.g., about 0.5% (w/v) to about 2% (w/v), about 1% (w/v) to about 7% (w/v), about 5% (w/v) to about 10% (w/v), and/or about 6% (w/v) to about 8% (w/v)), PEG 600 at a concentration of about 0.1% (w/v) to about 30% (w/v) (e.g., about 1% (w/v) to about 4% (w/v) and/or about 1% (w/v) to about 2% (w/v)), PEG 400 at a concentration of about 0.1% (w/v) to about 20% (w/v) (e.g., about 0.5% (w/v) to about 10% (w/v), about 0.2% (w/v) to about 2% (w/v) and/or about 6% (w/v) to about 12% (w/v)), PEG 200 at a concentration of about 0.1% (w/v) to about 10% (w/v) (e.g., about 1% (w/v) to about 4% (w/v) and/or about 0.05% (w/v) to about 5% (w/v)), glycerol (also referred to as glycerin) at a concentration of about 0.1% (w/v) to about 15% (w/v) (e.g., about 0.7% (w/v) to about 2.5% (w/v) and/or about 0.5% (w/v) to about 4% (w/v)), polyvinylpyrrolidone (PVP), for example, 10K PVP, at a concentration of about 0.001% (w/v) to about 10% (w/v) (e.g., about 0.01% (w/v) to about 1% (w/v) and/or about 0.005% (w/v) to about 2% (w/v)), calcium chloride at a concentration of about 1 to about 150 mM (e.g., about 5 to about 50 mM, about 10 to about 30 mM, about 20 to about 40 mM, about 30 to about 50 mM, about 40 to about 80 mM, about 50 to about 100 mM, or about 25 mM), proline at a concentration of about 0.1 to about 450 mM (e.g., about 50 to about 300 mM), PEG 15 hydroxystearate at a concentration of about 0.1% (w/v) to about 20% (w/v) (e.g., about 2.5% (w/v) to about 5% (w/v)), arginine at a concentration of about 0.1 to about 450 mM (e.g., about 60 to about 90 mM), dextran at a concentration of about 0.1% (w/v) to about 15% (w/v) (e.g., about 2% (w/v) to about 10% (w/v)), imidazole at a concentration of about 0.1% (w/v) to about 15% (w/v) (e.g., about 1% (w/v) to about 2% (w/v)), N-acetyl arginine at a concentration of about 0.1 to about 450 mM (e.g., about 90 to about 150 mM), inositol at a concentration of about 0.1 to about 450 mM (e.g., about 180 to about 250 mM), taurine at a concentration of about 0.1 to about 450 mM (e.g., about 100 to about 150 mM), citruline at a concentration of about 0.1 to about 450 mM (e.g., about 100 to about 150 mM), betaine at a concentration of about 0.1 to about 450 mM (e.g., about 100 to about 150 mM), sarcosine at a concentration of about 0.1 to about 450 mM (e.g., about 100 to about 150 mM), glycolic acid at a concentration of about 0.1 to about 300 mM (e.g., about 50 to about 70 mM), PCA at a concentration of about 0.1% (w/v) to about 15% (w/v) (e.g., about 0.05% (w/v) to about 2% (w/v)), gelatin at a concentration of about 0.1% (w/v) to about 15% (w/v) (e.g., about 0.5% (w/v) to about 2% (w/v)), hyaluronic acid at a concentration of about 0.05% (w/v) to about 2.5% (w/v) (e.g., about 0.1% (w/v) to about 0.05% (w/v)), N-acetyl proline at a concentration of about 0.1 to about 450 mM (e.g., about 100 to about 150 mM), N-acetyl ornithine at a concentration of about 0.1 to about 450 mM (e.g., about 100 to about 150 mM), ornithine at a concentration of about 0.1 to about 450 mM (e.g., about 100 to about 150 mM), beta-alanine at a concentration of about 0.1 to about 450 mM (e.g., about 100 to about 150 mM), niacinamide at a concentration of about 0.1 to about 450 mM (e.g., about 100 to about 270 mM and/or about 100 to about 150 mM), medronic acid at a concentration of about 0.1 to about 450 mM (e.g., about 100 to about 150 mM), methane sulfonic acid (MSA) at a concentration of about 0.1 to about 150 mM (e.g., about 0.1 to about 50 mM and/or about 20 to about 125 mM), triethanolamine (TEA) at a concentration of about 0.1 to about 170 mM (e.g., about 30 to about 150 mM), monoethanolamide hydrochloride (MEA-HCl) at a concentration of about 0.1 to about 150 mM (e.g., about 0.1 to about 40 mM), monoethanolamide (MEA) at a concentration of about 0.1 to about 300 mM (e.g., about 0.1 to about 50 mM, about 0.1 to about 170 mM, and/or about 30 to about 160 mM), ethanol at a concentration of about 0.05% (w/v) to about 2.5% (w/v) (e.g., about 0.25% (w/v) to about 1.4% (w/v)), benzene sulfonic acid at a concentration of about 0.1 to about 300 mM (e.g., about 75 to about 150 mM), adipic acid at a concentration of about 0.1 to about 300 mM (e.g., about 120 to about 180 mM), sodium borate at a concentration of about 0.1 to about 150 mM (e.g., about 60 to about 90 mM), sodium bicarbonate at a concentration of about 0.1 to about 150 mM (e.g., about 60 to about 90 mM), sodium sulfate at a concentration of about 0.1 to about 150 mM (e.g., about 60 to about 90 mM), calcium sulfate at a concentration of about 0.1 to about 150 mM (e.g., about 10 to about 30 mM), ammonium sulfate at a concentration of about 0.1 to about 150 mM (e.g., about 60 to about 90 mM), sodium chloride at a concentration of about 10 to about 100 mM (e.g., about 60 to about 90 mM, about 15 to about 50 mM, and/or about 35 mM), magnesium chloride at a concentration of about 0.1 to about 150 mM (e.g., about 60 to about 90 mM), alanine at a concentration of about 0.1 to about 450 mM (e.g., about 80 to about 120 mM), asparagine at a concentration of about 0.1 to about 450 mM (e.g., about 80 to about 120 mM), isoleucine at a concentration of about 0.1 to about 450 mM (e.g., about 80 to about 120 mM), serine at a concentration of about 0.1 to about 450 mM (e.g., about 80 to about 120 mM), aspartic acid at a concentration of about 0.1 to about 450 mM (e.g., about 10 to about 30 mM), creatine at a concentration of about 0.1 to about 450 mM (e.g., about 15 to about 35 mM), glutamine at a concentration of about 0.1 to about 450 mM (e.g., about 40 to about 60 mM), leucine at a concentration of about 0.1 to about 450 mM (e.g., about 40 to about 60 mM), phenylalanine at a concentration of about 0.1 to about 450 mM (e.g., about 40 to about 60 mM), tryptophan at a concentration of about 0.1 to about 450 mM (e.g., about 15 to about 35 mM), benzalkonium chloride at a concentration of about 0.001% (w/v) to about 1% (w/v) (e.g., about 0.005% (w/v) to about 0.05% (w/v)), guanidine HCl at a concentration of about 0.001% (w/v) to about 1% (w/v) (e.g., about 0.005% (w/v) to about 0.05% (w/v)), lecithin at a concentration of about 0.001% (w/v) to about 1% (w/v) (e.g., about 0.005% (w/v) to about 0.05% (w/v)), oleic acid at a concentration of about 0.001% (w/v) to about 1% (w/v) (e.g., about 0.005% (w/v) to about 0.05% (w/v)), sucrose at a concentration of about 0.1% (w/v) to about 15% (w/v) (e.g., about 4% (w/v) to about 10% (w/v), about 4% (w/v) to about 9% (w/v), about 6.5% (w/v), about 6.8% (w/v), about 6.9% (w/v), or about 9% (w/v)), sorbitol at a concentration of about 0.1% (w/v) to about 10% (w/v) (e.g., about 3% (w/v) to about 5% (w/v) and/or about 4% (w/v)), Pluronic F68 at a concentration of about 0.001% (w/v) to about 10% (w/v) (e.g., about 0.005% (w/v) to about 1% (w/v), about 0.05% (w/v) to about 0.4% (w/v), about 0.05% (w/v) to about 0.1% (w/v), about 0.01% (w/v), about 0.05% (w/v), and/or about 0.1% (w/v)), Polysorbate 20 at a concentration of about 0.001% (w/v) to about 2% (w/v) (e.g., about 0.005% (w/v) to about 0.1% (w/v)), Polysorbate 80 at a concentration of about 0.001% (w/v) to about 2% (w/v) (e.g., about 0.005% (w/v) to about 0.1% (w/v), about 0.005% (w/v) to about 0.05% (w/v), about 0.03% (w/v) to about 0.1% (w/v), about 0.04% (w/v) to about 0.1% (w/v), about 0.03% (w/v), about 0.04% (w/v), and/or about 0.1% (w/v)), polyvinyl alcohol, for example, 31K or 205 K polyvinyl alcohol, at a concentration of about 0.01% (w/v) to about 10% (w/v) (e.g., about 0.05% (w/v) to about 0.5% (w/v)), and protamine sulfate at a concentration of about 0.001% (w/v) to about 2% (w/v) (e.g., about 0.005% (w/v) to about 0.05% (w/v)). Optionally, the glutamate-containing stable aqueous adalimumab formulation has a pH of about 4.8 to about 5.7, for example, about 4.9 to about 5.6, about 5.0 to about 5.5, about 5.1 to about 5.4, about 5.1 to about 5.3, about 5.1 to about 5.2, about 5.2 to about 5.3, and/or about 5.2. Optionally, the pH of the stable aqueous adalimumab formulation is adjusted using a strong acid and/or a strong base including, but not limited to, hydrochloric acid, sodium hydroxide, calcium hydroxide, MSA, and/or MEA.

In an embodiment, the stable aqueous adalimumab formulation includes adalimumab at a concentration of about 90 to about 120 mg/mL, glutamate at a concentration of about 10 mM to about 25 mM, proline at a concentration of about 250 mM to about 350 mM, and has a pH of about 5.0 to about 5.5. Optionally, the pH of the stable aqueous adalimumab formulation is adjusted within this range with MEA or sodium hydroxide.

In an embodiment, the stable aqueous adalimumab formulation includes adalimumab at a concentration of about 90 to about 120 mg/mL, glutamate at a concentration of about 10 mM to about 25 mM, PEG 3350 at a concentration of about 5% (w/v) to about 10% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PEG 3350 at a concentration of about 5% (w/v) to about 10% (w/v), calcium chloride at a concentration of about 30 to about 60 mM, and has a pH of about 5.0 to about 5.5.

In an embodiment, the stable aqueous adalimumab formulation includes adalimumab at a concentration of about 90 to about 140 mg/mL, glutamate at a concentration of about 10 mM to about 25 mM, dextran at a concentration of about 5% (w/v) to about 15% (w/v), and has a pH of about 5.0 to about 5.5.

In an embodiment, the stable aqueous adalimumab formulation includes adalimumab at a concentration of about 90 to about 140 mg/mL, glutamate at a concentration of about 10 mM to about 25 mM, dextran at a concentration of about 5% (w/v) to about 15% (w/v), calcium chloride at a concentration of about 30 to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PEG 200 at a concentration of about 0.5% (w/v) to about 2% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PEG 200 at a concentration of about 0.5% (w/v) to about 2% (w/v), calcium chloride at a concentration of about 30 to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PEG 600 at a concentration of about 1.5% (w/v) to about 4% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PEG 600 at a concentration of about 1.5% (w/v) to about 4% (w/v), calcium chloride at a concentration of about 30 to about 60 mM, and has a pH of about 5.0 to about 5.5.

In an embodiment, the stable aqueous adalimumab formulation includes adalimumab at a concentration of about 90 to about 140 mg/mL, glutamate at a concentration of about 10 mM to about 25 mM, proline at a concentration of about 200 to about 300 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PEG 3350 at a concentration of about 0.5% (w/v) to about 2% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, MSA at a concentration of about 50 mM to about 150 mM, TEA at a concentration of about 25 mM to about 75 mM, and has a pH of about 5.0 to about 5.5.

In an embodiment, the stable aqueous adalimumab formulation includes adalimumab at a concentration of about 170 to about 190 mg/mL, glutamate at a concentration of about 10 mM to about 25 mM, sodium borate at a concentration of about 50 mM to about 100 mM, proline at a concentration of about 50 mM to about 150 mM, and has a pH of about 5.0 to about 5.5.

In an embodiment, the stable aqueous adalimumab formulation includes adalimumab at a concentration of about 170 to about 190 mg/mL, glutamate at a concentration of about 10 mM to about 25 mM, sodium bicarbonate at a concentration of about 50 mM to about 100 mM, proline at a concentration of about 50 mM to about 150 mM, and has a pH of about 5.0 to about 5.5.

In an embodiment, the stable aqueous adalimumab formulation includes adalimumab at a concentration of about 170 to about 190 mg/mL, glutamate at a concentration of about 10 mM to about 25 mM, sodium sulfate at a concentration of about 50 mM to about 100 mM, proline at a concentration of about 50 mM to about 150 mM, and has a pH of about 5.0 to about 5.5.

In an embodiment, the stable aqueous adalimumab formulation includes adalimumab at a concentration of about 170 to about 190 mg/mL, glutamate at a concentration of about 10 mM to about 25 mM, calcium sulfate at a concentration of about 10 mM to about 30 mM, proline at a concentration of about 50 mM to about 150 mM, and has a pH of about 5.0 to about 5.5.

In an embodiment, the stable aqueous adalimumab formulation includes adalimumab at a concentration of about 170 to about 190 mg/mL, glutamate at a concentration of about 10 mM to about 25 mM, ammonium sulfate at a concentration of about 50 mM to about 100 mM, proline at a concentration of about 50 mM to about 150 mM, and has a pH of about 5.0 to about 5.5.

In an embodiment, the stable aqueous adalimumab formulation includes adalimumab at a concentration of about 170 to about 190 mg/mL, glutamate at a concentration of about 10 mM to about 25 mM, calcium chloride at a concentration of about 50 mM to about 100 mM, proline at a concentration of about 50 mM to about 150 mM, and has a pH of about 5.0 to about 5.5.

In an embodiment, the stable aqueous adalimumab formulation includes adalimumab at a concentration of about 170 to about 190 mg/mL, glutamate at a concentration of about 10 mM to about 25 mM, sodium chloride at a concentration of about 50 mM to about 100 mM, proline at a concentration of about 50 mM to about 150 mM, and has a pH of about 5.0 to about 5.5.

In an embodiment, the stable aqueous adalimumab formulation includes adalimumab at a concentration of about 170 to about 200 mg/mL, glutamate at a concentration of about 10 mM to about 25 mM, magnesium chloride at a concentration of about 50 mM to about 100 mM, proline at a concentration of about 50 mM to about 150 mM, and has a pH of about 5.0 to about 5.5.

In an embodiment, the stable aqueous adalimumab formulation includes adalimumab at a concentration of about 170 to about 190 mg/mL, glutamate at a concentration of about 10 mM to about 25 mM, MEA at a concentration of about 20 mM to about 50 mM, and has a pH of about 5.0 to about 5.5.

In an embodiment, the stable aqueous adalimumab formulation includes adalimumab at a concentration of about 170 to about 190 mg/mL, glutamate at a concentration of about 10 mM to about 25 mM, MEA at a concentration of about 70 mM to about 90 mM, and has a pH of about 5.0 to about 5.5.

In an embodiment, the stable aqueous adalimumab formulation includes adalimumab at a concentration of about 170 to about 190 mg/mL, glutamate at a concentration of about 10 mM to about 25 mM, MEA at a concentration of about 100 mM to about 130 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, ethanol at a concentration of about 1% (w/v) to about 2% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, ethanol at a concentration of about 0.3% (w/v) to about 0.8% (w/v), calcium chloride at a concentration of about 30 mM to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, ethanol at a concentration of about 0.3% (w/v) to about 0.8% (w/v), PEG 3350 at a concentration of about 0.7% (w/v) to about 1.5% (w/v), calcium chloride at a concentration of about 30 mM to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, TEA at a concentration of about 100 mM to about 200 mM, calcium chloride at a concentration of about 30 mM to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, TEA at a concentration of about 20 mM to about 40 mM, calcium chloride at a concentration of about 60 mM to about 90 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, ethanol at a concentration of about 0.3% (w/v) to about 0.8% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, ethanol at a concentration of about 0.3% (w/v) to about 0.8% (w/v), PEG 200 at a concentration of about 1.5% (w/v) to about 4% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, ethanol at a concentration of about 0.1% (w/v) to about 0.4% (w/v), PEG 200 at a concentration of about 1.5% (w/v) to about 4% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, ethanol at a concentration of about 0.3% (w/v) to about 0.8% (w/v), MSA at a concentration of about 80 mM to about 120 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, ethanol at a concentration of about 0.3% (w/v) to about 0.8% (w/v), 10K PVP at a concentration of about 0.3% (w/v) to about 0.8% (w/v), MSA at a concentration of about 80 mM to about 120 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, ethanol at a concentration of about 0.3% (w/v) to about 0.8% (w/v), MEA at a concentration of about 80 mM to about 120 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, alanine at a concentration of about 80 mM to about 120 mM, calcium chloride at a concentration of about 30 mM to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, asparagine at a concentration of about 80 mM to about 120 mM, calcium chloride at a concentration of about 30 mM to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, isoleucine at a concentration of about 80 mM to about 120 mM, calcium chloride at a concentration of about 30 mM to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, serine at a concentration of about 80 mM to about 120 mM, calcium chloride at a concentration of about 30 mM to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, aspartic acid at a concentration of about 10 mM to about 30 mM, proline at a concentration of about 60 mM to about 100 mM, calcium chloride at a concentration of about 30 mM to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, creatine at a concentration of about 15 mM to about 35 mM, proline at a concentration of about 60 mM to about 90 mM, calcium chloride at a concentration of about 30 mM to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, glutamine at a concentration of about 40 mM to about 60 mM, proline at a concentration of about 40 mM to about 60 mM, calcium chloride at a concentration of about 30 mM to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, leucine at a concentration of about 40 mM to about 60 mM, proline at a concentration of about 40 mM to about 60 mM, calcium chloride at a concentration of about 30 mM to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, phenylalanine at a concentration of about 40 mM to about 60 mM, proline at a concentration of about 40 mM to about 60 mM, calcium chloride at a concentration of about 30 mM to about 60 mM, and has a pH of about 5.0 to about 5.5.

In an embodiment, the stable aqueous adalimumab formulation includes adalimumab at a concentration of about 80 to about 120 mg/mL, glutamate at a concentration of about 10 mM to about 25 mM, tryptophan at a concentration of about 10 mM to about 40 mM, proline at a concentration of about 60 mM to about 90 mM, calcium chloride at a concentration of about 30 mM to about 60 mM, and has a pH of about 5.0 to about 5.5.

In an embodiment, the stable aqueous adalimumab formulation includes adalimumab at a concentration of about 80 to about 120 mg/mL, glutamate at a concentration of about 10 mM to about 25 mM, benzalkonium chloride at a concentration of about 0.005% (w/v) to about 0.05% (w/v), proline at a concentration of about 250 mM to about 350 mM, and has a pH of about 5.0 to about 5.5.

In an embodiment, the stable aqueous adalimumab formulation includes adalimumab at a concentration of about 80 to about 120 mg/mL, glutamate at a concentration of about 10 mM to about 25 mM, guanidine HCl at a concentration of about 0.005% (w/v) to about 0.05% (w/v), proline at a concentration of about 250 mM to about 350 mM, and has a pH of about 5.0 to about 5.5.

In an embodiment, the stable aqueous adalimumab formulation includes adalimumab at a concentration of about 80 to about 120 mg/mL, glutamate at a concentration of about 10 mM to about 25 mM, lecithin at a concentration of about 0.005% (w/v) to about 0.05% (w/v), proline at a concentration of about 250 mM to about 350 mM, and has a pH of about 5.0 to about 5.5.

In an embodiment, the stable aqueous adalimumab formulation includes adalimumab at a concentration of about 80 to about 120 mg/mL, glutamate at a concentration of about 10 mM to about 25 mM, oleic acid at a concentration of about 0.005% (w/v) to about 0.05% (w/v), proline at a concentration of about 250 mM to about 350 mM, and has a pH of about 5.0 to about 5.5.

In an embodiment, the stable aqueous adalimumab formulation includes adalimumab at a concentration of about 80 to about 120 mg/mL, glutamate at a concentration of about 10 mM to about 25 mM, Polysorbate 80 at a concentration of about 0.005% (w/v) to about 0.05% (w/v), proline at a concentration of about 250 mM to about 350 mM, and has a pH of about 5.0 to about 5.5.

In an embodiment, the stable aqueous adalimumab formulation includes adalimumab at a concentration of about 80 to about 120 mg/mL, glutamate at a concentration of about 10 mM to about 25 mM, polyvinyl alcohol 205K at a concentration of about 0.05% (w/v) to about 0.5% (w/v), proline at a concentration of about 250 mM to about 350 mM, and has a pH of about 5.0 to about 5.5.

In an embodiment, the stable aqueous adalimumab formulation includes adalimumab at a concentration of about 80 to about 120 mg/mL, glutamate at a concentration of about 10 mM to about 25 mM, polyvinyl alcohol 31K at a concentration of about 0.05% (w/v) to about 0.5% (w/v), proline at a concentration of about 250 mM to about 350 mM, and has a pH of about 5.0 to about 5.5.

In an embodiment, the stable aqueous adalimumab formulation includes adalimumab at a concentration of about 80 to about 120 mg/mL, glutamate at a concentration of about 10 mM to about 25 mM, PVP at a concentration of about 0.005% (w/v) to about 0.05% (w/v), proline at a concentration of about 250 mM to about 350 mM, and has a pH of about 5.0 to about 5.5.

In an embodiment, the stable aqueous adalimumab formulation includes adalimumab at a concentration of about 80 to about 120 mg/mL, glutamate at a concentration of about 10 mM to about 25 mM, protamine sulfate at a concentration of about 0.005% (w/v) to about 0.05% (w/v), proline at a concentration of about 250 mM to about 350 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PEG 400 at a concentration of about 5% (w/v) to about 12% (w/v), glycerol at a concentration of about 0.7% (w/v) to about 1.5% (w/v), and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PEG 400 at a concentration of about 2% (w/v) to about 6% (w/v), glycerol at a concentration of about 0.7% (w/v) to about 1.5% (w/v), and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PEG 400 at a concentration of about 0.5% (w/v) to about 2% (w/v), glycerol at a concentration of about 1.5% (w/v) to about 4% (w/v), and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PEG 400 at a concentration of about 8% (w/v) to about 12% (w/v), and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PVP at a concentration of about 0.7% (w/v) to about 1.5% (w/v), and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, calcium chloride at a concentration of about 30 to about 60 mM, proline at a concentration of about 80 to about 120 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PEG 15 hydroxystearate at a concentration of about 1.5% (w/v) to about 4% (w/v), and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PEG 15 hydroxystearate at a concentration of about 1.5% (w/v) to about 4% (w/v), arginine at a concentration of about 60 to about 90 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PEG 15 hydroxystearate at a concentration of about 3% (w/v) to about 8% (w/v), calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PEG 15 hydroxystearate at a concentration of about 3% (w/v) to about 8% (w/v), calcium chloride at a concentration of about 30 to about 60 mM, proline at a concentration of about 80 to about 120 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, dextran at a concentration of about 1.5% (w/v) to about 4% (w/v), and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, imidazole at a concentration of about 1.5% (w/v) to about 4% (w/v), and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, imidazole at a concentration of about 0.7% (w/v) to about 1.5% (w/v), calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, N-acetyl arginine at a concentration of about 100 to about 150 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, N-acetyl arginine at a concentration of about 100 to about 150 mM, calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, inositol at a concentration of about 200 to about 300 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, inositol at a concentration of about 200 to about 300 mM, calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PEG 3350 at a concentration of about 0.7% (w/v) to about 1.5% (w/v), calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, taurine at a concentration of about 100 to about 150 mM, calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, citruline at a concentration of about 100 to about 150 mM, calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, betaine at a concentration of about 100 to about 150 mM, calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, sarcosine at a concentration of about 100 to about 150 mM, calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PEG 400 at a concentration of about 1% (w/v) to about 1.5% (w/v), glycolic acid at a concentration of about 40 to about 80 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, glycolic acid at a concentration of about 40 to about 80 mM, calcium chloride at a concentration of about 60 to about 90 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PCA at a concentration of about 0.7% (w/v) to about 1.5% (w/v), and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PCA at a concentration of about 0.7% (w/v) to about 1.5% (w/v), calcium chloride at a concentration of about 60 to about 90 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, gelatin at a concentration of about 0.7% (w/v) to about 1.5% (w/v), calcium chloride at a concentration of about 60 to about 90 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, hyaluronic acid at a concentration of about 0.1% (w/v) to about 0.5% (w/v), and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, hyaluronic acid at a concentration of about 0.1% (w/v) to about 0.5% (w/v), calcium chloride at a concentration of about 60 to about 90 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, N-acetyl proline at a concentration of about 100 to about 150 mM, calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, N-acetyl ornithine at a concentration of about 100 to about 150 mM, calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, ornithine at a concentration of about 100 to about 150 mM, calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, beta-alanine at a concentration of about 100 to about 150 mM, calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, niacinamide at a concentration of about 100 to about 150 mM, calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, medronic acid at a concentration of about 100 to about 150 mM, calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PEG 200 at a concentration of about 0.7% (w/v) to about 1.5% (w/v), and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PEG 200 at a concentration of about 0.7% (w/v) to about 1.5% (w/v), calcium chloride at a concentration of about 30 to about 60 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PEG 600 at a concentration of about 1.5% (w/v) to about 4% (w/v), and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, PEG 600 at a concentration of about 1.5% (w/v) to about 4% (w/v), and calcium chloride at a concentration of about 30 to about 60 mM, and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, MSA at a concentration of about 80 to about 120 mM, TEA at a concentration of about 30 to about 70 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, MSA at a concentration of about 110 to about 140 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, niacinamide at a concentration of about 250 to about 300 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, niacinamide at a concentration of about 80 to about 120 mM, and optionally Pluronic F68 at a concentration of about 0.05% (w/v) to about 0.4%

(w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, niacinamide at a concentration of about 80 to about 120 mM, calcium chloride at a concentration of about 60 to about 100 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, niacinamide at a concentration of about 80 to about 120 mM, MSA at a concentration of about 60 to about 100 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, niacinamide at a concentration of about 80 to about 120 mM, PEG 200 at a concentration of about 0.7% (w/v) to about 1.5% (w/v), and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, ethanol at a concentration of about 0.25% (w/v) to about 0.75% (w/v), and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, ethanol at a concentration of about 0.25% (w/v) to about 0.75% (w/v), PEG 200 at a concentration of about 1.5% (w/v) to about 4% (w/v), and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, ethanol at a concentration of about 0.1% (w/v) to about 0.4% (w/v), PEG 200 at a concentration of about 1.5% (w/v) to about 4% (w/v), and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, ethanol at a concentration of about 0.1% (w/v) to about 0.4% (w/v), PEG 200 at a concentration of about 1.5% (w/v) to about 4% (w/v), MSA at a concentration of about 80 to about 120 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, ethanol at a concentration of about 0.25% (w/v) to about 0.75% (w/v), MSA at a concentration of about 80 to about 120 mM, 10K PVP at a concentration of about 0.25% (w/v) to about 0.75% (w/v), and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, ethanol at a concentration of about 0.25% (w/v) to about 0.75% (w/v), MEA at a concentration of about 80 to about 120 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, benzene sulfonic acid at a concentration of about 100 to about 200 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5. Optionally, the pH of the formulation is adjusted within this range with sodium hydroxide or calcium hydroxide.

In an embodiment, the stable aqueous adalimumab formulation includes adalimumab at a concentration of about 90 to about 120 mg/mL, glutamate at a concentration of about 10 mM to about 25 mM, benzene sulfonic acid at a concentration of about 60 to about 90 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, benzene sulfonic acid at a concentration of about 60 to about 90 mM, calcium chloride at a concentration of about 25 to about 75 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, benzene sulfonic acid at a concentration of about 60 to about 90 mM, MEA at a concentration of about 60 to about 90 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 90 to about 120 mg/mL, glutamate at a concentration of about 10 mM to about 25 mM, adipic acid at a concentration of about 100 to about 200 mM, and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

In an embodiment, the stable aqueous adalimumab formulation includes adalimumab at a concentration of about 170 to about 190 mg/mL, glutamate at a concentration of about 10 mM to about 25 mM, PEG 400 at a concentration of about 0.25% (w/v) to about 0.75% (w/v), calcium chloride at a concentration of about 40 to about 80 mM, glycerin at a concentration of about 0.5% (w/v) to about 1% (w/v), and optionally Pluronic F68 at a concentration of about 0.05% (w/v) to about 0.4% (w/v) or Polysorbate 80 at a concentration of about 0.005% (w/v) to about 0.1% (w/v), and has a pH of about 5.0 to about 5.5.

Exemplary aqueous adalimumab formulations are provided in Table A. Each formulation in Table A may optionally include Pluronic F68 at a concentration of about 0.001% (w/v) to about 10% (w/v) (e.g., about 0.005% (w/v) to about 1% (w/v), about 0.05% (w/v) to about 0.4% (w/v), about 0.05% (w/v) to about 0.1% (w/v), about 0.01% (w/v), about 0.05% (w/v), and/or about 0.1% (w/v)), Polysorbate 20 at a concentration of about 0.001% (w/v) to about 2% (w/v) (e.g., about 0.005% (w/v) to about 0.1% (w/v)), or Polysorbate 80 at a concentration of about 0.001% (w/v) to about 2% (w/v) (e.g., about 0.005% (w/v) to about 0.1% (w/v), about 0.03% (w/v) to about 0.1% (w/v), about 0.04% (w/v) to about 0.1% (w/v), about 0.03% (w/v), about 0.04% (w/v), and/or about 0.1% (w/v)). Each formulation in Table A has a pH of about 5.0 to about 5.5, e.g., about 5.1 to about 5.3 and/or about 5.2. Optionally, the pH of each formulation in Table A is adjusted using a strong acid and/or strong base including, but not limited to, hydrochloric acid, sodium hydroxide, calcium hydroxide, MSA, and/or MEA.

TABLE A

| Protein conc. | Buffer | Excipient(s)[1] |
|---|---|---|
| 100 mg/mL | 15 mM glutamate | 8% PEG 400 |
| | | 1% glycerol |
| 100 mg/mL | 15 mM glutamate | 4% PEG 200 |
| | | 1% glycerol |
| 100 mg/mL | 15 mM glutamate | 1% PEG 400 |
| | | 2.5% glycerol |
| 100 mg/mL | 15 mM glutamate | 10% PEG 400 |
| 100 mg/mL | 15 mM glutamate | 1% PVP |
| 110 mg/mL | 20 mM glutamate | 45 mM $CaCl_2$ |
| 110 mg/mL | 20 mM glutamate | 45 mM $CaCl_2$ |
| | | 100 mM proline |
| 110 mg/mL | 20 mM glutamate | 2.5% PEG 15 hydroxystearate |
| 110 mg/mL | 20 mM glutamate | 2.5% PEG 15 hydroxystearate |
| | | 75 mM arginine |
| 110 mg/mL | 20 mM glutamate | 5% PEG 15 hydroxystearate |
| | | 45 mM $CaCl_2$ |
| 110 mg/mL | 20 mM glutamate | 5% PEG 15 hydroxystearate |
| | | 45 mM $CaCl_2$ |
| | | 100 mM proline |
| 110 mg/mL | 20 mM glutamate | 2% dextran |
| 110 mg/mL | 20 mM glutamate | 2% imidazole |
| 110 mg/mL | 20 mM glutamate | 1% imidazole |
| | | 45 mM $CaCl_2$ |
| 110 mg/mL | 20 mM glutamate | 120 mM N-acetyl arginine |
| 110 mg/mL | 20 mM glutamate | 120 mM N-acetyl arginine |
| | | 45 mM $CaCl_2$ |
| 105 mg/mL | 20 mM glutamic acid | 250 mM inositol |
| 105 mg/mL | 20 mM glutamic acid | 180 mM inositol |
| | | 40 mM $CaCl_2$ |
| 105 mg/mL | 20 mM glutamic acid | 1% PEG 3350 |
| | | 40 mM $CaCl_2$ |
| 105 mg/mL | 20 mM glutamic acid | 120 mM taurine |
| | | 40 mM $CaCl_2$ |
| 105 mg/mL | 20 mM glutamic acid | 120 mM citruline |
| | | 40 mM $CaCl_2$ |
| 105 mg/mL | 20 mM glutamic acid | 120 mM betaine |
| | | 40 mM $CaCl_2$ |
| 105 mg/mL | 20 mM glutamic acid | 120 mM sarcosine |
| | | 40 mM $CaCl_2$ |
| 105 mg/mL | 20 mM glutamic acid | 1.2% PEG 400 |
| | | 60 mM glycolic acid |
| 105 mg/mL | 20 mM glutamic acid | 60 mM glycolic acid |
| | | 75 mM $CaCl_2$ |
| 105 mg/mL | 20 mM glutamic acid | 1% PCA |
| 105 mg/mL | 20 mM glutamic acid | 1% PCA |
| | | 75 mM $CaCl_2$ |
| 110 mg/mL | 20 mM glutamic acid | 1% Type B gelatin |
| | | 75 mM $CaCl_2$ |
| 110 mg/mL | 20 mM glutamic acid | 0.25% hyaluronic acid |
| 110 mg/mL | 20 mM glutamic acid | 0.25% hyaluronic acid |
| | | 75 mM $CaCl_2$ |
| 110 mg/mL | 20 mM glutamic acid | 120 mM N-acetyl proline |
| | | 40 mM $CaCl_2$ |

TABLE A-continued

| Protein conc. | Buffer | Excipient(s)[1] |
|---|---|---|
| 110 mg/mL | 20 mM glutamic acid | 120 mM N-acetyl ornithine<br>40 mM CaCl$_2$ |
| 110 mg/mL | 20 mM glutamic acid | 120 mM ornithine<br>40 mM CaCl$_2$ |
| 110 mg/mL | 20 mM glutamic acid | 120 mM beta-alanine<br>40 mM CaCl$_2$ |
| 110 mg/mL | 20 mM glutamic acid | 120 mM niacinamide<br>40 mM CaCl$_2$ |
| 110 mg/mL | 20 mM glutamic acid | 120 mM medronic acid<br>40 mM CaCl$_2$ |
| 110 mg/mL | 20 mM glutamic acid | 1% PEG 200 |
| 110 mg/mL | 20 mM glutamic acid | 1% PEG 200<br>40 mM CaCl$_2$ |
| 110 mg/mL | 20 mM glutamic acid | 2% PEG 600 |
| 110 mg/mL | 20 mM glutamic acid | 2% PEG 600<br>40 mM CaCl2 |
| 110 mg/mL | 20 mM glutamic acid | 100 mM MSA<br>50 mM TEA |
| 110 mg/mL | 20 mM glutamic acid | 125 mM MSA |
| 110 mg/mL | 20 mM glutamic acid | 270 mM niacinamide |
| 110 mg/mL | 20 mM glutamic acid | 100 mM niacinamide |
| 110 mg/mL | 20 mM glutamic acid | 100 mM niacinamide<br>80 mM CaCl$_2$ |
| 110 mg/mL | 20 mM glutamic acid | 100 mM niacinamide<br>80 mM MSA |
| 110 mg/mL | 20 mM glutamic acid | 100 mM niacinamide<br>1% PEG 200 |
| 110 mg/mL | 20 mM glutamic acid | 0.5% ethanol |
| 110 mg/mL | 20 mM glutamic acid | 0.5% ethanol<br>2% PEG 200 |
| 110 mg/mL | 20 mM glutamic acid | 0.25% ethanol<br>2% PEG 200 |
| 110 mg/mL | 20 mM glutamic acid | 0.25% ethanol<br>2% PEG 200<br>100 mM MSA |
| 110 mg/mL | 20 mM glutamic acid | 0.5% ethanol<br>100 mM MSA<br>0.5% 10K PVP |
| 110 mg/mL | 20 mM glutamic acid | 0.5% ethanol<br>100 mM MEA |
| 110 mg/mL | 20 mM glutamic acid | 150 mM benzene sulfonic acid (adjust pH with NaOH) |
| 110 mg/mL | 20 mM glutamic acid | 150 mM benzene sulfonic acid (adjust pH with Ca(OH)$_2$) |
| 110 mg/mL | 20 mM glutamic acid | 75 mM benzene sulfonic acid |
| 110 mg/mL | 20 mM glutamic acid | 75 mM benzene sulfonic acid<br>50 mM CaCl$_2$ |
| 110 mg/mL | 20 mM glutamic acid | 75 mM benzene sulfonic acid<br>75 mM MEA |
| 110 mg/mL | 20 mM glutamic acid | 150 mM adipic acid |
| 180 mg/mL | 20 mM glutamic acid | 0.5% PEG 400<br>60 mM CaCl$_2$<br>0.7% glycerin |

[1]All percentages are (w/v).

In an embodiment, a lyophilized form of any one of the foregoing glutamate-containing adalimumab formulations is provided.

Formulations of Adalimumab with Adipate Buffer

In an embodiment, the stable aqueous adalimumab formulation includes adalimumab at a concentration of about 40 to about 200 mg/mL, such as about 170 to about 190 mg/mL, about 90 to about 120 mg/mL, about 160 to about 190 mg/mL, about 40 to about 60 mg/mL, about 50 mg/mL, about 100 mg/mL, or about 170 mg/mL, adipate at a concentration of about 5 mM to about 50 mM (e.g., about 10 mM to about 25 mM, about 15 mM to about 20 mM, about 10 mM, about 15 mM, about 20 mM, and/or about 25 mM), and one or more excipients. Suitable excipients include certain stabilizers such as certain amino acids and amino acid derivatives, certain polyethylene glycols and polyethylene glycol derivatives, certain polyols, certain acids, certain amines, certain salts, and certain surfactants. Examples of suitable amino acids and amino acid derivatives include proline (e.g., at a concentration of about 0.1 to about 450 mM or about 50 to about 300 mM) and N-acetyl arginine (e.g., at a concentration of about 0.1 to about 450 mM or about 100 to about 150 mM). Examples of suitable polyethylene glycols and polyethylene glycol derivatives include PEG 400 (e.g., at a concentration of about 0.1% (w/v) to about 20% (w/v) or about 0.3% (w/v) to about 1.5% (w/v)) and PEG 3350 (e.g., at a concentration of about 0.1% (w/v) to about 30% (w/v) or about 0.5% (w/v) to about 2% (w/v)). Examples of suitable polyols include glycerol (e.g., at a concentration of about 0.1% (w/v) to about 15% (w/v) or about 1% (w/v) to about 2% (w/v)), sucrose (e.g., at a concentration of about 0.1% (w/v) to about 15% (w/v), about 4% (w/v) to about 10% (w/v), about 4% (w/v) to about 9% (w/v), about 6.5% (w/v), about 6.8% (w/v), about 6.9% (w/v), or about 9% (w/v)), and sorbitol (e.g., at a concentration of about 0.1% (w/v) to about 10% (w/v), about 3%

(w/v) to about 5% (w/v), and/or about 4% (w/v)). Examples of suitable acids include MSA (e.g., at a concentration of about 0.1 to about 150 mM, about 0.1 to about 50 mM, and/or about 10 to about 40 mM). Examples of suitable amines include monoethanolamine hydrochloride (MEA-HCl) (e.g., at a concentration of about 0.1 to about 150 mM, about 0.1 to about 40 mM, or about 50 to about 100 mM) and methanolamine (MEA) (e.g., at a concentration of about 0.1 to about 150 mM, about 0.1 to about 50 mM, or about 50 to about 100 mM). Examples of suitable salts include calcium chloride (e.g., at a concentration of about 1 to about 150 mM, about 20 to about 75 mM, about 5 to about 50 mM, about 10 to about 30 mM, about 20 to about 40 mM, about 30 to about 50 mM, about 40 to about 80 mM, about 50 to about 100 mM, or about 25 mM) and sodium chloride (e.g., at a concentration of about 10 to about 100 mM, about 60 to about 90 mM, about 15 to about 50 mM, and/or about 35 mM). Examples of suitable surfactants Pluronic F68 (e.g., at a concentration of about 0.001% (w/v) to about 10% (w/v), about 0.005% (w/v) to about 1% (w/v), about 0.05% (w/v) to about 0.4% (w/v), about 0.05% (w/v) to about 0.1% (w/v), about 0.01% (w/v), about 0.05% (w/v), and/or about 0.1% (w/v)), Polysorbate 20 (e.g., at a concentration of about 0.001% (w/v) to about 2% (w/v) or about 0.005% (w/v) to about 0.1% (w/v)), and Polysorbate 80 (e.g., at a concentration of about 0.001% (w/v) to about 2% (w/v), about 0.005% (w/v) to about 0.1% (w/v), about 0.005% (w/v) to about 0.05% (w/v), about 0.03% (w/v) to about 0.1% (w/v), about 0.04% (w/v) to about 0.1% (w/v), about 0.03% (w/v), about 0.04% (w/v), and/or about 0.1% (w/v)). Examples of other suitable excipients include imidazole (e.g., at a concentration of about 0.1% (w/v) to about 15% (w/v) or about 1% (w/v) to about 1.5% (w/v)) and PVP, for example, 10K PVP, (e.g., at a concentration of about 0.1% (w/v) to about 10% (w/v) or about 0.5% (w/v) to about 2% (w/v)). Optionally, the adipate-containing stable aqueous adalimumab formulation has a pH of about 4.8 to about 5.7, for example, about 4.9 to about 5.6, about 5.0 to about 5.5, about 5.1 to about 5.4, about 5.1 to about 5.3, about 5.1 to about 5.2, about 5.2 to about 5.3, and/or about 5.2. Optionally, the pH of the stable aqueous adalimumab formulation is adjusted using a strong acid and/or a strong base including, but not limited to, hydrochloric acid, sodium hydroxide, calcium hydroxide, MSA, and/or MEA.

In an embodiment, the stable aqueous adalimumab formulation includes adalimumab at a concentration of about 40 to about 200 mg/mL, such as about 170 to about 190 mg/mL, about 90 to about 120 mg/mL, about 160 to about 190 mg/mL, about 40 to about 60 mg/mL, about 50 mg/mL, about 100 mg/mL, or about 170 mg/mL, adipate at a concentration of about 5 mM to about 50 mM (e.g., about 10 mM to about 25 mM, about 15 mM to about 20 mM, about 10 mM, about 15 mM, about 20 mM, and/or about 25 mM), and one or more excipients selected from the group consisting of N-acetyl arginine at a concentration of about 0.1 to about 450 mM (e.g., about 100 to about 150 mM), PEG 400 at a concentration of about 0.1% (w/v) to about 20% (w/v) (e.g., about 0.3% (w/v) to about 1.5% (w/v)), MSA at a concentration of about 0.1 to about 150 mM (e.g., about 0.1 to about 50 mM and/or about 10 to about 40 mM), calcium chloride at a concentration of about 1 to about 150 mM (e.g., about 20 to about 75 mM, about 5 to about 50 mM, about 10 to about 30 mM, about 20 to about 40 mM, about 30 to about 50 mM, about 40 to about 80 mM, about 50 to about 100 mM, or about 25 mM), monoethanolamide hydrochloride (MEA-HCl) at a concentration of about 0.1 to about 150 mM (e.g., about 0.1 to about 40 mM or about 50 to about 100 mM), monoethanolamide (MEA) at a concentration of about 0.1 to about 150 mM (e.g., about 0.1 to about 50 mM or about 50 to about 100 mM), glycerol at a concentration of about 0.1% (w/v) to about 15% (w/v) (e.g., about 1% (w/v) to about 2% (w/v)), imidazole at a concentration of about 0.1% (w/v) to about 15% (w/v) (e.g., about 1% (w/v) to about 1.5% (w/v)), PVP, for example, 10K PVP, at a concentration of about 0.1% (w/v) to about 10% (w/v) (e.g., about 0.5% (w/v) to about 2% (w/v)), PEG 3350 at a concentration of about 0.1% (w/v) to about 30% (w/v) (e.g., about 0.5% (w/v) to about 2% (w/v)), sodium chloride at a concentration of about 10 to about 100 mM (e.g., about 60 to about 90 mM, about 15 to about 50 mM, and/or about 35 mM), proline at a concentration of about 0.1 to about 450 mM (e.g., about 50 to about 300 mM), sucrose at a concentration of about 0.1% (w/v) to about 15% (w/v) (e.g., about 4% (w/v) to about 10% (w/v), about 4% (w/v) to about 9% (w/v), about 6.5% (w/v), about 6.8% (w/v), about 6.9% (w/v), or about 9% (w/v)), sorbitol at a concentration of about 0.1% (w/v) to about 10% (w/v) (e.g., about 3% (w/v) to about 5% (w/v) and/or about 4% (w/v)), Pluronic F68 at a concentration of about 0.001% (w/v) to about 10% (w/v) (e.g., about 0.005% (w/v) to about 1% (w/v), about 0.05% (w/v) to about 0.4% (w/v), about 0.05% (w/v) to about 0.1% (w/v), about 0.01% (w/v), about 0.05% (w/v), and/or about 0.1% (w/v)), Polysorbate 20 at a concentration of about 0.001% (w/v) to about 2% (w/v) (e.g., about 0.005% (w/v) to about 0.1% (w/v)), and Polysorbate 80 at a concentration of about 0.001% (w/v) to about 2% (w/v) (e.g., about 0.005% (w/v) to about 0.1% (w/v), about 0.005% (w/v) to about 0.05% (w/v), about 0.03% (w/v) to about 0.1% (w/v), about 0.04% (w/v) to about 0.1% (w/v), about 0.03% (w/v), about 0.04% (w/v), and/or about 0.1% (w/v)). Optionally, the adipate-containing stable aqueous adalimumab formulation has a pH of about 4.8 to about 5.7, for example, about 4.9 to about 5.6, about 5.0 to about 5.5, about 5.1 to about 5.4, about 5.1 to about 5.3, about 5.1 to about 5.2, about 5.2 to about 5.3, and/or about 5.2. Optionally, the pH of the stable aqueous adalimumab formulation is adjusted using a strong acid and/or a strong base including, but not limited to, hydrochloric acid, sodium hydroxide, calcium hydroxide, MSA, and/or MEA.

In an embodiment, the stable aqueous adalimumab formulation includes adalimumab at a concentration of about 170 to about 190 mg/mL, adipate at a concentration of about 10 mM to about 25 mM, N-acetyl arginine at a concentration of about 100 to about 150 mM, PEG 400 at a concentration of about 0.5% (w/v) to about 1% (w/v), and MSA at a concentration of about 10 to about 30 mM, and has a pH of about 5.0 to about 5.5.

In an embodiment, the stable aqueous adalimumab formulation includes adalimumab at a concentration of about 170 to about 190 mg/mL, adipate at a concentration of about 10 mM to about 25 mM, N-acetyl arginine at a concentration of about 100 to about 150 mM, calcium chloride at a concentration of about 30 to about 50 mM, and MSA at a concentration of about 10 to about 30 mM, and has a pH of about 5.0 to about 5.5.

In an embodiment, the stable aqueous adalimumab formulation includes adalimumab at a concentration of about 170 to about 190 mg/mL, adipate at a concentration of about 10 mM to about 25 mM, N-acetyl arginine at a concentration of about 100 to about 150 mM, MEA-HCl at a concentration of about 30 to about 70 mM, and MSA at a concentration of about 5 to about 15 mM, and has a pH of about 5.0 to about 5.5.

In an embodiment, the stable aqueous adalimumab formulation includes adalimumab at a concentration of about 170 to about 190 mg/mL, adipate at a concentration of about 10 mM to about 25 mM, glycerol at a concentration of about 1% (w/v) to about 2% (w/v), and MSA at a concentration of about 30 to about 50 mM, and has a pH of about 5.0 to about 5.5.

In an embodiment, the stable aqueous adalimumab formulation includes adalimumab at a concentration of about 170 to about 190 mg/mL, adipate at a concentration of about 10 mM to about 25 mM, PEG 400 at a concentration of about 0.5% (w/v) to about 2% (w/v), and MSA at a concentration of about 30 to about 50 mM, and has a pH of about 5.0 to about 5.5.

In an embodiment, the stable aqueous adalimumab formulation includes adalimumab at a concentration of about 170 to about 190 mg/mL, adipate at a concentration of about 10 mM to about 25 mM, and imidazole at a concentration of about 1% (w/v) to about 1.5% (w/v), and has a pH of about 5.0 to about 5.5.

In an embodiment, the stable aqueous adalimumab formulation includes adalimumab at a concentration of about 170 to about 190 mg/mL, adipate at a concentration of about 10 mM to about 25 mM, calcium chloride at a concentration of about 60 to about 90 mM, PEG 400 at a concentration of about 0.1% (w/v) to about 0.5% (w/v), and 10K PVP at a concentration of about 0.5% (w/v) to about 2% (w/v), and has a pH of about 5.0 to about 5.5.

In an embodiment, the stable aqueous adalimumab formulation includes adalimumab at a concentration of about 170 to about 190 mg/mL, adipate at a concentration of about 10 mM to about 25 mM, MEA-HCl at a concentration of about 80 to about 120 mM, PEG 400 at a concentration of about 0.1% (w/v) to about 0.5% (w/v), and 10K PVP at a concentration of about 0.5% (w/v) to about 2% (w/v), and has a pH of about 5.0 to about 5.5.

In an embodiment, the stable aqueous adalimumab formulation includes adalimumab at a concentration of about 170 to about 190 mg/mL, adipate at a concentration of about 10 mM to about 25 mM, PEG 400 at a concentration of about 0.5% (w/v) to about 2% (w/v), and calcium chloride at a concentration of about 30 to about 50 mM, and has a pH of about 5.0 to about 5.5.

In an embodiment, the stable aqueous adalimumab formulation includes adalimumab at a concentration of about 170 to about 190 mg/mL, adipate at a concentration of about 10 mM to about 25 mM, PEG 3350 at a concentration of about 0.5% (w/v) to about 2% (w/v), and calcium chloride at a concentration of about 60 to about 90 mM, and has a pH of about 5.0 to about 5.5.

In an embodiment, the stable aqueous adalimumab formulation includes adalimumab at a concentration of about 170 to about 190 mg/mL, adipate at a concentration of about 10 mM to about 25 mM, PEG 3350 at a concentration of about 0.5% (w/v) to about 2% (w/v), PEG 400 at a concentration of about 1% (w/v) to about 3% (w/v), and calcium chloride at a concentration of about 10 to about 30 mM, and has a pH of about 5.0 to about 5.5.

In an embodiment, the stable aqueous adalimumab formulation includes adalimumab at a concentration of about 170 to about 190 mg/mL, adipate at a concentration of about 10 mM to about 25 mM, PEG 3350 at a concentration of about 0.5% (w/v) to about 2% (w/v), PEG 400 at a concentration of about 0.5% (w/v) to about 2% (w/v), and calcium chloride at a concentration of about 30 to about 50 mM, and has a pH of about 5.0 to about 5.5.

Exemplary aqueous adalimumab formulations are provided in Table B. Each formulation in Table B may optionally include Pluronic F68 at a concentration of about 0.001% (w/v) to about 10% (w/v) (e.g., about 0.005% (w/v) to about 1% (w/v), about 0.05% (w/v) to about 0.4% (w/v), about 0.05% (w/v) to about 0.1% (w/v), about 0.01% (w/v), about 0.05% (w/v), and/or about 0.1% (w/v)), Polysorbate 20 at a concentration of about 0.001% (w/v) to about 2% (w/v) (e.g., about 0.005% (w/v) to about 0.1% (w/v)), or Polysorbate 80 at a concentration of about 0.001% (w/v) to about 2% (w/v) (e.g., about 0.005% (w/v) to about 0.1% (w/v), about 0.03% (w/v) to about 0.1% (w/v), about 0.04% (w/v) to about 0.1% (w/v), about 0.03% (w/v), about 0.04% (w/v), and/or about 0.1% (w/v)). Each formulation in Table B has a pH of about 5.0 to about 5.5, e.g., about 5.1 to about 5.3 and/or about 5.2. Optionally, the pH of each formulation in Table B is adjusted using a strong acid and/or strong base including, but not limited to, hydrochloric acid, sodium hydroxide, calcium hydroxide, MSA, and/or MEA.

TABLE B

| Protein conc. | Buffer | Excipient(s) |
| --- | --- | --- |
| 180 mg/mL | 15 mM adipate | 120 mM N-acetyl arginine<br>0.7% PEG 400<br>20 mM MSA |
| 180 mg/mL | 15 mM adipate | 120 mM N-acetyl arginine<br>40 mM CaCl$_2$<br>20 mM MSA |
| 180 mg/mL | 15 mM adipate | 120 mM N-acetyl arginine<br>50 mM MEA-HCl<br>10 mM MSA |
| 180 mg/mL | 15 mM adipate | 1.4% glycerol<br>40 mM MSA |
| 180 mg/mL | 15 mM adipate | 1% PEG 400<br>40 mM MSA |
| 180 mg/mL | 15 mM adipate | 1.2% imidazole |
| 180 mg/mL | 20 mM adipate | 75 mM CaCl$_2$<br>0.3% PEG 400<br>1% PVP 10K |
| 180 mg/mL | 20 mM adipate | 100 mM MEA-HCl<br>0.3% PEG 400<br>1% PVP 10K |
| 180 mg/mL | 20 mM adipate | 1% PEG 400<br>40 mM CaCl$_2$ |
| 180 mg/mL | 20 mM adipate | 1% PEG 3350<br>75 mM CaCl$_2$ |
| 180 mg/mL | 20 mM adipate | 1% PEG 3350<br>1.5% PEG 400<br>20 mM CaCl2 |
| 180 mg/mL | 20 mM adipate | 1% PEG 3350<br>1% PEG 400<br>40 mM CaCl$_2$ |

In an embodiment, a lyophilized form of any one of the foregoing adipate-containing adalimumab formulations is provided.

Formulations of Adalimumab with Glucuronate Buffer

In an embodiment, the stable aqueous adalimumab formulation includes adalimumab at a concentration of about 40 to about 200 mg/mL, such as about 170 to about 190 mg/mL, about 90 to about 120 mg/mL, about 160 to about 190 mg/mL, about 40 to about 60 mg/mL, about 50 mg/mL, about 100 mg/mL, or about 170 mg/mL, glucuronate at a concentration of about 5 mM to about 50 mM (e.g., about 10 mM to about 30 mM, about 10 mM, about 15 mM, about 20 mM, and/or about 25 mM), and one or more excipients. Suitable excipients include certain stabilizers such as certain amino acids and amino acid derivatives, certain polyols, certain acids, certain amines, certain salts, and certain surfactants. Examples of suitable amino acids and amino acid derivatives include proline (e.g., at a concentration of about 0.1 to about 450 mM, about 250 to about 350 mM, or about 50 to about 300 mM). Examples of suitable polyols include sucrose (e.g., at a concentration of about 0.1% (w/v) to about 15% (w/v), about 4% (w/v) to about 10% (w/v), about 4% (w/v) to about 9% (w/v), about 6.5% (w/v), about 6.8% (w/v), about 6.9% (w/v), or about 9% (w/v)) and sorbitol (e.g., at a concentration of about 0.1% (w/v) to about 10% (w/v), about 3% (w/v) to about 5% (w/v), and/or about 4% (w/v)). Examples of suitable acids include methane sulfonic acid (MSA) (e.g., at a concentration of about 0.1 to about 150 mM or about 0.1 to about 50 mM). Examples of suitable amines include monoethanolamide hydrochloride (MEA-HCl) (e.g., at a concentration of about 0.1 to about 150 mM or about 0.1 to about 40 mM) and monoethanolamide (MEA) (e.g., at a concentration of about 0.1 to about 300 mM or about 0.1 to about 50 mM). Examples of suitable salts include sodium chloride (e.g., at a concentration of about 10 to about 100 mM, about 60 to about 90 mM, about 15 to about 50 mM, and/or about 35 mM) and calcium chloride (e.g., at a concentration of about 1 to about 150 mM, about 5 to about 50 mM, about 10 to about 30 mM, about 20 to about 40 mM, about 30 to about 50 mM, about 40 to about 80 mM, about 50 to about 100 mM, or about 25 mM). Examples of suitable surfactants include Pluronic F68 (e.g., at a concentration of about 0.001% (w/v) to about 10% (w/v), about 0.005% (w/v) to about 1% (w/v), about 0.05% (w/v) to about 0.4% (w/v), about 0.05% (w/v) to about 0.1% (w/v), about 0.01% (w/v), about 0.05% (w/v), and/or about 0.1% (w/v)), Polysorbate 20 (e.g., at a concentration of about 0.001% (w/v) to about 2% (w/v) or about 0.005% (w/v) to about 0.1% (w/v)), and Polysorbate 80 (e.g., at a concentration of about 0.001% (w/v) to about 2% (w/v), about 0.005% (w/v) to about 0.1% (w/v), about 0.005% (w/v) to about 0.05% (w/v), about 0.03% (w/v) to about 0.1% (w/v), about 0.04% (w/v) to about 0.1% (w/v), about 0.03% (w/v), about 0.04% (w/v), and/or about 0.1% (w/v)). Optionally, the glucuronate-containing stable aqueous adalimumab formulation has a pH of about 4.8 to about 5.7, for example, about 4.9 to about 5.6, about 5.0 to about 5.5, about 5.1 to about 5.4, about 5.1 to about 5.3, about 5.1 to about 5.2, about 5.2 to about 5.3, and/or about 5.2. Optionally, the pH of the stable aqueous adalimumab formulation is adjusted using a strong acid and/or a strong base including, but not limited to, hydrochloric acid, sodium hydroxide, calcium hydroxide, MSA, and/or MEA.

In an embodiment, the stable aqueous adalimumab formulation includes adalimumab at a concentration of about 40 to about 200 mg/mL, such as about 170 to about 190 mg/mL, about 90 to about 120 mg/mL, about 160 to about 190 mg/mL, about 40 to about 60 mg/mL, about 50 mg/mL, about 100 mg/mL, or about 170 mg/mL, glucuronate at a concentration of about 5 mM to about 50 mM (e.g., about 10 mM to about 30 mM, about 10 mM, about 15 mM, about 20 mM, and/or about 25 mM), and one or more excipients selected from the group consisting of proline at a concentration of about 0.1 to about 450 mM (e.g., about 250 to about 350 mM or about 50 to about 300 mM), sodium chloride at a concentration of about 10 to about 100 mM (e.g., about 60 to about 90 mM, about 15 to about 50 mM, and/or about 35 mM), calcium chloride at a concentration of about 1 to about 150 mM (e.g., about 5 to about 50 mM, about 10 to about 30 mM, about 20 to about 40 mM, about 30 to about 50 mM, about 40 to about 80 mM, about 50 to about 100 mM, or about 25 mM), sucrose at a concentration of about 0.1% (w/v) to about 15% (w/v) (e.g., about 4% (w/v) to about 10% (w/v), about 4% (w/v) to about 9% (w/v), about 6.5% (w/v), about 6.8% (w/v), about 6.9% (w/v), or about 9% (w/v)), sorbitol at a concentration of about 0.1% (w/v) to about 10% (w/v) (e.g., about 3% (w/v) to about 5% (w/v) and/or about 4% (w/v)), methane sulfonic acid (MSA) at a concentration of about 0.1 to about 150 mM (e.g., about 0.1 to about 50 mM), monoethanolamide hydrochloride (MEA-HCl) at a concentration of about 0.1 to about 150 mM (e.g., about 0.1 to about 40 mM), monoethanolamide (MEA) at a concentration of about 0.1 to about 300 mM (e.g., about 0.1 to about 50 mM), Pluronic F68 at a concentration of about 0.001% (w/v) to about 10% (w/v) (e.g., about 0.005% (w/v) to about 1% (w/v), about 0.05% (w/v) to about 0.4% (w/v), about 0.05% (w/v) to about 0.1% (w/v), about 0.01% (w/v), about 0.05% (w/v), and/or about 0.1% (w/v)), Polysorbate 20 at a concentration of about 0.001% (w/v) to about 2% (w/v) (e.g., about 0.005% (w/v) to about 0.1% (w/v)), and Polysorbate 80 at a concentration of about 0.001% (w/v) to about 2% (w/v) (e.g., about 0.005% (w/v) to about 0.1% (w/v), about 0.005% (w/v) to about 0.05% (w/v), about 0.03% (w/v) to about 0.1% (w/v), about 0.04% (w/v) to about 0.1% (w/v), about 0.03% (w/v), about 0.04% (w/v), and/or about 0.1% (w/v)). Optionally, the glucuronate-containing stable aqueous adalimumab formulation has a pH of about 4.8 to about 5.7, for example, about 4.9 to about 5.6, about 5.0 to about 5.5, about 5.1 to about 5.4, about 5.1 to about 5.3, about 5.1 to about 5.2, about 5.2 to about 5.3, and/or about 5.2. Optionally, the pH of the stable aqueous adalimumab formulation is adjusted using a strong acid and/or a strong base including, but not limited to, hydrochloric acid, sodium hydroxide, calcium hydroxide, MSA, and/or MEA.

In an embodiment, the stable aqueous adalimumab formulation includes adalimumab at a concentration of about 90 to about 120 mg/mL, glucuronate at a concentration of about 10 mM to about 30 mM, and proline at a concentration of about 250 to about 350 mM, and has a pH of about 5.0 to about 5.5.

Exemplary aqueous adalimumab formulations are provided in Table C. Each formulation in Table C may optionally include Pluronic F68 at a concentration of about 0.001% (w/v) to about 10% (w/v) (e.g., about 0.005% (w/v) to about 1% (w/v), about 0.05% (w/v) to about 0.4% (w/v), about 0.05% (w/v) to about 0.1% (w/v), about 0.01% (w/v), about 0.05% (w/v), and/or about 0.1% (w/v)), Polysorbate 20 at a concentration of about 0.001% (w/v) to about 2% (w/v) (e.g., about 0.005% (w/v) to about 0.1% (w/v)), or Polysorbate 80 at a concentration of about 0.001% (w/v) to about 2% (w/v) (e.g., about 0.005% (w/v) to about 0.1% (w/v), about 0.03% (w/v) to about 0.1% (w/v), about 0.04% (w/v) to about 0.1% (w/v), about 0.03% (w/v), about 0.04% (w/v), and/or about 0.1% (w/v)). Each formulation in Table C has a pH of about 5.0 to about 5.5, e.g., about 5.1 to about 5.3 and/or about 5.2. Optionally, the pH of each formulation in Table C is adjusted using a strong acid and/or strong base including, but not limited to, hydrochloric acid, sodium hydroxide, calcium hydroxide, MSA, and/or MEA.

TABLE C

| Protein conc. | Buffer | Excipient(s) |
| --- | --- | --- |
| 105 mg/mL | 20 mM MEA glucuronate | 300 mM proline |
| 105 mg/mL | 20 mM Na glucuronate | 300 mM proline |

In an embodiment, a lyophilized form of any one of the foregoing glucuronate-containing adalimumab formulations is provided.

Formulations of Adalimumab with Acetate Buffer

In an embodiment, the stable aqueous adalimumab formulation includes adalimumab at a concentration of about 40 to about 200 mg/mL, such as about 90 to about 120 mg/mL, about 90 to about 110 mg/mL, about 100 to about 110 mg/mL, about 120 to about 160 mg/mL, about 130 to about 150 mg/mL, about 160 to about 190 mg/mL, about 160 to about 180 mg/mL, about 170 to about 180 mg/mL, about 40 to about 60 mg/mL, about 40 to about 50 mg/mL, about 50 mg/mL, about 100 mg/mL, or about 170 mg/mL, acetic acid and/or acetate at a concentration of about 0.1 mM to about 300 mM (e.g., about 2 mM to about 30 mM, about 5 mM to about 50 mM, about 5 mM to about 15 mM, about 10 mM to about 20 mM, about 10 mM to about 30 mM, about 15 mM to about 25 mM, about 30 mM to about 40 mM, about 35 mM to about 45 mM, about 40 mM to about 50 mM, about 10 mM, about 15 mM, about 20 mM, and/or about 25 mM), and one or more excipients. Suitable excipients include certain stabilizers such as certain amino acids and amino acid derivatives, certain polyols, certain acids, certain amines, certain salts, certain polysaccharides or polysaccharide derivatives, and certain surfactants. Examples of suitable amino acids and amino acid derivatives include arginine-HCl (e.g., at a concentration of about 0.1 to about 450 mM, about 20 to about 200 mM, about 50 to about 150 mM, about 80 to about 120 mM, and/or about 100 mM) and proline (e.g., at a concentration of about 0.1 to about 450 mM, about 20 to about 400 mM, about 50 to about 350 mM, about 50 to about 300 mM, about 80 to about 300 mM, about 100 to about 250 mM, about 150 to about 230 mM, about 100 to about 140 mM, about 130 to about 170 mM, about 160 to about 200 mM, about 190 to about 230 mM, about 220 to about 260 mM, about 250 to about 290 mM and/or about 220 mM). Examples of suitable polyols include sucrose (e.g., at a concentration of about 0.1% (w/v) to about 15% (w/v) about 4% (w/v) to about 12% (w/v), about 4% (w/v) to about 10% (w/v), about 4% (w/v) to about 9% (w/v), about 5% (w/v) to about 10% (w/v), about 6% (w/v) to about 8% (w/v), about 8% (w/v) to about 10% (w/v), about 8.5% (w/v) to about 9.5% (w/v), about 9% (w/v), about 5.8% (w/v) to about 6.6% (w/v), about 6% (w/v) to about 6.4% (w/v), about 6.2% (w/v), about 6.1% (w/v) to about 6.9% (w/v), about 6.3% (w/v) to about 6.7% (w/v), about 6.5% (w/v), about 6.4% (w/v) to about 7.2% (w/v), about 6.6% (w/v) to about 7% (w/v), about 6.8% (w/v) to about 7.3% (w/v), about 6.7% (w/v) to about 7.1% (w/v), about 6.9% (w/v) to about 6.6% (w/v), about 7.4% (w/v), about 6.8% (w/v) to about 7.2% (w/v), about 7% (w/v), about 6.9% (w/v) to about 7.7% (w/v), about 7.1% (w/v) to about 7.5% (w/v), and/or about 7.3% (w/v)) and sorbitol (e.g., at a concentration of about 0.1% (w/v) to about 10% (w/v), about 3% (w/v) to about 5% (w/v), and/or about 4% (w/v)). Examples of suitable acids include MSA (e.g., at a concentration of about 0.1 to about 150 mM, about 0.1 to about 50 mM, about 10 to about 50 mM, about 20 to about 40 mM, about 30 mM, about 30 to about 50 mM, about 40 to about 60 mM, about 50 to about 70 mM, about 60 to about 80 mM, about 70 to about 90 mM, and/or about 80 to about 100 mM). Examples of suitable amines include MEA-HCl (e.g., at a concentration of about 0.1 to about 150 mM, about 0.1 to about 40 mM, about 10 to about 50 mM, about 20 to about 40 mM, about 30 mM, about 30 to about 50 mM, about 40 to about 60 mM, about 50 to about 70 mM, about 60 to about 80 mM, about 70 to about 90 mM, and/or about 80 to about 100 mM) and MEA (e.g., at a concentration of about 0.1 to about 300 mM, about 0.1 to about 50 mM, about 10 to about 50 mM, about 20 to about 40 mM, about 30 mM, about 30 to about 50 mM, about 40 to about 60 mM, about 50 to about 70 mM, about 60 to about 80 mM, about 70 to about 90 mM, and/or about 80 to about 100 mM). Examples of suitable salts include calcium chloride (e.g., at a concentration of about 1 to about 150 mM, about 5 to about 50 mM, about 5 to about 15 mM, about 10 to about 40 mM, about 10 to about 30 mM, about 15 to about 35 mM, about 20 to about 30 mM, about 20 to about 40 mM, about 30 to about 50 mM, about 40 to about 50 mM, about 40 to about 60 mM, about 40 to about 80 mM, about 50 to about 100 mM, about 10 mM, about 25 mM, and/or about 45 mM) and sodium chloride (e.g., at a concentration of about 10 to about 100 mM, about 60 to about 90 mM, about 15 to about 50 mM, and/or about 35 mM). Examples of suitable polysaccharides or polysaccharide derivatives include sodium carboxymethylcellulose (NaCMC) (e.g., at a concentration of about 0.1% (w/v) to about 15% (w/v), about 0.1% (w/v) to about 5% (w/v), about 0.1% (w/v) to about 2% (w/v), about 0.1% (w/v) to about 1% (w/v), and/or about 0.1% (w/v) to about 0.5% (w/v)). Examples of suitable surfactants include guanidine hydrochloride (GnHCl) (e.g., at a concentration of about 0.1 to about 150 mM, 5 to about 50 mM, about 10 to about 40 mM, about 15 to about 30 mM, and/or about 20 mM), Pluronic F68 (e.g., at a concentration of about 0.001% (w/v) to about 10% (w/v), about 0.005% (w/v) to about 1% (w/v), about 0.01% (w/v) to about 0.1% (w/v), about 0.01% (w/v) to about 1% (w/v), about 0.05% (w/v) to about 0.1% (w/v), about 0.05% (w/v) to about 0.4% (w/v), about 0.05% (w/v) to about 0.5% (w/v), about 0.1% (w/v) to about 2% (w/v), about 0.2% (w/v) to about 1% (w/v), about 0.01% (w/v), about 0.05% (w/v), about 0.1% (w/v), and/or about 0.4% (w/v)), Docusate sodium (e.g., at a concentration of about 0.001% (w/v) to about 1% (w/v) or about 0.005% (w/v) to about 0.05% (w/v)), benzalkonium chloride (e.g., at a concentration of about 0.001% (w/v) to about 1% (w/v) or about 0.05% (w/v) to about 0.5% (w/v)), Span 40 (e.g., at a concentration of about 0.001% (w/v) to about 1% (w/v) or about 0.05% (w/v) to about 0.5% (w/v)), Triton X-100 (e.g., at a concentration of about 0.001% (w/v) to about 1% (w/v), about 0.002% (w/v) to about 0.01% (w/v), about 0.005% (w/v) to about 0.05% (w/v), about 0.02% (w/v) to about 0.1% (w/v), and/or about 0.05% (w/v) to about 0.2% (w/v)), Polysorbate 20 (e.g., at a concentration of about 0.001% (w/v) to about 2% (w/v), about 0.002% (w/v) to about 0.01% (w/v), about 0.005% (w/v) to about 0.05% (w/v), about 0.005% (w/v) to about 0.1% (w/v), about 0.02% (w/v) to about 0.1% (w/v), and/or about 0.05% (w/v) to about 0.2% (w/v)), and Polysorbate 80 (e.g., at a concentration of about 0.001% (w/v) to about 2% (w/v), about 0.002% (w/v) to about 0.01% (w/v), about 0.005% (w/v) to about 0.1% (w/v), about 0.005% (w/v) to about 0.05% (w/v), about 0.02% (w/v) to about 0.1% (w/v), about 0.03% (w/v) to about 0.1% (w/v), 0.04% (w/v) to about 0.1% (w/v), about 0.05% (w/v) to about 0.2% (w/v), about 0.03% (w/v), about 0.04% (w/v), and/or about 0.1% (w/v)). Optionally, the acetate-containing stable aqueous adalimumab formulation has a pH of about 4.8 to about 5.7, for example, about 4.9 to about 5.6, about 5.0 to about 5.5, about 5.1 to about 5.4, about 5.1 to about 5.3, about 5.1 to about 5.2, about 5.2 to about 5.3, and/or about 5.2. Optionally, the pH of the stable aqueous adalimumab formulation is adjusted using a strong acid and/or a strong base including, but not limited to, hydrochloric acid, sodium hydroxide, calcium hydroxide, MSA, and/or MEA.

In an embodiment, the stable aqueous adalimumab formulation includes adalimumab at a concentration of about 40 to about 200 mg/mL, such as about 90 to about 120 mg/mL, about 90 to about 110 mg/mL, about 100 to about 110 mg/mL, about 120 to about 160 mg/mL, about 130 to about 150 mg/mL, about 160 to about 190 mg/mL, about 160 to about 180 mg/mL, about 170 to about 180 mg/mL, about 40 to about 60 mg/mL, about 40 to about 50 mg/mL, about 50 mg/mL, about 100 mg/mL, or about 170 mg/mL, acetic acid and/or acetate at a concentration of about 0.1 mM to about 300 mM (e.g., about 2 mM to about 30 mM, about 5 mM to about 50 mM, about 5 mM to about 15 mM, about 10 mM to about 20 mM, about 10 mM to about 30 mM, about 15 mM to about 25 mM, about 30 mM to about 40 mM, about 35 mM to about 45 mM, about 40 mM to about 50 mM, about 10 mM, about 15 mM, about 20 mM, and/or about 25 mM), and one or more excipients selected from the group consisting of sucrose at a concentration of about 0.1% (w/v) to about 15% (w/v) (e.g., about 4% (w/v) to about 12% (w/v), about 4% (w/v) to about 10% (w/v), about 4% (w/v) to about 9% (w/v), about 5% (w/v) to about 10% (w/v), about 6% (w/v) to about 8% (w/v), about 8% (w/v) to about 10% (w/v), about 8.5% (w/v) to about 9.5% (w/v), about 9% (w/v), about 5.8% (w/v) to about 6.6% (w/v), about 6% (w/v) to about 6.4% (w/v), about 6.2% (w/v), about 6.1% (w/v) to about 6.9% (w/v), about 6.3% (w/v) to about 6.7% (w/v), about 6.5% (w/v), about 6.4% (w/v) to about 7.2% (w/v), about 6.6% (w/v) to about 7% (w/v), about 6.8% (w/v), about 6.5% (w/v) to about 7.3% (w/v), about 6.7% (w/v) to about 7.1% (w/v), about 6.9% (w/v), about 6.6% (w/v) to about 7.4% (w/v), about 6.8% (w/v) to about 7.2% (w/v), about 7% (w/v), about 6.9% (w/v) to about 7.7% (w/v), about 7.1% (w/v) to about 7.5% (w/v), and/or about 7.3% (w/v)), sorbitol at a concentration of about 0.1% (w/v) to about 10% (w/v) (e.g., about 3% (w/v) to about 5% (w/v) and/or about 4% (w/v)), calcium chloride at a concentration of about 1 to about 150 mM (e.g., about 5 to about 50 mM, about 5 to about 15 mM, about 10 to about 40 mM, about 10 to about 30 mM, about 15 to about 35 mM, about 20 to about 30 mM, about 20 to about 40 mM, about 30 to about 50 mM, about 40 to about 50 mM, about 40 to about 60 mM, about 40 to about 80 mM, about 50 to about 100 mM, about 10 mM, about 25 mM, and/or about 45 mM), sodium chloride at a concentration of about 10 to about 100 mM (e.g., about 60 to about 90 mM, about 15 to about 50 mM, and/or about 35 mM), MSA at a concentration of about 0.1 to about 150 mM (e.g., about 0.1 to about 50 mM, about 10 to about 50 mM, about 20 to about 40 mM, about 30 mM, about 30 to about 50 mM, about 40 to about 60 mM, about 50 to about 70 mM, about 60 to about 80 mM, about 70 to about 90 mM, and/or about 80 to about 100 mM), MEA-HCl at a concentration of about 0.1 to about 150 mM (e.g., about 0.1 to about 40 mM, about 10 to about 50 mM, about 20 to about 40 mM, about 30 mM, about 30 to about 50 mM, about 40 to about 60 mM, about 50 to about 70 mM, about 60 to about 80 mM, about 70 to about 90 mM, and/or about 80 to about 100 mM), MEA at a concentration of about 0.1 to about 300 mM (e.g., about 0.1 to about 50 mM, about 10 to about 50 mM, about 20 to about 40 mM, about 30 mM, about 30 to about 50 mM, about 40 to about 60 mM, about 50 to about 70 mM, about 60 to about 80 mM, about 70 to about 90 mM, and/or about 80 to about 100 mM), guanidine hydrochloride (GnHCl) at a concentration of about 0.1 to about 150 mM (e.g., 5 to about 50 mM, about 10 to about 40 mM, about 15 to about 30 mM, and/or 20 mM), sodium carboxymethylcellulose (NaCMC) at a concentration of about 0.1% (w/v) to about 15% (w/v) (e.g., about 0.1% (w/v) to about 5% (w/v), about 0.1% (w/v) to about 2% (w/v), about 0.1% (w/v) to about 1% (w/v), and/or about 0.1% (w/v) to about 0.5% (w/v)), arginine-HCl at a concentration of about 0.1 to about 450 mM (e.g., about 20 to about 200 mM, about 50 to about 150 mM, about 80 to about 120 mM, and/or about 100 mM), proline at a concentration of about 0.1 to about 450 mM (e.g., about 20 to about 400 mM, about 50 to about 350 mM, about 50 to about 300 mM, about 80 to about 300 mM, about 100 to about 250 mM, about 150 to about 230 mM, about 100 to about 140 mM, about 130 to about 170 mM, about 160 to about 200 mM, about 190 to about 230 mM, about 220 to about 260 mM, about 250 to about 290 mM and/or about 220 mM), Pluronic F68 at a concentration of about 0.001% (w/v) to about 10% (w/v) (e.g., about 0.005% (w/v) to about 1% (w/v), about 0.01% (w/v) to about 0.1% (w/v), about 0.01% (w/v) to about 1% (w/v), about 0.05% (w/v) to about 0.1% (w/v), about 0.05% (w/v) to about 0.4% (w/v), about 0.05% (w/v) to about 0.5% (w/v), about 0.1% (w/v) to about 2% (w/v), about 0.2% (w/v) to about 1% (w/v), about 0.01% (w/v), about 0.05% (w/v), about 0.1% (w/v), and/or about 0.4% (w/v)), Docusate sodium at a concentration of about 0.001% (w/v) to about 1% (w/v) (e.g., about 0.005% (w/v) to about 0.05% (w/v)), benzalkonium chloride at a concentration of about 0.001% (w/v) to about 1% (w/v) (e.g., about 0.05% (w/v) to about 0.5% (w/v)), Span 40 at a concentration of about 0.001% (w/v) to about 1% (w/v) (e.g., about 0.05% (w/v) to about 0.5% (w/v)), Triton X-100 at a concentration of about 0.001% (w/v) to about 1% (w/v) (e.g., about 0.002% (w/v) to about 0.01% (w/v), about 0.005% (w/v) to about 0.05% (w/v), about 0.02% (w/v) to about 0.1% (w/v), and/or about 0.05% (w/v) to about 0.2% (w/v)), Polysorbate 20 at a concentration of about 0.001% (w/v) to about 2% (w/v) (e.g., about 0.002% (w/v) to about 0.01% (w/v), about 0.005% (w/v) to about 0.05% (w/v), about 0.005% (w/v) to about 0.1% (w/v), about 0.02% (w/v) to about 0.1% (w/v), and/or about 0.05% (w/v) to about 0.2% (w/v)), and Polysorbate 80 at a concentration of about 0.001% (w/v) to about 2% (w/v) (e.g., about 0.002% (w/v) to about 0.01% (w/v), about 0.005% (w/v) to about 0.1% (w/v), about 0.005% (w/v) to about 0.05% (w/v), about 0.02% (w/v) to about 0.1% (w/v), about 0.03% (w/v) to about 0.1% (w/v), 0.04% (w/v) to about 0.1% (w/v), about 0.05% (w/v) to about 0.2% (w/v), about 0.03% (w/v), about 0.04% (w/v), and/or about 0.1% (w/v)). Optionally, the acetate-containing stable aqueous adalimumab formulation has a pH of about 4.8 to about 5.7, for example, about 4.9 to about 5.6, about 5.0 to about 5.5, about 5.1 to about 5.4, about 5.1 to about 5.3, about 5.1 to about 5.2, about 5.2 to about 5.3, and/or about 5.2. Optionally, the pH of the stable aqueous adalimumab formulation is adjusted using a strong acid and/or a strong base including, but not limited to, hydrochloric acid, sodium hydroxide, calcium hydroxide, MSA, and/or MEA.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Polysorbate 20 at a concentration of about 0.05% (w/v) to about 0.5% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Polysorbate 80 at a concentration of about 0.05% (w/v) to about 0.5% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Pluronic F68 at a concentration of about 0.05% (w/v) to about 0.5% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Docusate sodium at a concentration of about 0.005% (w/v) to about 0.05% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and benzalkonium chloride at a concentration of about 0.05% (w/v) to about 0.5% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Span 40 at a concentration of about 0.05% (w/v) to about 0.5% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Triton X-100 at a concentration of about 0.05% (w/v) to about 0.5% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, and arginine-HCl at a concentration of about 80 to about 120 mM, and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Polysorbate 80 at a concentration of about 0.0025% (w/v) to about 0.025% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Polysorbate 80 at a concentration of about 0.005% (w/v) to about 0.05% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Polysorbate 80 at a concentration of about 0.025% (w/v) to about 0.25% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Polysorbate 20 at a concentration of about 0.0025% (w/v) to about 0.025% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Polysorbate 20 at a concentration of about 0.005% (w/v) to about 0.05% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Polysorbate 20 at a concentration of about 0.025% (w/v) to about 0.25% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Triton X-100 at a concentration of about 0.0025% (w/v) to about 0.025% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Triton X-100 at a concentration of about 0.005% (w/v) to about 0.05% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Triton X-100 at a concentration of about 0.025% (w/v) to about 0.25% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Pluronic F68 at a concentration of about 0.025% (w/v) to about 0.25% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Pluronic F68 at a concentration of about 0.05% (w/v) to about 0.5% (w/v), and has a pH of about 5.1 to 5.3.

In an embodiment, the stable aqueous adalimumab formulation includes adalimumab at a concentration of about 120 to about 160 mg/mL, acetate at a concentration of about 15 mM to about 25 mM, calcium chloride at a concentration of about 30 to about 60 mM, arginine-HCl at a concentration of about 80 to about 120 mM, and Pluronic F68 at a concentration of about 0.2% (w/v) to about 0.6% (w/v), and has a pH of about 5.1 to 5.3.

In an embodiment, the stable aqueous adalimumab formulation includes adalimumab at a concentration of about 150 to about 180 mg/mL, acetate at a concentration of about 5 mM to about 10 mM, sucrose at a concentration of about 7% (w/v) to about 10% (w/v), and Polysorbate 80 at a concentration of about 0.05% (w/v) to about 0.2% (w/v), and has a pH of about 5.1 to 5.3. Optionally, the pH of the formulation is adjusted within this range with MSA and/or MEA.

In an embodiment, the stable aqueous adalimumab formulation includes adalimumab at a concentration of about 40 to about 50 mg/mL, acetate at a concentration of about 5 mM to about 15 mM, sucrose at a concentration of about 6.5% (w/v) to about 7.1% (w/v), calcium chloride at a concentration of about 15 to about 35 mM, and Pluronic F68 at a concentration of about 0.05% (w/v) to about 0.5% (w/v), and has a pH of about 5.1 to 5.3.

In an embodiment, the stable aqueous adalimumab formulation includes adalimumab at a concentration of about 40 to about 50 mg/mL, acetate at a concentration of about 5 mM to about 15 mM, sucrose at a concentration of about 6.0% (w/v) to about 6.5% (w/v), calcium chloride at a concentration of about 15 to about 35 mM, and Pluronic F68 at a concentration of about 0.05% (w/v) to about 0.5% (w/v), and has a pH of about 5.1 to 5.3.

In an embodiment, the stable aqueous adalimumab formulation includes adalimumab at a concentration of about 40 to about 50 mg/mL, acetate at a concentration of about 5 mM to about 15 mM, sucrose at a concentration of about 6.6% (w/v) to about 7.2% (w/v), MEA-HCl at a concentration of about 20 to about 40 mM, and Pluronic F68 at a concentration of about 0.05% (w/v) to about 0.5% (w/v), and has a pH of about 5.1 to 5.3.

In an embodiment, the stable aqueous adalimumab formulation includes adalimumab at a concentration of about 40 to about 50 mg/mL, acetate at a concentration of about 5 mM to about 15 mM, sucrose at a concentration of about 6.7% (w/v) to about 7.3% (w/v), calcium chloride at a concentration of about 5 to about 15 mM, guanidine hydrochloride (GnHCl) at a concentration of about 10 to about 30 mM, and Pluronic F68 at a concentration of about 0.05% (w/v) to about 0.5% (w/v), and has a pH of about 5.1 to 5.3.

In an embodiment, the stable aqueous adalimumab formulation includes adalimumab at a concentration of about 40 to about 50 mg/mL, acetate at a concentration of about 5 mM to about 15 mM, sucrose at a concentration of about 6.7% (w/v) to about 7.3% (w/v), calcium chloride at a concentration of about 5 to about 15 mM, NaCMC at a concentration of about 0.2% (w/v) to about 1% (w/v), and Pluronic F68 at a concentration of about 0.05% (w/v) to about 0.5% (w/v), and has a pH of about 5.1 to 5.3.

In an embodiment, the stable aqueous adalimumab formulation includes adalimumab at a concentration of about 40 to about 60 mg/mL, acetate at a concentration of about 5 mM to about 15 mM, and sucrose at a concentration of about 8% (w/v) to about 10% (w/v), and has a pH of about 5.1 to 5.3. Optionally, the pH of the formulation is adjusted within this range with HCl and/or NaOH.

In an embodiment, the stable aqueous adalimumab formulation includes adalimumab at a concentration of about 40 to about 60 mg/mL, acetate at a concentration of about 5 mM to about 15 mM, sucrose at a concentration of about 8% (w/v) to about 10% (w/v), and Polysorbate 80 at a concentration of about 0.05% (w/v) to about 0.5% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 40 to about 60 mg/mL, acetate at a concentration of about 5 mM to about 15 mM, sucrose at a concentration of about 8.5% (w/v) to about 9.5% (w/v), and Polysorbate 80 at a concentration of about 0.05% (w/v) to about 0.2% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, sucrose at a concentration of about 8% (w/v) to about 10% (w/v), and Pluronic F68 at a concentration of about 0.05% (w/v) to about 0.5% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 110 mg/mL, acetate at a concentration of about 5 mM to about 15 mM, sucrose at a concentration of about 8.5% (w/v) to about 9.5% (w/v), and Pluronic F68 at a concentration of about 0.05% (w/v) to about 0.2% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, sucrose at a concentration of about 6.4% (w/v) to about 7.2% (w/v), calcium chloride at a concentration of about 15 to about 35 mM, and Pluronic F68 at a concentration of about 0.05% (w/v) to about 0.5% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, proline at a concentration of about 190 to about 250 mM, calcium chloride at a concentration of about 15 to about 35 mM, and Pluronic F68 at a concentration of about 0.05% (w/v) to about 0.5% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, sucrose at a concentration of about 6.5% (w/v) to about 7.3% (w/v), MEA-HCl at a concentration of about 20 to about 40 mM, and Pluronic F68 at a concentration of about 0.05% (w/v) to about 0.5% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, sucrose at a concentration of about 6.9% (w/v) to about 7.7% (w/v), MSA at a concentration of about 20 to about 40 mM, and Pluronic F68 at a concentration of about 0.05% (w/v) to about 0.5% (w/v), and has a pH of about 5.1 to 5.3. Optionally, the pH of the formulation is adjusted within this range with NaOH, Ca(OH)$_2$, or MEA.

In an embodiment, the stable aqueous adalimumab formulation includes adalimumab at a concentration of about 90 to about 120 mg/mL, acetate at a concentration of about 5 mM to about 15 mM, sucrose at a concentration of about 6.5% (w/v) to about 7.3% (w/v), sodium chloride at a concentration of about 20 to about 45 mM, and Pluronic F68 at a concentration of about 0.05% (w/v) to about 0.5% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, sucrose at a concentration of about 8% (w/v) to about 10% (w/v), and Pluronic F68 at a concentration of about 0.01% (w/v) to about 0.1% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 110 mg/mL, acetate at a concentration of about 5 mM to about 15 mM, sucrose at a concentration of about 8.5% (w/v) to about 9.5% (w/v), and Pluronic F68 at a concentration of about 0.03% (w/v) to about 0.1% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, sucrose at a concentration of about 6.4% (w/v) to about 7.2% (w/v), calcium chloride at a concentration of about 15 to about 35 mM, and Pluronic F68 at a concentration of about 0.01% (w/v) to about 0.1% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, proline at a concentration of about 190 to about 250 mM, calcium chloride at a concentration of about 15 to about 35 mM, and Pluronic F68 at a concentration of about 0.01% (w/v) to about 0.1% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, sucrose at a concentration of about 6.5% (w/v) to about 7.3% (w/v), MEA-HCl at a concentration of about 20 to about 40 mM, and Pluronic F68 at a concentration of about 0.01% (w/v) to about 0.1% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, sucrose at a concentration of about 6.9% (w/v) to about 7.7% (w/v), MSA at a concentration of about 20 to about 40 mM, and Pluronic F68 at a concentration of about 0.01% (w/v) to about 0.1% (w/v), and has a pH of about 5.1 to 5.3. Optionally, the pH of the formulation is adjusted within this range with NaOH, Ca(OH)$_2$, or MEA.

In an embodiment, the stable aqueous adalimumab formulation includes adalimumab at a concentration of about 90 to about 120 mg/mL, acetate at a concentration of about 5 mM to about 15 mM, sucrose at a concentration of about 6.5% (w/v) to about 7.3% (w/v), sodium chloride at a concentration of about 20 to about 45 mM, and Pluronic F68 at a concentration of about 0.01% (w/v) to about 0.1% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, sucrose at a concentration of about 8% (w/v) to about 10% (w/v), and Polysorbate 80 at a concentration of about 0.05% (w/v) to about 0.5% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, sucrose at a concentration of about 6.4% (w/v) to about 7.2% (w/v), calcium chloride at a concentration of about 15 to about 35 mM, and Polysorbate 80 at a concentration of about 0.05% (w/v) to about 0.5% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, proline at a concentration of about 190 to about 250 mM, calcium chloride at a concentration of about 15 to about 35 mM, and Polysorbate 80 at a concentration of about 0.05% (w/v) to about 0.5% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, sucrose at a concentration of about 6.5% (w/v) to about 7.3% (w/v), MEA-HCl at a concentration of about 20 to about 40 mM, and Polysorbate 80 at a concentration of about 0.05% (w/v) to about 0.5% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, sucrose at a concentration of about 6.9% (w/v) to about 7.7% (w/v), MSA at a concentration of about 20 to about 40 mM, and Polysorbate 80 at a concentration of about 0.05% (w/v) to about 0.5% (w/v), and has a pH of about 5.1 to 5.3. Optionally, the pH of the formulation is adjusted within this range with NaOH, Ca(OH)$_2$, or MEA.

In an embodiment, the stable aqueous adalimumab formulation includes adalimumab at a concentration of about 90 to about 120 mg/mL, acetate at a concentration of about 5 mM to about 15 mM, sucrose at a concentration of about 6.5% (w/v) to about 7.3% (w/v), sodium chloride at a concentration of about 20 to about 45 mM, and Polysorbate 80 at a concentration of about 0.05% (w/v) to about 0.5% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, sucrose at a concentration of about 8% (w/v) to about 10% (w/v), and Polysorbate 80 at a concentration of about 0.01% (w/v) to about 0.1% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 110 mg/mL, acetate at a concentration of about 5 mM to about 15 mM, sucrose at a concentration of about 8.5% (w/v) to about 9.5% (w/v), and Polysorbate 80 at a concentration of about 0.03% (w/v) to about 0.1% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, sucrose at a concentration of about 6.4% (w/v) to about 7.2% (w/v), calcium chloride at a concentration of about 15 to about 35 mM, and Polysorbate 80 at a concentration of about 0.01% (w/v) to about 0.1% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 110 mg/mL, acetate at a concentration of about 5 mM to about 15 mM, sucrose at a concentration of about 6.6% (w/v) to about 7% (w/v), calcium chloride at a concentration of about 20 to about 30 mM, and Polysorbate 80 at a concentration of about 0.03% (w/v) to about 0.1% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, proline at a concentration of about 190 to about 250 mM, calcium chloride at a concentration of about 15 to about 35 mM, and Polysorbate 80 at a concentration of about 0.01% (w/v) to about 0.1% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, sucrose at a concentration of about 6.5% (w/v) to about 7.3% (w/v), MEA-HCl at a concentration of about 20 to about 40 mM, and Polysorbate 80 at a concentration of about 0.01% (w/v) to about 0.1% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, sucrose at a concentration of about 6.9% (w/v) to about 7.7% (w/v), MSA at a concentration of about 20 to about 40 mM, and Polysorbate 80 at a concentration of about 0.01% (w/v) to about 0.1% (w/v), and has a pH of about 5.1 to 5.3. Optionally, the pH of the formulation is adjusted within this range with NaOH, Ca(OH)$_2$, or MEA.

In an embodiment, the stable aqueous adalimumab formulation includes adalimumab at a concentration of about 90 to about 120 mg/mL, acetate at a concentration of about 5 mM to about 15 mM, sucrose at a concentration of about 6.5% (w/v) to about 7.3% (w/v), sodium chloride at a concentration of about 20 to about 45 mM, and Polysorbate 80 at a concentration of about 0.01% (w/v) to about 0.1% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 110 mg/mL, acetate at a concentration of about 5 mM to about 15 mM, sucrose at a concentration of about 6.7% (w/v) to about 7.1% (w/v), sodium chloride at a concentration of about 25 to about 40 mM, and Polysorbate 80 at a concentration of about 0.03% (w/v) to about 0.1% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, sucrose at a concentration of about 8% (w/v) to about 10% (w/v), and Polysorbate 20 at a concentration of about 0.05% (w/v) to about 0.5% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, sucrose at a concentration of about 6.4% (w/v) to about 7.2% (w/v), calcium chloride at a concentration of about 15 to about 35 mM, and Polysorbate 20 at a concentration of about 0.05% (w/v) to about 0.5% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, proline at a concentration of about 190 to about 250 mM, calcium chloride at a concentration of about 15 to about 35 mM, and Polysorbate 20 at a concentration of about 0.05% (w/v) to about 0.5% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, sucrose at a concentration of about 6.5% (w/v) to about 7.3% (w/v), MEA-HCl at a concentration of about 20 to about 40 mM, and Polysorbate 20 at a concentration of about 0.05% (w/v) to about 0.5% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, sucrose at a concentration of about 6.9% (w/v) to about 7.7% (w/v), MSA at a concentration of about 20 to about 40 mM, and Polysorbate 20 at a concentration of about 0.05% (w/v) to about 0.5% (w/v), and has a pH of about 5.1 to 5.3. Optionally, the pH of the formulation is adjusted within this range with NaOH, Ca(OH)$_2$, or MEA.

In an embodiment, the stable aqueous adalimumab formulation includes adalimumab at a concentration of about 90 to about 120 mg/mL, acetate at a concentration of about 5 mM to about 15 mM, sucrose at a concentration of about 6.5% (w/v) to about 7.3% (w/v), sodium chloride at a concentration of about 20 to about 45 mM, and Polysorbate 20 at a concentration of about 0.05% (w/v) to about 0.5% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, sucrose at a concentration of about 8% (w/v) to about 10% (w/v), and Polysorbate 20 at a concentration of about 0.01% (w/v) to about 0.1% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, sucrose at a concentration of about 6.4% (w/v) to about 7.2% (w/v), calcium chloride at a concentration of about 15 to about 35 mM, and Polysorbate 20 at a concentration of about 0.01% (w/v) to about 0.1% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, proline at a concentration of about 190 to about 250 mM, calcium chloride at a concentration of about 15 to about 35 mM, and Polysorbate 20 at a concentration of about 0.01% (w/v) to about 0.1% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, sucrose at a concentration of about 6.5% (w/v) to about 7.3% (w/v), MEA-HCl at a concentration of about 20 to about 40 mM, and Polysorbate 20 at a concentration of about 0.01% (w/v) to about 0.1% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, acetate at a concentration of about 5 mM to about 15 mM, sucrose at a concentration of about 6.9% (w/v) to about 7.7% (w/v), MSA at a concentration of about 20 to about 40 mM, and Polysorbate 20 at a concentration of about 0.01% (w/v) to about 0.1% (w/v), and has a pH of about 5.1 to 5.3. Optionally, the pH of the formulation is adjusted within this range with NaOH, Ca(OH)$_2$, or MEA.

In an embodiment, the stable aqueous adalimumab formulation includes adalimumab at a concentration of about 90 to about 120 mg/mL, acetate at a concentration of about 5 mM to about 15 mM, sucrose at a concentration of about 6.5% (w/v) to about 7.3% (w/v), sodium chloride at a concentration of about 20 to about 45 mM, and Polysorbate 20 at a concentration of about 0.01% (w/v) to about 0.1% (w/v), and has a pH of about 5.1 to 5.3. Optionally, the pH of the formulation is adjusted within this range with HCl, NaOH, Ca(OH)$_2$, MEA, and/or MSA.

Exemplary aqueous adalimumab formulations are provided in Table D. Each formulation in Table D may optionally include Pluronic F68 at a concentration of about 0.001% (w/v) to about 10% (w/v) (e.g., about 0.005% (w/v) to about 1% (w/v), about 0.01% (w/v) to about 0.1% (w/v), about 0.01% (w/v) to about 1% (w/v), about 0.05% (w/v) to about 0.1% (w/v), about 0.05% (w/v) to about 0.4% (w/v), about 0.05% (w/v) to about 0.5% (w/v), about 0.1% (w/v) to about 2% (w/v), about 0.2% (w/v) to about 1% (w/v), about 0.01% (w/v), about 0.05% (w/v), about 0.1% (w/v), and/or about 0.4% (w/v)), Polysorbate 20 at a concentration of about 0.001% (w/v) to about 2% (w/v) (e.g., about 0.002% (w/v) to about 0.01% (w/v), about 0.005% (w/v) to about 0.05% (w/v), about 0.005% (w/v) to about 0.1% (w/v), about 0.02% (w/v) to about 0.1% (w/v), and/or about 0.05% (w/v) to about 0.2% (w/v)), or Polysorbate 80 at a concentration of about 0.001% (w/v) to about 2% (w/v) (e.g., about 0.002% (w/v) to about 0.01% (w/v), about 0.005% (w/v) to about 0.1% (w/v), about 0.005% (w/v) to about 0.05% (w/v), about 0.02% (w/v) to about 0.1% (w/v), about 0.03% (w/v) to about 0.1% (w/v), 0.04% (w/v) to about 0.1% (w/v), about 0.05% (w/v) to about 0.2% (w/v), about 0.03% (w/v), about 0.04% (w/v), and/or about 0.1% (w/v)). Each formulation in Table D has a pH of about 5.0 to about 5.5, e.g., about 5.1 to about 5.3 and/or about 5.2. Optionally, the pH of each formulation in Table D is adjusted using a strong acid and/or strong base including, but not limited to, hydrochloric acid, sodium hydroxide, calcium hydroxide, MSA, and/or MEA.

TABLE D

| Protein conc. | Buffer | Excipient(s) |
| --- | --- | --- |
| 50 mg/mL | 10 mM sodium acetate | 6.8% (w/v) sucrose<br>25 mM CaCl$_2$ |
| 50 mg/mL | 10 mM calcium acetate | 6.2% (w/v) sucrose<br>25 mM CaCl$_2$ |
| 50 mg/mL | 10 mM sodium acetate | 6.9% (w/v) sucrose<br>30 mM MEA-HCl |
| 50 mg/mL | 10 mM sodium acetate | 7% (w/v) sucrose<br>10 mM CaCl$_2$<br>20 mM GnHCl |
| 50 mg/mL | 10 mM sodium acetate | 7% (w/v) sucrose<br>10 mM CaCl$_2$<br>0.5% NaCMC |
| 50 mg/mL | 10 mM acetate | 9% (w/v) sucrose |
| 100 mg/mL | 10 mM acetate | 9% (w/v) sucrose |
| 100 mg/mL | 10 mM acetate | 6.8% (w/v) sucrose<br>25 mM CaCl$_2$ |
| 100 mg/mL | 10 mM acetate | 220 mM proline<br>25 mM CaCl$_2$ |
| 100 mg/mL | 10 mM acetate | 6.9% (w/v) sucrose<br>30 mM MEA-HCl |
| 100 mg/mL | 10 mM acetate | 7.3% (w/v) sucrose<br>30 mM MSA |
| 100 mg/mL | 10 mM acetate | 6.9% (w/v) sucrose<br>35 mM NaCl |

Exemplary aqueous adalimumab formulations are provided in Table E. Each formulation in Table E has a pH of about 5.0 to about 5.5, e.g., about 5.1 to about 5.3 and/or about 5.2. Optionally, the pH of each formulation in Table E is adjusted using a strong acid and/or strong base including, but not limited to, hydrochloric acid, sodium hydroxide, calcium hydroxide, MSA, and/or MEA.

TABLE E

| Protein conc. | Buffer | Excipient(s) | Surfactant |
|---|---|---|---|
| 50 mg/mL | 10 mM sodium acetate | 6.8% (w/v) sucrose 25 mM CaCl$_2$ | 0.1% (w/v) Pluronic F68 |
| 50 mg/mL | 10 mM calcium acetate | 6.2% (w/v) sucrose 25 mM CaCl$_2$ | 0.1% (w/v) Pluronic F68 |
| 50 mg/mL | 10 mM sodium acetate | 6.9% (w/v) sucrose 30 mM MEA-HCl | 0.1% (w/v) Pluronic F68 |
| 50 mg/mL | 10 mM sodium acetate | 7% (w/v) sucrose 10 mM CaCl$_2$ 20 mM GnHCl | 0.1% (w/v) Pluronic F68 |
| 50 mg/mL | 10 mM sodium acetate | 7% (w/v) sucrose 10 mM CaCl$_2$ 0.5% NaCMC | 0.1% (w/v) Pluronic F68 |
| 50 mg/mL | 10 mM acetate | 9% (w/v) sucrose | 0.1% (w/v) Polysorbate 80 |
| 100 mg/mL | 10 mM acetate | 9% (w/v) sucrose | 0.1% (w/v) Pluronic F68 |
| 100 mg/mL | 10 mM acetate | 6.8% (w/v) sucrose 25 mM CaCl$_2$ | 0.1% (w/v) Pluronic F68 |
| 100 mg/mL | 10 mM acetate | 220 mM proline 25 mM CaCl$_2$ | 0.1% (w/v) Pluronic F68 |
| 100 mg/mL | 10 mM acetate | 6.9% (w/v) sucrose 30 mM MEA-HCl | 0.1% (w/v) Pluronic F68 |
| 100 mg/mL | 10 mM acetate | 7.3% (w/v) sucrose 30 mM MSA | 0.1% (w/v) Pluronic F68 |
| 100 mg/mL | 10 mM acetate | 6.9% (w/v) sucrose 35 mM NaCl | 0.1% (w/v) Pluronic F68 |
| 100 mg/mL | 10 mM acetate | 9% (w/v) sucrose | 0.05% (w/v) Pluronic F68 |
| 100 mg/mL | 10 mM acetate | 6.8% (w/v) sucrose 25 mM CaCl$_2$ | 0.05% (w/v) Pluronic F68 |
| 100 mg/mL | 10 mM acetate | 220 mM proline 25 mM CaCl$_2$ | 0.05% (w/v) Pluronic F68 |
| 100 mg/mL | 10 mM acetate | 6.9% (w/v) sucrose 30 mM MEA-HCl | 0.05% (w/v) Pluronic F68 |
| 100 mg/mL | 10 mM acetate | 7.3% (w/v) sucrose 30 mM MSA | 0.05% (w/v) Pluronic F68 |
| 100 mg/mL | 10 mM acetate | 6.9% (w/v) sucrose 35 mM NaCl | 0.05% (w/v) Pluronic F68 |
| 100 mg/mL | 10 mM acetate | 9% (w/v) sucrose | 0.1% (w/v) Polysorbate 80 |
| 100 mg/mL | 10 mM acetate | 6.8% (w/v) sucrose 25 mM CaCl$_2$ | 0.1% (w/v) Polysorbate 80 |
| 100 mg/mL | 10 mM acetate | 220 mM proline 25 mM CaCl$_2$ | 0.1% (w/v) Polysorbate 80 |
| 100 mg/mL | 10 mM acetate | 6.9% (w/v) sucrose 30 mM MEA-HCl | 0.1% (w/v) Polysorbate 80 |
| 100 mg/mL | 10 mM acetate | 7.3% (w/v) sucrose 30 mM MSA | 0.1% (w/v) Polysorbate 80 |
| 100 mg/mL | 10 mM acetate | 6.9% (w/v) sucrose 35 mM NaCl | 0.1% (w/v) Polysorbate 80 |
| 100 mg/mL | 10 mM acetate | 9% (w/v) sucrose | 0.05% (w/v) Polysorbate 80 |
| 100 mg/mL | 10 mM acetate | 6.8% (w/v) sucrose 25 mM CaCl$_2$ | 0.05% (w/v) Polysorbate 80 |
| 100 mg/mL | 10 mM acetate | 220 mM proline 25 mM CaCl$_2$ | 0.05% (w/v) Polysorbate 80 |
| 100 mg/mL | 10 mM acetate | 6.9% (w/v) sucrose 30 mM MEA-HCl | 0.05% (w/v) Polysorbate 80 |
| 100 mg/mL | 10 mM acetate | 7.3% (w/v) sucrose 30 mM MSA | 0.05% (w/v) Polysorbate 80 |
| 100 mg/mL | 10 mM acetate | 6.9% (w/v) sucrose 35 mM NaCl | 0.05% (w/v) Polysorbate 80 |
| 100 mg/mL | 10 mM acetate | 9% (w/v) sucrose | 0.1% (w/v) Polysorbate 20 |
| 100 mg/mL | 10 mM acetate | 6.8% (w/v) sucrose 25 mM CaCl$_2$ | 0.1% (w/v) Polysorbate 20 |
| 100 mg/mL | 10 mM acetate | 220 mM proline 25 mM CaCl$_2$ | 0.1% (w/v) Polysorbate 20 |

TABLE E-continued

| Protein conc. | Buffer | Excipient(s) | Surfactant |
|---|---|---|---|
| 100 mg/mL | 10 mM acetate | 6.9% (w/v) sucrose 30 mM MEA-HCl | 0.1% (w/v) Polysorbate 20 |
| 100 mg/mL | 10 mM acetate | 7.3% (w/v) sucrose 30 mM MSA | 0.1% (w/v) Polysorbate 20 |
| 100 mg/mL | 10 mM acetate | 6.9% (w/v) sucrose 35 mM NaCl | 0.1% (w/v) Polysorbate 20 |
| 100 mg/mL | 10 mM acetate | 9% (w/v) sucrose | 0.05% (w/v) Polysorbate 20 |
| 100 mg/mL | 10 mM acetate | 6.8% (w/v) sucrose 25 mM CaCl$_2$ | 0.05% (w/v) Polysorbate 20 |
| 100 mg/mL | 10 mM acetate | 220 mM proline 25 mM CaCl$_2$ | 0.05% (w/v) Polysorbate 20 |
| 100 mg/mL | 10 mM acetate | 6.9% (w/v) sucrose 30 mM MEA-HCl | 0.05% (w/v) Polysorbate 20 |
| 100 mg/mL | 10 mM acetate | 7.3% (w/v) sucrose 30 mM MSA | 0.05% (w/v) Polysorbate 20 |
| 100 mg/mL | 10 mM acetate | 6.9% (w/v) sucrose 35 mM NaCl | 0.05% (w/v) Polysorbate 20 |

Exemplary aqueous adalimumab formulations are provided in Table F.

TABLE F

| Protein conc. | Buffer | Excipient(s) | pH Adjusting Agent | Surfactant | pH |
|---|---|---|---|---|---|
| 50 mg/mL | 10 mM sodium acetate | 6.8% (w/v) sucrose 25 mM CaCl$_2$ | HCl/NaOH, HCl/Ca(OH)$_2$, HCl/MEA, MSA/Ca(OH)$_2$, or MSA/MEA | 0.1% (w/v) Pluronic F68 | 5.2 |
| 50 mg/mL | 10 mM calcium acetate | 6.2% (w/v) sucrose 25 mM CaCl$_2$ | HCl/NaOH, HCl/Ca(OH)$_2$, HCl/MEA, MSA/Ca(OH)$_2$, or MSA/MEA | 0.1% (w/v) Pluronic F68 | 5.2 |
| 50 mg/mL | 10 mM sodium acetate | 6.9% (w/v) sucrose 30 mM MEA-HCl | HCl/NaOH, HCl/Ca(OH)$_2$, HCl/MEA, MSA/Ca(OH)$_2$, or MSA/MEA | 0.1% (w/v) Pluronic F68 | 5.2 |
| 50 mg/mL | 10 mM sodium acetate | 7% (w/v) sucrose 10 mM CaCl$_2$ 20 mM GnHCl | HCl/NaOH, HCl/Ca(OH)$_2$, HCl/MEA, MSA/Ca(OH)$_2$, or MSA/MEA | 0.1% (w/v) Pluronic F68 | 5.2 |
| 50 mg/mL | 10 mM sodium acetate | 7% (w/v) sucrose 10 mM CaCl$_2$ 0.5% NaCMC | HCl/NaOH, HCl/Ca(OH)$_2$, HCl/MEA, MSA/Ca(OH)$_2$, or MSA/MEA | 0.1% (w/v) Pluronic F68 | 5.2 |
| 50 mg/mL | 10 mM acetate | 9% (w/v) sucrose | HCl/NaOH, HCl/Ca(OH)$_2$, HCl/MEA, MSA/Ca(OH)$_2$, or MSA/MEA | 0.1% (w/v) Polysorbate 80 | 5.2 |
| 100 mg/mL | 10 mM acetate | 9% (w/v) sucrose | HCl/NaOH, HCl/Ca(OH)$_2$, HCl/MEA, MSA/Ca(OH)$_2$, or MSA/MEA | 0.1% (w/v) Pluronic F68 | 5.2 |
| 100 mg/mL | 10 mM acetate | 6.8% (w/v) sucrose 25 mM CaCl$_2$ | HCl/NaOH, HCl/Ca(OH)$_2$, HCl/MEA, | 0.1% (w/v) Pluronic F68 | 5.2 |

TABLE F-continued

| Protein conc. | Buffer | Excipient(s) | pH Adjusting Agent | Surfactant | pH |
|---|---|---|---|---|---|
| 100 mg/mL | 10 mM acetate | 220 mM proline 25 mM CaCl$_2$ | MSA/Ca(OH)$_2$, or MSA/MEA HCl/NaOH, HCl/Ca(OH)$_2$, HCl/MEA, MSA/Ca(OH)$_2$, or MSA/MEA | 0.1% (w/v) Pluronic F68 | 5.2 |
| 100 mg/mL | 10 mM acetate | 6.9% (w/v) sucrose 30 mM MEA-HCl | HCl/NaOH, HCl/Ca(OH)$_2$, HCl/MEA, MSA/Ca(OH)$_2$, or MSA/MEA | 0.1% (w/v) Pluronic F68 | 5.2 |
| 100 mg/mL | 10 mM acetate | 7.3% (w/v) sucrose 30 mM MSA | NaOH, Ca(OH)$_2$, or MEA | 0.1% (w/v) Pluronic F68 | 5.2 |
| 100 mg/mL | 10 mM acetate | 6.9% (w/v) sucrose 35 mM NaCl | HCl/NaOH, HCl/Ca(OH)$_2$, HCl/MEA, MSA/Ca(OH)$_2$, or MSA/MEA | 0.1% (w/v) Pluronic F68 | 5.2 |
| 100 mg/mL | 10 mM acetate | 9% (w/v) sucrose | HCl/NaOH, HCl/Ca(OH)$_2$, HCl/MEA, MSA/Ca(OH)$_2$, or MSA/MEA | 0.05% (w/v) Pluronic F68 | 5.2 |
| 100 mg/mL | 10 mM acetate | 6.8% (w/v) sucrose 25 mM CaCl$_2$ | HCl/NaOH, HCl/Ca(OH)$_2$, HCl/MEA, MSA/Ca(OH)$_2$, or MSA/MEA | 0.05% (w/v) Pluronic F68 | 5.2 |
| 100 mg/mL | 10 mM acetate | 220 mM proline 25 mM CaCl$_2$ | HCl/NaOH, HCl/Ca(OH)$_2$, HCl/MEA, MSA/Ca(OH)$_2$, or MSA/MEA | 0.05% (w/v) Pluronic F68 | 5.2 |
| 100 mg/mL | 10 mM acetate | 6.9% (w/v) sucrose 30 mM MEA-HCl | HCl/NaOH, HCl/Ca(OH)$_2$, HCl/MEA, MSA/Ca(OH)$_2$, or MSA/MEA | 0.05% (w/v) Pluronic F68 | 5.2 |
| 100 mg/mL | 10 mM acetate | 7.3% (w/v) sucrose 30 mM MSA | NaOH, Ca(OH)$_2$, or MEA | 0.05% (w/v) Pluronic F68 | 5.2 |
| 100 mg/mL | 10 mM acetate | 6.9% (w/v) sucrose 35 mM NaCl | HCl/NaOH, HCl/Ca(OH)$_2$, HCl/MEA, MSA/Ca(OH)$_2$, or MSA/MEA | 0.05% (w/v) Pluronic F68 | 5.2 |
| 100 mg/mL | 10 mM acetate | 9% (w/v) sucrose | HCl/NaOH, HCl/Ca(OH)$_2$, HCl/MEA, MSA/Ca(OH)$_2$, or MSA/MEA | 0.1% (w/v) Polysorbate 80 | 5.2 |
| 100 mg/mL | 10 mM acetate | 6.8% (w/v) sucrose 25 mM CaCl$_2$ | HCl/NaOH, HCl/Ca(OH)$_2$, HCl/MEA, MSA/Ca(OH)$_2$, or MSA/MEA | 0.1% (w/v) Polysorbate 80 | 5.2 |
| 100 mg/mL | 10 mM acetate | 220 mM proline 25 mM CaCl$_2$ | HCl/NaOH, HCl/Ca(OH)$_2$, HCl/MEA, MSA/Ca(OH)$_2$, or MSA/MEA | 0.1% (w/v) Polysorbate 80 | 5.2 |
| 100 mg/mL | 10 mM acetate | 6.9% (w/v) sucrose 30 mM MEA-HCl | HCl/NaOH, HCl/Ca(OH)$_2$, | 0.1% (w/v) Polysorbate 80 | 5.2 |

TABLE F-continued

| Protein conc. | Buffer | Excipient(s) | pH Adjusting Agent | Surfactant | pH |
|---|---|---|---|---|---|
| 100 mg/mL | 10 mM acetate | 7.3% (w/v) sucrose 30 mM MSA | HCl/MEA, MSA/Ca(OH)$_2$, or MSA/MEA NaOH, Ca(OH)$_2$, or MEA | 0.1% (w/v) Polysorbate 80 | 5.2 |
| 100 mg/mL | 10 mM acetate | 6.9% (w/v) sucrose 35 mM NaCl | HCl/NaOH, HCl/Ca(OH)$_2$, HCl/MEA, MSA/Ca(OH)$_2$, or MSA/MEA | 0.1% (w/v) Polysorbate 80 | 5.2 |
| 100 mg/mL | 10 mM acetate | 9% (w/v) sucrose | HCl/NaOH, HCl/Ca(OH)$_2$, HCl/MEA, MSA/Ca(OH)$_2$, or MSA/MEA | 0.05% (w/v) Polysorbate 80 | 5.2 |
| 100 mg/mL | 10 mM acetate | 6.8% (w/v) sucrose 25 mM CaCl$_2$ | HCl/NaOH, HCl/Ca(OH)$_2$, HCl/MEA, MSA/Ca(OH)$_2$, or MSA/MEA | 0.05% (w/v) Polysorbate 80 | 5.2 |
| 100 mg/mL | 10 mM acetate | 220 mM proline 25 mM CaCl$_2$ | HCl/NaOH, HCl/Ca(OH)$_2$, HCl/MEA, MSA/Ca(OH)$_2$, or MSA/MEA | 0.05% (w/v) Polysorbate 80 | 5.2 |
| 100 mg/mL | 10 mM acetate | 6.9% (w/v) sucrose 30 mM MEA-HCl | HCl/NaOH, HCl/Ca(OH)$_2$, HCl/MEA, MSA/Ca(OH)$_2$, or MSA/MEA | 0.05% (w/v) Polysorbate 80 | 5.2 |
| 100 mg/mL | 10 mM acetate | 7.3% (w/v) sucrose 30 mM MSA | NaOH, Ca(OH)$_2$, or MEA | 0.05% (w/v) Polysorbate 80 | 5.2 |
| 100 mg/mL | 10 mM acetate | 6.9% (w/v) sucrose 35 mM NaCl | HCl/NaOH, HCl/Ca(OH)$_2$, HCl/MEA, MSA/Ca(OH)$_2$, or MSA/MEA | 0.05% (w/v) Polysorbate 80 | 5.2 |
| 100 mg/mL | 10 mM acetate | 9% (w/v) sucrose | HCl/NaOH, HCl/Ca(OH)$_2$, HCl/MEA, MSA/Ca(OH)$_2$, or MSA/MEA | 0.04% (w/v) Polysorbate 80 | 5.2 |
| 100 mg/mL | 10 mM acetate | 6.8% (w/v) sucrose 25 mM CaCl$_2$ | HCl/NaOH, HCl/Ca(OH)$_2$, HCl/MEA, MSA/Ca(OH)$_2$, or MSA/MEA | 0.04% (w/v) Polysorbate 80 | 5.2 |
| 100 mg/mL | 10 mM acetate | 220 mM proline 25 mM CaCl$_2$ | HCl/NaOH, HCl/Ca(OH)$_2$, HCl/MEA, MSA/Ca(OH)$_2$, or MSA/MEA | 0.04% (w/v) Polysorbate 80 | 5.2 |
| 100 mg/mL | 10 mM acetate | 6.9% (w/v) sucrose 30 mM MEA-HCl | HCl/NaOH, HCl/Ca(OH)$_2$, HCl/MEA, MSA/Ca(OH)$_2$, or MSA/MEA | 0.04% (w/v) Polysorbate 80 | 5.2 |
| 100 mg/mL | 10 mM acetate | 7.3% (w/v) sucrose 30 mM MSA | NaOH, Ca(OH)$_2$, or MEA | 0.04% (w/v) Polysorbate 80 | 5.2 |
| 100 mg/mL | 10 mM acetate | 6.9% (w/v) sucrose 35 mM NaCl | HCl/NaOH, HCl/Ca(OH)$_2$, HCl/MEA, MSA/Ca(OH)$_2$, | 0.04% (w/v) Polysorbate 80 | 5.2 |

TABLE F-continued

| Protein conc. | Buffer | Excipient(s) | pH Adjusting Agent | Surfactant | pH |
|---|---|---|---|---|---|
| 100 mg/mL | 10 mM acetate | 9% (w/v) sucrose | or MSA/MEA HCl/NaOH, HCl/Ca(OH)$_2$, HCl/MEA, MSA/Ca(OH)$_2$, or MSA/MEA | 0.03% (w/v) Polysorbate 80 | 5.2 |
| 100 mg/mL | 10 mM acetate | 6.8% (w/v) sucrose 25 mM CaCl$_2$ | HCl/NaOH, HCl/Ca(OH)$_2$, HCl/MEA, MSA/Ca(OH)$_2$, or MSA/MEA | 0.03% (w/v) Polysorbate 80 | 5.2 |
| 100 mg/mL | 10 mM acetate | 220 mM proline 25 mM CaCl$_2$ | HCl/NaOH, HCl/Ca(OH)$_2$, HCl/MEA, MSA/Ca(OH)$_2$, or MSA/MEA | 0.03% (w/v) Polysorbate 80 | 5.2 |
| 100 mg/mL | 10 mM acetate | 6.9% (w/v) sucrose 30 mM MEA-HCl | HCl/NaOH, HCl/Ca(OH)$_2$, HCl/MEA, MSA/Ca(OH)$_2$, or MSA/MEA | 0.03% (w/v) Polysorbate 80 | 5.2 |
| 100 mg/mL | 10 mM acetate | 7.3% (w/v) sucrose 30 mM MSA | NaOH, Ca(OH)$_2$, or MEA | 0.03% (w/v) Polysorbate 80 | 5.2 |
| 100 mg/mL | 10 mM acetate | 6.9% (w/v) sucrose 35 mM NaCl | HCl/NaOH, HCl/Ca(OH)$_2$, HCl/MEA, MSA/Ca(OH)$_2$, or MSA/MEA | 0.03% (w/v) Polysorbate 80 | 5.2 |
| 100 mg/mL | 10 mM acetate | 9% (w/v) sucrose | HCl/NaOH, HCl/Ca(OH)$_2$, HCl/MEA, MSA/Ca(OH)$_2$, or MSA/MEA | 0.1% (w/v) Polysorbate 20 | 5.2 |
| 100 mg/mL | 10 mM acetate | 6.8% (w/v) sucrose 25 mM CaCl$_2$ | HCl/NaOH, HCl/Ca(OH)$_2$, HCl/MEA, MSA/Ca(OH)$_2$, or MSA/MEA | 0.1% (w/v) Polysorbate 20 | 5.2 |
| 100 mg/mL | 10 mM acetate | 220 mM proline 25 mM CaCl$_2$ | HCl/NaOH, HCl/Ca(OH)$_2$, HCl/MEA, MSA/Ca(OH)$_2$, or MSA/MEA | 0.1% (w/v) Polysorbate 20 | 5.2 |
| 100 mg/mL | 10 mM acetate | 6.9% (w/v) sucrose 30 mM MEA-HCl | HCl/NaOH, HCl/Ca(OH)$_2$, HCl/MEA, MSA/Ca(OH)$_2$, or MSA/MEA | 0.1% (w/v) Polysorbate 20 | 5.2 |
| 100 mg/mL | 10 mM acetate | 7.3% (w/v) sucrose 30 mM MSA | NaOH, Ca(OH)$_2$, or MEA | 0.1% (w/v) Polysorbate 20 | 5.2 |
| 100 mg/mL | 10 mM acetate | 6.9% (w/v) sucrose 35 mM NaCl | HCl/NaOH, HCl/Ca(OH)$_2$, HCl/MEA, MSA/Ca(OH)$_2$, or MSA/MEA | 0.1% (w/v) Polysorbate 20 | 5.2 |
| 100 mg/mL | 10 mM acetate | 9% (w/v) sucrose | HCl/NaOH, HCl/Ca(OH)$_2$, HCl/MEA, MSA/Ca(OH)$_2$, or MSA/MEA | 0.05% (w/v) Polysorbate 20 | 5.2 |
| 100 mg/mL | 10 mM acetate | 6.8% (w/v) sucrose 25 mM CaCl$_2$ | HCl/NaOH, HCl/Ca(OH)$_2$, HCl/MEA, | 0.05% (w/v) Polysorbate 20 | 5.2 |

TABLE F-continued

| Protein conc. | Buffer | Excipient(s) | pH Adjusting Agent | Surfactant | pH |
|---|---|---|---|---|---|
| 100 mg/mL | 10 mM acetate | 220 mM proline 25 mM CaCl$_2$ | MSA/Ca(OH)$_2$, or MSA/MEA HCl/NaOH, HCl/Ca(OH)$_2$, HCl/MEA, MSA/Ca(OH)$_2$, or MSA/MEA | 0.05% (w/v) Polysorbate 20 | 5.2 |
| 100 mg/mL | 10 mM acetate | 6.9% (w/v) sucrose 30 mM MEA-HCl | HCl/NaOH, HCl/Ca(OH)$_2$, HCl/MEA, MSA/Ca(OH)$_2$, or MSA/MEA | 0.05% (w/v) Polysorbate 20 | 5.2 |
| 100 mg/mL | 10 mM acetate | 7.3% (w/v) sucrose 30 mM MSA | NaOH, Ca(OH)$_2$, or MEA | 0.05% (w/v) Polysorbate 20 | 5.2 |
| 100 mg/mL | 10 mM acetate | 6.9% (w/v) sucrose 35 mM NaCl | HCl/NaOH, HCl/Ca(OH)$_2$, HCl/MEA, MSA/Ca(OH)$_2$, or MSA/MEA | 0.05% (w/v) Polysorbate 20 | 5.2 |

Exemplary aqueous adalimumab formulations are also provided in Tables 8, 9, 12, 14 and 15. In an embodiment, the stable aqueous adalimumab formulation is one of the acetate formulations described in Tables D, E, F, 8, 9, 12, 14 or 15 provided herein.

In an embodiment, a lyophilized form of any one of the foregoing acetate-containing adalimumab formulations is provided.

Formulations of Adalimumab with Benzoate Buffer

In an embodiment, the stable aqueous adalimumab formulation includes adalimumab at a concentration of about 40 to about 200 mg/mL, such as about 90 to about 120 mg/mL, about 170 to about 190, about 160 to about 190 mg/mL, about 60 to about 90 mg/mL, about 40 to about 60 mg/mL, about 50 mg/mL, about 100 mg/mL, or about 170 mg/mL, benzoate at a concentration of about 5 mM to about 50 mM (e.g., about 10 mM to about 30 mM, about 10 mM, about 15 mM, about 20 mM, and/or about 25 mM), and one or more excipients. Suitable excipients include certain stabilizers such as certain amino acids and amino acid derivatives, certain polyols, certain acids, certain amines, certain salts, and certain surfactants. Examples of suitable amino acids and amino acid derivatives include proline (e.g., at a concentration of about 0.1 to about 450 mM, about 50 to about 300 mM, or about 250 mM to about 350 mM). Examples of suitable polyols include sucrose (e.g., at a concentration of about 0.1% (w/v) to about 15% (w/v), about 4% (w/v) to about 10% (w/v), about 4% (w/v) to about 9% (w/v), about 6.5% (w/v), about 6.8% (w/v), about 6.9% (w/v), about 9% (w/v)) and sorbitol (e.g., at a concentration of about 0.1% (w/v) to about 10% (w/v), about 3% (w/v) to about 5% (w/v), and/or about 4% (w/v)). Examples of suitable acids include methane sulfonic acid (MSA) (e.g., at a concentration of about 0.1 to about 150 mM or about 0.1 to about 50 mM). Examples of suitable amines include MEA-HCl (e.g., at a concentration of about 0.1 to about 150 mM or about 0.1 to about 40 mM) and MEA (e.g., at a concentration of about 0.1 to about 300 mM or about 0.1 to about 50 mM). Examples of suitable salts include sodium chloride (e.g., at a concentration of about 10 to about 100 mM, about 60 to about 90 mM, about 15 to about 50 mM, and/or about 35 mM) and calcium chloride (e.g., at a concentration of about 1 to about 150 mM, about 5 to about 50 mM, about 10 to about 30 mM, about 20 to about 40 mM, about 30 to about 50 mM, about 40 to about 80 mM, about 50 to about 100 mM, or about 25 mM). Examples of suitable surfactants include Pluronic F68 (e.g., at a concentration of about 0.001% (w/v) to about 10% (w/v), about 0.005% (w/v) to about 1% (w/v), about 0.05% (w/v) to about 0.4% (w/v), about 0.05% (w/v) to about 0.1% (w/v), about 0.01% (w/v), about 0.05% (w/v), and/or about 0.1% (w/v)), Polysorbate 20 (e.g., at a concentration of about 0.001% (w/v) to about 2% (w/v) or about 0.005% (w/v) to about 0.1% (w/v)), and Polysorbate 80 (e.g., at a concentration of about 0.001% (w/v) to about 2% (w/v), about 0.005% (w/v) to about 0.1% (w/v), about 0.005% (w/v) to about 0.05% (w/v), about 0.03% (w/v) to about 0.1% (w/v), about 0.04% (w/v) to about 0.1% (w/v), about 0.03% (w/v), about 0.04% (w/v), and/or about 0.1% (w/v)). Optionally, the benzoate-containing stable aqueous adalimumab formulation has a pH of about 4.8 to about 5.7, for example, about 4.9 to about 5.6, about 5.0 to about 5.5, about 5.1 to about 5.4, about 5.1 to about 5.3, about 5.1 to about 5.2, about 5.2 to about 5.3, and/or about 5.2. Optionally, the pH of the stable aqueous adalimumab formulation is adjusted using a strong acid and/or a strong base including, but not limited to, hydrochloric acid, sodium hydroxide, calcium hydroxide, MSA, and/or MEA.

In an embodiment, the stable aqueous adalimumab formulation includes adalimumab at a concentration of about 40 to about 200 mg/mL, such as about 90 to about 120 mg/mL, about 170 to about 190, about 160 to about 190 mg/mL, about 60 to about 90 mg/mL, about 40 to about 60 mg/mL, about 50 mg/mL, about 100 mg/mL, or about 170 mg/mL, benzoate at a concentration of about 5 mM to about 50 mM (e.g., about 10 mM to about 30 mM, about 10 mM, about 15 mM, about 20 mM, and/or about 25 mM), and one or more excipients selected from the group consisting of proline at a concentration of about 0.1 to about 450 mM (e.g., about 50 to about 300 mM or about 250 mM to about 350 mM), sodium chloride at a concentration of about 10 to about 100 mM (e.g., about 60 to about 90 mM, about 15 to about 50 mM, and/or about 35 mM), calcium chloride at a concentration of about 1 to about 150 mM (e.g., about 5 to about 50 mM, about 10 to about 30 mM, about 20 to about 40 mM, about 30 to about 50 mM, about 40 to about 80 mM, about 50 to about 100 mM, or about 25 mM), sucrose at a concentration of about 0.1% (w/v) to about 15% (w/v) (e.g., about 4% (w/v) to about 10% (w/v), about 4% (w/v) to about 9% (w/v), about 6.5% (w/v), about 6.8% (w/v), about 6.9% (w/v), about 9% (w/v)), sorbitol at a concentration of about 0.1% (w/v) to about 10% (w/v) (e.g., about 3% (w/v) to about 5% (w/v) and/or about 4% (w/v)), methane sulfonic acid (MSA) at a concentration of about 0.1 to about 150 mM (e.g., about 0.1 to about 50 mM), MEA-HCl at a concentration of about 0.1 to about 150 mM (e.g., about 0.1 to about 40 mM), MEA at a concentration of about 0.1 to about 300 mM (e.g., about 0.1 to about 50 mM), Pluronic F68 at a concentration of about 0.001% (w/v) to about 10% (w/v) (e.g., about 0.005% (w/v) to about 1% (w/v), about 0.05% (w/v) to about 0.4% (w/v), about 0.01% (w/v), about 0.05% (w/v) to about 0.1% (w/v), about 0.05% (w/v), and/or about 0.1% (w/v)), Polysorbate 20 at a concentration of about 0.001% (w/v) to about 2% (w/v) (e.g., about 0.005% (w/v) to about 0.1% (w/v)), and Polysorbate 80 at a concentration of about 0.001% (w/v) to about 2% (w/v) (e.g., about 0.005% (w/v) to about 0.1% (w/v), about 0.005% (w/v) to about 0.05% (w/v), about 0.03% (w/v) to about 0.1% (w/v), about 0.04% (w/v) to about 0.1% (w/v), about 0.03% (w/v), about 0.04% (w/v), and/or about 0.1% (w/v)). Optionally, the benzoate-containing stable aqueous adalimumab formulation has a pH of about 4.8 to about 5.7, for example, about 4.9 to about 5.6, about 5.0 to about 5.5, about 5.1 to about 5.4, about 5.1 to about 5.3, about 5.1 to about 5.2, about 5.2 to about 5.3, and/or about 5.2. Optionally, the pH of the stable aqueous adalimumab formulation is adjusted using a strong acid and/or a strong base including, but not limited to, hydrochloric acid, sodium hydroxide, calcium hydroxide, MSA, and/or MEA.

In an embodiment, the stable aqueous adalimumab formulation includes adalimumab at a concentration of about 60 to about 90 mg/mL, benzoate at a concentration of about 10 mM to about 30 mM, and proline at a concentration of about 250 to about 350 mM, and has a pH of about 5.1 to 5.3. Optionally, the pH of the formulation is adjusted within this range with MEA.

In an embodiment, the stable aqueous adalimumab formulation includes adalimumab at a concentration of about 90 to about 120 mg/mL, benzoate at a concentration of about 10 mM to about 30 mM, and proline at a concentration of about 250 to about 350 mM, and has a pH of about 5.1 to 5.3. Optionally, the pH of the formulation is adjusted within this range with NaOH.

In an embodiment, a lyophilized form of any one of the foregoing benzoate-containing adalimumab formulations is provided.

Formulations of Adalimumab with Glycolate Buffer

In an embodiment, the stable aqueous adalimumab formulation includes adalimumab at a concentration of about 40 to about 200 mg/mL, such as about 90 to about 120 mg/mL, about 170 to about 190, about 160 to about 190 mg/mL, about 60 to about 90 mg/mL, about 40 to about 60 mg/mL, about 50 mg/mL, about 100 mg/mL, or about 170 mg/mL, glycolate at a concentration of about 5 mM to about 50 mM (e.g., about 10 mM to about 30 mM, about 10 mM, about 15 mM, about 20 mM, and/or about 25 mM), and one or more excipients. Suitable excipients include certain stabilizers such as certain amino acids and amino acid derivatives, certain polyols, certain acids, certain amines, certain salts, and certain surfactants. Examples of suitable amino acids and amino acid derivatives include proline (e.g., at a concentration of about 0.1 to about 450 mM, about 250 mM to about 350 mM, or about 50 to about 300 mM). Examples of suitable polyols include sucrose (e.g., at a concentration of about 0.1% (w/v) to about 15% (w/v), about 4% (w/v) to about 10% (w/v), about 4% (w/v) to about 9% (w/v), about 6.5% (w/v), about 6.8% (w/v), about 6.9% (w/v), about 9% (w/v)) and sorbitol (e.g., at a concentration of about 0.1% (w/v) to about 10% (w/v), about 3% (w/v) to about 5% (w/v), and/or about 4% (w/v)). Examples of suitable acids include methane sulfonic acid (MSA) (e.g., at a concentration of about 0.1 to about 150 mM or about 0.1 to about 50 mM). Examples of suitable amines include MEA-HCl (e.g., at a concentration of about 0.1 to about 150 mM or about 0.1 to about 40 mM) and MEA (e.g., at a concentration of about 0.1 to about 300 mM or about 0.1 to about 50 mM). Examples of suitable salts include sodium chloride (e.g., at a concentration of about 10 to about 100 mM, about 60 to about 90 mM, about 15 to about 50 mM, and/or about 35 mM) and calcium chloride (e.g., at a concentration of about 1 to about 150 mM, about 5 to about 50 mM, about 10 to about 30 mM, about 20 to about 40 mM, about 30 to about 50 mM, about 40 to about 80 mM, about 50 to about 100 mM, or about 25 mM). Examples of suitable surfactants include Pluronic F68 (e.g., at a concentration of about 0.001% (w/v) to about 10% (w/v), about 0.005% (w/v) to about 1% (w/v), about 0.05% (w/v) to about 0.4% (w/v), about 0.05% (w/v) to about 0.1% (w/v), about 0.01% (w/v), about 0.05% (w/v), and/or about 0.1% (w/v)), Polysorbate 20 (e.g., at a concentration of about 0.001% (w/v) to about 2% (w/v) or about 0.005% (w/v) to about 0.1% (w/v)), and Polysorbate 80 (e.g., at a concentration of about 0.001% (w/v) to about 2% (w/v), about 0.005% (w/v) to about 0.1% (w/v), about 0.005% (w/v) to about 0.05% (w/v), about 0.03% (w/v) to about 0.1% (w/v), about 0.04% (w/v) to about 0.1% (w/v), about 0.03% (w/v), about 0.04% (w/v), and/or about 0.1% (w/v)). Optionally, the glycolate-containing stable aqueous adalimumab formulation has a pH of about 4.8 to about 5.7, for example, about 4.9 to about 5.6, about 5.0 to about 5.5, about 5.1 to about 5.4, about 5.1 to about 5.3, about 5.1 to about 5.2, about 5.2 to about 5.3, and/or about 5.2. Optionally, the pH of the stable aqueous adalimumab formulation is adjusted using a strong acid and/or a strong base including, but not limited to, hydrochloric acid, sodium hydroxide, calcium hydroxide, MSA, and/or MEA.

In an embodiment, the stable aqueous adalimumab formulation includes adalimumab at a concentration of about 40 to about 200 mg/mL, such as about 90 to about 120 mg/mL, about 170 to about 190, about 160 to about 190 mg/mL, about 60 to about 90 mg/mL, about 40 to about 60 mg/mL, about 50 mg/mL, about 100 mg/mL, or about 170 mg/mL, glycolate at a concentration of about 5 mM to about 50 mM (e.g., about 10 mM to about 30 mM, about 10 mM, about 15 mM, about 20 mM, and/or about 25 mM), and one or more excipients selected from the group consisting of proline at a concentration of about 0.1 to about 450 mM (e.g., about 250 mM to about 350 mM or about 50 to about 300 mM), sodium chloride at a concentration of about 10 to about 100 mM (e.g., about 60 to about 90 mM, about 15 to about 50 mM, and/or about 35 mM), calcium chloride at a concentration of about 1 to about 150 mM (e.g., about 5 to about 50 mM, about 10 to about 30 mM, about 20 to about 40 mM, about 30 to about 50 mM, about 40 to about 80 mM, about 50 to about 100 mM, or about 25 mM), sucrose at a concentration of about 0.1% (w/v) to about 15% (w/v) (e.g., about 4% (w/v) to about 10% (w/v), about 4% (w/v) to about 9% (w/v), about 6.5% (w/v), about 6.8% (w/v), about 6.9% (w/v), about 9% (w/v)), sorbitol at a concentration of about 0.1% (w/v) to about 10% (w/v) (e.g., about 3% (w/v) to about 5% (w/v) and/or about 4% (w/v)), methane sulfonic acid (MSA) at a concentration of about 0.1 to about 150 mM (e.g., about 0.1 to about 50 mM), MEA-HCl at a concentration of about 0.1 to about 150 mM (e.g., about 0.1 to about 40 mM), MEA at a concentration of about 0.1 to about 300 mM (e.g., about 0.1 to about 50 mM), Pluronic F68 at a concentration of about 0.001% (w/v) to about 10% (w/v) (e.g., about 0.005% (w/v) to about 1% (w/v), about 0.05% (w/v) to about 0.4% (w/v), about 0.05% (w/v) to about 0.1% (w/v), about 0.01% (w/v), about 0.05% (w/v), and/or about 0.1% (w/v)), Polysorbate 20 at a concentration of about 0.001% (w/v) to about 2% (w/v) (e.g., about 0.005% (w/v) to about 0.1% (w/v)), and Polysorbate 80 at a concentration of about 0.001% (w/v) to about 2% (w/v) (e.g., about 0.005% (w/v) to about 0.1% (w/v), about 0.005% (w/v) to about 0.05% (w/v), about 0.03% (w/v) to about 0.1% (w/v), about 0.04% (w/v) to about 0.1% (w/v), about 0.03% (w/v), about 0.04% (w/v), and/or about 0.1% (w/v)). Optionally, the glycolate-containing stable aqueous adalimumab formulation has a pH of about 4.8 to about 5.7, for example, about 4.9 to about 5.6, about 5.0 to about 5.5, about 5.1 to about 5.4, about 5.1 to about 5.3, about 5.1 to about 5.2, about 5.2 to about 5.3, and/or about 5.2. Optionally, the pH of the stable aqueous adalimumab formulation is adjusted using a strong acid and/or a strong base including, but not limited to, hydrochloric acid, sodium hydroxide, calcium hydroxide, MSA, and/or MEA.

In an embodiment, the stable aqueous adalimumab formulation includes adalimumab at a concentration of about 90 to about 120 mg/mL, glycolate at a concentration of about 10 mM to about 30 mM, and proline at a concentration of about 250 to about 350 mM, and has a pH of about 5.1 to 5.3. Optionally, the pH of the formulation is adjusted within this range with MEA or NaOH.

In an embodiment, a lyophilized form of any one of the foregoing glycolate-containing adalimumab formulations is provided.

Formulations of Adalimumab with Lactate Buffer

In an embodiment, the stable aqueous adalimumab formulation includes adalimumab at a concentration of about 40 to about 200 mg/mL, such as about 90 to about 120 mg/mL, about 160 to 190 mg/mL, about 40 to about 60 mg/mL, about 50 mg/mL, about 100 mg/mL, or about 170 mg/mL, lactic acid and/or lactate at a concentration of about 0.1 mM to about 300 mM (e.g., about 2 mM to about 30 mM, about 10 mM to about 30 mM, about 5 mM to about 15 mM, about 10 mM, about 15 mM, about 20 mM, and/or about 25 mM), and one or more excipients. Suitable excipients include certain stabilizers such as certain amino acids and amino acid derivatives, certain polyethylene glycols and polyethylene glycol derivatives, certain salts, certain polyols, certain acids, certain amines, and certain surfactants. Examples of suitable amino acids include proline (e.g., at a concentration of about 0.1 to about 450 mM, about 50 to about 300 mM, about 110 to about 300 mM, about 250 to about 350 mM, about 190 to about 250 mM, and/or about 220 mM). Examples of suitable polyethylene glycols include PEG 600 (e.g., at a concentration of about 0.1% (w/v) to about 30% (w/v) or about 4% (w/v) to about 13% (w/v)), PEG 400 (e.g., at a concentration of about 0.1% (w/v) to about 20% (w/v) or about 0.5% (w/v) to about 2% (w/v)), and PEG 200 (e.g., at a concentration of about 0.1% (w/v) to about 10% (w/v) or about 1.6% (w/v) to about 3.8% (w/v)). Examples of suitable salts include calcium chloride (e.g., at a concentration of about 1 to about 150 mM, about 5 to about 50 mM, about 10 to about 30 mM, about 20 to about 30 mM, about 20 to about 40 mM, about 30 to about 50 mM, about 40 to about 80 mM, about 50 to about 100 mM, or about 25 mM) and sodium chloride (e.g., at a concentration of about 10 to about 100 mM, about 60 to about 90 mM, about 15 to about 50 mM, or about 35 mM). Examples of suitable polyols include sucrose (e.g., at a concentration of about 0.1% (w/v) to about 15% (w/v), about 4% (w/v) to about 10% (w/v), about 4% (w/v) to about 9% (w/v), about 6.5% (w/v), about 6.8% (w/v), about 6.9% (w/v), about 9% (w/v)) and sorbitol (e.g., at a concentration of about 0.1% (w/v) to about 10% (w/v), about 3% (w/v) to about 5% (w/v), and/or about 4% (w/v)). Examples of suitable acids include methane sulfonic acid (MSA) (e.g., at a concentration of about 0.1 to about 150 mM or about 0.1 to about 50 mM). Examples of suitable amines include monoethanolamide hydrochloride (MEA-HCl) (e.g., at a concentration of about 0.1 to about 150 mM or about 0.1 to about 40 mM) and monoethanolamide (MEA) (e.g., at a concentration of about 0.1 to about 300 mM or about 0.1 to about 50 mM). Examples of suitable surfactants include Pluronic F68 (e.g., at a concentration of about 0.001% (w/v) to about 10% (w/v), about 0.005% (w/v) to about 1% (w/v), about 0.05% (w/v) to about 0.5% (w/v), about 0.05% (w/v) to about 0.4% (w/v), about 0.05% (w/v) to about 0.1% (w/v), about 0.01% (w/v), about 0.05% (w/v), and/or about 0.1% (w/v)), Polysorbate 20 (e.g., at a concentration of about 0.001% (w/v) to about 2% (w/v) or about 0.005% (w/v) to about 0.1% (w/v)), and Polysorbate 80 (e.g., at a concentration of about 0.001% (w/v) to about 2% (w/v), about 0.005% (w/v) to about 0.1% (w/v), about 0.005% (w/v) to about 0.05% (w/v), about 0.03% (w/v) to about 0.1% (w/v), 0.04% (w/v) to about 0.1% (w/v), about 0.05% (w/v) to about 0.1% (w/v), about 0.03% (w/v), about 0.04% (w/v), and/or about 0.1% (w/v)). Optionally, the lactate-containing stable aqueous adalimumab formulation has a pH of about 4.8 to about 5.7, for example, about 4.9 to about 5.6, about 5.0 to about 5.5, about 5.1 to about 5.4, about 5.1 to about 5.3, about 5.1 to about 5.2, about 5.2 to about 5.3, and/or about 5.2. Optionally, the pH of the stable aqueous adalimumab formulation is adjusted using a strong acid and/or a strong base including, but not limited to, hydrochloric acid, sodium hydroxide, calcium hydroxide, MSA, and/or MEA.

In an embodiment, the stable aqueous adalimumab formulation includes adalimumab at a concentration of about 40 to about 200 mg/mL, such as about 90 to about 120 mg/mL, about 160 to 190 mg/mL, or about 40 to about 60 mg/mL, about 50 mg/mL, about 100 mg/mL, or about 170 mg/mL, lactic acid and/or lactate at a concentration of about 0.1 mM to about 300 mM (e.g., about 2 mM to about 30 mM, about 10 mM to about 30 mM, about 5 mM to about 15 mM, about 10 mM, about 15 mM, about 20 mM, and/or about 25 mM), and one or more excipients selected from the group consisting of proline at a concentration of about 0.1 to about 450 mM (e.g., about 50 to about 300 mM, about 110 to about 300 mM, about 250 to about 350 mM, about 190 to about 250 mM, and/or about 220 mM), PEG 600 at a concentration of about 0.1% (w/v) to about 30% (w/v) (e.g., about 4% (w/v) to about 13% (w/v)), PEG 400 at a concentration of about 0.1% (w/v) to about 20% (w/v) (e.g., about 0.5% (w/v) to about 2% (w/v)), PEG 200 at a concentration of about 0.1% (w/v) to about 10% (w/v) (e.g., about 1.6% (w/v) to about 3.8% (w/v)), calcium chloride at a concentration of about 1 to about 150 mM (e.g., about 5 to about 50 mM, about 10 to about 30 mM, about 20 to about 30 mM, about 20 to about 40 mM, about 30 to about 50 mM, about 40 to about 80 mM, about 50 to about 100 mM, or about 25 mM), sodium chloride at a concentration of about 10 to about 100 mM (e.g., about 60 to about 90 mM, about 15 to about 50 mM, and/or about 35 mM), sucrose at a concentration of about 0.1% (w/v) to about 15% (w/v) (e.g., about 4% (w/v) to about 10% (w/v), about 4% (w/v) to about 9% (w/v), about 6.5% (w/v), about 6.8% (w/v), about 6.9% (w/v), about 9% (w/v)), sorbitol at a concentration of about 0.1% (w/v) to about 10% (w/v) (e.g., about 3% (w/v) to about 5% (w/v) and/or about 4% (w/v)), methane sulfonic acid (MSA) at a concentration of about 0.1 to about 150 mM (e.g., about 0.1 to about 50 mM), monoethanolamide hydrochloride (MEA-HCl) at a concentration of about 0.1 to about 150 mM (e.g., about 0.1 to about 40 mM), monoethanolamide (MEA) at a concentration of about 0.1 to about 300 mM (e.g., about 0.1 to about 50 mM), Pluronic F68 at a concentration of about 0.001% (w/v) to about 10% (w/v) (e.g., about 0.005% (w/v) to about 1% (w/v), about 0.05% (w/v) to about 0.5% (w/v), about 0.05% (w/v) to about 0.4% (w/v), about 0.05% (w/v) to about 0.1% (w/v), about 0.01% (w/v), about 0.05% (w/v), and/or about 0.1% (w/v)), Polysorbate 20 at a concentration of about 0.001% (w/v) to about 2% (w/v) (e.g., about 0.005% (w/v) to about 0.1% (w/v)), and Polysorbate 80 at a concentration of about 0.001% (w/v) to about 2% (w/v) (e.g., about 0.005% (w/v) to about 0.1% (w/v), about 0.005% (w/v) to about 0.05% (w/v), about 0.03% (w/v) to about 0.1% (w/v), 0.04% (w/v) to about 0.1% (w/v), about 0.05% (w/v) to about 0.1% (w/v), about 0.03% (w/v), about 0.04% (w/v), and/or about 0.1% (w/v)). Optionally, the lactate-containing stable aqueous adalimumab formulation has a pH of about 4.8 to about 5.7, for example, about 4.9 to about 5.6, about 5.0 to about 5.5, about 5.1 to about 5.4, about 5.1 to about 5.3, about 5.1 to about 5.2, about 5.2 to about 5.3, and/or about 5.2. Optionally, the pH of the stable aqueous adalimumab formulation is adjusted using a strong acid and/or a strong base including, but not limited to, hydrochloric acid, sodium hydroxide, calcium hydroxide, MSA, and/or MEA.

In an embodiment, the stable aqueous adalimumab formulation includes adalimumab at a concentration of about 90 to about 120 mg/mL, lactate at a concentration of 10 mM to about 30 mM, and proline at a concentration of about 250 to about 350 mM, and has a pH of about 5.1 to 5.3. Optionally, the pH of the formulation is adjusted within this range with MEA or NaOH.

In an embodiment, the stable aqueous adalimumab formulation includes adalimumab at a concentration of about 90 to about 120 mg/mL, lactate at a concentration of 5 mM to about 15 mM, PEG 600 at a concentration of about 8% (w/v) to about 9% (w/v), and Pluronic F68 at a concentration of about 0.05% (w/v) to about 0.5% (w/v), and has a pH of about 5.1 to 5.3.

In an embodiment, the stable aqueous adalimumab formulation includes adalimumab at a concentration of about 90 to about 120 mg/mL, lactate at a concentration of 5 mM to about 15 mM, PEG 600 at a concentration of about 3% (w/v) to about 5% (w/v), PEG 200 at a concentration of about 1.2% (w/v) to about 2% (w/v), and Pluronic F68 at a concentration of about 0.05% (w/v) to about 0.5% (w/v), and has a pH of about 5.1 to 5.3.

In an embodiment, the stable aqueous adalimumab formulation includes adalimumab at a concentration of about 160 to about 190 mg/mL, lactate at a concentration of about 5 mM to about 15 mM, PEG 600 at a concentration of about 8% (w/v) to about 9% (w/v), and Pluronic F68 at a concentration of about 0.05% (w/v) to about 0.5% (w/v), and has a pH of about 5.1 to 5.3.

In an embodiment, the stable aqueous adalimumab formulation includes adalimumab at a concentration of about 160 to about 190 mg/mL, lactate at a concentration of about 5 mM to about 15 mM, PEG 600 at a concentration of about 3% (w/v) to about 5% (w/v), PEG 200 at a concentration of about 1.2% (w/v) to about 2% (w/v), and Pluronic F68 at a concentration of about 0.05% (w/v) to about 0.5% (w/v), and has a pH of about 5.1 to 5.3.

In an embodiment, the stable aqueous adalimumab formulation includes adalimumab at a concentration of about 160 to about 190 mg/mL, lactate at a concentration of about 5 mM to about 15 mM, PEG 200 at a concentration of about 3.5% (w/v) to about 4.2% (w/v), and Pluronic F68 at a concentration of about 0.05% (w/v) to about 0.5% (w/v), and has a pH of about 5.1 to 5.3.

In an embodiment, the stable aqueous adalimumab formulation includes adalimumab at a concentration of about 160 to about 190 mg/mL, lactate at a concentration of about 5 mM to about 15 mM, proline at a concentration of about 190 to about 250 mM, and Pluronic F68 at a concentration of about 0.05% (w/v) to about 0.5% (w/v), and has a pH of about 5.1 to 5.3.

In an embodiment, the stable aqueous adalimumab formulation includes adalimumab at a concentration of about 90 to about 120 mg/mL, lactate at a concentration of about 5 mM to about 15 mM, proline at a concentration of about 190 to about 240 mM, calcium chloride at a concentration of about 15 to about 35 mM, and Pluronic F68 at a concentration of about 0.05% (w/v) to about 0.5% (w/v), and has a pH of about 5.1 to 5.3. Optionally, the pH of the formulation is adjusted within this range with MSA and/or MEA.

In an embodiment, the stable aqueous adalimumab formulation includes adalimumab at a concentration of about 160 to about 190 mg/mL, lactate at a concentration of about 5 mM to about 15 mM, proline at a concentration of about 200 to about 250 mM, calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MSA and/or MEA.

In an embodiment, the stable aqueous adalimumab formulation includes adalimumab at a concentration of about 160 to about 190 mg/mL, lactate at a concentration of about 5 mM to about 15 mM, PEG 600 at a concentration of about 11% (w/v) to about 15% (w/v), calcium chloride at a concentration of about 20 to about 40 mM, and Pluronic F68 at a concentration of about 0.05% (w/v) to about 0.5% (w/v), and has a pH of about 5.1 to 5.3. Optionally, the pH of the formulation is adjusted within this range with MSA and/or MEA.

In an embodiment, the stable aqueous adalimumab formulation includes adalimumab at a concentration of about 160 to about 190 mg/mL, lactate at a concentration of about 5 mM to about 15 mM, PEG 600 at a concentration of about 11% (w/v) to about 15% (w/v), calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MSA and/or MEA.

In an embodiment, the stable aqueous adalimumab formulation includes adalimumab at a concentration of about 160 to about 190 mg/mL, lactate at a concentration of about 5 mM to about 15 mM, PEG 600 at a concentration of about 8% (w/v) to about 9% (w/v), calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MSA and/or MEA.

In an embodiment, the stable aqueous adalimumab formulation includes adalimumab at a concentration of about 160 to about 190 mg/mL, lactate at a concentration of about 5 mM to about 15 mM, PEG 600 at a concentration of about 3% (w/v) to about 5% (w/v), PEG 200 at a concentration of about 1.2% (w/v) to about 2% (w/v), calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MSA and/or MEA.

In an embodiment, the stable aqueous adalimumab formulation includes adalimumab at a concentration of about 160 to about 190 mg/mL, lactate at a concentration of about 5 mM to about 15 mM, PEG 200 at a concentration of about 3.5% (w/v) to about 4.2% (w/v), calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MSA and/or MEA.

In an embodiment, the stable aqueous adalimumab formulation includes adalimumab at a concentration of about 160 to about 190 mg/mL, lactate at a concentration of about 5 mM to about 15 mM, PEG 600 at a concentration of about 5% (w/v) to about 5.7% (w/v), calcium chloride at a concentration of about 10 to about 30 mM, proline at a concentration of about 90 to about 130 mM, and Pluronic F68 at a concentration of about 0.05% (w/v) to about 0.5% (w/v), and has a pH of about 5.1 to 5.3. Optionally, the pH of the formulation is adjusted within this range with MSA and/or MEA.

In an embodiment, the stable aqueous adalimumab formulation includes adalimumab at a concentration of about 160 to about 190 mg/mL, lactate at a concentration of about 5 mM to about 15 mM, calcium chloride at a concentration of about 10 to about 30 mM, proline at a concentration of about 190 to about 250 mM, and Pluronic F68 at a concentration of about 0.05% (w/v) to about 0.5% (w/v), and has a pH of about 5.1 to 5.3. Optionally, the pH of the formulation is adjusted within this range with MSA and/or MEA.

In an embodiment, the stable aqueous adalimumab formulation includes adalimumab at a concentration of about 90 to about 120 mg/mL, lactate at a concentration of about 5 mM to about 15 mM, calcium chloride at a concentration of about 15 to about 35 mM, proline at a concentration of about 190 to about 250 mM, and Pluronic F68 at a concentration of about 0.05% (w/v) to about 0.5% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, lactate at a concentration of about 5 mM to about 15 mM, calcium chloride at a concentration of about 15 to about 35 mM, proline at a concentration of about 190 to about 250 mM, and Pluronic F68 at a concentration of about 0.01% (w/v) to about 0.1% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, lactate at a concentration of about 5 mM to about 15 mM, sucrose at a concentration of about 8% (w/v) to about 10% (w/v), and Pluronic F68 at a concentration of about 0.05% (w/v) to about 0.5% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, lactate at a concentration of about 5 mM to about 15 mM, sucrose at a concentration of about 8% (w/v) to about 10% (w/v), and Pluronic F68 at a concentration of about 0.01% (w/v) to about 0.1% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 110 mg/mL, lactate at a concentration of about 5 mM to about 15 mM, sucrose at a concentration of about 8.5% (w/v) to about 9.5% (w/v), and Pluronic F68 at a concentration of about 0.03% (w/v) to about 0.1% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, lactate at a concentration of about 5 mM to about 15 mM, sucrose at a concentration of about 8% (w/v) to about 10% (w/v), calcium chloride at a concentration of about 15 mM to about 35 mM, and Pluronic F68 at a concentration of about 0.005% (w/v) to about 0.05% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, lactate at a concentration of about 5 mM to about 15 mM, sucrose at a concentration of about 8% (w/v) to about 10% (w/v), calcium chloride at a concentration of about 15 mM to about 35 mM, and Pluronic F68 at a concentration of about 0.01% (w/v) to about 0.1% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, lactate at a concentration of about 5 mM to about 15 mM, calcium chloride at a concentration of about 15 to about 35 mM, proline at a concentration of about 190 to about 250 mM, and Polysorbate 80 at a concentration of about 0.05% (w/v) to about 0.5% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, lactate at a concentration of about 5 mM to about 15 mM, calcium chloride at a concentration of about 15 to about 35 mM, proline at a concentration of about 190 to about 250 mM, and Polysorbate 80 at a concentration of about 0.01% (w/v) to about 0.1% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, lactate at a concentration of about 5 mM to about 15 mM, sucrose at a concentration of about 8% (w/v) to about 10% (w/v), and Polysorbate 80 at a concentration of about 0.05% (w/v) to about 0.5% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, lactate at a concentration of about 5 mM to about 15 mM, sucrose at a concentration of about 8% (w/v) to about 10% (w/v), and Polysorbate 80 at a concentration of about 0.01% (w/v) to about 0.1% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, lactate at a concentration of about 5 mM to about 15 mM, calcium chloride at a concentration of about 15 to about 35 mM, proline at a concentration of about 190 to about 250 mM, and Polysorbate 20 at a concentration of about 0.05% (w/v) to about 0.5% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, lactate at a concentration of about 5 mM to about 15 mM, calcium chloride at a concentration of about 15 to about 35 mM, proline at a concentration of about 190 to about 250 mM, and Polysorbate 20 at a concentration of about 0.01% (w/v) to about 0.1% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, lactate at a concentration of about 5 mM to about 15 mM, sucrose at a concentration of about 8% (w/v) to about 10% (w/v), and Polysorbate 20 at a concentration of about 0.05% (w/v) to about 0.5% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 90 to about 120 mg/mL, lactate at a concentration of about 5 mM to about 15 mM, sucrose at a concentration of about 8% (w/v) to about 10% (w/v), and Polysorbate 20 at a concentration of about 0.01% (w/v) to about 0.1% (w/v), and has a pH of about 5.1 to 5.3. Optionally, the pH of the formulation is adjusted within this range with HCl, NaOH, Ca(OH)$_2$, MEA, and/or MSA.

In an embodiment, the stable aqueous adalimumab formulation includes adalimumab at a concentration of about 40 mg/ml to about 200 mg/ml, or about 160 mg/ml to about 190 mg/mL, or about 80 mg/ml to about 120 mg/ml, or about 90 mg/ml to about 110 mg/ml, or about 95 mg/ml to about 105 mg/ml, or about 40 mg/ml, or about 45 mg/ml, or about 50 mg/ml, or about 55 mg/ml, or about 60 mg/ml, or about 65 mg/ml, or about 70 mg/ml, or about 75 mg/ml, or about 80 mg/ml, or about 85 mg/ml, or about 90 mg/ml, or about 95 mg/ml, or about 100 mg/ml, or about 105 mg/ml, or about 110 mg/ml, or about 115 mg/ml, or about 120 mg/ml, or about 125 mg/ml, or about 130 mg/ml, or about 135 mg/ml, or about 140 mg/ml, or about 145 mg/ml, or about 150 mg/ml, or about 155 mg/ml, or about 160 mg/ml, or about 165 mg/ml, or about 170 mg/ml, or about 175 mg/ml, or about 180 mg/ml, or about 185 mg/ml, or about 190 mg/mL, with the following excipients:

(a) lactate buffer at a concentration of about 5 mM to about 15 mM, or about 7 mM to about 12 mM, or about 9 mM to about 11 mM, or about 5 mM, or about 6 mM, or about 7 mM, or about 8 mM, or about 8 mM, or about 9 mM, or about 10 mM, or about 11 mM, or about 12 mM, or about 13 mM, or about 14 mM, or about 15 mM;

(b) calcium chloride at a concentration of about 5 to about 30 mM, about 10 to about 20 mM, or about 12.5 mM to about 17.5 mM, or about 14 mM to about 16 mM, or about 10 mM, or about 10.5 mM, or about 11 mM, or about 11.5 mM, or about 12 mM, or about 12.5 mM, or about 13 mM, or about 13.5 mM, or about 14 mM, or about 14.5 mM, or about 15 mM, or about 15.5 mM, or about 16 mM, or about 16.5 mM, or about 17 mM, or about 17.5 mM, or about 18 mM, or about 18.5 mM, or about 19 mM, or about 19.5 mM, or about 20 mM;

(c) sucrose at a concentration of about 4% (w/v) to about 10% (w/v), or about 6% (w/v) to about 8.5% (w/v), or about 4% (w/v), or about 4.5% (w/v), or about 5% (w/v), or about 5.5% (w/v), or about 6% (w/v), or about 6.5% (w/v), or about 7% (w/v), or about 7.1% (w/v), or about 7.2% (w/v), or about 7.3% (w/v), or about 7.4% (w/v), or about 7.5% (w/v), or about 7.6% (w/v), or about 7.7% (w/v), or about 7.8% (w/v), or about 8% (w/v), or about 8.5% (w/v);

(d) Pluronic F68 at a concentration of about 0.03% (w/v) to about 0.09% (w/v), or about 0.03% (w/v) to about 0.06% (w/v), about 0.01% (w/v) to about 0.2% (w/v), about 0.01% (w/v) to about 0.1% (w/v), about 0.03% (w/v) to about 0.1% (w/v), or about 0.05% (w/v) to about 0.07% (w/v), or about 0.03% (w/v), or about 0.04% (w/v), or about 0.05% (w/v), or about 0.06% (w/v), or about 0.07% (w/v), or about 0.08% (w/v), about 0.09% (w/v), or about 0.1% (w/v); and (e) has a pH of about 3.5 to about 8, or about 4 to about 7, or about 4.5 to about 6, or about 5 to about 5.5, or about 3.5, or about 4, or about 4.5, or about 4.6, or about 4.7, or about 4.8, or about 4.9, or about 5.0, or about 5.1, or about 5.2, or about 5.3, or about 5.4, or about 5.5, or about 5.6, or about 5.7, or about 5.8, or about 5.9, or about 6.0, or about 6.5, or about 7.0, or about 7.5, or about 8.0.

In an embodiment, the stable aqueous adalimumab formulation includes adalimumab at a concentration or about 40 mg/ml to 200 mg/ml, lactate buffer at a concentration of about 5 mM to about 15 mM, sucrose at a concentration of about 4% (w/v) to about 10% (w/v), calcium chloride at a concentration of about 5 to about 30 mM, and Pluronic F68 at a concentration of about 0.03% (w/v) to about 0.1% (w/v), and has a pH of about 3.5 to 8.

In an embodiment, the stable aqueous adalimumab formulation includes adalimumab at a concentration or about 40 mg/ml to 200 mg/ml, lactate buffer at a concentration of about 1 mM to about 15 mM, sucrose at a concentration of about 4% (w/v) to about 10% (w/v), calcium chloride at a concentration of about 10 to about 20 mM, and Pluronic F68 at a concentration of about 0.03% (w/v) to about 0.1% (w/v), and has a pH of about 3.5 to 8.

In an embodiment, the stable aqueous adalimumab formulation includes adalimumab at a concentration of about 80 mg/ml to about 120 mg/mL, lactate buffer at a concentration of about 7 mM to about 12 mM, sucrose at a concentration of about 4% (w/v) to about 10% (w/v), calcium chloride at a concentration of about 12.5 to about 17.5 mM, and Pluronic F68 at a concentration of about 0.03% (w/v) to about 0.07% (w/v), and a pH of about 4 to about 7.

In an embodiment, the stable aqueous adalimumab formulation includes adalimumab at a concentration of about 90 mg/ml to about 110 mg/mL, lactate buffer at a concentration of about 9 mM to about 11 mM, sucrose at a concentration of about 6% (w/v) to about 8.5% (w/v), calcium chloride at a concentration of about 14 to about 16 mM, and Pluronic F68 at a concentration of about 0.03% (w/v) to about 0.07% (w/v), and a pH of about 5.0 to about 5.5.

In an embodiment, the stable aqueous adalimumab formulation includes adalimumab at a concentration of about 100 mg/mL, lactate buffer at a concentration of about 10 mM, sucrose at a concentration of about 7.4% (w/v), calcium chloride at a concentration of about 15 mM, and Pluronic F68 at a concentration of about 0.06% (w/v), and a pH of about 5.2.

Exemplary aqueous adalimumab formulations are provided in Table G. Each formulation in Table G may optionally include Pluronic F68 at a concentration of about 0.001% (w/v) to about 10% (w/v) (e.g., about 0.005% (w/v) to about 1% (w/v), about 0.01% (w/v) to about 0.1% (w/v), about 0.01% (w/v) to about 1% (w/v), about 0.05% (w/v) to about 0.1% (w/v), about 0.05% (w/v) to about 0.4% (w/v), about 0.01% (w/v), about 0.05% (w/v) to about 0.5% (w/v), about 0.1% (w/v) to about 2% (w/v), about 0.2% (w/v) to about 1% (w/v), about 0.05% (w/v), about 0.1% (w/v), and/or about 0.4% (w/v)), Polysorbate 20 at a concentration of about 0.001% (w/v) to about 2% (w/v) (e.g., about 0.002% (w/v) to about 0.01% (w/v), about 0.005% (w/v) to about 0.05% (w/v), about 0.005% (w/v) to about 0.1% (w/v), about 0.02% (w/v) to about 0.1% (w/v), and/or about 0.05% (w/v) to about 0.2% (w/v)), or Polysorbate 80 at a concentration of about 0.001% (w/v) to about 2% (w/v) (e.g., about 0.002% (w/v) to about 0.01% (w/v), about 0.005% (w/v) to about 0.1% (w/v), about 0.005% (w/v) to about 0.05% (w/v), about 0.02% (w/v) to about 0.1% (w/v), about 0.03% (w/v) to about 0.1% (w/v), 0.04% (w/v) to about 0.1% (w/v), about 0.05% (w/v) to about 0.2% (w/v), about 0.03% (w/v), about 0.04% (w/v), and/or about 0.1% (w/v)). Each formulation in Table G has a pH of about 5.0 to about 5.5, e.g., about 5.1 to about 5.3 and/or about 5.2. Optionally, the pH of each formulation in Table G is adjusted using a strong acid and/or strong base including, but not limited to, hydrochloric acid, sodium hydroxide, calcium hydroxide, MSA, and/or MEA.

TABLE G

| Protein conc. | Buffer | Excipient(s) |
|---|---|---|
| 100 mg/mL | 10 mM lactate | 220 mM proline<br>25 mM CaCl$_2$ |
| 100 mg/mL | 10 mM lactate | 9% (w/v) sucrose |
| 100 mg/mL | 10 mM lactate | 9% (w/v) sucrose<br>25 mM CaCl$_2$ |

Exemplary aqueous adalimumab formulations are provided in Table H. Each formulation in Table H has a pH of about 5.0 to about 5.5, e.g., about 5.1 to about 5.3 and/or about 5.2. Optionally, the pH of each formulation in Table H is adjusted using a strong acid and/or strong base including, but not limited to, hydrochloric acid, sodium hydroxide, calcium hydroxide, MSA, and/or MEA.

TABLE H

| Protein conc. | Buffer | Excipient(s) | Surfactant |
|---|---|---|---|
| 100 mg/mL | 10 mM lactate | 220 mM proline<br>25 mM CaCl$_2$ | 0.1% (w/v) Pluronic F68 |
| 100 mg/mL | 10 mM lactate | 9% (w/v) sucrose | 0.1% (w/v) Pluronic F68 |
| 100 mg/mL | 10 mM lactate | 9% (w/v) sucrose<br>25 mM CaCl$_2$ | 0.1% (w/v) Pluronic F68 |
| 100 mg/mL | 10 mM lactate | 220 mM proline<br>25 mM CaCl$_2$ | 0.05% (w/v) Pluronic F68 |
| 100 mg/mL | 10 mM lactate | 9% (w/v) sucrose | 0.05% (w/v) Pluronic F68 |
| 100 mg/mL | 10 mM lactate | 9% (w/v) sucrose<br>25 mM CaCl$_2$ | 0.05% (w/v) Pluronic F68 |
| 100 mg/mL | 10 mM lactate | 220 mM proline<br>25 mM CaCl$_2$ | 0.01% (w/v) Pluronic F68 |
| 100 mg/mL | 10 mM lactate | 9% (w/v) sucrose | 0.01% (w/v) Pluronic F68 |
| 100 mg/mL | 10 mM lactate | 9% (w/v) sucrose<br>25 mM CaCl$_2$ | 0.01% (w/v) Pluronic F68 |
| 100 mg/mL | 10 mM lactate | 220 mM proline<br>25 mM CaCl$_2$ | 0.1% (w/v) Polysorbate 80 |
| 100 mg/mL | 10 mM lactate | 9% (w/v) sucrose | 0.1% (w/v) Polysorbate 80 |
| 100 mg/mL | 10 mM lactate | 220 mM proline<br>25 mM CaCl$_2$ | 0.05% (w/v) Polysorbate 80 |
| 100 mg/mL | 10 mM lactate | 9% (w/v) sucrose | 0.05% (w/v) Polysorbate 80 |
| 100 mg/mL | 10 mM lactate | 220 mM proline<br>25 mM CaCl$_2$ | 0.1% (w/v) Polysorbate 20 |
| 100 mg/mL | 10 mM lactate | 9% (w/v) sucrose | 0.1% (w/v) Polysorbate 20 |
| 100 mg/mL | 10 mM lactate | 220 mM proline<br>25 mM CaCl$_2$ | 0.05% (w/v) Polysorbate 20 |
| 100 mg/mL | 10 mM lactate | 9% (w/v) sucrose | 0.05% (w/v) Polysorbate 20 |

Exemplary aqueous adalimumab formulations are provided in Table I.

TABLE I

| Protein conc | Buffer | Excipient(s) | pH Adjusting Agent | Surfactant | pH |
|---|---|---|---|---|---|
| 100 mg/mL | 10 mM lactate | 220 mM proline 25 mM CaCl$_2$ | HCl/NaOH, HCl/Ca(OH)$_2$, HCl/MEA, MSA/Ca(OH)$_2$, or MSA/MEA | 0.1% (w/v) Pluronic F68 | 5.2 |
| 100 mg/mL | 10 mM lactate | 9% (w/v) sucrose | HCl/NaOH, HCl/Ca(OH)$_2$, HCl/MEA, MSA/Ca(OH)$_2$, or MSA/MEA | 0.1% (w/v) Pluronic F68 | 5.2 |
| 100 mg/mL | 10 mM lactate | 9% (w/v) sucrose 25 mM CaCl$_2$ | HCl/NaOH, HCl/Ca(OH)$_2$, HCl/MEA, MSA/Ca(OH)$_2$, or MSA/MEA | 0.1% (w/v) Pluronic F68 | 5.2 |
| 100 mg/mL | 10 mM lactate | 220 mM proline 25 mM CaCl$_2$ | HCl/NaOH, HCl/Ca(OH)$_2$, HCl/MEA, MSA/Ca(OH)$_2$, or MSA/MEA | 0.05% (w/v) Pluronic F68 | 5.2 |
| 100 mg/mL | 10 mM lactate | 9% (w/v) sucrose | HCl/NaOH, HCl/Ca(OH)$_2$, HCl/MEA, MSA/Ca(OH)$_2$, or MSA/MEA | 0.05% (w/v) Pluronic F68 | 5.2 |
| 100 mg/mL | 10 mM lactate | 9% (w/v) sucrose 25 mM CaCl$_2$ | HCl/NaOH, HCl/Ca(OH)$_2$, HCl/MEA, MSA/Ca(OH)$_2$, or MSA/MEA | 0.05% (w/v) Pluronic F68 | 5.2 |
| 100 mg/mL | 10 mM lactate | 220 mM proline 25 mM CaCl$_2$ | HCl/NaOH, HCl/Ca(OH)$_2$, HCl/MEA, MSA/Ca(OH)$_2$, or MSA/MEA | 0.01% (w/v) Pluronic F68 | 5.2 |
| 100 mg/mL | 10 mM lactate | 9% (w/v) sucrose | HCl/NaOH, HCl/Ca(OH)$_2$, HCl/MEA, MSA/Ca(OH)$_2$, or MSA/MEA | 0.01% (w/v) Pluronic F68 | 5.2 |
| 100 mg/mL | 10 mM lactate | 9% (w/v) sucrose 25 mM CaCl$_2$ | HCl/NaOH, HCl/Ca(OH)$_2$, HCl/MEA, MSA/Ca(OH)$_2$, or MSA/MEA | 0.01% (w/v) Pluronic F68 | 5.2 |
| 100 mg/mL | 10 mM lactate | 220 mM proline 25 mM CaCl$_2$ | HCl/NaOH, HCl/Ca(OH)$_2$, HCl/MEA, MSA/Ca(OH)$_2$, or MSA/MEA | 0.1% (w/v) Polysorbate 80 | 5.2 |
| 100 mg/mL | 10 mM lactate | 9% (w/v) sucrose | HCl/NaOH, HCl/Ca(OH)$_2$, HCl/MEA, MSA/Ca(OH)$_2$, or MSA/MEA | 0.1% (w/v) Polysorbate 80 | 5.2 |
| 100 mg/mL | 10 mM lactate | 220 mM proline 25 mM CaCl$_2$ | HCl/NaOH, HCl/Ca(OH)$_2$, HCl/MEA, MSA/Ca(OH)$_2$, or MSA/MEA | 0.05% (w/v) Polysorbate 80 | 5.2 |
| 100 mg/mL | 10 mM lactate | 9% (w/v) sucrose | HCl/NaOH, HCl/Ca(OH)$_2$, HCl/MEA, | 0.05% (w/v) Polysorbate 80 | 5.2 |

TABLE I-continued

| Protein conc | Buffer | Excipient(s) | pH Adjusting Agent | Surfactant | pH |
|---|---|---|---|---|---|
| 100 mg/mL | 10 mM lactate | 220 mM proline 25 mM CaCl$_2$ | MSA/Ca(OH)$_2$, or MSA/MEA HCl/NaOH, HCl/Ca(OH)$_2$, HCl/MEA, MSA/Ca(OH)$_2$, or MSA/MEA | 0.1% (w/v) Polysorbate 20 | 5.2 |
| 100 mg/mL | 10 mM lactate | 9% (w/v) sucrose | HCl/NaOH, HCl/Ca(OH)$_2$, HCl/MEA, MSA/Ca(OH)$_2$, or MSA/MEA | 0.1% (w/v) Polysorbate 20 | 5.2 |
| 100 mg/mL | 10 mM lactate | 220 mM proline 25 mM CaCl$_2$ | HCl/NaOH, HCl/Ca(OH)$_2$, HCl/MEA, MSA/Ca(OH)$_2$, or MSA/MEA | 0.05% (w/v) Polysorbate 20 | 5.2 |
| 100 mg/mL | 10 mM lactate | 9% (w/v) sucrose | HCl/NaOH, HCl/Ca(OH)$_2$, HCl/MEA, MSA/Ca(OH)$_2$, or MSA/MEA | 0.05% (w/v) Polysorbate 20 | 5.2 |

Exemplary aqueous adalimumab lactate formulations are also provided in Tables 1, 11, 12, 13, 15, 16 and 17. In an embodiment, the stable aqueous adalimumab formulation is one of the lactate buffer formulations described in Tables G, H, I, 1, 11, 12, 13, 15, 16 or 17 provided herein.

In an embodiment, a lyophilized form of any one of the foregoing lactate-containing adalimumab formulations is provided.

Formulations of Adalimumab with Histidine Buffer

In an embodiment, the stable aqueous adalimumab formulation includes adalimumab at a concentration of about 40 to about 200 mg/mL, such as about 90 to about 120 mg/mL, about 160 to 190 mg/mL, about 40 to about 60 mg/mL, about 50 mg/mL, about 100 mg/mL, or about 170 mg/mL, histidine at a concentration of about 5 mM to about 50 mM (e.g., about 5 mM to about 15 mM, about 10 mM, about 15 mM, about 20 mM, and/or about 25 mM), and one or more excipients. Suitable excipients include certain stabilizers such as certain amino acids and amino acid derivatives, certain salts, certain polyols, certain acids, certain amines, and certain surfactants. Examples of suitable amino acids and amino acid derivatives include proline (e.g., at a concentration of about 0.1 to about 450 mM, about 50 to about 300 mM, or about 270 to about 370 mM). Examples of suitable salts include calcium chloride (e.g., at a concentration of about 1 to about 150 mM, about 5 to about 50 mM, about 10 to about 30 mM, about 20 to about 40 mM, about 30 to about 50 mM, about 40 to about 80 mM, about 50 to about 100 mM, or about 25 mM) and sodium chloride (e.g., at a concentration of about 10 to about 100 mM, about 60 to about 90 mM, about 15 to about 50 mM, and/or about 35 mM). Examples of suitable polyols include sucrose (e.g., at a concentration of about 0.1% (w/v) to about 15% (w/v), about 4% (w/v) to about 10% (w/v), about 4% (w/v) to about 9% (w/v), about 6.5% (w/v), about 6.8% (w/v), about 6.9% (w/v), about 9% (w/v)) and sorbitol (e.g., at a concentration of about 0.1% (w/v) to about 10% (w/v), about 3% (w/v) to about 5% (w/v), and/or about 4% (w/v)). Examples of suitable acids include methane sulfonic acid (MSA) (e.g., at a concentration of about 0.1 to about 150 mM or about 0.1 to about 50 mM). Examples of suitable amines include MEA-HCl (e.g., at a concentration of about 0.1 to about 150 mM or about 0.1 to about 40 mM) and MEA (e.g., at a concentration of about 0.1 to about 300 mM or about 0.1 to about 50 mM). Examples of suitable surfactants include Pluronic F68 (e.g., at a concentration of about 0.001% (w/v) to about 10% (w/v), about 0.005% (w/v) to about 1% (w/v), about 0.05% (w/v) to about 0.4% (w/v), about 0.05% (w/v) to about 0.1% (w/v), about 0.01% (w/v), about 0.05% (w/v), and/or about 0.1% (w/v)), Polysorbate 20 (e.g., at a concentration of about 0.001% (w/v) to about 2% (w/v) or about 0.005% (w/v) to about 0.1% (w/v)), and Polysorbate 80 (e.g., at a concentration of about 0.001% (w/v) to about 2% (w/v), about 0.005% (w/v) to about 0.1% (w/v), about 0.005% (w/v) to about 0.05% (w/v), about 0.03% (w/v) to about 0.1% (w/v), about 0.04% (w/v) to about 0.1% (w/v), about 0.03% (w/v), about 0.04% (w/v), and/or about 0.1% (w/v)). Optionally, the histidine-containing stable aqueous adalimumab formulation has a pH of about 4.8 to about 5.7, for example, about 4.9 to about 5.6, about 5.0 to about 5.5, about 5.1 to about 5.4, about 5.1 to about 5.3, about 5.1 to about 5.2, about 5.2 to about 5.3, about 6.4 to about 7.2, about 6.5 to about 7.1, about 6.6 to about 7.0, about 6.7 to about 6.9, about 6.7 to about 6.8, about 6.8 to about 6.9, about 5.2, and/or about 6.8. Optionally, the pH of the stable aqueous adalimumab formulation is adjusted using a strong acid and/or a strong base including, but not limited to, hydrochloric acid, sodium hydroxide, calcium hydroxide, MSA, and/or MEA.

In an embodiment, the stable aqueous adalimumab formulation includes adalimumab at a concentration of about 40 to about 200 mg/mL, such as about 90 to about 120 mg/mL, about 160 to 190 mg/mL, about 40 to about 60 mg/mL, about 50 mg/mL, about 100 mg/mL, or about 170 mg/mL, histidine at a concentration of about 5 mM to about 50 mM (e.g., about 5 mM to about 15 mM, about 10 mM, about 15 mM, about 20 mM, and/or about 25 mM), and one or more excipients selected from the group consisting of proline at a concentration of about 0.1 to about 450 mM (e.g., about 50 to about 300 mM or about 270 to about 370 mM), calcium chloride at a concentration of about 1 to about 150 mM (e.g., about 5 to about 50 mM, about 10 to about 30 mM, about 20 to about 40 mM, about 30 to about 50 mM, about 40 to about 80 mM, about 50 to about 100 mM, or about 25 mM), sodium chloride at a concentration of about 10 to about 100 mM (e.g., about 60 to about 90 mM, about 15 to about 50 mM, and/or about 35 mM), sucrose at a concentration of about 0.1% (w/v) to about 15% (w/v) (e.g., about 4% (w/v) to about 10% (w/v), about 4% (w/v) to about 9% (w/v), about 6.5% (w/v), about 6.8% (w/v), about 6.9% (w/v), about 9% (w/v)), sorbitol at a concentration of about 0.1% (w/v) to about 10% (w/v) (e.g., about 3% (w/v) to about 5% (w/v) and/or about 4% (w/v)), methane sulfonic acid (MSA) at a concentration of about 0.1 to about 150 mM (e.g., about 0.1 to about 50 mM), MEA-HCl at a concentration of about 0.1 to about 150 mM (e.g., about 0.1 to about 40 mM), MEA at a concentration of about 0.1 to about 300 mM (e.g., about 0.1 to about 50 mM), Pluronic F68 at a concentration of about 0.001% (w/v) to about 10% (w/v) (e.g., about 0.005% (w/v) to about 1% (w/v), about 0.05% (w/v) to about 0.4% (w/v), about 0.05% (w/v) to about 0.1% (w/v), about 0.01% (w/v), about 0.05% (w/v), and/or about 0.1% (w/v)), Polysorbate 20 at a concentration of about 0.001% (w/v) to about 2% (w/v) (e.g., about 0.005% (w/v) to about 0.1% (w/v)), and Polysorbate 80 at a concentration of about 0.001% (w/v) to about 2% (w/v) (e.g., about 0.005% (w/v) to about 0.1% (w/v), about 0.005% (w/v) to about 0.05% (w/v), about 0.03% (w/v) to about 0.1% (w/v), about 0.04% (w/v) to about 0.1% (w/v), about 0.03% (w/v), about 0.04% (w/v), and/or about 0.1% (w/v)). Optionally, the histidine-containing stable aqueous adalimumab formulation has a pH of about 4.8 to about 5.7, for example, about 4.9 to about 5.6, about 5.0 to about 5.5, about 5.1 to about 5.4, about 5.1 to about 5.3, about 5.1 to about 5.2, about 5.2 to about 5.3, about 6.4 to about 7.2, about 6.5 to about 7.1, about 6.6 to about 7.0, about 6.7 to about 6.9, about 6.7 to about 6.8, about 6.8 to about 6.9, about 5.2, and/or about 6.8. Optionally, the pH of the stable aqueous adalimumab formulation is adjusted using a strong acid and/or a strong base including, but not limited to, hydrochloric acid, sodium hydroxide, calcium hydroxide, MSA, and/or MEA.

In an embodiment, the stable aqueous adalimumab formulation includes adalimumab at a concentration of about 90 to about 120 mg/mL, histidine at a concentration of about 5 mM to about 15 mM, proline at a concentration of about 270 to about 370 mM, and calcium chloride at a concentration of about 10 to about 30 mM, and has a pH of about 6.7 to 6.9. Optionally, the pH of the formulation is adjusted within this range with MEA and/or MSA.

Exemplary aqueous adalimumab formulations are provided in Table J.

In an embodiment, a lyophilized form of any one of the foregoing histidine-containing adalimumab formulations is provided.

Formulations of Adalimumab without Buffer

In an embodiment, the stable aqueous adalimumab formulation includes adalimumab at a concentration of about 40 to about 200 mg/mL, such as about 90 to about 120 mg/mL, about 160 to 190 mg/mL, about 40 to about 60 mg/mL, about 50 mg/mL, about 100 mg/mL, or about 170 mg/mL, and one or more excipients. Suitable excipients include certain stabilizers such as certain amino acids and amino acid derivatives, certain polyethylene glycols and polyethylene glycol derivatives, certain salts, certain polyols, certain acids, certain amines, and certain surfactants. Examples of suitable amino acids and amino acid derivatives include proline (e.g., at a concentration of about 0.1 to about 450 mM, about 50 to about 300 mM, or about 60 to about 300 mM). Examples of suitable polyethylene glycols and polyethylene glycol derivatives include PEG 600 (e.g., at a concentration of about 0.1% (w/v) to about 30% (w/v) or about 1.2% (w/v) to about 14.5% (w/v)) and PEG 200 (e.g., at a concentration of about 0.1% (w/v) to about 10% (w/v) or about 0.6% (w/v) to about 4.8% (w/v)). Examples of suitable salts include calcium chloride (e.g., at a concentration of about 1 to about 150 mM, about 5 to about 50 mM, about 10 to about 30 mM, about 20 to about 40 mM, about 30 to about 50 mM, about 40 to about 80 mM, about 20 to about 100 mM, about 50 to about 100 mM, or about 25 mM) and sodium chloride (e.g., at a concentration of about 10 to about 100 mM, about 60 to about 90 mM, about 15 to about 50 mM, and/or about 35 mM). Examples of suitable polyols include sorbitol (e.g., at a concentration of about 0.1% (w/v) to about 10% (w/v), about 3% (w/v) to about 5% (w/v), and/or about 4% (w/v)) and sucrose (e.g., at a concentration of about 0.1% (w/v) to about 15% (w/v), about 4% (w/v) to about 10% (w/v), about 4% (w/v) to about 9% (w/v), about 6.5% (w/v) to about 7.3% (w/v), about 6.5% (w/v), about 6.8% (w/v), about 6.9% (w/v), about 9% (w/v)). Examples of suitable acids include MSA (e.g., at a concentration of about 0.1 to about 150 mM, about 0.1 to about 50 mM, or about 20 to about 90 mM). Examples of suitable amines include MEA-HCl (e.g., at a concentration of about 0.1 to about 150 mM, about 0.1 to about 40 mM, or about 60 to about 90 mM) and MEA (e.g., at a concentration of about 0.1 to about 300 mM, about 0.1 to about 50 mM, or about 60 to about 90 mM). Examples of suitable surfactants include Pluronic F68 (e.g., at a concentration of about 0.001% (w/v) to about 10% (w/v), about 0.005% (w/v) to about 1% (w/v), about 0.05% (w/v) to about 0.5% (w/v), about 0.05% (w/v) to about 0.4% (w/v), about 0.05% (w/v) to about 0.1% (w/v), about 0.01% (w/v), about 0.05% (w/v), and/or about 0.1% (w/v)), Polysorbate 20 (e.g., at a concentration of about 0.001% (w/v) to about 2% (w/v) or about 0.005% (w/v) to about 0.1% (w/v)), and Polysorbate 80 (e.g., at a concentration of about 0.001% (w/v) to about 2% (w/v), about

TABLE J

| Protein conc. | Buffer | Excipient(s) | pH Adjusting Agent | pH |
|---|---|---|---|---|
| 100 mg/mL | 10 mM histidine | 320 mM proline 20 mM CaCl$_2$ | HCl/NaOH, HCl/Ca(OH)$_2$, HCl/MEA, MSA/Ca(OH)$_2$, or MSA/MEA | 5.2 |

0.005% (w/v) to about 0.1% (w/v), about 0.005% (w/v) to about 0.05% (w/v), about 0.03% (w/v) to about 0.1% (w/v), 0.04% (w/v) to about 0.1% (w/v), about 0.05% (w/v) to about 0.1% (w/v), about 0.03% (w/v), about 0.04% (w/v), and/or about 0.1% (w/v)). Optionally, the stable aqueous adalimumab formulation without buffer has a pH of about 4.8 to about 5.7, for example, about 4.9 to about 5.6, about 5.0 to about 5.5, about 5.1 to about 5.4, about 5.1 to about 5.3, about 5.1 to about 5.2, about 5.2 to about 5.3, and/or about 5.2. Optionally, the pH of the stable aqueous adalimumab formulation is adjusted using a strong acid and/or a strong base including, but not limited to, hydrochloric acid, sodium hydroxide, calcium hydroxide, MSA, and/or MEA.

In an embodiment, the stable aqueous adalimumab formulation includes adalimumab at a concentration of about 40 to about 200 mg/mL, such as about 90 to about 120 mg/mL, about 160 to 190 mg/mL, about 40 to about 60 mg/mL, about 50 mg/mL, about 100 mg/mL, or about 170 mg/mL, and one or more excipients selected from the group consisting of proline at a concentration of about 0.1 to about 450 mM (e.g., about 50 to about 300 mM or about 60 to about 300 mM), PEG 600 at a concentration of about 0.1% (w/v) to about 30% (w/v) (e.g., about 1.2% (w/v) to about 14.5% (w/v)), PEG 200 at a concentration of about 0.1% (w/v) to about 10% (w/v) (e.g., about 0.6% (w/v) to about 4.8% (w/v)), calcium chloride at a concentration of about 1 to about 150 mM (e.g., about 5 to about 50 mM, about 10 to about 30 mM, about 20 to about 40 mM, about 30 to about 50 mM, about 40 to about 80 mM, about 20 to about 100 mM, about 50 to about 100 mM, or about 25 mM), sodium chloride at a concentration of about 10 to about 100 mM (e.g., about 60 to about 90 mM, about 15 to about 50 mM, and/or about 35 mM), MSA at a concentration of about 0.1 to about 150 mM (e.g., about 0.1 to about 50 mM or about 20 to about 90 mM), MEA-HCl at a concentration of about 0.1 to about 150 mM (e.g., about 0.1 to about 40 mM or about 60 to about 90 mM), MEA at a concentration of about 0.1 to about 300 mM (e.g., about 0.1 to about 50 mM or about 60 to about 90 mM), sorbitol at a concentration of about 0.1% (w/v) to about 10% (w/v) (e.g., about 3% (w/v) to about 5% (w/v), and/or about 4% (w/v)), sucrose at a concentration of about 0.1% (w/v) to about 15% (w/v) (e.g., about 4% (w/v) to about 10% (w/v), about 4% (w/v) to about 9% (w/v), about 6.5% (w/v) to about 7.3% (w/v), about 6.5% (w/v), about 6.8% (w/v), about 6.9% (w/v), about 9% (w/v)), Pluronic F68 at a concentration of about 0.001% (w/v) to about 10% (w/v) (e.g., about 0.005% (w/v) to about 1% (w/v), about 0.05% (w/v) to about 0.5% (w/v), about 0.05% (w/v) to about 0.4% (w/v), about 0.05% (w/v) to about 0.1% (w/v), about 0.01% (w/v), about 0.05% (w/v), and/or about 0.1% (w/v)), Polysorbate 20 at a concentration of about 0.001% (w/v) to about 2% (w/v) (e.g., about 0.005% (w/v) to about 0.1% (w/v)), and Polysorbate 80 at a concentration of about 0.001% (w/v) to about 2% (w/v) (e.g., about 0.005% (w/v) to about 0.1% (w/v), about 0.005% (w/v) to about 0.05% (w/v), about 0.03% (w/v) to about 0.1% (w/v), 0.04% (w/v) to about 0.1% (w/v), about 0.05% (w/v) to about 0.1% (w/v), about 0.03% (w/v), about 0.04% (w/v), and/or about 0.1% (w/v)). Optionally, the stable aqueous adalimumab formulation without buffer has a pH of about 4.8 to about 5.7, for example, about 4.9 to about 5.6, about 5.0 to about 5.5, about 5.1 to about 5.4, about 5.1 to about 5.3, about 5.1 to about 5.2, about 5.2 to about 5.3, and/or about 5.2. Optionally, the pH of the stable aqueous adalimumab formulation is adjusted using a strong acid and/or a strong base including, but not limited to, hydrochloric acid, sodium hydroxide, calcium hydroxide, MSA, and/or MEA.

In an embodiment, the stable aqueous adalimumab formulation includes adalimumab at a concentration of about 90 to about 120 mg/mL, MSA at a concentration of about 10 to about 30 mM, and proline at a concentration of about 250 to about 350 mM, and has a pH of about 5.1 to 5.3. Optionally, the pH of the formulation is adjusted within this range with MEA or NaOH.

In an embodiment, the stable aqueous adalimumab formulation includes adalimumab at a concentration of about 90 to about 120 mg/mL, PEG 600 at a concentration of about 8% (w/v) to about 10% (w/v), calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, PEG 600 at a concentration of about 6.5% (w/v) to about 7.3% (w/v), PEG 200 at a concentration of about 0.3% (w/v) to about 1% (w/v), calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, PEG 600 at a concentration of about 4% (w/v) to about 5% (w/v), PEG 200 at a concentration of about 1.5% (w/v) to about 2.1% (w/v), calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, PEG 600 at a concentration of about 0.9% (w/v) to about 1.5% (w/v), PEG 200 at a concentration of about 2.5% (w/v) to about 3.5% (w/v), calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, PEG 200 at a concentration of about 3% (w/v) to about 5% (w/v), calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, PEG 600 at a concentration of about 6.9% (w/v) to about 7.7% (w/v), proline at a concentration of about 40 to about 80 mM, calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, PEG 600 at a concentration of about 5% (w/v) to about 6% (w/v), proline at a concentration of about 90 to about 150 mM, calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, PEG 600 at a concentration of about 2% (w/v) to about 3% (w/v), proline at a concentration of about 150 to about 210 mM, calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, proline at a concentration of about 200 to about 300 mM, calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, sorbitol at a concentration of about 3% (w/v) to about 5% (w/v), calcium chloride at a concentration of about 15 to about 35 mM, and Pluronic F68 at a concentration of about 0.05% (w/v) to about 0.5% (w/v), and has a pH of about 5.1 to 5.3. Optionally, the pH of the formulation is adjusted within this range with HCl, NaOH, $CaCl_2$), MEA, and/or MSA.

In an embodiment, the stable aqueous adalimumab formulation includes adalimumab at a concentration of about 90 to about 110 mg/mL, sorbitol at a concentration of about 3.5% (w/v) to about 4.5% (w/v), calcium chloride at a concentration of about 20 to about 30 mM, and Pluronic F68 at a concentration of about 0.05% (w/v) to about 0.2% (w/v), and has a pH of about 5.1 to 5.3. Optionally, the pH of the formulation is adjusted within this range with HCl, NaOH, $CaCl_2$), MEA, and/or MSA.

In an embodiment, the stable aqueous adalimumab formulation includes adalimumab at a concentration of about 90 to about 120 mg/mL, sorbitol at a concentration of about 3% (w/v) to about 5% (w/v), calcium chloride at a concentration of about 15 to about 35 mM, and Pluronic F68 at a concentration of about 0.01% (w/v) to about 0.1% (w/v), and has a pH of about 5.1 to 5.3. Optionally, the pH of the formulation is adjusted within this range with HCl, NaOH, $CaCl_2$), MEA, and/or MSA.

In an embodiment, the stable aqueous adalimumab formulation includes adalimumab at a concentration of about 90 to about 110 mg/mL, sorbitol at a concentration of about 3.5% (w/v) to about 4.5% (w/v), calcium chloride at a concentration of about 20 to about 30 mM, and Pluronic F68 at a concentration of about 0.03% (w/v) to about 0.1% (w/v), and has a pH of about 5.1 to 5.3. Optionally, the pH of the formulation is adjusted within this range with HCl, NaOH, $CaCl_2$), MEA, and/or MSA.

In an embodiment, the stable aqueous adalimumab formulation includes adalimumab at a concentration of about 90 to about 120 mg/mL, sorbitol at a concentration of about 3% (w/v) to about 5% (w/v), calcium chloride at a concentration of about 15 to about 35 mM, and Polysorbate 80 at a concentration of about 0.05% (w/v) to about 0.5% (w/v), and has a pH of about 5.1 to 5.3. Optionally, the pH of the formulation is adjusted within this range with HCl, NaOH, $CaCl_2$), MEA, and/or MSA.

In an embodiment, the stable aqueous adalimumab formulation includes adalimumab at a concentration of about 90 to about 120 mg/mL, sorbitol at a concentration of about 3% (w/v) to about 5% (w/v), calcium chloride at a concentration of about 15 to about 35 mM, and Polysorbate 80 at a concentration of about 0.01% (w/v) to about 0.1% (w/v), and has a pH of about 5.1 to 5.3. Optionally, the pH of the formulation is adjusted within this range with HCl, NaOH, $CaCl_2$), MEA, and/or MSA.

In an embodiment, the stable aqueous adalimumab formulation includes adalimumab at a concentration of about 90 to about 120 mg/mL, sorbitol at a concentration of about 3% (w/v) to about 5% (w/v), calcium chloride at a concentration of about 15 to about 35 mM, and Polysorbate 20 at a concentration of about 0.05% (w/v) to about 0.5% (w/v), and has a pH of about 5.1 to 5.3. Optionally, the pH of the formulation is adjusted within this range with HCl, NaOH, $CaCl_2$), MEA, and/or MSA.

In an embodiment, the stable aqueous adalimumab formulation includes adalimumab at a concentration of about 90 to about 120 mg/mL, sorbitol at a concentration of about 3% (w/v) to about 5% (w/v), calcium chloride at a concentration of about 15 to about 35 mM, and Polysorbate 20 at a concentration of about 0.01% (w/v) to about 0.1% (w/v), and has a pH of about 5.1 to 5.3. Optionally, the pH of the formulation is adjusted within this range with HCl, NaOH, $CaCl_2$), MEA, and/or MSA.

In an embodiment, the stable aqueous adalimumab formulation includes adalimumab at a concentration of about 90 to about 120 mg/mL, sucrose at a concentration of about 5% (w/v) to about 8% (w/v), calcium chloride at a concentration of about 15 to about 35 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, sucrose at a concentration of about 6.1% (w/v) to about 6.9% (w/v), calcium chloride at a concentration of about 15 to about 35 mM, and Pluronic F68 at a concentration of about 0.05% (w/v) to about 0.5% (w/v), and has a pH of about 5.1 to 5.3. Optionally, the pH of the formulation is adjusted within this range with HCl, NaOH, $CaCl_2$), MEA, and/or MSA.

In an embodiment, the stable aqueous adalimumab formulation includes adalimumab at a concentration of about 90 to about 110 mg/mL, sucrose at a concentration of about 6.3% (w/v) to about 6.7% (w/v), calcium chloride at a concentration of about 20 to about 30 mM, and Pluronic F68 at a concentration of about 0.05% (w/v) to about 0.2% (w/v), and has a pH of about 5.1 to 5.3. Optionally, the pH of the formulation is adjusted within this range with HCl, NaOH, $CaCl_2$), MEA, and/or MSA.

In an embodiment, the stable aqueous adalimumab formulation includes adalimumab at a concentration of about 90 to about 120 mg/mL, sucrose at a concentration of about 6.1% (w/v) to about 6.9% (w/v), calcium chloride at a concentration of about 15 to about 35 mM, and Pluronic F68 at a concentration of about 0.01% (w/v) to about 0.1% (w/v), and has a pH of about 5.1 to 5.3. Optionally, the pH of the formulation is adjusted within this range with HCl, NaOH, CaCl$_2$), MEA, and/or MSA.

In an embodiment, the stable aqueous adalimumab formulation includes adalimumab at a concentration of about 90 to about 110 mg/mL, sucrose at a concentration of about 6.3% (w/v) to about 6.7% (w/v), calcium chloride at a concentration of about 20 to about 30 mM, and Pluronic F68 at a concentration of about 0.03% (w/v) to about 0.1% (w/v), and has a pH of about 5.1 to 5.3. Optionally, the pH of the formulation is adjusted within this range with HCl, NaOH, CaCl$_2$), MEA, and/or MSA.

In an embodiment, the stable aqueous adalimumab formulation includes adalimumab at a concentration of about 90 to about 120 mg/mL, sucrose at a concentration of about 6.1% (w/v) to about 6.9% (w/v), calcium chloride at a concentration of about 15 to about 35 mM, and Polysorbate 80 at a concentration of about 0.05% (w/v) to about 0.5% (w/v), and has a pH of about 5.1 to 5.3. Optionally, the pH of the formulation is adjusted within this range with HCl, NaOH, CaCl$_2$), MEA, and/or MSA.

In an embodiment, the stable aqueous adalimumab formulation includes adalimumab at a concentration of about 90 to about 120 mg/mL, sucrose at a concentration of about 6.1% (w/v) to about 6.9% (w/v), calcium chloride at a concentration of about 15 to about 35 mM, and Polysorbate 80 at a concentration of about 0.01% (w/v) to about 0.1% (w/v), and has a pH of about 5.1 to 5.3. Optionally, the pH of the formulation is adjusted within this range with HCl, NaOH, CaCl$_2$), MEA, and/or MSA.

In an embodiment, the stable aqueous adalimumab formulation includes adalimumab at a concentration of about 90 to about 120 mg/mL, sucrose at a concentration of about 6.1% (w/v) to about 6.9% (w/v), calcium chloride at a concentration of about 15 to about 35 mM, and Polysorbate 20 at a concentration of about 0.05% (w/v) to about 0.5% (w/v), and has a pH of about 5.1 to 5.3. Optionally, the pH of the formulation is adjusted within this range with HCl, NaOH, CaCl$_2$), MEA, and/or MSA.

In an embodiment, the stable aqueous adalimumab formulation includes adalimumab at a concentration of about 90 to about 120 mg/mL, sucrose at a concentration of about 6.1% (w/v) to about 6.9% (w/v), calcium chloride at a concentration of about 15 to about 35 mM, and Polysorbate 20 at a concentration of about 0.01% (w/v) to about 0.1% (w/v), and has a pH of about 5.1 to 5.3. Optionally, the pH of the formulation is adjusted within this range with HCl, NaOH, CaCl$_2$), MEA, and/or MSA.

In an embodiment, the stable aqueous adalimumab formulation includes adalimumab at a concentration of about 90 to about 120 mg/mL, proline at a concentration of about 200 to about 250 mM, calcium chloride at a concentration of about 15 to about 35 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, PEG 600 at a concentration of about 11% (w/v) to about 15% (w/v), calcium chloride at a concentration of about 20 to about 40 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 160 to about 190 mg/mL, sucrose at a concentration of about 5% (w/v) to about 8% (w/v), calcium chloride at a concentration of about 15 to about 35 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, sucrose at a concentration of about 6.9% (w/v) to about 7.7% (w/v), calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, PEG 200 at a concentration of about 4.5% (w/v) to about 5.1% (w/v), calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, sorbitol at a concentration of about 3% (w/v) to about 5% (w/v), calcium chloride at a concentration of about 15 to about 35 mM, and Pluronic F68 at a concentration of about 0.05% (w/v) to about 0.5% (w/v), and has a pH of about 5.1 to 5.3. Optionally, the pH of the formulation is adjusted within this range with HCl.

In an embodiment, the stable aqueous adalimumab formulation includes adalimumab at a concentration of about 90 to about 120 mg/mL, PEG 600 at a concentration of about 13% (w/v) to about 16% (w/v), calcium chloride at a concentration of about 10 to about 30 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 90 to about 120 mg/mL, PEG 600 at a concentration of about 3% (w/v) to about 3.6% (w/v), calcium chloride at a concentration of about 10 to about 30 mM, proline at a concentration of about 150 to about 210 mM, and Pluronic F68 at a concentration of about 0.05% (w/v) to about 0.5% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 40 to about 60 mg/mL and PEG 600 at a concentration of about 10% (w/v) to about 11% (w/v), and has a pH of about 5.1 to 5.3. Optionally, the pH of the formulation is adjusted within this range with MEA and/or MSA.

In an embodiment, the stable aqueous adalimumab formulation includes adalimumab at a concentration of about 40 to about 60 mg/mL, PEG 600 at a concentration of about 8% (w/v) to about 9% (w/v), and calcium chloride at a concentration of about 15 to about 35 mM, and has a pH of about 5.1 to 5.3. Optionally, the pH of the formulation is adjusted within this range with MEA and/or MSA.

In an embodiment, the stable aqueous adalimumab formulation includes adalimumab at a concentration of about 40 to about 60 mg/mL, PEG 600 at a concentration of about 6% (w/v) to about 7% (w/v), and calcium chloride at a concentration of about 40 to about 60 mM, and has a pH of about 5.1 to 5.3. Optionally, the pH of the formulation is adjusted within this range with MEA and/or MSA.

In an embodiment, the stable aqueous adalimumab formulation includes adalimumab at a concentration of about 40 to about 60 mg/mL, PEG 600 at a concentration of about 3.4% (w/v) to about 4% (w/v), and calcium chloride at a concentration of about 65 to about 85 mM, and has a pH of about 5.1 to 5.3. Optionally, the pH of the formulation is adjusted within this range with MEA and/or MSA.

In an embodiment, the stable aqueous adalimumab formulation includes adalimumab at a concentration of about 40 to about 60 mg/mL and calcium chloride at a concentration of about 80 to about 120 mM, and has a pH of about 5.1 to 5.3. Optionally, the pH of the formulation is adjusted within this range with MEA and/or MSA.

In an embodiment, the stable aqueous adalimumab formulation includes adalimumab at a concentration of about 40 to about 60 mg/mL and proline at a concentration of about 250 to about 350 mM, and has a pH of about 5.1 to 5.3. Optionally, the pH of the formulation is adjusted within this range with MEA and/or MSA.

In an embodiment, the stable aqueous adalimumab formulation includes adalimumab at a concentration of about 40 to about 60 mg/mL, proline at a concentration of about 200 to about 250 mM, and calcium chloride at a concentration of about 15 to about 35 mM, and has a pH of about 5.1 to 5.3. Optionally, the pH of the formulation is adjusted within this range with MEA and/or MSA.

In an embodiment, the stable aqueous adalimumab formulation includes adalimumab at a concentration of about 40 to about 60 mg/mL, proline at a concentration of about 120 to about 180 mM, and calcium chloride at a concentration of about 40 to about 60 mM, and has a pH of about 5.1 to 5.3. Optionally, the pH of the formulation is adjusted within this range with MEA and/or MSA.

In an embodiment, the stable aqueous adalimumab formulation includes adalimumab at a concentration of about 40 to about 60 mg/mL, proline at a concentration of about 60 to about 90 mM, and calcium chloride at a concentration of about 65 to about 85 mM, and has a pH of about 5.1 to 5.3. Optionally, the pH of the formulation is adjusted within this range with MEA and/or MSA.

In an embodiment, the stable aqueous adalimumab formulation includes adalimumab at a concentration of about 40 to about 60 mg/mL, proline at a concentration of about 200 to about 300 mM, MEA at a concentration of about 40 to about 80 mM, and MSA at a concentration of about 40 to about 80 mM, and has a pH of about 5.1 to 5.3. Optionally, the pH of the formulation is adjusted within this range with MEA and/or MSA.

In an embodiment, the stable aqueous adalimumab formulation includes adalimumab at a concentration of about 40 to about 60 mg/mL, proline at a concentration of about 150 to about 210 mM, MEA at a concentration of about 40 to about 80 mM, and MSA at a concentration of about 40 to about 80 mM, and has a pH of about 5.1 to 5.3. Optionally, the pH of the formulation is adjusted within this range with MEA and/or MSA.

In an embodiment, the stable aqueous adalimumab formulation includes adalimumab at a concentration of about 40 to about 60 mg/mL, proline at a concentration of about 90 to about 150 mM, MEA at a concentration of about 70 to about 110 mM, and MSA at a concentration of about 70 to about 110 mM, and has a pH of about 5.1 to 5.3. Optionally, the pH of the formulation is adjusted within this range with MEA and/or MSA.

Exemplary aqueous adalimumab formulations are provided in Table J. Each formulation in Table J may optionally include Pluronic F68 at a concentration of about 0.001% (w/v) to about 10% (w/v) (e.g., about 0.005% (w/v) to about 1% (w/v), about 0.01% (w/v) to about 0.1% (w/v), about 0.01% (w/v) to about 1% (w/v), about 0.05% (w/v) to about 0.1% (w/v), about 0.05% (w/v) to about 0.4% (w/v), about 0.01% (w/v), about 0.05% (w/v) to about 0.5% (w/v), about 0.1% (w/v) to about 2% (w/v), about 0.2% (w/v) to about 1% (w/v), about 0.05% (w/v), about 0.1% (w/v), and/or about 0.4% (w/v)), Polysorbate 20 at a concentration of about 0.001% (w/v) to about 2% (w/v) (e.g., about 0.002% (w/v) to about 0.01% (w/v), about 0.005% (w/v) to about 0.05% (w/v), about 0.005% (w/v) to about 0.1% (w/v), about 0.02% (w/v) to about 0.1% (w/v), and/or about 0.05% (w/v) to about 0.2% (w/v)), or Polysorbate 80 at a concentration of about 0.001% (w/v) to about 2% (w/v) (e.g., about 0.002% (w/v) to about 0.01% (w/v), about 0.005% (w/v) to about 0.1% (w/v), about 0.005% (w/v) to about 0.05% (w/v), about 0.02% (w/v) to about 0.1% (w/v), about 0.03% (w/v) to about 0.1% (w/v), 0.04% (w/v) to about 0.1% (w/v), about 0.05% (w/v) to about 0.2% (w/v), about 0.03% (w/v), about 0.04% (w/v), and/or about 0.1% (w/v)). Each formulation in Table J has a pH of about 5.0 to about 5.5, e.g., about 5.1 to about 5.3 and/or about 5.2. Optionally, the pH of each formulation in Table J is adjusted using a strong acid and/or strong base including, but not limited to, hydrochloric acid, sodium hydroxide, calcium hydroxide, MSA, and/or MEA.

TABLE J

| Protein conc. | Excipient(s) |
| --- | --- |
| 100 mg/mL | 4% (w/v) sorbitol<br>25 mM $CaCl_2$ |
| 100 mg/mL | 6.5% (w/v) sucrose<br>25 mM $CaCl_2$ |

Exemplary aqueous adalimumab formulations are provided in Table K. Each formulation in Table K has a pH of about 5.0 to about 5.5, e.g., about 5.1 to about 5.3 and/or about 5.2. Optionally, the pH of each formulation in Table K is adjusted using a strong acid and/or strong base including, but not limited to, hydrochloric acid, sodium hydroxide, calcium hydroxide, MSA, and/or MEA.

TABLE K

| Protein conc. | Excipient(s) | Surfactant |
| --- | --- | --- |
| 100 mg/mL | 4% (w/v) sorbitol<br>25 mM $CaCl_2$ | 0.1% (w/v) Pluronic F68 |
| 100 mg/mL | 6.5% (w/v) sucrose<br>25 mM $CaCl_2$ | 0.1% (w/v) Pluronic F68 |
| 100 mg/mL | 4% (w/v) sorbitol<br>25 mM $CaCl_2$ | 0.05% (w/v) Pluronic F68 |
| 100 mg/mL | 6.5% (w/v) sucrose<br>25 mM $CaCl_2$ | 0.05% (w/v) Pluronic F68 |
| 100 mg/mL | 4% (w/v) sorbitol<br>25 mM $CaCl_2$ | 0.1% (w/v) Polysorbate 80 |
| 100 mg/mL | 6.5% (w/v) sucrose<br>25 mM $CaCl_2$ | 0.1% (w/v) Polysorbate 80 |
| 100 mg/mL | 4% (w/v) sorbitol<br>25 mM $CaCl_2$ | 0.05% (w/v) Polysorbate 80 |

TABLE K-continued

| Protein conc. | Excipient(s) | Surfactant |
| --- | --- | --- |
| 100 mg/mL | 6.5% (w/v) sucrose 25 mM CaCl$_2$ | 0.05% (w/v) Polysorbate 80 |
| 100 mg/mL | 4% (w/v) sorbitol 25 mM CaCl$_2$ | 0.1% (w/v) Polysorbate 20 |
| 100 mg/mL | 6.5% (w/v) sucrose 25 mM CaCl$_2$ | 0.1% (w/v) Polysorbate 20 |
| 100 mg/mL | 4% (w/v) sorbitol 25 mM CaCl$_2$ | 0.05% (w/v) Polysorbate 20 |
| 100 mg/mL | 6.5% (w/v) sucrose 25 mM CaCl$_2$ | 0.05% (w/v) Polysorbate 20 |

Exemplary aqueous adalimumab formulations are provided in Table L.

TABLE L

| Protein conc. | Excipient(s) | pH Adjusting Agent | Surfactant | pH |
| --- | --- | --- | --- | --- |
| 100 mg/mL | 4% (w/v) sorbitol 25 mM CaCl$_2$ | HCl/NaOH, HCl/Ca(OH)$_2$, HCl/MEA, MSA/Ca(OH)$_2$, or MSA/MEA | 0.1% (w/v) Pluronic F68 | 5.2 |
| 100 mg/mL | 6.5% (w/v) sucrose 25 mM CaCl$_2$ | HCl/NaOH, HCl/Ca(OH)$_2$, HCL/MEA, MSA/Ca(OH)$_2$, or MSA/MEA | 0.1% (w/v) Pluronic F68 | 5.2 |
| 100 mg/mL | 4% (w/v) sorbitol 25 mM CaCl$_2$ | HCl/NaOH, HCl/Ca(OH)$_2$, HCl/MEA, MSA/Ca(OH)$_2$, or MSA/MEA | 0.05% (w/v) Pluronic F68 | 5.2 |
| 100 mg/mL | 6.5% (w/v) sucrose 25 mM CaCl$_2$ | HCl/NaOH, HCl/Ca(OH)$_2$, HCl/MEA, MSA/Ca(OH)$_2$, or MSA/MEA | 0.05% (w/v) Pluronic F68 | 5.2 |
| 100 mg/mL | 4% (w/v) sorbitol 25 mM CaCl$_2$ | HCl/NaOH, HCl/Ca(OH)$_2$, HCl/MEA, MSA/Ca(OH)$_2$, or MSA/MEA | 0.1% (w/v) Polysorbate 80 | 5.2 |
| 100 mg/mL | 6.5% (w/v) sucrose 25 mM CaCl$_2$ | HCl/NaOH, HCl/Ca(OH)$_2$, HCl/MEA, MSA/Ca(OH)$_2$, or MSA/MEA | 0.1% (w/v) Polysorbate 80 | 5.2 |
| 100 mg/mL | 4% (w/v) sorbitol 25 mM CaCl$_2$ | HCl/NaOH, HCl/Ca(OH)$_2$, HCl/MEA, MSA/Ca(OH)$_2$, or MSA/MEA | 0.05% (w/v) Polysorbate 80 | 5.2 |
| 100 mg/mL | 6.5% (w/v) sucrose 25 mM CaCl$_2$ | HCl/NaOH, HCl/Ca(OH)$_2$, HCl/MEA, MSA/Ca(OH)$_2$, or MSA/MEA | 0.05% (w/v) Polysorbate 80 | 5.2 |
| 100 mg/mL | 4% (w/v) sorbitol 25 mM CaCl$_2$ | HCl/NaOH, HCl/Ca(OH)$_2$, HCl/MEA, MSA/Ca(OH)$_2$, or MSA/MEA | 0.1% (w/v) Polysorbate 20 | 5.2 |
| 100 mg/mL | 6.5% (w/v) sucrose 25 mM CaCl$_2$ | HCl/NaOH, HCl/Ca(OH)$_2$, HCl/MEA, MSA/Ca(OH)$_2$, or MSA/MEA | 0.1% (w/v) Polysorbate 20 | 5.2 |
| 100 mg/mL | 4% (w/v) sorbitol 25 mM CaCl$_2$ | HCl/NaOH, HCl/Ca(OH)$_2$, HCl/MEA, MSA/Ca(OH)$_2$, or MSA/MEA | 0.05% (w/v) Polysorbate 20 | 5.2 |
| 100 mg/mL | 6.5% (w/v) sucrose 25 mM CaCl$_2$ | HCl/NaOH, HCl/Ca(OH)$_2$, HCl/MEA, MSA/Ca(OH)$_2$, or MSA/MEA | 0.05% (w/v) Polysorbate 20 | 5.2 |

In an embodiment, a lyophilized form of any one of the foregoing adalimumab formulations without buffer is provided.

Methods of Treatment

The invention provides for methods of treating a patient suffering from a TNF-α associated disease or disorder comprising administering to the patient any of the stable aqueous adalimumab formulations of the invention (or lyophilized formulations thereof once reconstituted, e.g., with sterile water for injection). The TNF-α diseases and disorders include, but are not limited to, inflammatory diseases and disorders, intestinal diseases and disorders, autoimmune diseases and disorders, eye diseases and disorders, pulmonary diseases and disorders, and infectious diseases and disorders. The term "patient" includes humans and non-human animal subjects.

The invention also provides for compositions comprising any of the stable aqueous or lyophilized adalimumab formulations of the invention for the treatment of a TNF-α associated disease or disorder, such as inflammatory diseases and disorders, intestinal diseases and disorders, autoimmune diseases and disorders, eye diseases and disorders, pulmonary diseases and disorders, and infectious diseases and disorders.

The invention further provides for use of the stable aqueous or lyophilized adalimumab formulations of the invention for the preparation of a medicament for the treatment of TNF-α associated diseases or disorders, such as inflammatory diseases and disorders, intestinal diseases and disorders, autoimmune diseases and disorders, eye diseases and disorders, pulmonary diseases and disorders, and infectious diseases and disorders.

Inflammatory diseases and disorders include, but are not limited to, arthritis, adult and juvenile rheumatoid arthritis, juvenile idiopathic arthritis, polyarticular juvenile idiopathic arthritis, psoriatic arthritis, osteoarthritis including erosive osteoarthritis and hund osteoarthritis, plaque psoriasis, general pustular psoriasis, nail and scalp psoriasis, hidradenitis suppurativa, ankylosing spondylitis, interstitial cystitis, spondyloarthritis including peripheral spondyloarthritis and axial spondyloarthritis, spondylarthropathy, pulmonary inflammation disorder, allergy, uveitis, chronic pulmonary inflammation disease, vascular inflammation, enthesitis related arthritis, enthesopathy, coronary atherosclerosis, inflammatory bone disorders, bone resorption disease, hepatitis including alcoholic hepatitis, chronic pouchitis, inflammatory bowel disease, adult and pediatric Crohn's disease, ulcerative colitis, schleritis, sarcoidosis, cutaneous sarcoidosis, Netherton syndrome, and giant cell arteritis.

Intestinal diseases and disorders include, but are not limited to, chronic pouchitis, inflammatory bowel disease, adult and pediatric Crohn's disease, ulcerative colitis, small bowel lesions, anal squamous intraepithelial lesions, anal fissures, and intestinal Behcet's disease.

Autoimmune diseases and disorders include, but are not limited to, adult and juvenile rheumatoid arthritis, juvenile idiopathic arthritis, psoriasis, plaque psoriasis, general pustular psoriasis, nail and scalp psoriasis, psoriasis vulgaris, psoriasis arthropica, psoriatic arthritis, pyoderma gangrenosum, gouty arthritis, allergy, multiple sclerosis, autoimmune diabetes, autoimmune uveitis, nephrotic syndrome, diabetic ulcers, and graft vs. host disease Eye diseases and disorders include, but are not limited to, uveitis, anterior uveitis, intermediate uveitis and posterior uveitis, refractory diabetic retinopathy, choroid diseases, choroidal neovascularization, macular degeneration including age-related macular degeneration, albinism, Behcet's syndrome, Hermanski-Pudluk syndrome, panuveitis, pars planitis, retinal degeneration, uveal diseases, retinal vascular disorders, and schleritis.

Infectious diseases and disorders include, but are not limited to, malaria, acquired immune deficiency (AIDS), cytomegalovirus infection and influenza.

Pulmonary disease and disorders include, but are not limited to, adult respiratory distress syndrome, asthma, refractory asthma, pulmonary inflammation disorder, shock lung, chronic pulmonary inflammatory disease, pulmonary sarcoidosis, pulmonary fibrosis and silicosis.

Other TNF-α associated diseases and disorders include, but are not limited to, mucopolysaccharidosis including mucopolysaccharidosis type I, mucopolysaccharidosis type II, mucopolysaccharidosis type IV, cancers, cachexia, ischemia of the heart, coagulation disturbances, acute disc prolapse, sleep apnea, anaplastic thyroid cancer and focal segmental glomeruloschelorisis.

Stable aqueous adalimumab formulations of the invention (or lyophilized formulations thereof once reconstituted, e.g., with sterile water for injection) may be administered subcutaneously, intravenously, parenterally, intradermally, intramuscularly, and/or intraperitoneally using standard techniques. For example, the stable aqueous adalimumab formulations of the invention may be prepared to be subcutaneously administered using a pre-filled syringe. Specifically, any of the formulations of the invention may be administered once every week or 6 to 8 days or 7 to 10 days, or every other week or every two weeks or 12 to 16 days or 7 to 14 days or 13 to 15 days, or every three weeks or 19 to 23 days, or every month or 26 to 30 days or 29 to 31 days, or every five weeks or 33 to 34 days, or every six weeks or 40 to 44 days, or every seven weeks or 47 to 51 days, or every two months or 54 to 58 days subcutaneously, intravenously, parenterally, intradermally, intramuscularly, and/or intraperitoneally at a therapeutically effective dosage and in the formulations described herein for an indefinite period of time for the treatment of the diseases and conditions described above.

Administration and dosage regimens of stable aqueous adalimumab formulations of the invention (or lyophilized formulations thereof once reconstituted, e.g., with sterile water for injection) can be adjusted to provide an effective amount for an optimum therapeutic response. For example, a single bolus can be administered, two or more divided doses can be administered over time or the dose can be proportionally reduced or increased as indicated by the exigencies of the therapeutic situation. For example, a unit dose can be administered over two consecutive days every two weeks. Unit dosing refers to a physically discrete amount of adalimumab or a biosimilar thereof suited as unitary dosages for the patients to be treated; each unit contains a predetermined quantity of active biopharmaceutical calculated to produce a desired therapeutic effect.

The dosing regimen of stable aqueous adalimumab formulations of the invention (or lyophilized formulations thereof once reconstituted, e.g., with sterile water for injection) may comprise administering a dose given on Day one, followed by the administration of the same dose every other week. For example, a dose of 40 mg adalimumab or biosimilar thereof is administered every other week in patients suffering from rheumatoid arthritis, psoriatic arthritis or ankylosing spondylitis. For patients suffering from juvenile idiopathic arthritis that are 10 kg (22 lbs) to less than 15 kg (33 lbs), a dose of 10 mg adalimumab or biosimilar thereof is administered every other week, for example. For patients suffering from juvenile idiopathic arthritis that are 15 kg (33 lbs) to less than 30 kg (66 lbs), a dose of 20 mg adalimumab or biosimilar thereof is administered every other week, for example. For patients suffering from juvenile idiopathic arthritis that are greater or equal to 30 kg (66 lbs), a dose of 40 mg adalimumab or biosimilar thereof is administered every other week, for example. This dosing regimen may also include administering methotrexate (MTX), other non-biologic DMARDS, glucocorticoid, nonsteroidal anti-inflammatory drugs (NSAIDS) and/or analgesics throughout the administration or for a portion of the time of administration of any of the stable aqueous adalimumab formulations of the invention.

The dosing regimen of stable aqueous adalimumab formulations of the invention may (or lyophilized formulations thereof once reconstituted, e.g., with sterile water for injection) comprise administering an initial dose given on day one or split over two consecutive days, followed by the administration of the same or a reduced dose two weeks later (Day 15), e.g. the initial dose reduced by half. The dosing regimen may further comprise administration of the same or further reduced dose two weeks later (Day 29); e.g. a dose that is a fourth of the initial dose which will be continued as a maintenance dose every two weeks. For example, for patients suffering from adult Crohn's disease or ulcerative colitis, an initial dose of 160 mg adalimumab or biosimilar thereof is administered on Day 1, a second dose of 80 mg adalimumab or biosimilar thereof is administered two weeks later (Day 15), followed by a maintenance dose of 40 mg adalimumab or biosimilar thereof administered two weeks later (Day 29) that is continued every other week. For patients suffering from pediatric Crohn's disease that are 17 kb (37 lbs) to less than 40 kg (88 lbs), an initial dose of 80 mg adalimumab or biosimilar thereof is administered on Day 1, a second dose of 40 mg adalimumab or biosimilar thereof is administered two weeks later (Day 15), followed by a maintenance dose of 20 mg adalimumab or biosimilar thereof administered two weeks later (Day 29) that is continued every other week, for example. For patients suffering from pediatric Crohn's disease that are greater than 40 kg (88 lbs), an initial dose of 160 mg adalimumab or biosimilar thereof is administered on Day 1, a second dose of 80 mg adalimumab or biosimilar thereof is administered two weeks later (Day 15), followed by a maintenance dose of 40 mg adalimumab or biosimilar thereof administered two weeks later (Day 29) that is continued every other week, for example. This dosing regimen may also include administering aminosalicylates and/or corticosteroids, azathioprine, 6-mercaptopurine (6-MP) or MTX throughout the administration or for a portion of the time of administration of any of the stable aqueous adalimumab formulations of the invention.

The dosing regimen of stable aqueous adalimumab formulations of the invention (or lyophilized formulations thereof once reconstituted, e.g., with sterile water for injection) may comprise administering an initial dose given on Day one or split over two consecutive days, followed by the administration of the same or a reduced dose two weeks later (Day 15), e.g. an initial dose reduced by half. The dosing regimen may further comprise administration of the same or further reduced dose two weeks later (Day 29), e.g. a dose that is a fourth of the initial dose. For example, an initial dose of 160 mg adalimumab or biosimilar thereof is administered on Day 1, a second dose of 80 mg adalimumab or biosimilar thereof is administered two weeks later (Day 15), and a third dose of 40 mg adalimumab or biosimilar thereof is administered on Day 29 followed by administration of 40 mg adalimumab or biosimilar thereof every week. This dosing regimen may be administered to patients suffering from hidradenitis suppurativa.

The dosing regimen of stable aqueous adalimumab formulations of the invention (or lyophilized formulations thereof once reconstituted, e.g., with sterile water for injection) may comprise administering an initial dose given on Day one or split over two consecutive days, followed by the administration of the same or a reduced dose one week after the initial dose e.g. an initial dose reduced by half and continued administration every other week. For example, an initial dose of 80 mg adalimumab or biosimilar thereof, followed by administration of 40 mg adalimumab or biosimilar thereof every other week starting one week after the initial dose. This dosing regimen may be administered to patients suffering from plaque psoriasis or uveitis.

The invention provides for a method of preparing a stable aqueous adalimumab formulations of the invention, comprising combining an aqueous solution comprising one or more excipients and an therapeutically effective amount of adalimumab using techniques standard in the art. The invention further provides for a method of preparing the stable lyophilized adalimumab formulations of the invention, comprising lyophilizing an aqueous adalimumab formulation comprising one or more excipients and a therapeutically effective amount of adalimumab using techniques standard in the art.

The foregoing detailed description is not intended to define every aspect of the invention, and other features and advantages of the present disclosure will be apparent to those skilled in the art. The present disclosure is intended to be related as a unified document, and it should be understood that all combinations of features described herein are contemplated, even if the combination of features are not found together in the same sentence, paragraph, or section of this disclosure. In addition, the disclosure includes, as an additional aspect, all embodiments of the invention narrower in scope in any way than the variations specifically mentioned above. With respect to aspects of the disclosure described or claimed with "a" or "an," it should be understood that these terms mean "one or more" unless context unambiguously requires a more restricted meaning. With respect to elements described as one or more within a set, it should be understood that all combinations within the set are contemplated. If aspects of the disclosure are described as "comprising" a feature, embodiments also are contemplated "consisting of" or "consisting essentially of" the feature. Additional features and variations of the disclosure will be apparent to those skilled in the art from the entirety of this application, and all such features are intended as aspects of the disclosure.

The present disclosure will be more readily understood by reference to the following examples, which are provided by way of illustration and are not intended to be limiting.

EXAMPLES

The following Examples describe formulations of the present disclosure.

General Materials: In the following examples, an adalimumab biosimilar as described in Velayudhan et al., BioDrugs 30:339-351 (2016) (i.e., ABP 501) was used.

General Analytical Methods: Cation-exchange high-performance liquid chromatography (CEX-HPLC) and size-exclusion high-performance liquid chromatography (SE-HPLC) were used to assess stability. CEX-HPLC examines changes in charge, mainly due to deamidation, which is measured as pre-peak or acidic growth, and SE-HPLC is used to resolve and measure soluble aggregation, also known as high molecular weight species (HMWS), which is determined as a growth in pre-peak area. To be considered significant, changes in degradation should be greater than the intermediate precision of the assays: the standard deviation is +/−0.16 for the CEX-HPLC method and +/−0.032 for the SE-HPLC method. CEX-HPLC was performed using, a Pro Pac WCX-10 analytical column, 4.0 mm×250 mm (Dionex, 054993) for the charge separation of protein in a gradient mobile phase. Mobile Phase A was 20 mM sodium phosphate, pH 6.8 and Mobile Phase B was 20 mM sodium phosphate, 0.5 M NaCl, pH 6.8. Samples were injected onto the column at a 50 µg mass load and detected at a wavelength of 230 nm. SE-HPLC was performed using an Agilent 1200 system. A TSK-GEL G3000SWXL column, 5 µM particle size, 7.8×300 nm (Tosoh Bioscience, 08541) to separate protein by size. A UV detector with a wavelength of 220 nm was used to detect samples injected at a mass load of 35 µg. The mobile phase which allows for separation on the column was 100 mM sodium phosphate, 250 mM sodium chloride, pH 6.8.

Opalescence measurement was also used to assess stability. Opalescence examines physical instability of a formulation due to the presence of aggregates. Opalescence was measured in a 2100 AN Turbidimeter, using 13 cm×100 mm glass tubes and a 13 mm sample tube adapter. Samples of at least 2.5 mL were used for each measurement. A standard curve was generated using Stablcal® turbidity standard (Hach Company) prepared to expected turbidimetry readings of 3, 6, 18 and 30 nephelometric turbidity units (NTUs) by diluting a stock standard in water.

Transport stress studies were also used to assess stability. Frozen formulations were thawed statically at room temperature protected from light using a TempTale® temperature monitor to monitor temperature conditions in the cold room during the thaw. After fully thawing, the cap on the bottle was tightened to avoid leakage. The bottle was placed on its side and rolled gently for 4-6 minutes to ensure thorough mixing. The bottle was then placed at −30° C. for 8 hours to re-freeze. Freezing was confirmed visually. The freeze-thaw process was repeated for a total of 3 cycles. Next, the formulation was mixed with an overhead mixer for 15 minutes to simulate shear from a mixing operation, and then filtered at 2-8° C. under pressure using a 0.2 µm PVDF filter. The formulation was sterile-filtered a second time prior to filling into syringes followed by stoppering. The formulations were pressure-filtered through a 0.2 µm PVDF filter, then hand-filled into syringes or vials. The hand-filled syringes were stoppered using an ASPU (autoclavable stopper placement unit) system. The filled and stoppered syringes were placed in a laminar air flow hood at room temperature for 3 days to mimic room temperature and light exposure stresses expected during manufacturing. Temperature was recorded using a TempTale® temperature monitor, and UV and visible light levels were recorded using a photometer. A portion of the filled syringes were subjected to simulated air and ground transportation stresses. Air and ground simulated transport stress studies were carried out, for a total duration of 91.5 hours, with air transportation vibration of 48 hours and truck transportation vibration for 43.5 hours. Samples were also subjected to the International Safe Transit Association (ISTA 3A) drop test sequence six times which included drops 1 thru 9 prior to the 91.5 hour air and ground vibrational simulation and drops 10 thru 17 after the air and ground vibrational transport simulation. The syringes were stored for 2 weeks at 40° C. Stability was assessed by SE-HPLC, CEX-HPLC, and micro-flow imaging (MFI). MFI measures the presence of sub-visible particles by passing a sample through a visual flow cell, counting particles as they pass through the cell, and categorizing into different bins based on size. An aspect ratio is applied to resolve silicone oil, if present, from proteinaceous particles. MFI (Micro-Flow Imaging) was performed on MFI 5200 systems. The size range of particles measured was from 1 to 70 µm. The sample volume measured was 1 mL, with pre filled syringes pooled into a clean glass vial to allow for adequate volume of at least 1 mL for measurement. Between each measurement, the system was flushed and a baseline established before proceeding. For each sample measurement, a digital camera is used to magnify, record the size, shape and morphology of visible particles.

Conductivity is the ability of an aqueous solution to conduct an electric current between two electrodes. Because a current flows via ion transport, the more ions in a particular solution, the higher the conductivity. Conductivity of the formulations described herein was assessed on a Model CDM83, Thermo Orion 4 or Model 5230 Seven Compact, Mettler Toledo instrument, using a conductivity cell. At minimum of at least 20 mL sample (Thermo Orion) or 3 mL sample (Mettler Toledo) was used for each measurement. The cell was rinsed with water and dried between sample measurements. Conductivity measurements were performed at ambient room temperature, and is reported using the standard SI unit of siemens per meter (S/m).

Osmolality is the concentration of a solution in terms of amount of solute quantity of solvent. For example, serum has an osmolality ranging from about 270-300 mOsM. Osmolality of the formulations described herein can be determined using, for example, Freezing Point Depression Osmometry.

Example 1

Effect of Buffer Composition on Formulation Stability

Adalimumab biosimilar was prepared in a target formulation buffer by centrifuge concentration using a 30 kD MW cutoff filter tube. 2 mL of adalimumab biosimilar was diluted with the target formulation buffer to a volume of 15 mL, followed by a centrifuge concentration step to a final volume of around 2 mL before repeating the dilution and centrifuge concentration step three times. Around 3 mL were collected after the last centrifuge concentration step, which was diluted with the desired formulation buffer to 100 mg/mL, sterile filtered and aliquoted into 5 cc glass vials. Following the filling step, samples were placed at 40° C. and examined for stability at approximately 1 week, 2 weeks and 4 weeks.

The formulation buffers used for the centrifuge concentration step contained various buffers, with the pH of the buffer adjusted to 5.2±0.1 using either NaOH or monoethanolamine (MEA). Each buffer contained isotonic proline as an additional excipient. Formulations without buffer were prepared by adjusting the pH of methane sulfonic acid (MSA) to pH 5.2±0.1 with MEA or NaOH. The composition of the formulation buffer, and the pH and antibody (Ab) concentration of the formulations are provided in Table 1.

TABLE 1

| Ref. | Buffer | Excipient | pH adjusting agent | pH | Ab conc. (mg/mL) |
|---|---|---|---|---|---|
| 1A | 20 mM benzoate | 300 mM proline | MEA | 5.2 | 73 |
| 1B | 20 mM benzoate | 300 mM proline | NaOH | 5.2 | 109 |
| 1C | 20 mM glutamate | 300 mM proline | MEA | 5.2 | 105 |
| 1D | 20 mM glutamate | 300 mM proline | NaOH | 5.1 | 111 |
| 1E | 20 mM glycolate | 300 mM proline | MEA | 5.2 | 110 |
| 1F | 20 mM glycolate | 300 mM proline | NaOH | 5.2 | 108 |
| 1G | 20 mM lactate | 300 mM proline | MEA | 5.1 | 109 |
| 1H | 20 mM lactate | 300 mM proline | NaOH | 5.1 | 104 |
| 1I | — | 20 mM MSA 300 mM proline | MEA | 5.3 | 100 |
| 1J | — | 20 mM MSA 300 mM proline | NaOH | 5.3 | 107 |

To assess stability, the % acidic peak was measured by CEX-HPLC after 0, 6, 13, and 28 days at 40° C. As shown in FIG. 1, the formulations containing lactate or glycolate buffers demonstrated less acidic peak growth over time compared to the formulations containing benzoate or glutamate buffers. The formulations without buffer, but including MSA, demonstrated stability comparable to the buffered formulations and improved compared to the benzoate and glutamate-buffered formulations at the 28 day time point.

Figure 2:
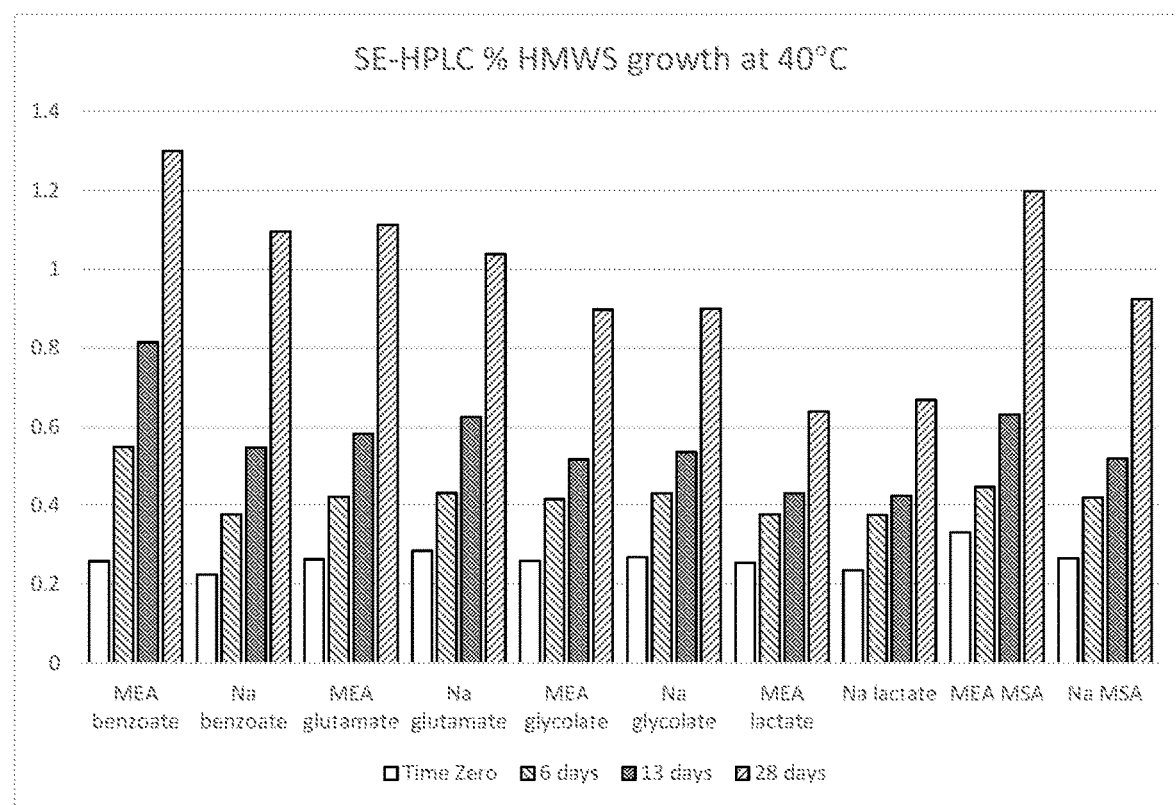
FIG. 2 is a bar graph of stability of adalimumab formulations as determined by size-exclusion high-performance liquid chromatography (SE-HPLC).

Stability also was assessed by measuring high molecular weight species (HMWS) by SE-HPLC after 0, 6, 13, and 28 days at 40° C. As shown in FIG. 2, the formulations containing lactate demonstrated significantly less HMWS growth over time compared to the other formulations. Compared to glycolic acid, lactic acid has a structure that differs only by including an additional methyl group. As shown in FIG. 2, HMWS were surprisingly lower for the formulations containing lactate compared to the formulations containing glycolate. The formulations without buffer, but including MSA, demonstrated stability comparable to the buffered formulations.

Example 2

Effect of PEG, Dextran, and Calcium Chloride on Formulation Stability

Adalimumab biosimilar solution at a concentration of 220 mg/mL ("UF DF stock") was prepared by ultrafiltration/diafiltration (UF DF) into a buffer of 20 mM glutamate, pH 5.1 using a Cogent μScale tangential flow filtration (TFF) system with a delta pressure set to about 23 psi. A Millipore Pellicon 3 Ultracell 30 kD 0.11 m² cassette was used as the exchange filter. The resulting material was then further concentrated to 220 mg/mL to obtain the UF DF stock.

Stock 2× excipient solutions were prepared, and were then diluted into UF DF stock adalimumab biosimilar solution. Upon final dilution and mixing in of the 2× excipients, the adalimumab biosimilar concentration was adjusted to about 100 mg/mL. If needed, the pH was adjusted to 5.2±0.2 using NaOH or HCl. The composition of the formulation buffer, and the pH and antibody concentration of the formulations are provided in Table 2. Following sterile filtration, aliquots were filled into 5 cc glass vials and stored at −30° C., 4° C., and 40° C.

TABLE 2

| Ref. | Buffer | Excipient(s) | pH | Ab conc. (mg/mL) |
|---|---|---|---|---|
| 2A | 20 mM glutamate | 7% PEG 3350 | 5.4 | 114 |
| 2B | 20 mM glutamate | 7% PEG 3350 45 mM calcium chloride | 5.3 | 114 |
| 2C | 20 mM glutamate | 10% dextran | 5.1 | 128 |
| 2D | 20 mM glutamate | 10% dextran 45 mM calcium chloride | 5.2 | 119 |
| 2E | 20 mM glutamate | 1% PEG 200 | 5.1 | 110 |
| 2F | 20 mM glutamate | 1% PEG 200 40 mM calcium chloride | 5.1 | 115 |
| 2G | 20 mM glutamate | 2% PEG 600 | 5.1 | 110 |
| 2H | 20 mM glutamate | 2% PEG 600 40 mM calcium chloride | 5.1 | 109 |

Figure 3:
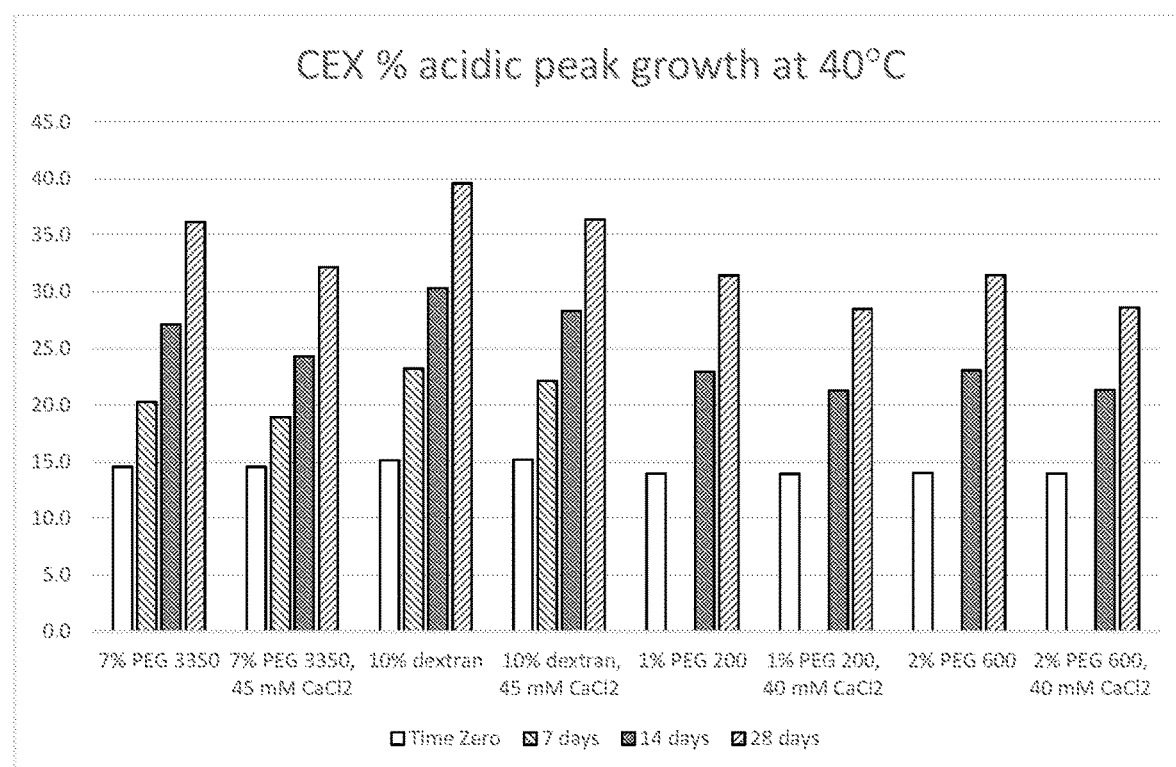
FIG. 3 is a bar graph of stability of adalimumab formulations as determined by CEX-HPLC.

To assess stability, the % acidic peak was measured by CEX-HPLC after 0, 7, 14, and 28 days at 40° C. As shown in FIG. 3, the formulations containing calcium chloride and one of PEG 200, PEG 600, PEG 3350, or dextran demonstrated less acidic peak growth over time compared to otherwise similar formulations without calcium chloride. In addition, the formulations containing PEG 200 or PEG 600 demonstrated less acidic peak growth over time compared to the formulations containing PEG 3350 or dextran.

Figure 4:
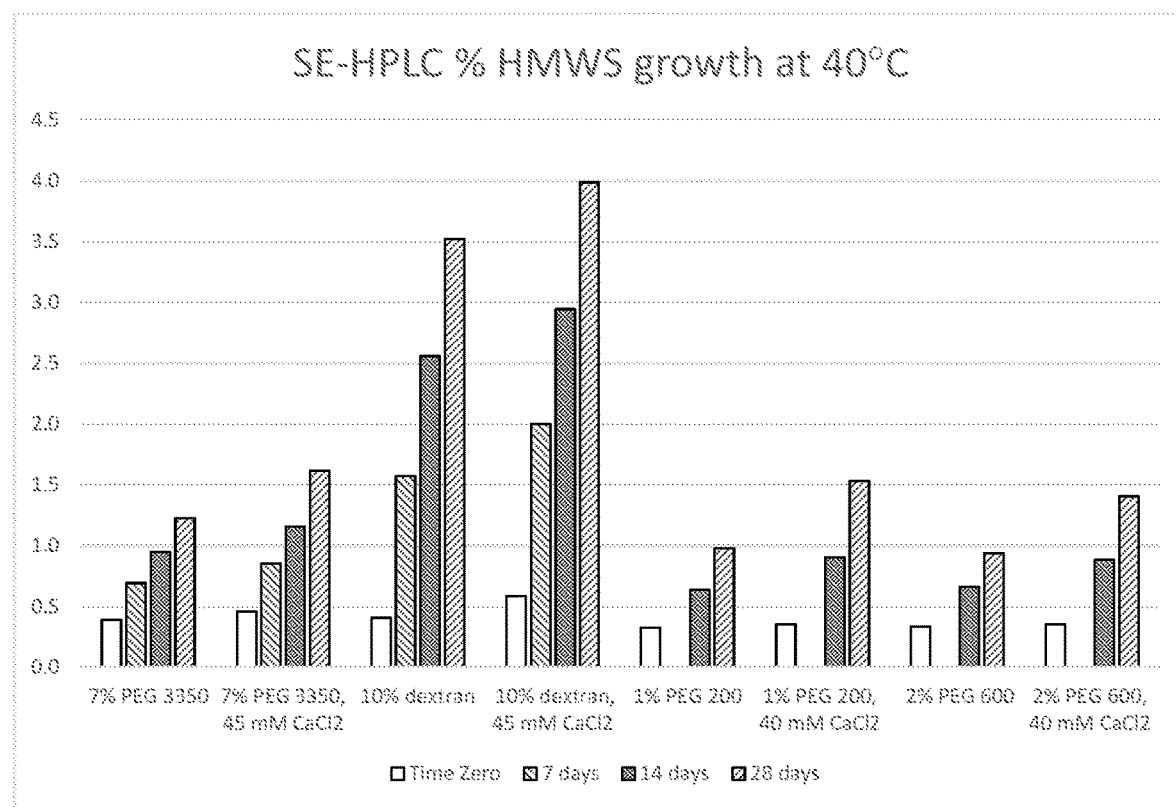
FIG. 4 is a bar graph of stability of adalimumab formulations as determined by SE-HPLC.

Stability also was assessed by measuring HMWS by SE-HPLC after 0, 7, 14, and 28 days at 40° C. As shown in FIG. 4, the formulations containing PEG 200, PEG 600, or PEG 3350 (alone or in combination with calcium chloride) demonstrated less HMWS growth over time compared to the formulations containing dextran.

Example 3

Effect of Proline, PEG, MSA, TEA, and Calcium Chloride on Frozen Stability

Stock 2× excipient solutions in 20 mM glutamate buffer, pH 5.2 were added to the UF DF stock adalimumab biosimilar solution described in Example 2 to a final protein concentration of 100 mg/mL. If needed, the pH was adjusted to 5.2±0.2 using NaOH or HCl. The final formulations were sterile filtered and placed into 5 cc glass vials for subsequent tests.

Three free thaw (F/T) cycles were executed, with room temperature thaws of samples stored at −30° C. at each cycle. After the freeze thaw cycles, each formulation was then analyzed for stability and the remainder of the material stored at −30° C. for long term storage stability. The composition of the formulation buffer, and the pH and antibody concentration of the formulations are provided in Table 3.

TABLE 3

| Ref. | Buffer | Excipient(s) | pH | Ab conc. (mg/mL) |
|---|---|---|---|---|
| 3A | 20 mM glutamate | 250 mM proline | 5.1 | 119 |
| 3B | 20 mM glutamate | 1% PEG 3350 | 5.4 | 114 |
| 2A | 20 mM glutamate | 7% PEG 3350 | 5.4 | 114 |
| 2B | 20 mM glutamate | 7% PEG 3350 45 mM calcium chloride | 5.3 | 114 |
| 2E | 20 mM glutamate | 1% PEG 200 | 5.1 | 110 |
| 2F | 20 mM glutamate | 1% PEG 200 40 mM calcium chloride | 5.1 | 115 |
| 2G | 20 mM glutamate | 2% PEG 600 | 5.1 | 109 |
| 2H | 20 mM glutamate | 2% PEG 600 40 mM calcium chloride | 5.1 | 109 |
| 3C | 20 mM glutamate | 100 mM MSA 50 mM TEA | 5.2 | 109 |

Figure 5:
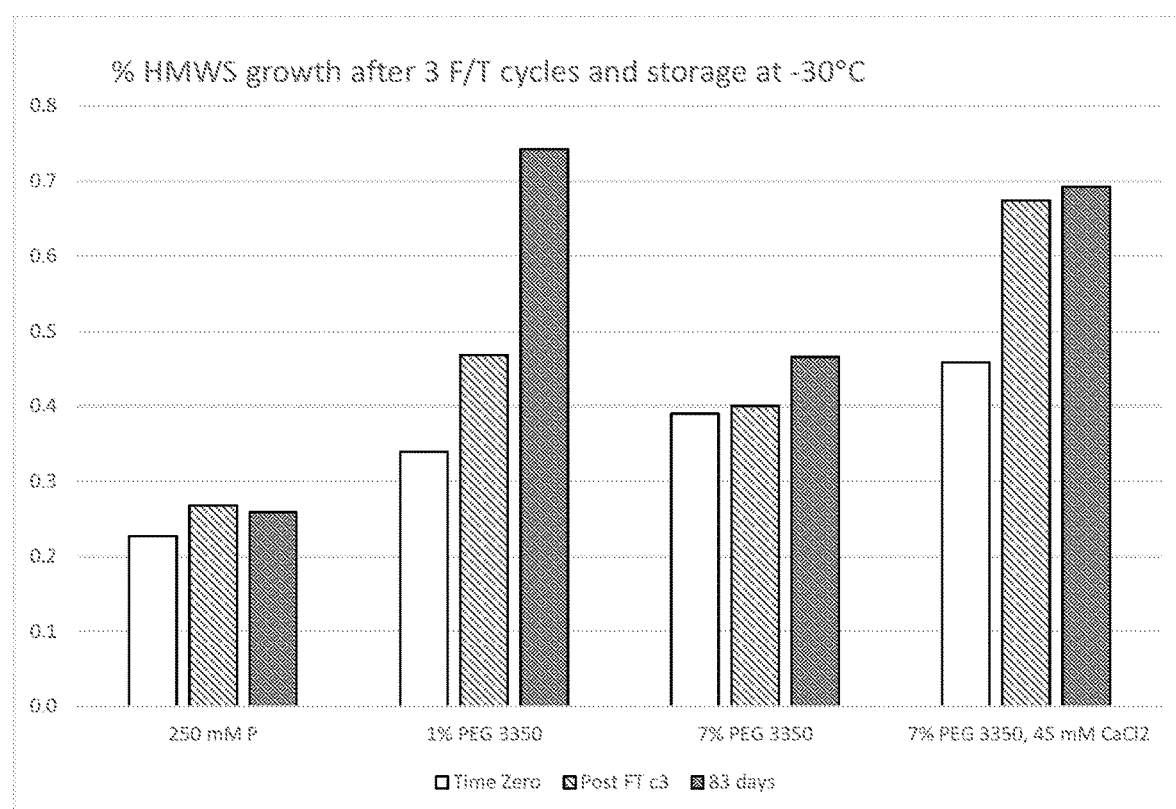
FIG. 5 is a bar graph of stability of adalimumab formulations as determined by SE-HPLC.

Stability was assessed by measuring HMWS by SE-HPLC after 0 days, after 3 F/T cycles, and after 83 days at −30° C. As shown in FIG. 5, the formulations containing proline demonstrated almost no HMWS growth over time.

Figure 6:
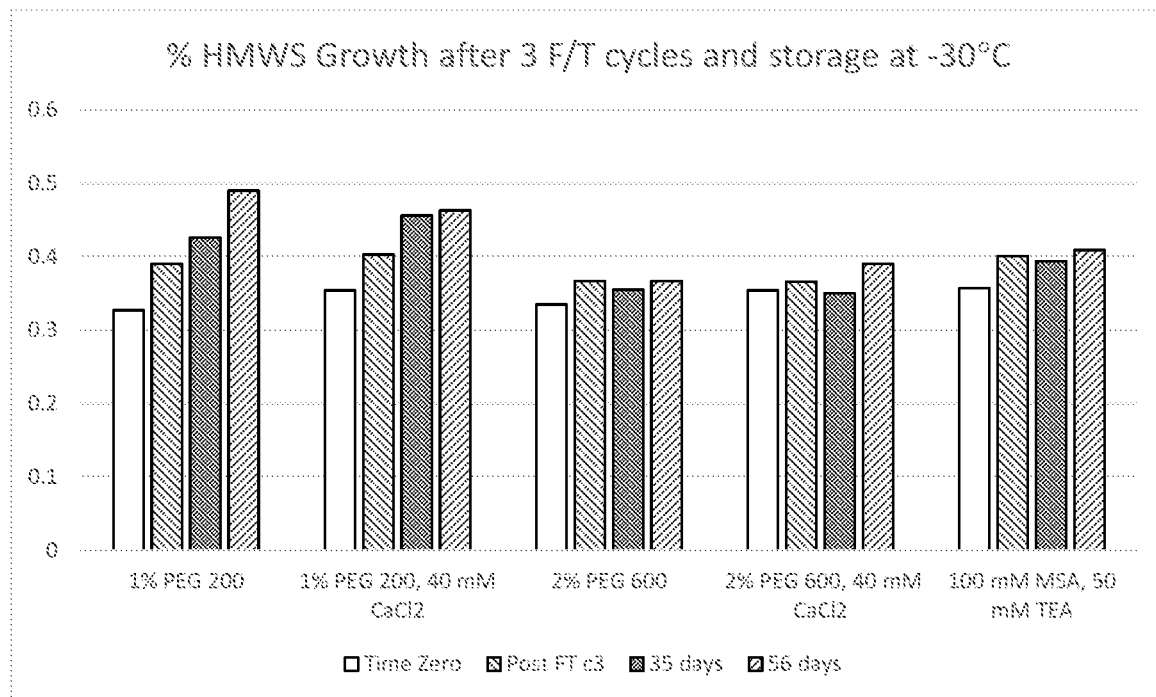
FIG. 6 is a bar graph of stability of adalimumab formulations as determined by SE-HPLC.

Stability was also assessed by measuring HMWS by SE-HPLC after 0 days, after 3 F/T cycles, after 35 days at −30° C., and after 56 days at −30° C. As shown in FIG. 6, the formulations containing PEG 600 and a formulation with MSA and triethanolamine (TEA) demonstrated a small decrease in HMWS growth upon F/T stress and storage at −30° C. compared to the formulations containing PEG 200.

Example 4

Effect of Salts on Formulation Stability

The OF DF stock adalimumab biosimilar solution described in Example 2 was diluted to 170 mg/mL with 20 mM glutamate, pH 5.2 buffer and various salts were added directly by weight until dissolved at a final concentration of 75 mM. A stock concentrated solution of proline in the 20 mM glutamate, pH 5.2 buffer was also added to achieve a final concentration of 100 mM. After preparing the protein solutions, the pH was adjusted if needed with either HCl or NaOH to 5.2±0.4. The composition of the formulation buffer, and the pH and antibody concentration of the formulations are provided in Table 4. Following sterile filtration, aliquots were filled into 5 cc glass vials and stored at −30° C., 4° C., and 40° C.

TABLE 4

| Ref. | Buffer | Excipient(s) | pH | Ab conc. (mg/mL) |
|---|---|---|---|---|
| 4A | 20 mM glutamate | 75 mM sodium borate 100 mM proline | 5.6 | 175 |
| 4B | 20 mM glutamate | 75 mM sodium bicarbonate 100 mM proline | 5.2 | 180 |
| 4C | 20 mM glutamate | 75 mM sodium sulfate 100 mM proline | 5.2 | 183 |
| 4D | 20 mM glutamate | 15 mM calcium sulfate 100 mM proline | 5.1 | 178 |
| 4E | 20 mM glutamate | 75 mM ammonium sulfate 100 mM proline | 5.2 | 175 |
| 4F | 20 mM glutamate | 75 mM calcium chloride 100 mM proline | 5.1 | 172 |
| 4G | 20 mM glutamate | 75 mM sodium chloride 100 mM proline | 5.2 | 167 |
| 4H | 20 mM glutamate | 75 mM magnesium chloride 100 mM proline | 5.1 | 193 |

Figure 7:
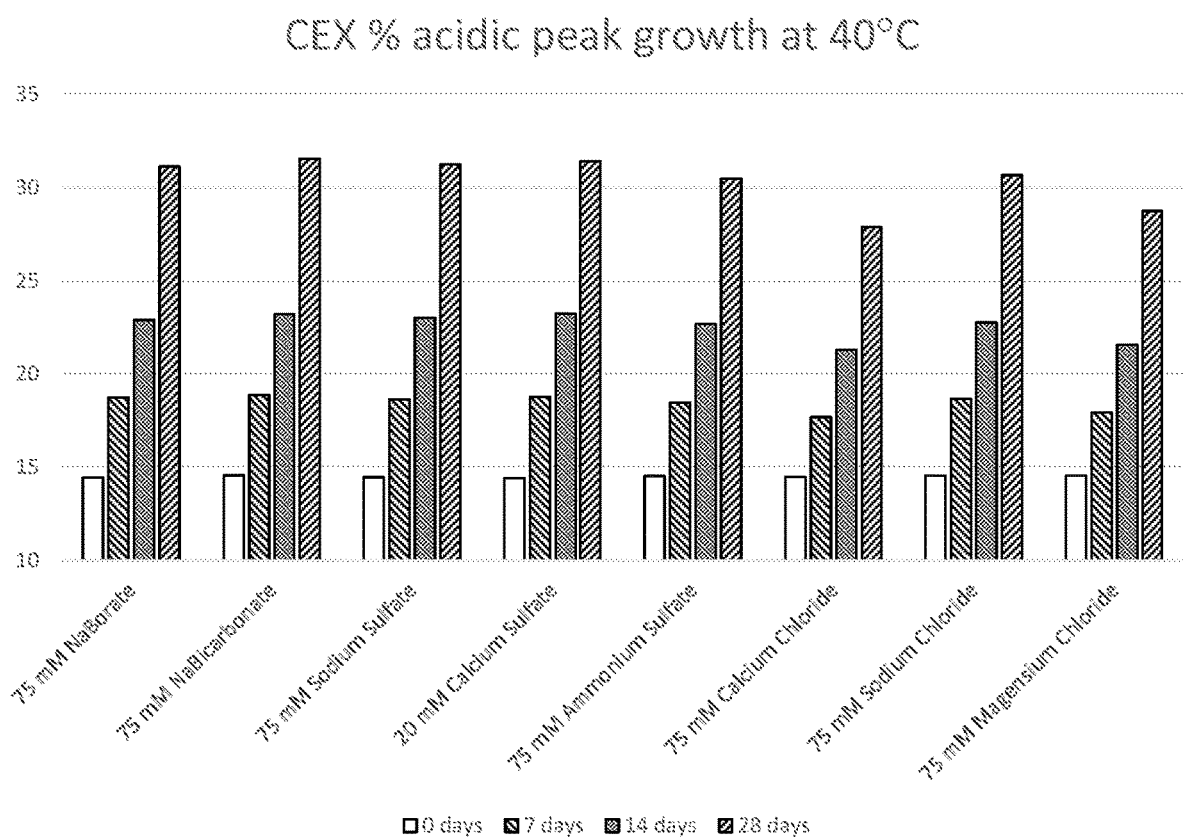
FIG. 7 is a bar graph of stability of adalimumab formulations as determined by CEX-HPLC.

To assess stability, the % acidic peak was measured by CEX-HPLC after 0, 7, 14, and 28 days at 40° C. As shown in FIG. 7, the formulations containing calcium chloride or magnesium chloride demonstrated less acidic peak growth over time compared to the formulations containing sodium borate, sodium bicarbonate, sodium sulfate, calcium sulfate, ammonium sulfate, or sodium chloride.

Figure 8:
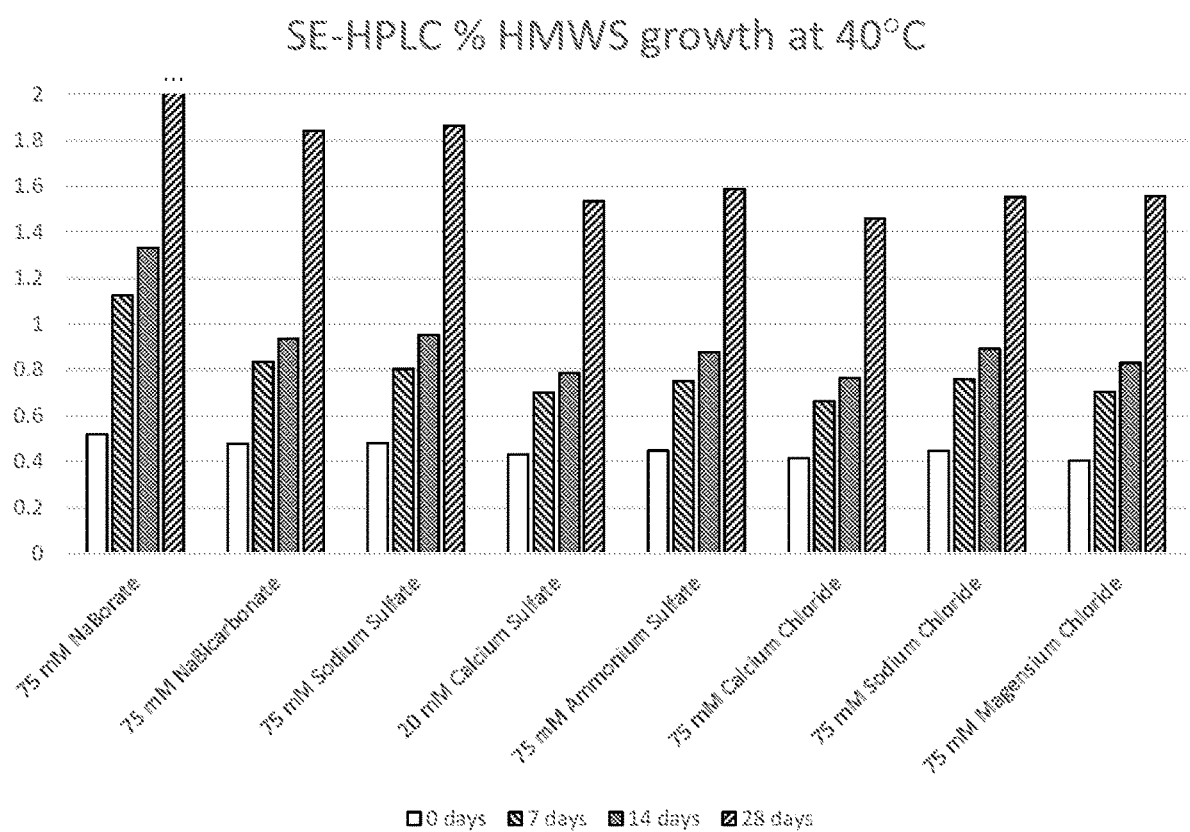
FIG. 8 is a bar graph of stability of adalimumab formulations as determined by SE-HPLC. The symbol " . . . " indicates a value above the maximum shown on the y-axis.

Stability also was assessed by measuring BMWS by SE-HPLC after 0, 7, 14, and 28 days at 40° C. As shown in FIG. 8, the formulations containing calcium sulfate, ammonium sulfate, calcium chloride, sodium chloride, or magnesium chloride demonstrated less HMWS growth over time compared to the formulations containing sodium borate, sodium bicarbonate, or sodium sulfate.

Example 5

Effect of MEA on Formulation Stability

The OF DF stock adalimumab biosimilar solution described in Example 2 was diluted with 20 mM glutamate buffer, pH 5.0 and 2M MEA in volumes needed to generate the final MEA concentrations shown in Table 5. After preparing the protein solutions, the pH was adjusted if needed with either HCl or NaOH to 5.2. The composition of the formulation buffer, and the pH and antibody concentration of the formulations are provided in Table 5. Following sterile filtration, aliquots were filled into 5 cc glass vials and stored at 4° C. or 40° C.

TABLE 5

| Ref. | Buffer | Excipient(s) | pH | Ab conc. (mg/mL) |
|---|---|---|---|---|
| 5A | 20 mM glutamate | 30 mM MEA | 5.2 | 182 |
| 5B | 20 mM glutamate | 80 mM MEA | 5.2 | 182 |
| 5C | 20 mM glutamate | 115 mM MEA | 5.2 | 185 |
| 5D | 20 mM glutamate | 160 mM MEA | 5.2 | 177 |

Figure 9:
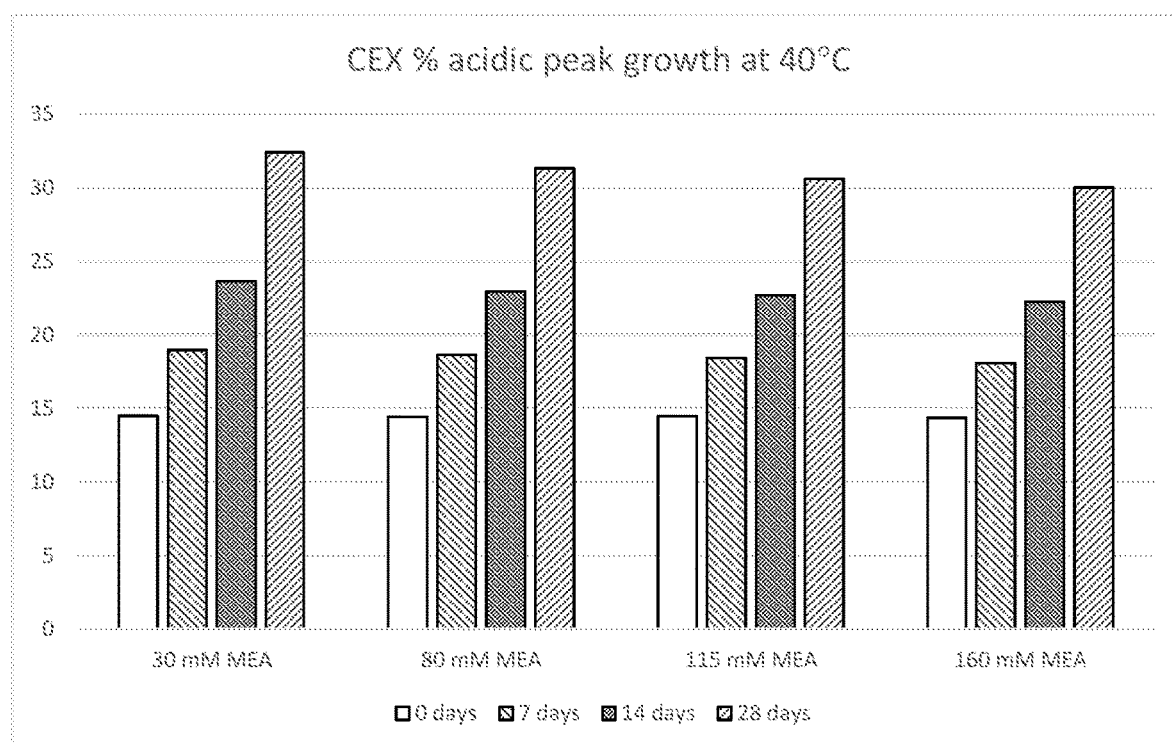
FIG. 9 is a bar graph of stability of adalimumab formulations as determined by CEX-HPLC.

To assess stability, the % acidic peak was measured by CEX-HPLC after 0, 7, 14, and 28 days at 40° C. As shown in FIG. 9, the formulations containing higher concentrations of MEA (e.g., 160 mM MEA) demonstrated less acidic peak growth over time compared to the formulations containing lower concentrations of MEA (e.g., 30 mM MEA). The ratio of % acidic peak after 28 days to the % acidic peak at 0 days was 2.23 for formulation 5A, 2.17 for formulation 5B, 2.11 for formulation 5C, and 2.09 for formulation 5D.

Figure 10:
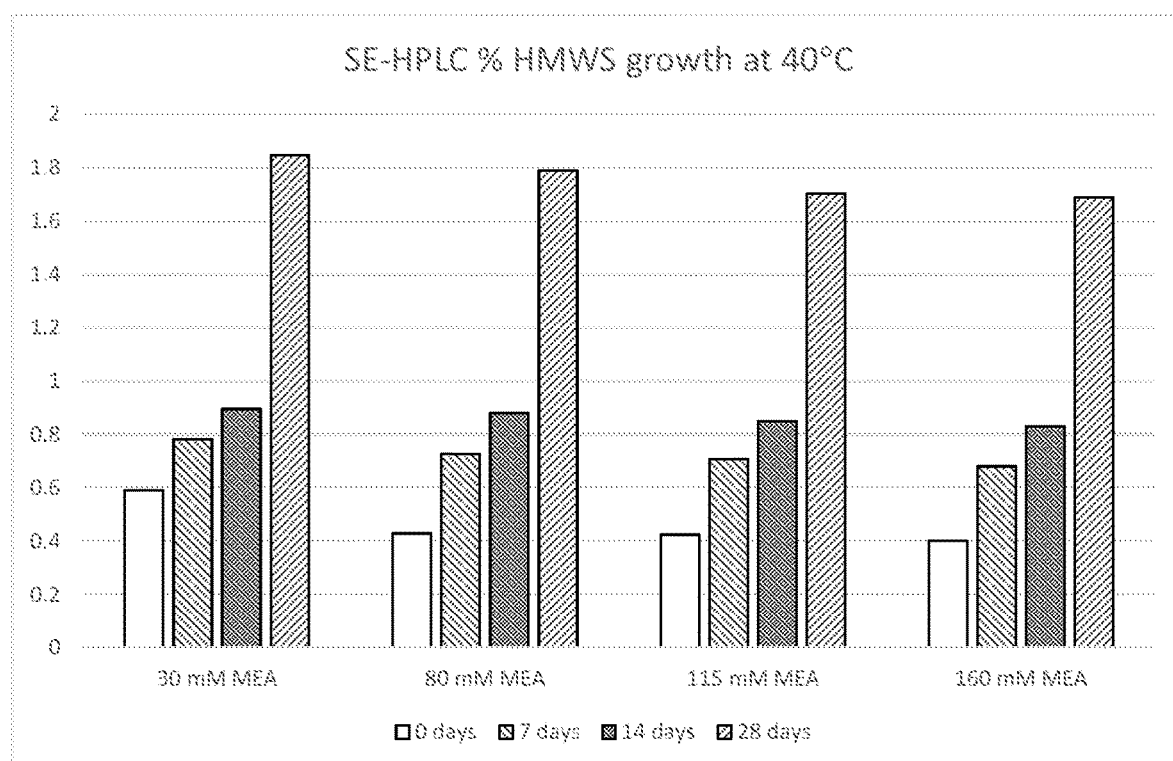
FIG. 10 is a bar graph of stability of adalimumab formulations as determined by SE-HPLC.

Stability also was assessed by measuring BMWS by SE-HPLC after 0, 7, 14, and 28 days at 40° C. As shown in FIG. 10, the formulations containing higher concentrations of MEA (e.g., 160 mM MEA) demonstrated slightly less HMWS growth over time compared to the formulations containing lower concentrations of MEA (e.g., 30 mM MEA).

Example 6

Effect of Excipients on Formulation Stability

The OF DF stock adalimumab biosimilar solution described in Example 2 was diluted to around 105 mg/mL once excipients were added. In each formulation, 2× stock excipient solutions in 20 mM glutamate buffer, pH 5.2 were added to a final protein concentration of around 105 mg/mL. The pH was adjusted to 5.2±0.1 with HCl or NaOH if needed. The final formulations were sterile filtered and placed into 5 cc glass vials for subsequent tests. The composition of the formulation buffer, and the pH and antibody concentration of the formulations are provided in Table 6.

TABLE 6

| Ref. | Buffer | Excipient(s) | pH | Ab conc. (mg/mL) |
|---|---|---|---|---|
| 6A | 20 mM glutamate | 1.4% ethanol | 5.1 | 102 |
| 6B | 20 mM glutamate | 0.5% ethanol 40 mM calcium chloride | 5.2 | 106 |
| 6C | 20 mM glutamate | 0.5% ethanol 1% PEG 3350 40 mM calcium chloride | 5.2 | 108 |
| 6D | 20 mM glutamate | 150 mM TEA 40 mM calcium chloride | 5.2 | 107 |
| 6E | 20 mM glutamate | 30 mM TEA 75 mM calcium chloride | 5.2 | 105 |
| 6F | 20 mM glutamate | 0.5% ethanol | 5.2 | 106 |
| 6G | 20 mM glutamate | 0.5% ethanol 2% PEG 200 | 5.2 | 106 |
| 6H | 20 mM glutamate | 0.25% ethanol 2% PEG 200 | 5.2 | 102 |
| 6I | 20 mM glutamate | 0.5% ethanol 100 mM MSA | 5.1 | 105 |
| 6J | 20 mM glutamate | 0.5% ethanol 0.5% poly(vinylpyrrolidone) (PVP) 10K 100 mM MSA | 5.2 | 105 |
| 6K | 20 mM glutamate | 0.5% ethanol 100 mM MEA | 5.2 | 101 |

Figure 11:
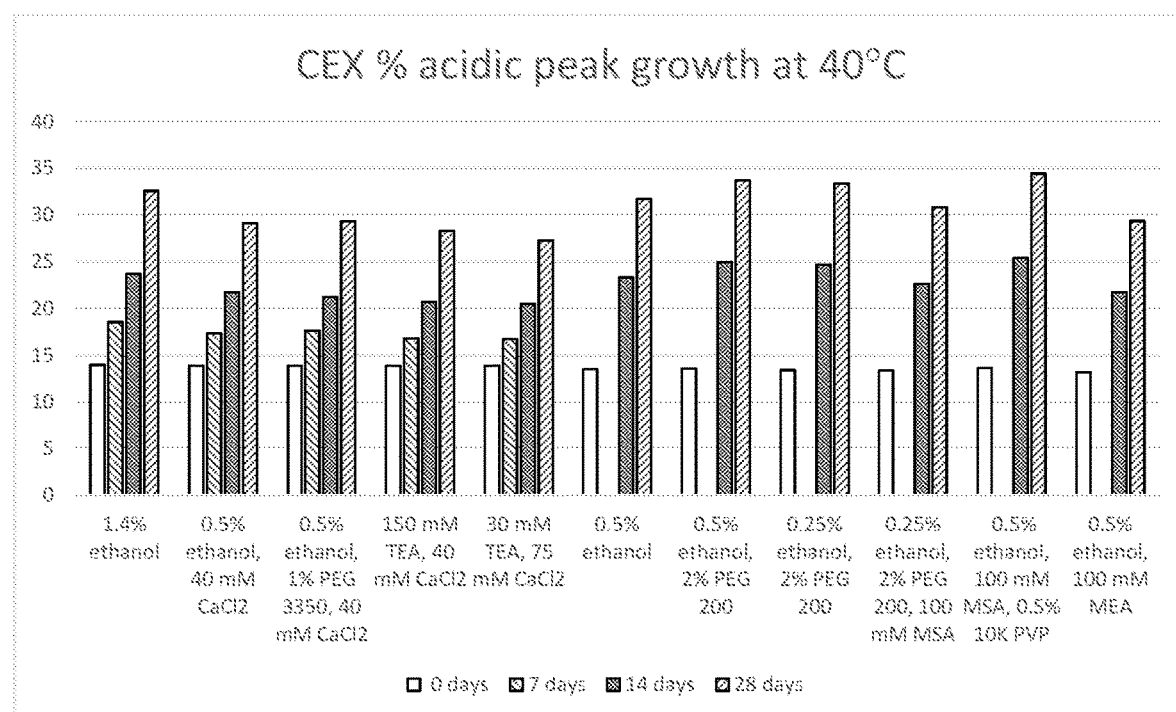
FIG. 11 is a bar graph of stability of adalimumab formulations as determined by CEX-HPLC.

To assess stability, the % acidic peak was measured by CEX-HPLC after 0, 7, 14, and 28 days at 40° C. As shown in FIG. 11, the formulations containing ethanol with calcium chloride, ethanol with calcium chloride and PEG 3350, TEA with calcium chloride, and ethanol with MEA demonstrated less than 30% of acidic peak after 4 weeks at 40° C. The formulations containing 1.4% ethanol with no additional excipients demonstrated stability comparable to the formulations containing 0.5% ethanol with no additional excipients at the 4 week time point.

Figure 12:
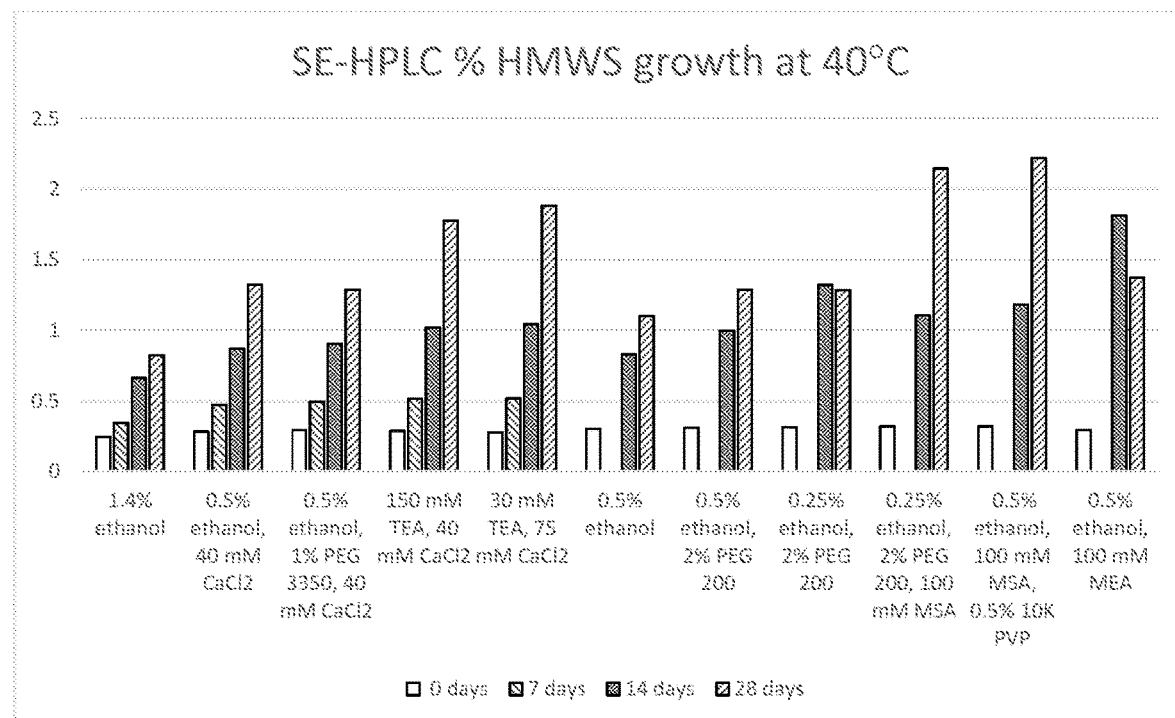
FIG. 12 is a bar graph of stability of adalimumab formulations as determined by SE-HPLC.

Stability also was assessed by measuring HMWS by SE-HPLC after 0, 7, 14, and 28 days at 40° C. As shown in FIG. 12, the formulation containing 1.4% ethanol with no additional excipients demonstrated less than 1% of HMWS after 4 weeks at 40° C. The formulations containing 0.5% ethanol, ethanol in combination with calcium chloride, ethanol in combination with calcium chloride and PEG 3350, ethanol in combination with PEG 200, and ethanol in combination with MEA demonstrated less than 1.5% of HMWS at the 4 week time point.

Example 7

Effect of Amino Acids on Formulation Stability

Adalimumab biosimilar was prepared in a buffer containing 15 mM glutamate, pH 5.2 using a Cogent μScale TFF system with a 30 kD Millipore cassette and a pressure difference of about 23 psi. The protein was concentrated to 114 mg/mL, and the resulting material in 15 mM glutamic acid, pH 5.2 buffer was then concentrated by centrifugation concentration to 186 mg/mL. In each formulation, 2× stock excipient solutions in 15 mM glutamate buffer, pH 5.2 were added to the starting material, resulting in a final protein concentration of around 90-100 mg/mL. The pH was adjusted to 5.2 with HCl or NaOH if needed. The final formulations were sterile filtered and placed into 5 cc glass vials for subsequent tests. The composition of the formulation buffer, and the pH and antibody concentration of the formulations are provided in Table 7.

TABLE 7

| Ref. | Buffer | Excipient(s) | pH | Ab conc. (mg/mL) |
|---|---|---|---|---|
| 7A | 15 mM glutamate | 100 mM alanine 45 mM calcium chloride | 5.2 | 92 |
| 7B | 15 mM glutamate | 100 mM asparagine 45 mM calcium chloride | 5.2 | 95 |
| 7C | 15 mM glutamate | 100 mM isoleucine 45 mM calcium chloride | 5.2 | 96 |
| 7D | 15 mM glutamate | 100 mM serine 45 mM calcium chloride | 5.2 | 98 |
| 7E | 15 mM glutamate | 20 mM aspartic acid 80 mM proline 45 mM calcium chloride | 5.2 | 96 |
| 7F | 15 mM glutamate | 25 mM creatine 75 mM proline 45 mM calcium chloride | 5.2 | 96 |
| 7G | 15 mM glutamate | 50 mM glutamine 50 mM proline 45 mM calcium chloride | 5.2 | 97 |
| 7H | 15 mM glutamate | 50 mM leucine 50 mM proline 45 mM calcium chloride | 5.2 | 97 |
| 7I | 15 mM glutamate | 50 mM phenylalanine 50 mM proline 45 mM calcium chloride | 5.2 | 97 |
| 7J | 15 mM glutamate | 25 mM tryptophan 75 mM proline 45 mM calcium chloride | 5.2 | 90 |

Figure 13:
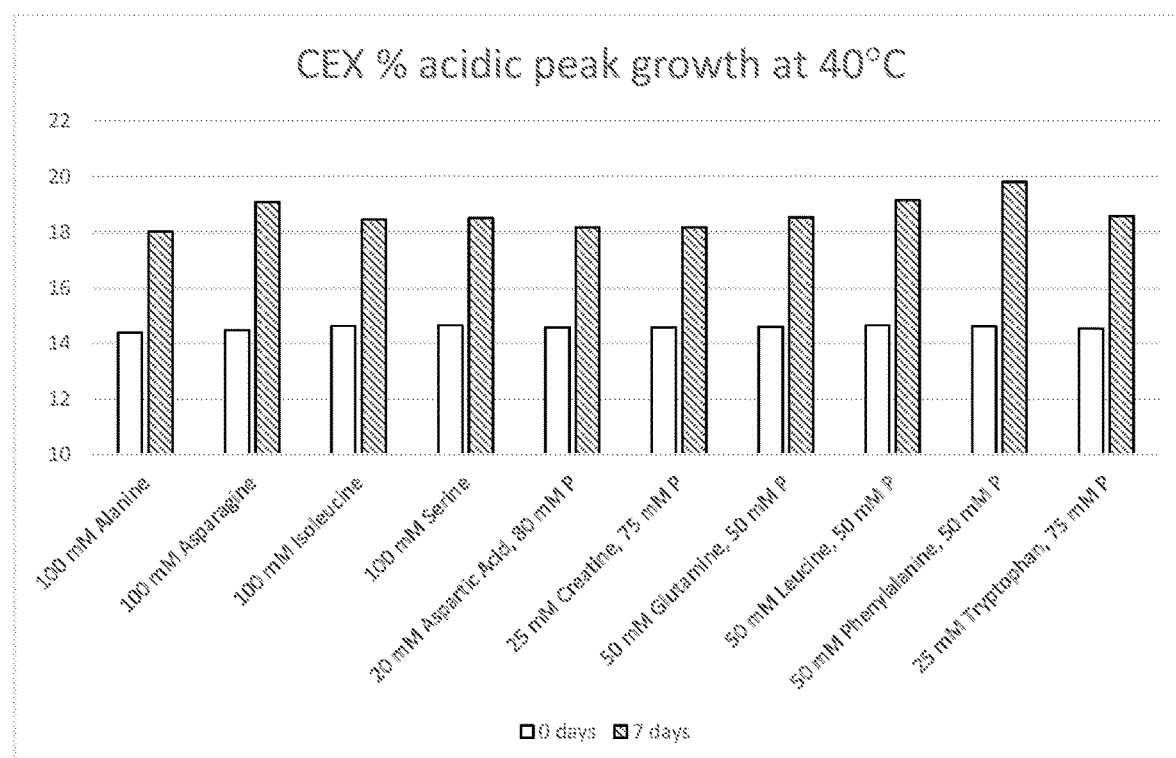
FIG. 13 is a bar graph of stability of adalimumab formulations as determined by CEX-HPLC.

To assess stability, the % acidic peak was measured by CEX-HPLC after 0 and 7 days at 40° C. As shown in FIG. 13, the formulations containing alanine, serine, proline in combination with glutamine, or proline in combination with creatine, for example, demonstrated 18-19% of acidic peak after 7 days incubation at 40° C., in comparison to the formulation containing proline in combination with phenylalanine, which demonstrated almost 20% of acidic peak after 7 days.

Figure 14:
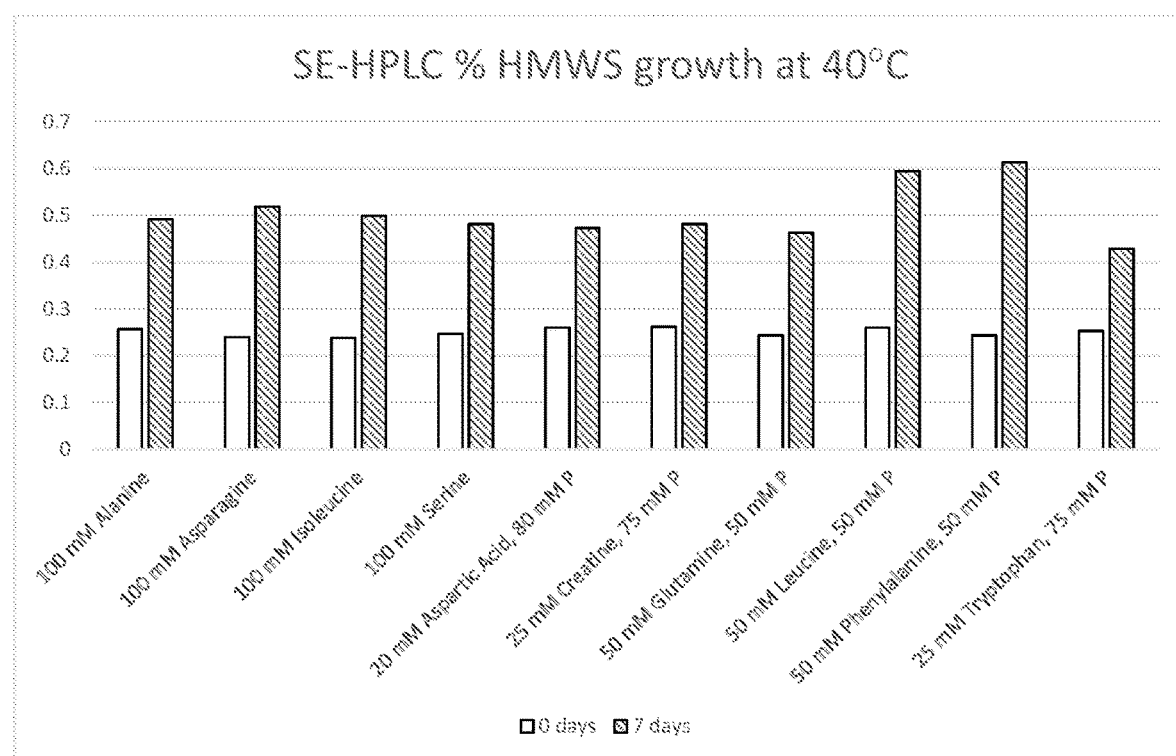
FIG. 14 is a bar graph of stability of adalimumab formulations as determined by SE-HPLC.

Stability also was assessed by measuring HMWS by SE-HPLC after 0 and 7 days at 40° C. As shown in FIG. 14, the formulations containing alanine, asparagine, isoleucine, serine, proline in combination with aspartic acid, proline in combination with creatine, proline in combination with glutamine, and proline in combination with tryptophan demonstrated about 0.5% or less of HMWS after 7 days at 40° C.

Example 8

Effect of Nonionic, Anionic, or Cationic Surfactants on Formulation Stability

Adalimumab biosimilar was prepared using a Cogent μScale TFF system with a 30 kD Millipore cassette and a pressure difference of about 23 psi in a buffer containing 20 mM acetate, 45 mM calcium chloride, and 100 mM arginine, with a final pH of 5.2. The resulting protein was concentrated to greater than 143 mg/mL. The material was then used for the addition of stock surfactant solutions to the final concentrations of surfactant and protein listed in Table 8. Final pH adjustment to 5.2 was accomplished with NaOH or HCl. For accelerated stability tests, aliquots were filled into 5 cc glass vials and examined for stability at 40° C. For shaking stress studies, 36 mL of each formulation in 50 cc containers was subjected to continued shaking stress at room temperature. The composition of the formulation buffer, and the pH and antibody concentration of the formulations are provided in Table 8.

TABLE 8

| Ref. | Buffer | Surfactant | Excipient(s) | pH | Ab conc. (mg/mL) |
|---|---|---|---|---|---|
| 8A | 20 mM acetate | 0.1% Polysorbate 20 | 45 mM calcium chloride 100 mM arginine-HCl | 5.2 | 140 |
| 8B | 20 mM acetate | 0.1% Polysorbate 80 | 45 mM calcium chloride 100 mM arginine-HCl | 5.2 | 140 |
| 8C | 20 mM acetate | 0.1% Pluronic F68 | 45 mM calcium chloride 100 mM arginine-HCl | 5.2 | 140 |
| 8D | 20 mM acetate | 0.01% Docusate sodium | 45 mM calcium chloride 100 mM arginine-HCl | 5.2 | 140 |
| 8E | 20 mM acetate | 0.1% benzalkonium chloride | 45 mM calcium chloride 100 mM arginine-HCl | 5.2 | 140 |
| 8F | 20 mM acetate | 0.1% Span 40 | 45 mM calcium chloride 100 mM arginine-HCl | 5.2 | 140 |
| 8G | 20 mM acetate | 0.1% Triton X-100 | 45 mM calcium chloride 100 mM arginine-HCl | 5.2 | 140 |
| 8H | 20 mM acetate | — | 45 mM calcium chloride 100 mM arginine-HCl | 5.2 | 140 |

Figure 15:
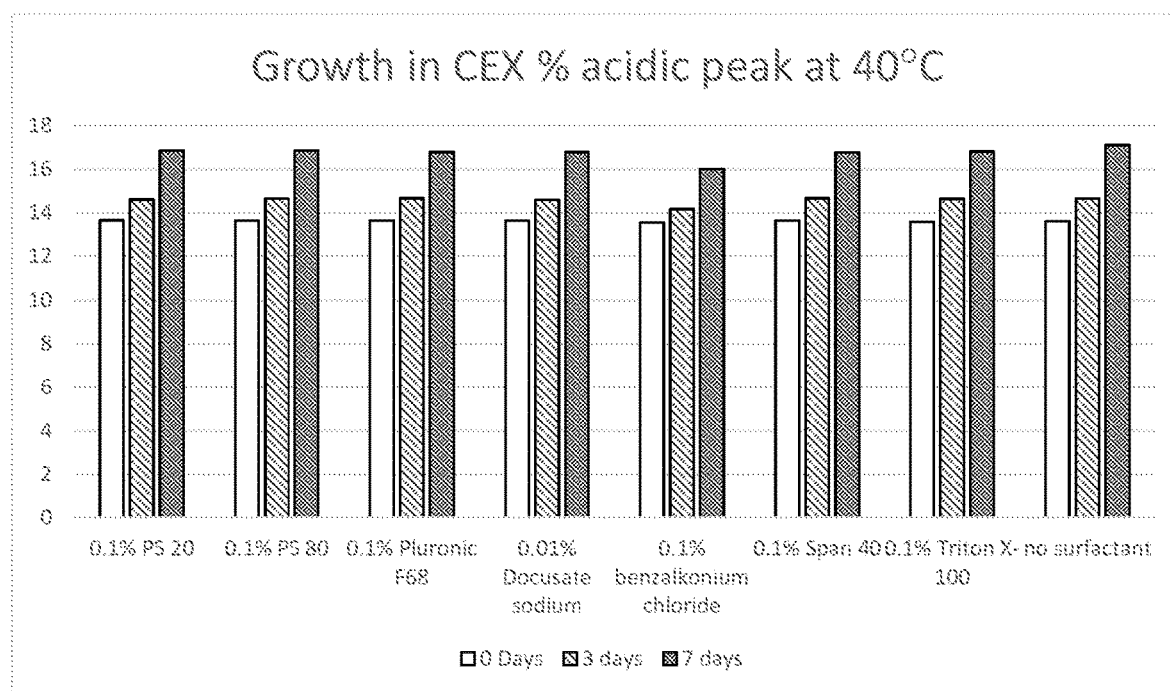
FIG. 15 is a bar graph of stability of adalimumab formulations as determined by CEX-HPLC.

To assess stability, the % acidic peak was measured by CEX-HPLC after 0, 3, and 7 days at 40° C. As shown in FIG. 15, the formulations containing nonionic, anionic, or cationic surfactants demonstrated similar amounts of acidic peak after 7 days at 40° C., in comparison to a formulation without surfactant.

Figure 16:
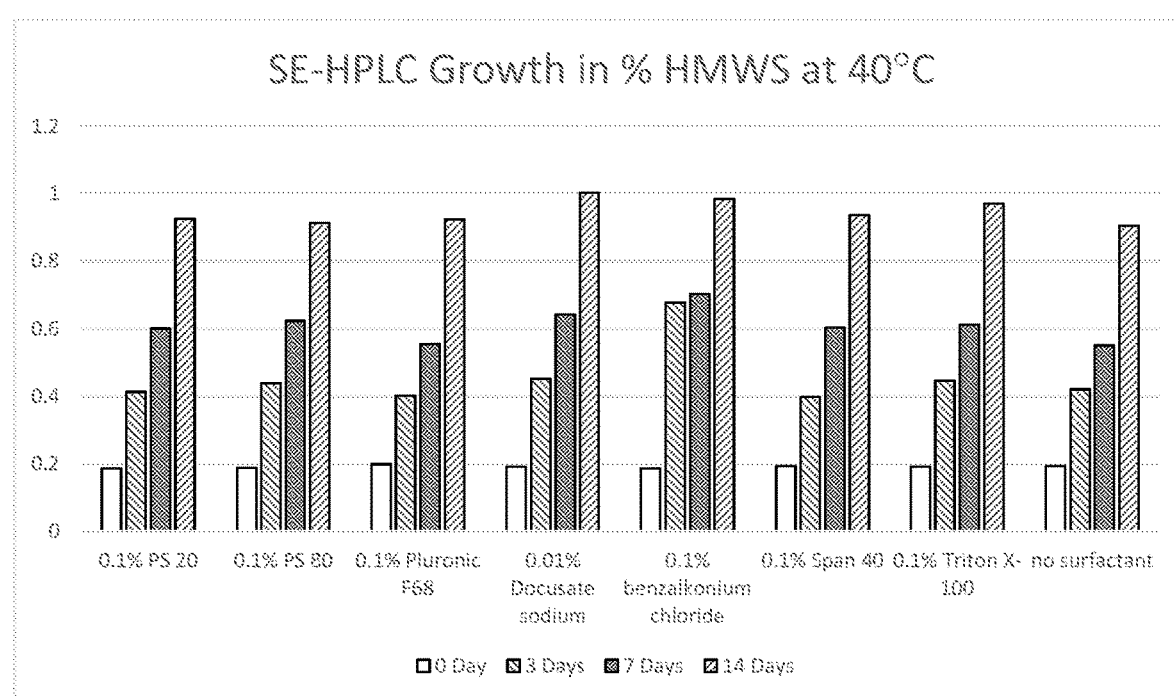
FIG. 16 is a bar graph of stability of adalimumab formulations as determined by SE-HPLC.

Stability also was assessed by measuring HMWS by SE-HPLC after 0, 3, 7, and 14 days at 40° C. As shown in FIG. 16, the formulations containing nonionic, anionic, or cationic surfactants demonstrated similar amounts of HMWS after 14 days at 40° C., in comparison to a formulation without surfactant.

Figure 17:
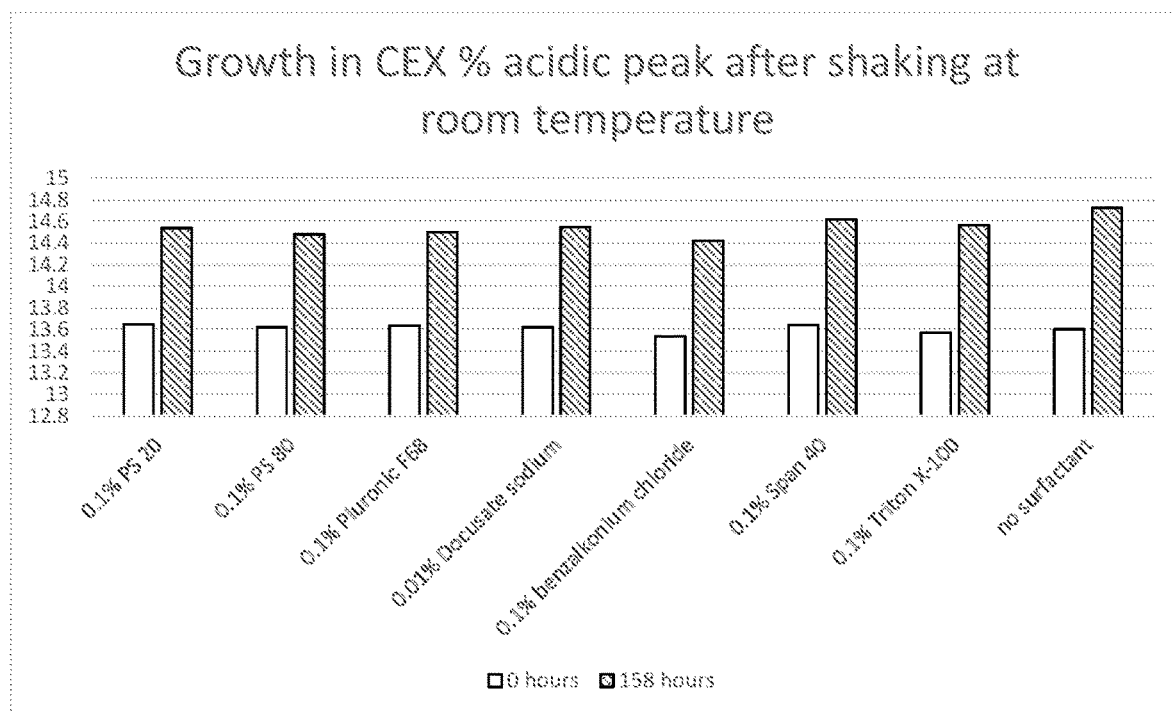
FIG. 17 is a bar graph of stability of adalimumab formulations as determined by CEX-HPLC.
Figure 18:
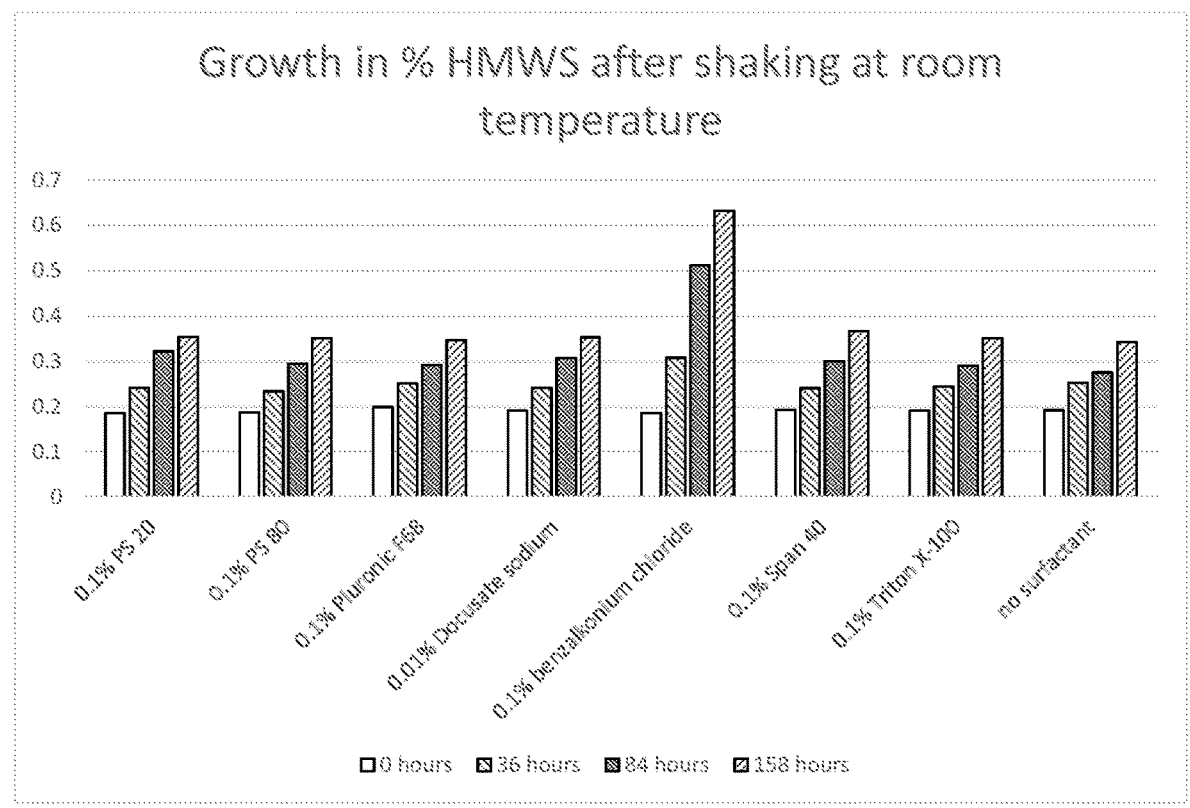
FIG. 18 is a bar graph of stability of adalimumab formulations as determined by SE-HPLC.

Stability was further assessed after subjecting the formulations to shaking stress. The % acidic peak was measured by CEX-HPLC after continuous shaking at room temperature for 0 and 158 hours. As shown in FIG. 17, the formulations containing surfactants demonstrated around 0.3% or less of acidic peak after continuous shaking at room temperature for 158 hours, in comparison to a formulation without surfactant. HMWS were measured by SE-HPLC after continuous shaking at room temperature for 0 and 158 hours. As shown in FIG. 18, the formulation containing benzalkonium chloride demonstrated about twice the percentage of HMWS, in comparison to the formulations containing other surfactants and a formulation without surfactant.

Example 9

Effect of Nonionic, Anionic, or Cationic Surfactants on Formulation Stability

Adalimumab biosimilar in a buffer consisting of 20 mM acetate, with 45 mM calcium chloride and 100 mM arginine, with a final pH set at 5.2 was used to assess stability upon stirring stress. The final formulation pH was adjusted to 5.2 using NaOH or HCl. Surfactants were chosen and selected at low, medium and high levels to assess stirring stability with adalimumab biosimilar at a final concentration of approximately 140 mg/mL. Stock surfactant solutions were made and diluted with the starting material to achieve the final surfactant concentrations as shown in Table 9. For each formulation condition, 30 mL were prepared, transferred to 50 cc containers and stirred continuously for 5 days at room temperature.

TABLE 9

| Ref. | Buffer | Surfactant | Excipient(s) | pH | Ab conc. (mg/mL) |
|---|---|---|---|---|---|
| 9A | 20 mM acetate | 0.005% Polysorbate 80 | 45 mM calcium chloride 100 mM arginine-HCl | 5.2 | 137 |
| 9B | 20 mM acetate | 0.01% Polysorbate 80 | 45 mM calcium chloride 100 mM arginine-HCl | 5.2 | 135 |
| 9C | 20 mM acetate | 0.05% Polysorbate 80 | 45 mM calcium chloride 100 mM arginine-HCl | 5.2 | 138 |
| 9D | 20 mM acetate | 0.005% Polysorbate 20 | 45 mM calcium chloride 100 mM arginine-HCl | 5.2 | 138 |

TABLE 9-continued

| Ref. | Buffer | Surfactant | Excipient(s) | pH | Ab conc. (mg/mL) |
|---|---|---|---|---|---|
| 9E | 20 mM acetate | 0.01% Polysorbate 20 | 45 mM calcium chloride 100 mM arginine-HCl | 5.2 | 136 |
| 9F | 20 mM acetate | 0.05% Polysorbate 20 | 45 mM calcium chloride 100 mM arginine-HCl | 5.2 | 136 |
| 9G | 20 mM acetate | 0.005% Triton X-100 | 45 mM calcium chloride 100 mM arginine-HCl | 5.2 | 134 |
| 9H | 20 mM acetate | 0.01% Triton X-100 | 45 mM calcium chloride 100 mM arginine-HCl | 5.2 | 139 |
| 9I | 20 mM acetate | 0.05% Triton X-100 | 45 mM calcium chloride 100 mM arginine-HCl | 5.2 | 138 |
| 9J | 20 mM acetate | 0.05% Pluronic F68 | 45 mM calcium chloride 100 mM arginine-HCl | 5.2 | 139 |
| 9K | 20 mM acetate | 0.1% Pluronic F68 | 45 mM calcium chloride 100 mM arginine-HCl | 5.2 | 139 |
| 9L | 20 mM acetate | 0.4% Pluronic F68 | 45 mM calcium chloride 100 mM arginine-HCl | 5.2 | 134 |

Figure 19:
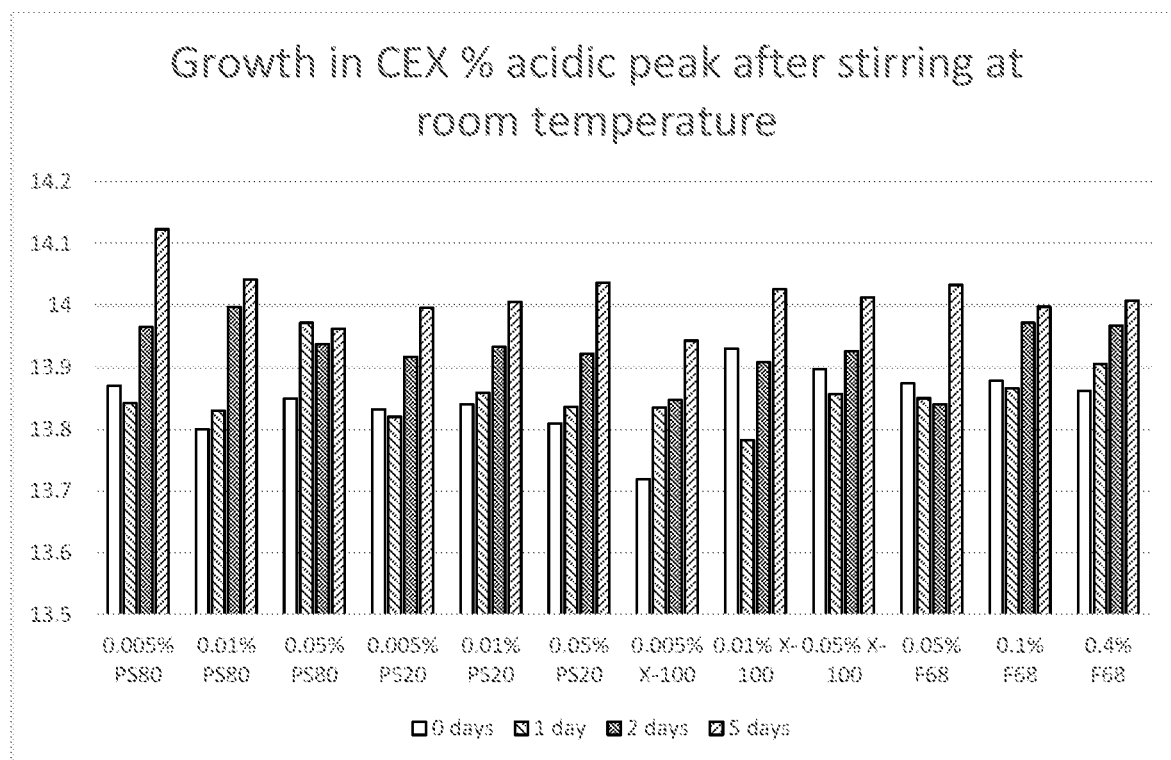
FIG. 19 is a bar graph of stability of adalimumab formulations as determined by CEX-HPLC.

To assess stability, the % acidic peak was measured by CEX-HPLC after stirring at room temperature for 0, 1, 2, and 5 days. The results are shown in FIG. 19. With the exception of the 0.005% Polysorbate 80 formulation (9A), which had a slightly higher level of % acidic peak, there was no meaningful difference due to the level of surfactant in the range tested on stability as measured by CEX-HPLC.

Figure 20:
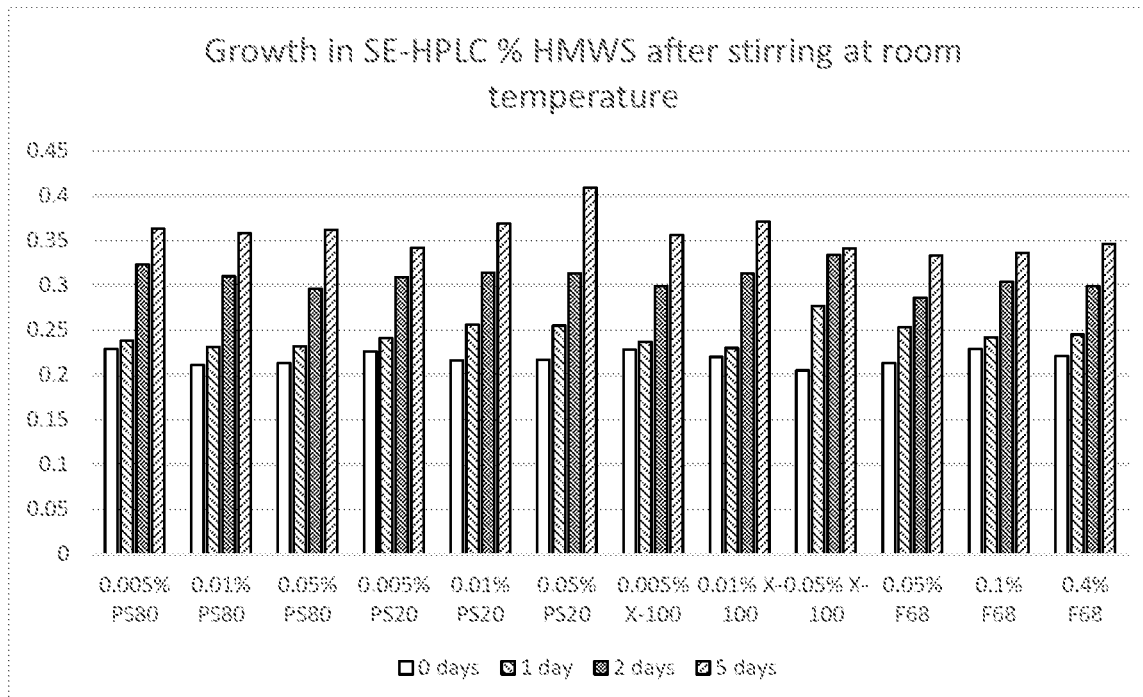
FIG. 20 is a bar graph of stability of adalimumab formulations as determined by SE-HPLC.

Stability also was assessed by measuring HMWS by SE-HPLC after stirring at room temperature for 0, 1, 2, and 5 days. The results are shown in FIG. 20. No meaningful differences in the amount of HMWS were observed in the concentration range of surfactants examined.

Figure 21:
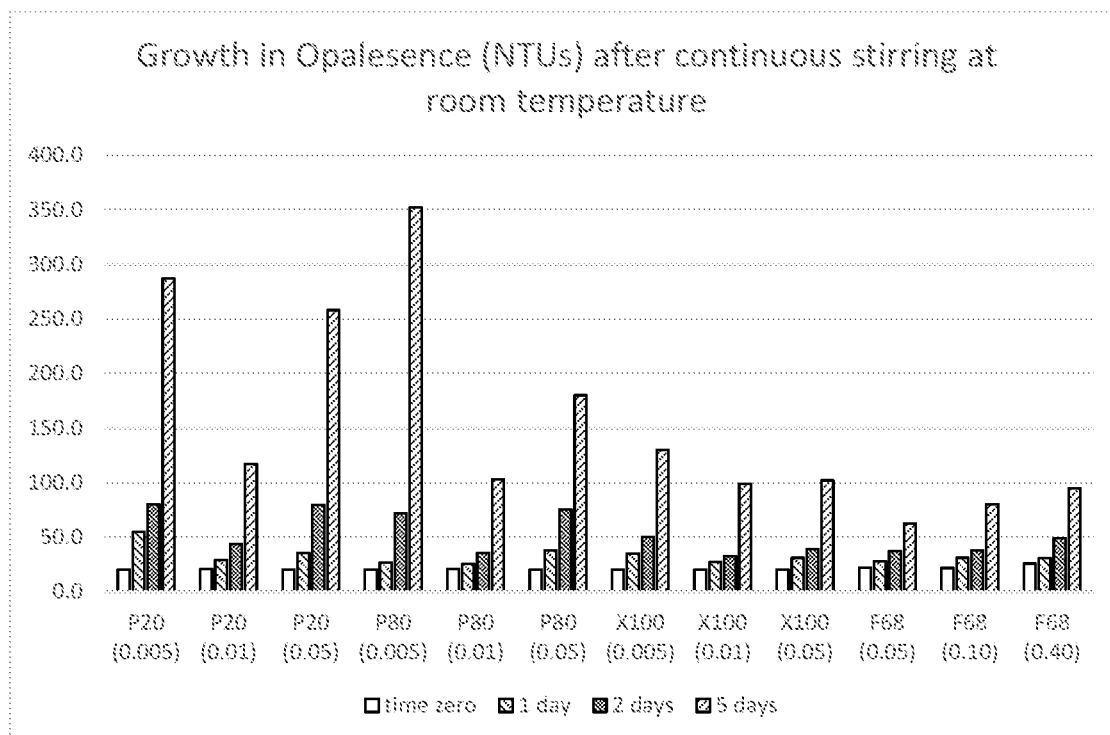
FIG. 21 is a bar graph of stability of adalimumab formulations as determined by opalescence measurement.

Stability additionally was assessed by measuring opalescence after stirring at room temperature for 0, 1, 2, and 5 days. As shown in FIG. 21, the formulations containing low levels of Polysorbate 20 or Polysorbate 80 demonstrated the highest opalescence of the formulations tested after stirring at room temperature for 5 days. In comparison, the formulations containing Pluronic F68 demonstrated the lowest opalescence of the formulations tested after stirring at room temperature for 5 days.

Example 10

Effect of Nontraditional Surfactants on Formulation Stability

Adalimumab biosimilar was prepared in a buffer containing 15 mM glutamate, 300 mM proline, pH 5.2 using the Cogent μScale TFF system described in Example 2. Surfactant stock solutions were then added to obtain a final protein concentration close to 110 mg/mL. The pH was adjusted to 5.2 using NaOH or HCl if needed. Aliquots were then filled into 5 cc glass vials for evaluation of stability at accelerated temperature. The composition of the formulation buffer, and the pH and antibody concentration of the formulations are provided in Table 10.

TABLE 10

| Ref. | Buffer | Surfactant | Excipient(s) | pH | Ab conc. (mg/mL) |
|---|---|---|---|---|---|
| 10A | 15 mM glutamate | 0.01% benzalkonium chloride | 300 mM proline | 5.2 | 109 |
| 10B | 15 mM glutamate | 0.01% guanidine HCl | 300 mM proline | 5.2 | 109 |
| 10C | 15 mM glutamate | 0.01% lecithin | 300 mM proline | 5.2 | 109 |
| 10D | 15 mM glutamate | 0.01% oleic acid | 300 mM proline | 5.2 | 109 |
| 10E | 15 mM glutamate | 0.01% Polysorbate 80 | 300 mM proline | 5.2 | 109 |
| 10F | 15 mM glutamate | 0.1% polyvinyl alcohol 205K | 300 mM proline | 5.2 | 100 |
| 10G | 15 mM glutamate | 0.1% polyvinyl alcohol 31K | 300 mM proline | 5.2 | 100 |
| 10H | 15 mM glutamate | 0.01% PVP | 300 mM proline | 5.2 | 109 |
| 10I | 15 mM glutamate | 0.01% protamine sulfate | 300 mM proline | 5.2 | 109 |

Figure 22:
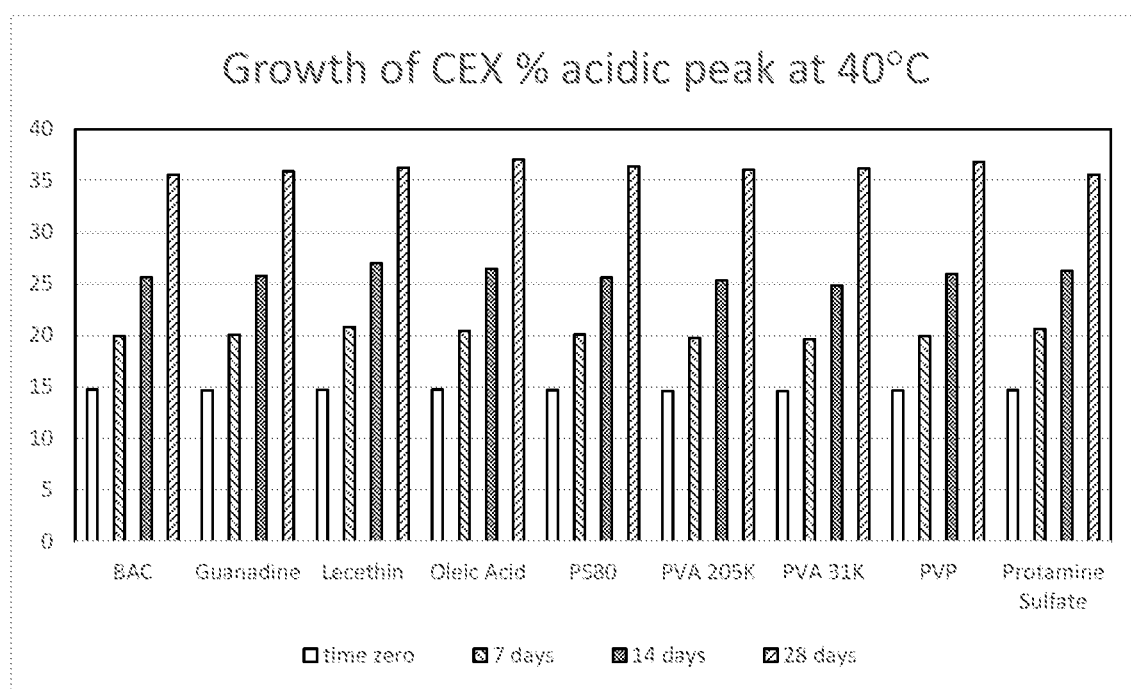
FIG. 22 is a bar graph of stability of adalimumab formulations as determined by CEX-HPLC.

To assess stability, the % acidic peak was measured by CEX-HPLC after 0, 7, 14, and 28 days at 40° C. The results are shown in FIG. 22. The amount of acidic peak formed after storage at 40° C. for 28 days was found to be similar. Meaningful differences were not observed.

Figure 23:
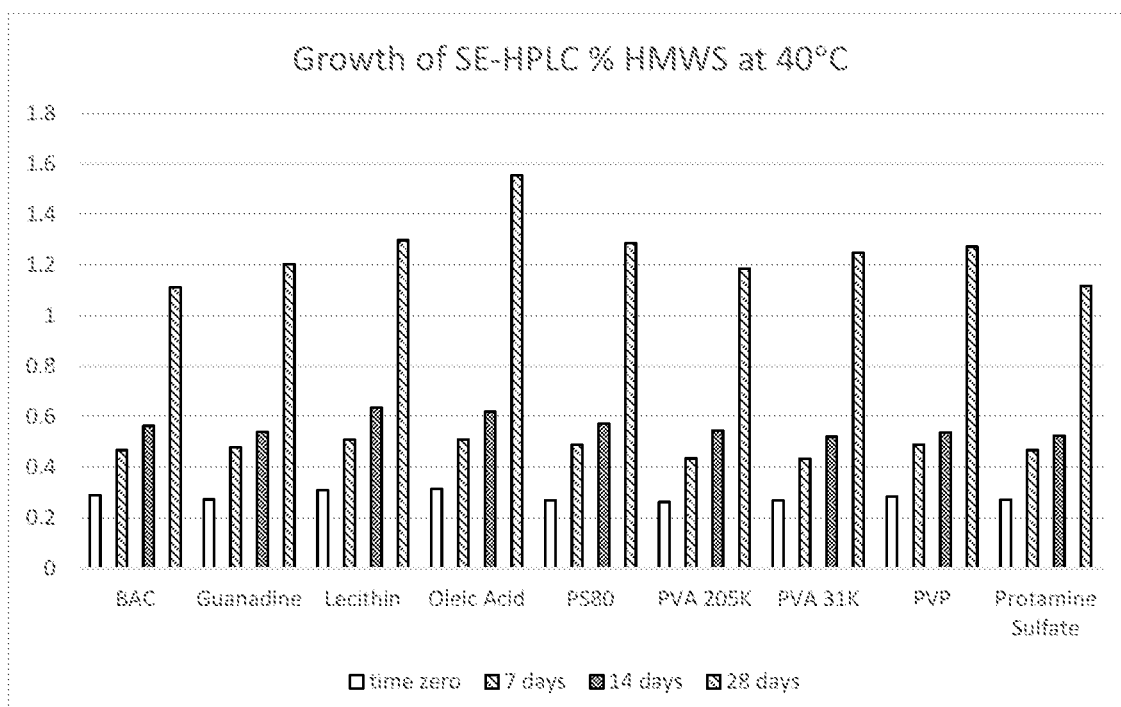
FIG. 23 is a bar graph of stability of adalimumab formulations as determined by SE-HPLC.

Stability also was assessed by measuring BMWS by SE-HPLC after 0, 7, 14, and 28 days at 40° C. The results are shown in FIG. 23. The formulations containing benzalkonium chloride and protamine sulfate (10A and 10I) appeared to have the lowest amount of HMWS after 28 days at 40° C.

Example 11

Effect of PEG, Proline, and Calcium Chloride on Formulation Stability

Adalimumab biosimilar frozen in a buffer with 20 mM glutamic acid, pH 5.2 was thawed and subjected to dialysis using dialysis tubing into one of the following buffers: 20 mM calcium chloride; 10 mM lactate; 4.2% mannitol; and 14.4 mM sodium phosphate with 7.7 mM citrate, 105 mM sodium chloride and 1.2% mannitol. Stock excipient solutions were then added to achieve the final concentrations as shown in Table 11. If needed, the pH was adjusted to 5.2±0.1 with MEA or MSA. Comparative formulations were also prepared and adjusted to pH 5.2±0.1 with NaOH or HCl as needed. The final formulation compositions, pH, and antibody concentration are listed in Table 11.

TABLE 11

| Ref. | Buffer/pH Adjusting Agent | Excipient(s) | Surfactant | pH | Ab conc. (mg/mL) | Osmolality (mOsm/kg) |
|---|---|---|---|---|---|---|
| Comp. 1A | —/HCl, NaOH | 4.2% mannitol | 0.1% polysorbate 80 | 5.2 | 102 | 271 |
| Comp. 2A | 7.7 mM citrate, 14.1 mM sodium phosphate | 105 mM NaCl 1.2% mannitol | 0.1% polysorbate 80 | 5.1 | 110 | 309 |
| 11A | —/MEA, MSA | 9% PEG 600 20 mM calcium chloride | 0.1% Pluronic F68 | 5.1 | 105 | 383 |
| 11B | —/MEA, MSA | 6.9% PEG 600 0.6% PEG 200 20 mM calcium chloride | 0.1% Pluronic F68 | 5.1 | 97 | 367 |
| 11C | —/MEA, MSA | 4.5% PEG 600 1.8% PEG 200 20 mM calcium chloride | 0.1% Pluronic F68 | 5.1 | 104 | 321 |
| 11D | —/MEA, MSA | 1.2% PEG 600 3% PEG 200 20 mM calcium chloride | 0.1% Pluronic F68 | 5.1 | 112 | 349 |
| 11E | —/MEA, MSA | 4% PEG 200 20 mM calcium chloride | 0.1% Pluronic F68 | 5.1 | 99 | 321 |
| 11F | —/MEA, MSA | 7.3% PEG 600 60 mM proline 20 mM calcium chloride | 0.1% Pluronic F68 | 5.2 | 114 | 439 |
| 11G | —/MEA, MSA | 5.5% PEG 600 120 mM proline 20 mM calcium chloride | 0.1% Pluronic F68 | 5.1 | 107 | 404 |
| 11H | —/MEA, MSA | 2.5% PEG 600 180 mM proline 20 mM calcium chloride | 0.1% Pluronic F68 | 5.2 | 105 | 410 |
| 11I | —/MEA, MSA | 240 mM proline 20 mM calcium chloride | 0.1% Pluronic F68 | 5.1 | 109 | 367 |
| 11J | 10 mM lactate | 8.4% PEG 600 | 0.1% Pluronic F68 | 5.1 | 107 | 379 |
| 11K | 10 mM lactate | 4% PEG 600 1.6% PEG 200 | 0.1% Pluronic F68 | 5.1 | 102 | 307 |
| Comp. 1B | —/HCl, NaOH | 4.2% mannitol | 0.1% polysorbate 80 | 5.2 | 173 | 301 |
| Comp. 2B | 7.7 mM citrate 14.1 mM sodium phosphate | 105 mM NaCl 1.2% mannitol | 0.1% polysorbate 80 | 5.1 | 174 | 317 |
| 11L | 10 mM lactate | 8.4% PEG 600 | 0.1% Pluronic F68 | 5.2 | 177 | 488 |
| 11M | 10 mM lactate | 4% PEG 600 1.6% PEG 200 | 0.1% Pluronic F68 | 5.2 | 178 | 413 |
| 11N | 10 mM lactate | 3.8% PEG 200 | 0.1% Pluronic F68 | 5.2 | 182 | 310 |
| 11O | 10 mM lactate | 220 mM proline | 0.1% Pluronic F68 | 5.2 | 170 | 389 |

Figure 24:
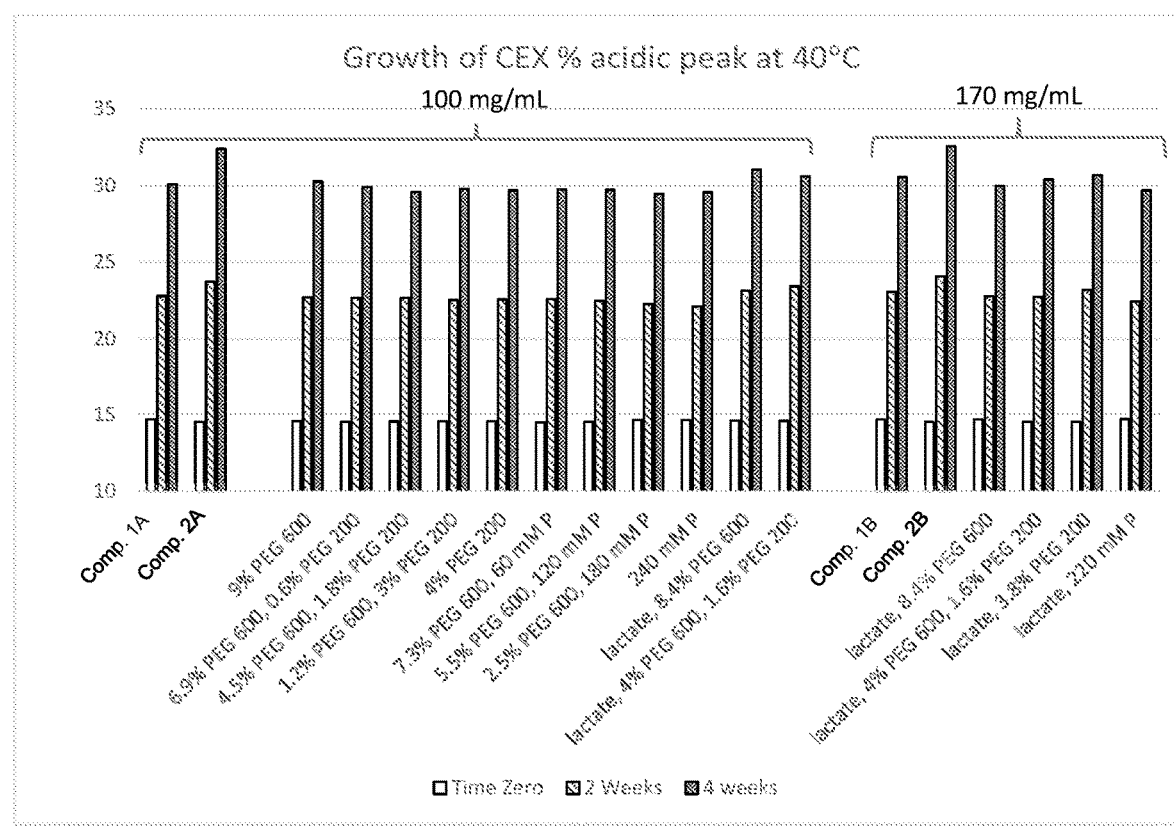
FIG. 24 is a bar graph of stability of adalimumab formulations as determined by CEX-HPLC.
Figure 25:
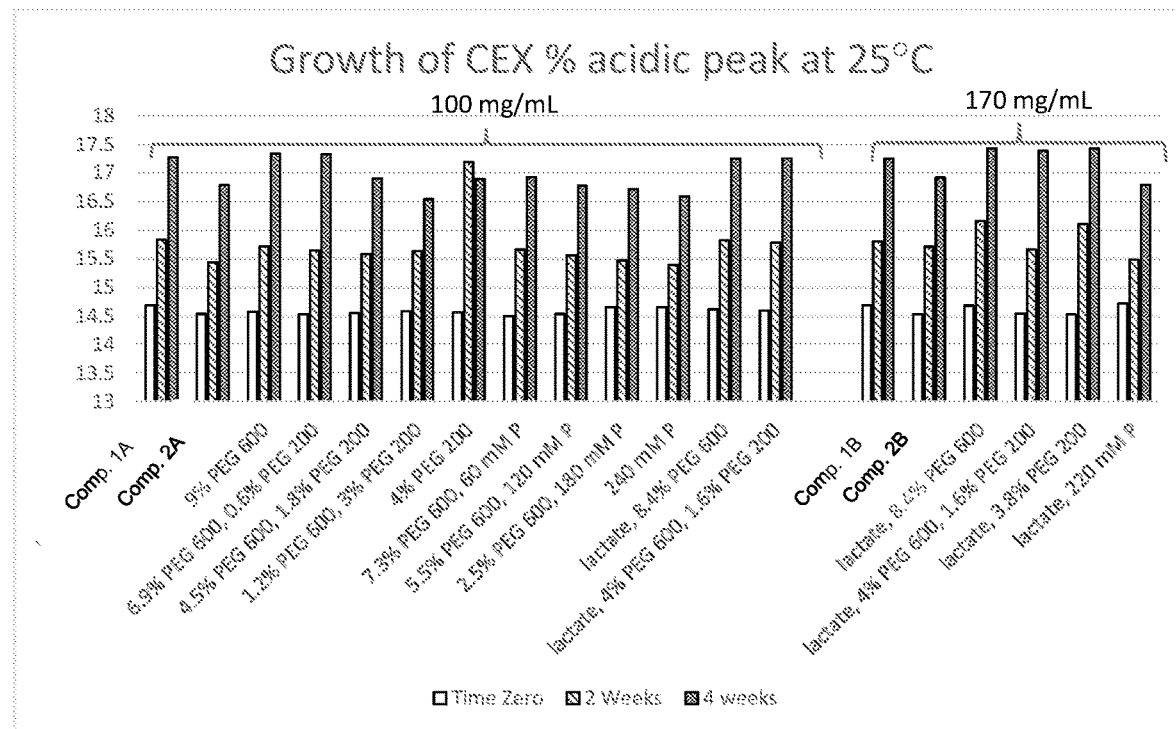
FIG. 25 is a bar graph of stability of adalimumab formulations as determined by CEX-HPLC.

To assess stability, the % acidic peak was measured by CEX-HPLC after 0, 2, and 4 weeks at 40° C. and at 25° C. The results are shown in FIG. 24 and FIG. 25. At 25° C., meaningful differences were not observed. After storage at 40° C., the formulations labeled 2A and 2B appeared to have higher growth of the % acidic peak, however the other formulations tested did not show apparent differences that could be considered meaningful.

Figure 26:
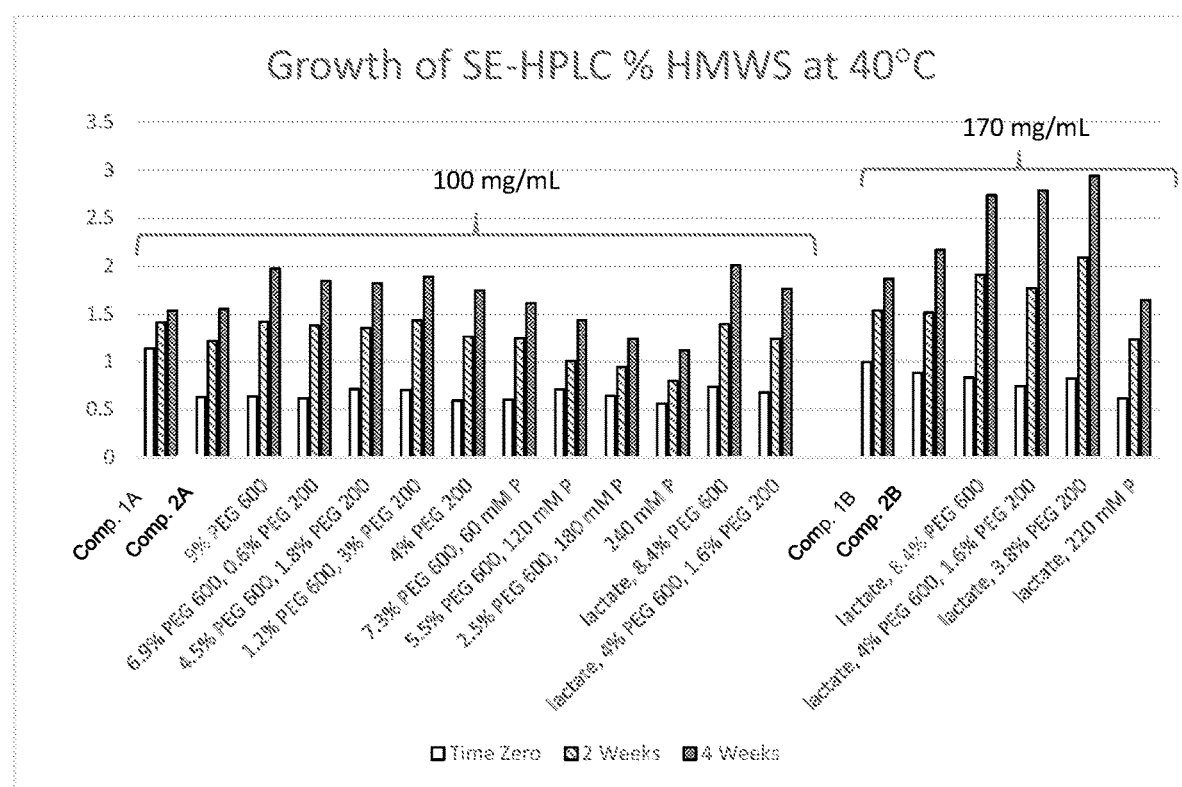
FIG. 26 is a bar graph of stability of adalimumab formulations as determined by SE-HPLC.
Figure 27:
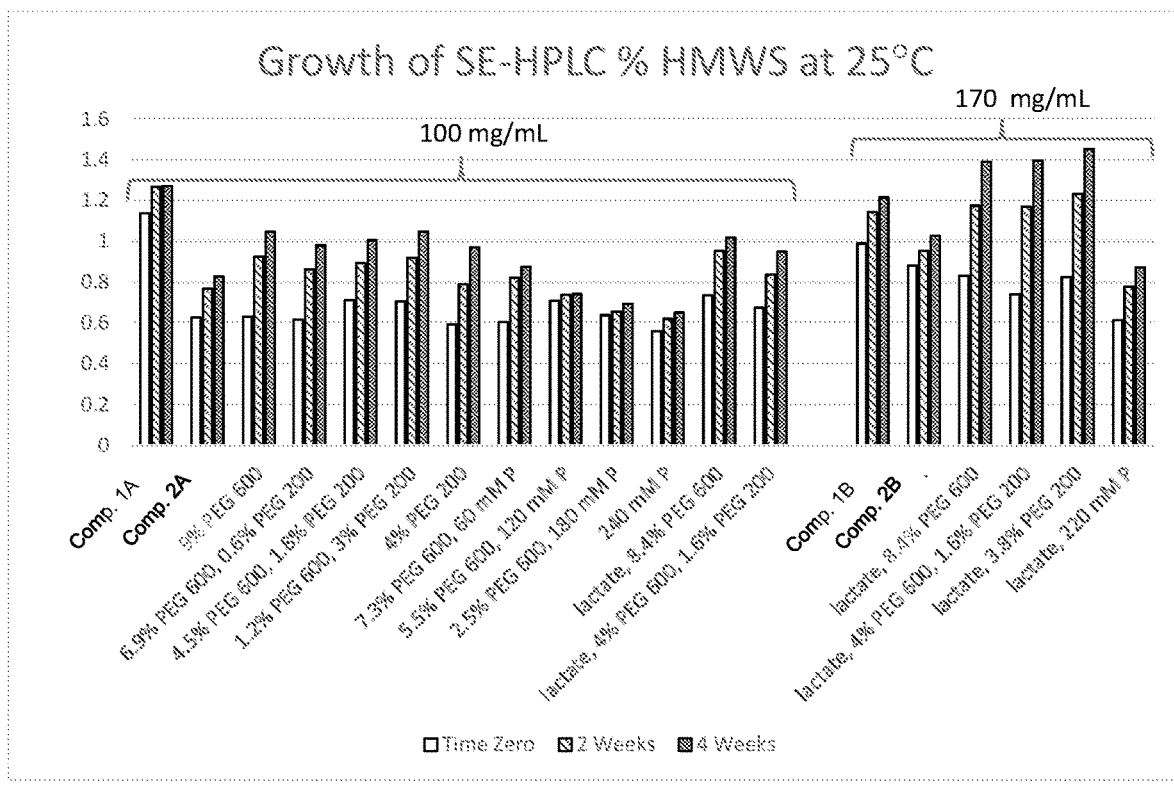
FIG. 27 is a bar graph of stability of adalimumab formulations as determined by SE-HPLC.

Stability also was assessed by measuring HMWS by SE-HPLC after 0, 2, and 4 weeks at 40° C. and at 25° C. The results are shown in FIG. 26 and FIG. 27. In formulations at a protein concentration of around 170 mg/mL, the formulation buffered with lactate and containing proline had superior stability, both at 25° C. and at 40° C. In formulations containing PEG 200 or PEG 600, stability was worse than the other formulations at 170 mg/mL. Formulations at approximately 100 mg/mL also showed a preference for proline in that the amount of HMWS was reduced as the proline concentration increased, a trend which was most apparent at 40° C. and to a lesser extent at 25° C.

Figure 28:
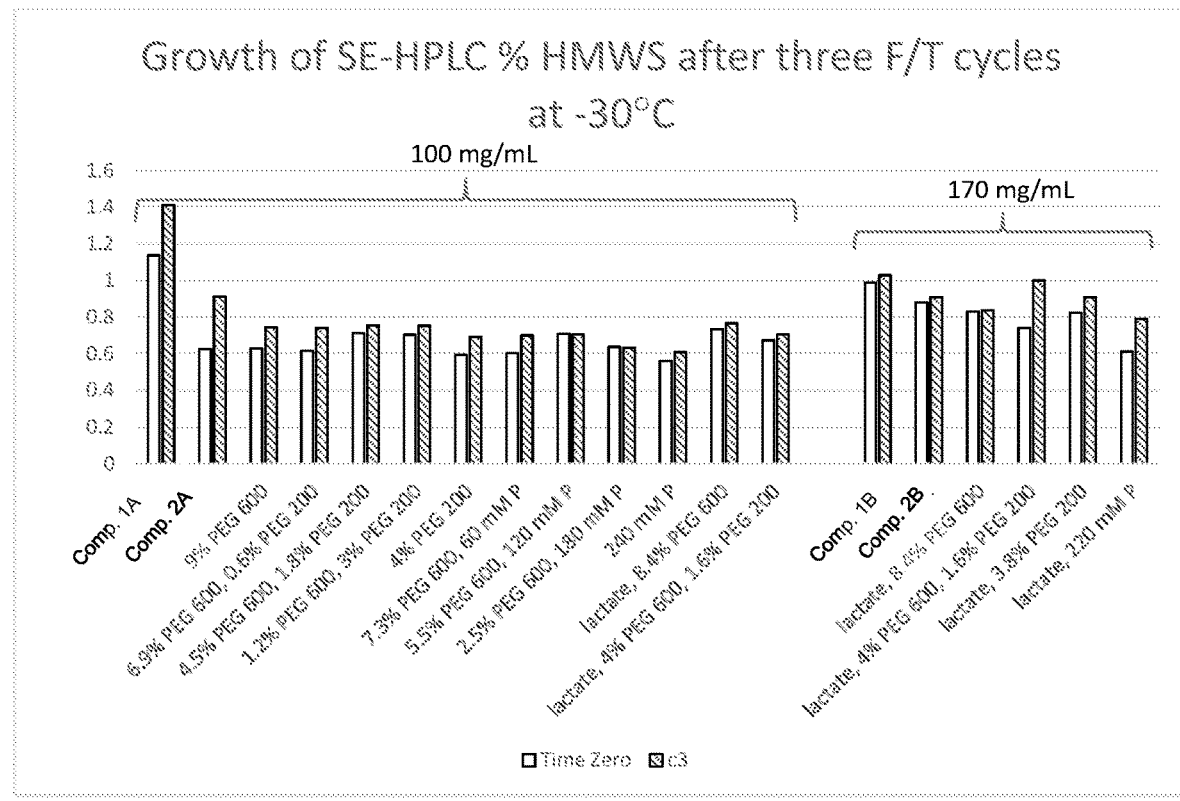
FIG. 28 is a bar graph of stability of adalimumab formulations as determined by SE-HPLC.

Stability was assessed after freeze/thaw cycling as described in Example 3. The percentage of HMWS was measured by SE-HPLC after 0 days and after 3 F/T cycles. The results are shown in FIG. 28. In general, at around 100 mg/mL, the comp 1A and comp 2A formulations appeared to have the largest increase in HMWS compared to the other formulations examined. At 170 mg/mL, the formulation with PEG 600 and PEG 200 (11M) appeared to have the largest increase in HMWS.

Example 12

Effect of Sorbitol, Sucrose, Proline, PEG, and Calcium Chloride on Formulation Stability Adalimumab biosimilar starting material was prepared using a Cogent μScale TFF with a 30 kD Millipore cassette and a pressure difference of about 23 psi in the following buffers: 4.2% mannitol; 14.4 mM sodium phosphate with 7.7 mM citrate, 105 mM sodium chloride and 1.2% mannitol; 7.3% sucrose with 20 mM calcium chloride; 20 mM calcium chloride; 4% sorbitol with 25 mM calcium chloride; 320 mM proline with 20 mM calcium chloride; 10 mM lactate with 225 mM proline and 20 mM calcium chloride; 10 mM lactate with 20 mM calcium chloride; 10 mM acetate with 9% sucrose. The pH was adjusted as shown in Table 12. The resulting protein was concentrated to achieve the concentration provided in Table 12, with the exception of Comp 3A which was diluted to 100 mg/mL with buffer from a bulk preparation at 170 mg/mL. The formulations are provided in Table 12. The formulations were stored at −30° C.

TABLE 12

| Ref. | Buffer/pH Adjusting Agent | Excipient(s) | Surfactant | pH | Ab conc. (mg/mL) |
| --- | --- | --- | --- | --- | --- |
| Comp. 3A | — | 4.2% mannitol | 0.1% Polysorbate 80 | 5.2 | 100 |
| Comp. 3B | — | 4.2% mannitol | 0.1% Polysorbate 80 | 5.2 | 170 |
| Comp. 4 | 14.1 mM sodium phosphate 7.7 mM citrate | 105 mM NaCl 1.2% mannitol | 0.1% Polysorbate 80 | 5.2 | 50 |
| 12A | —/MSA, MEA | 7.3% sucrose 20 mM calcium chloride | 0.1% Pluronic F68 | 5.2 | 100 |
| 12B | —/MSA, MEA | 4.8% PEG 200 20 mM calcium chloride | 0.1% Pluronic F68 | 5.2 | 100 |
| 12C | —/HCl | 4% sorbitol, 25 mM calcium chloride | 0.1% Pluronic F68 | 5.2 | 100 |
| 12D | —/MSA, MEA | 14.5% PEG 600 20 mM calcium chloride | 0.1% Pluronic F68 | 5.2 | 100 |
| 12E | 10 mM histidine/MSA, MEA | 320 mM proline 20 mM calcium chloride | — | 6.8 | 100 |
| 12F | 10 mM lactate/ MSA, MEA | 225 mM proline 20 mM calcium chloride | 0.1% Pluronic F68 | 5.2 | 170 |
| 12G | 10 mM lactate/ MSA, MEA | 13% PEG 600 20 mM calcium chloride | 0.1% Pluronic F68 | 5.2 | 170 |
| 12H | 10 mM acetate/ MSA, MEA | 9% sucrose | 0.1% Polysorbate 80 | 5.2 | 170 |

Figure 29:
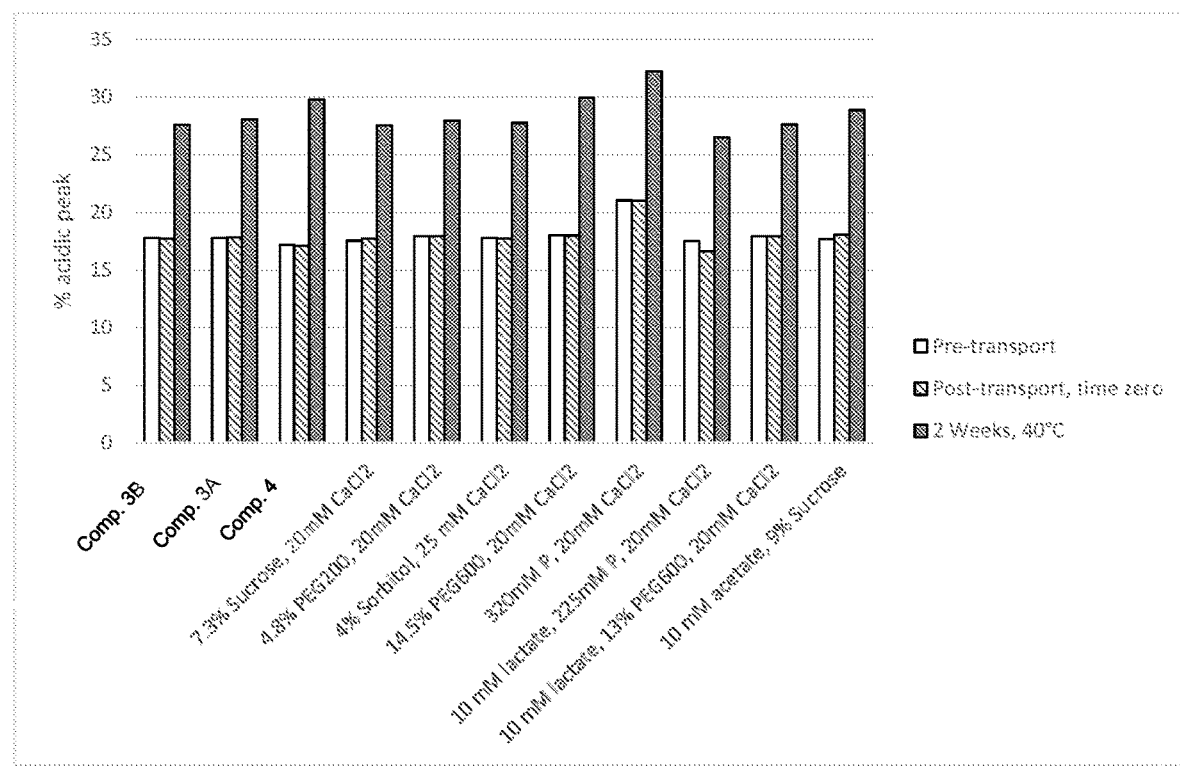
FIG. 29 is a bar graph of stability of adalimumab formulations as determined by CEX-HPLC.

To assess stability, the % acidic peak was measured by CEX-HPLC after 0 days, after transport, and after storing the transported sample at 40° C. for 2 weeks. The results are shown in FIG. 29. After 2 weeks at 40° C., the lowest amount of % acidic peak was found in the formulation buffered with lactate and containing calcium chloride (12F). Otherwise, formulations buffered with histidine, containing PEG 600 at a high concentration or the formulation buffered with sodium phosphate were less stable (12E, 12D, Comp 4). The antibody concentration of each formulation, i.e. whether at 50, 100 or 170 mg/mL did not appear to influence the amount of % acidic peak.

Figure 30:
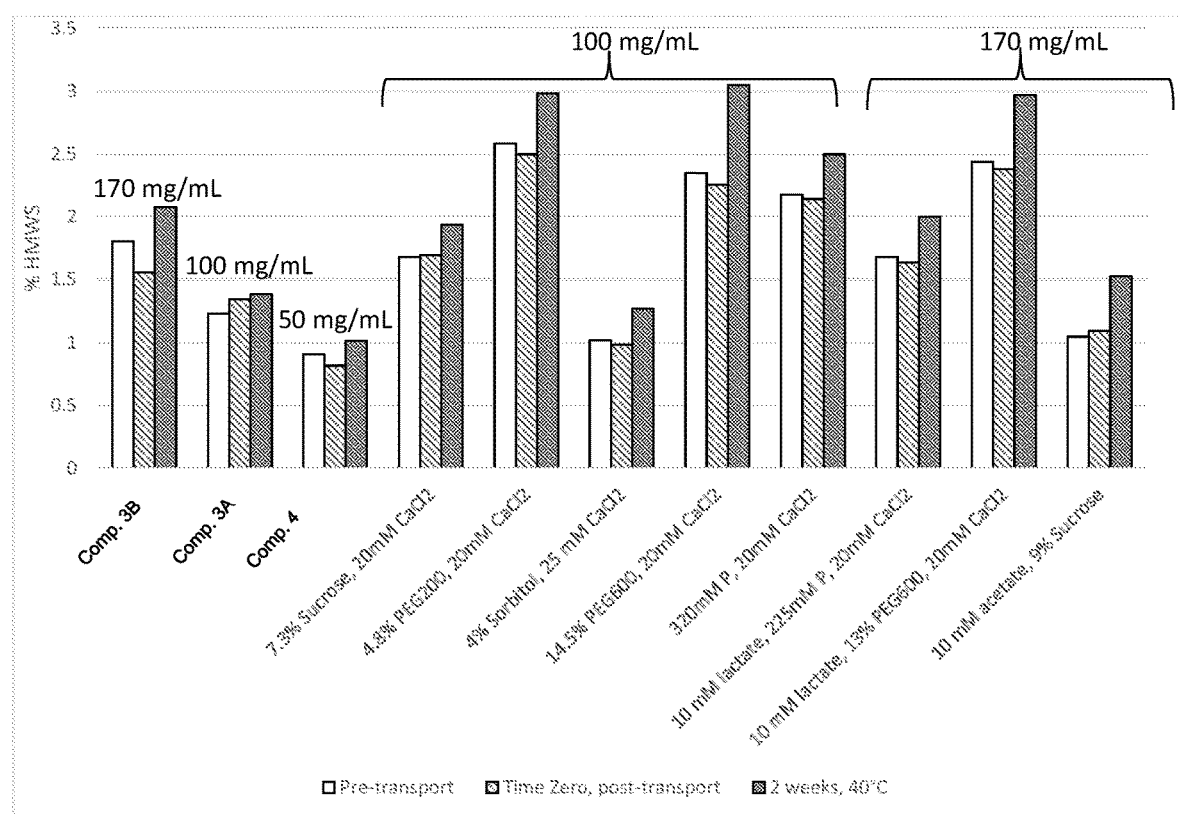
FIG. 30 is a bar graph of stability of adalimumab formulations as determined by SE-HPLC.
Figure 31:
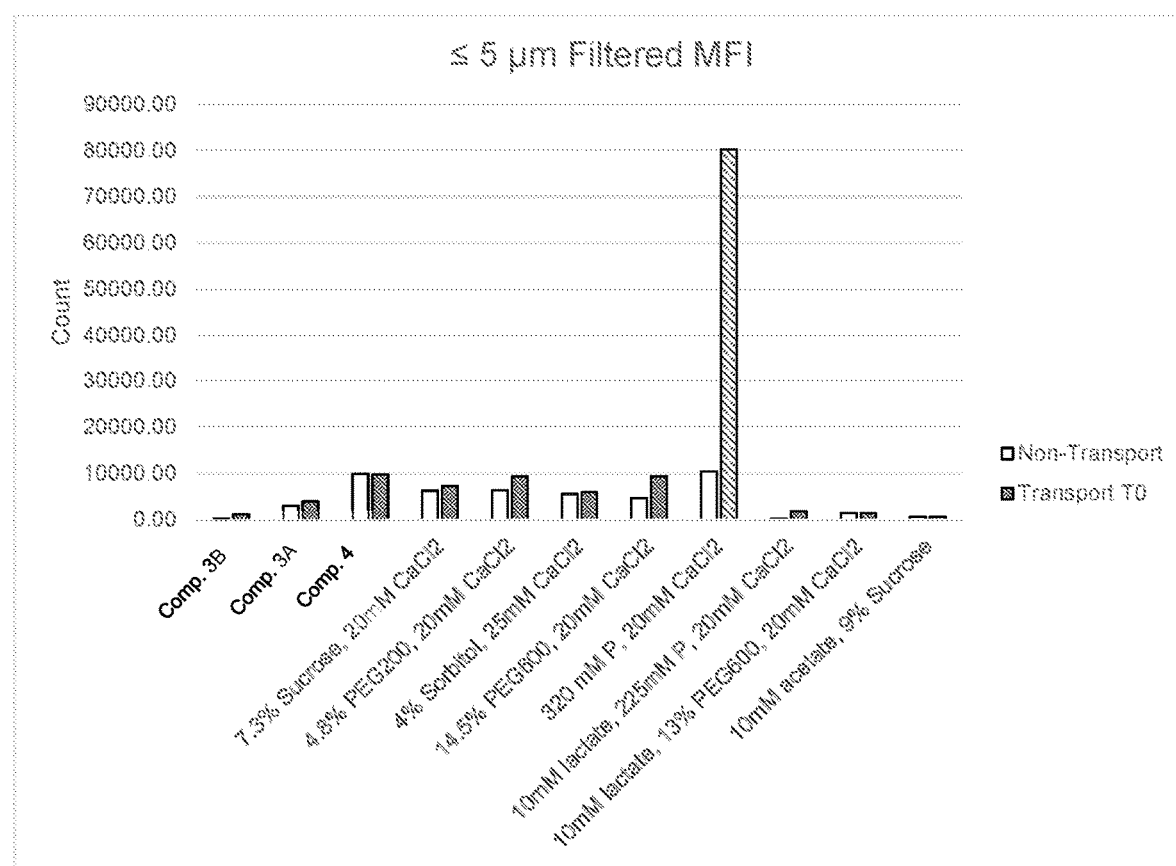
FIG. 31 is a bar graph of stability of adalimumab formulations as determined by micro-flow imaging (MFI).
Figure 32:
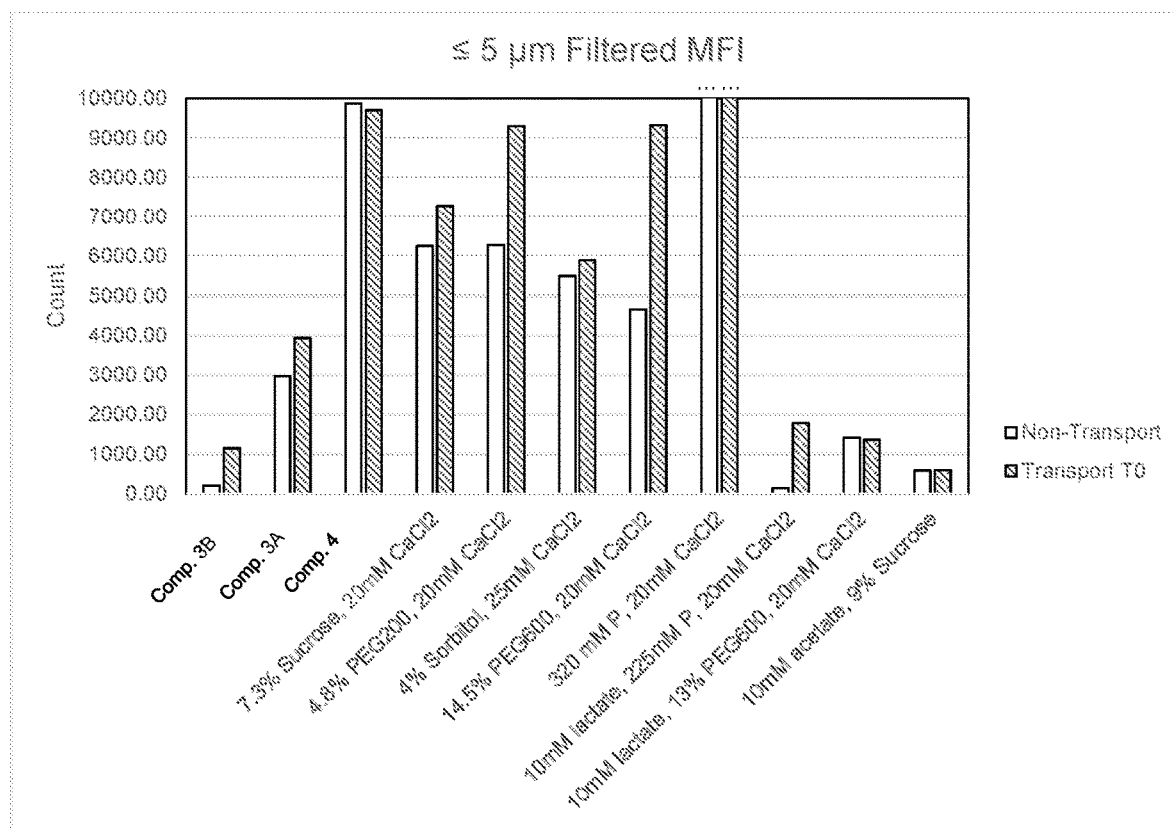
FIG. 32 is a bar graph of stability of adalimumab formulations as determined by MFI. The symbol " . . . " indicates a value above the maximum shown on the y-axis.
Figure 33:
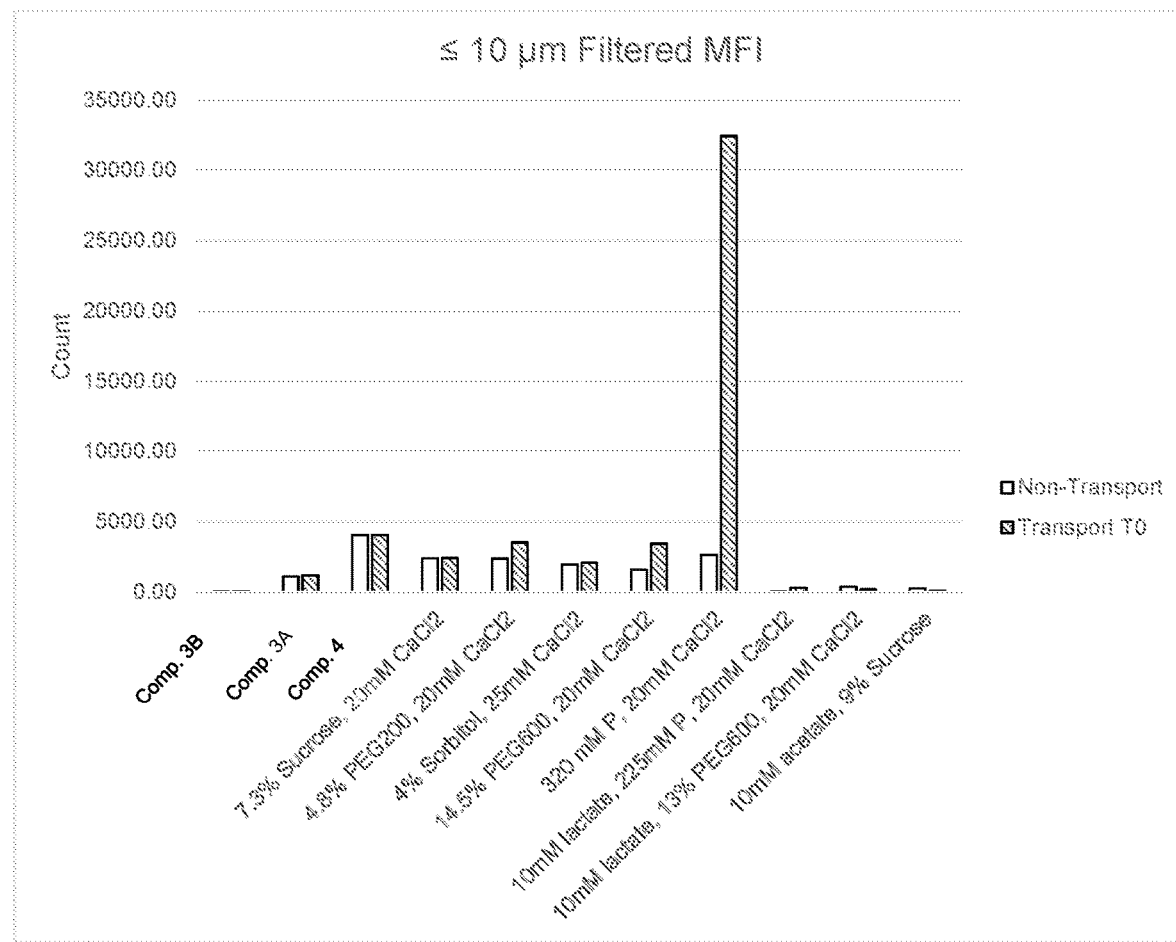
FIG. 33 is a bar graph of stability of adalimumab formulations as determined by MFI.
Figure 34:
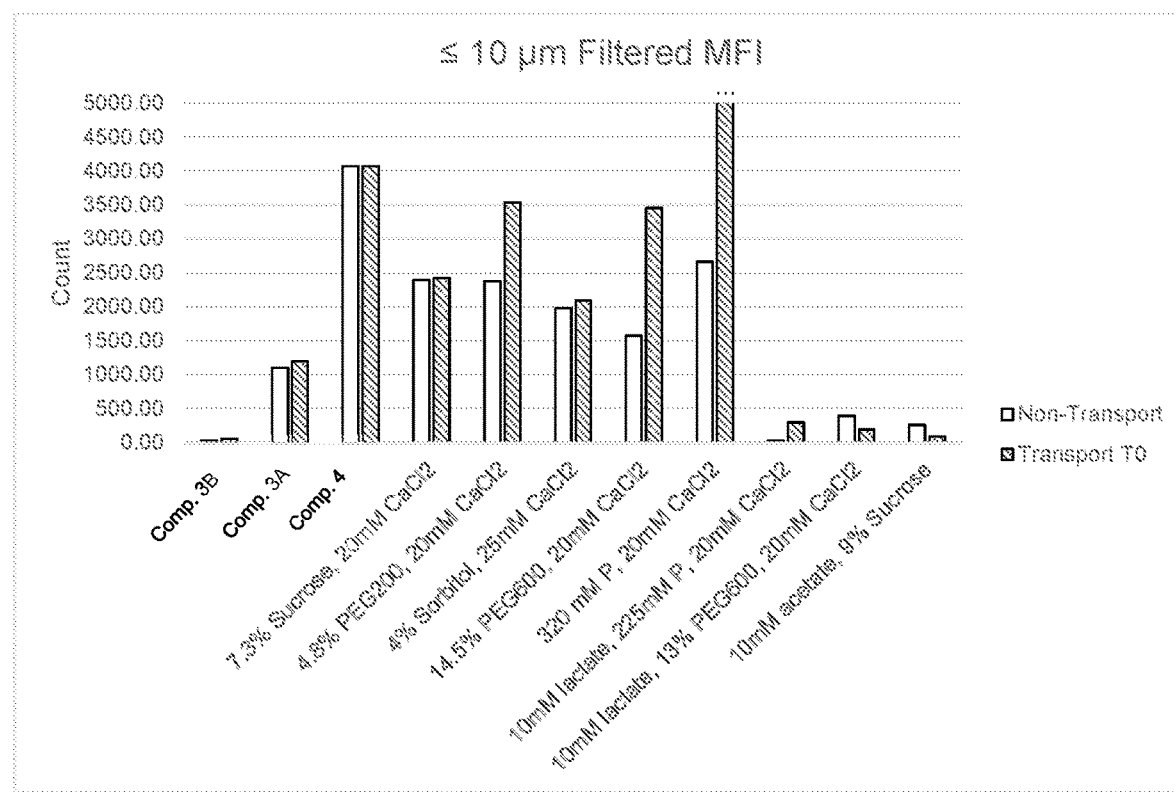
FIG. 34 is a bar graph of stability of adalimumab formulations as determined by MFI. The symbol " . . . " indicates a value above the maximum shown on the y-axis.
Figure 35:
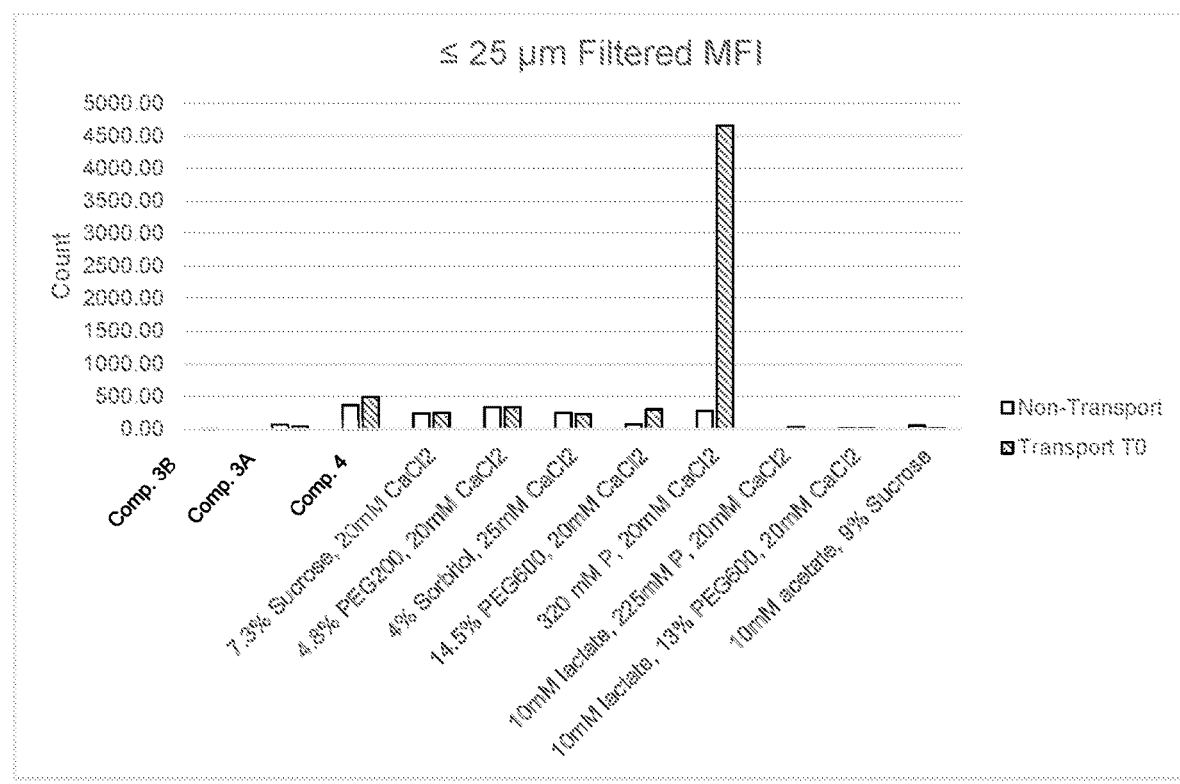
FIG. 35 is a bar graph of stability of adalimumab formulations as determined by MFI.
Figure 36:
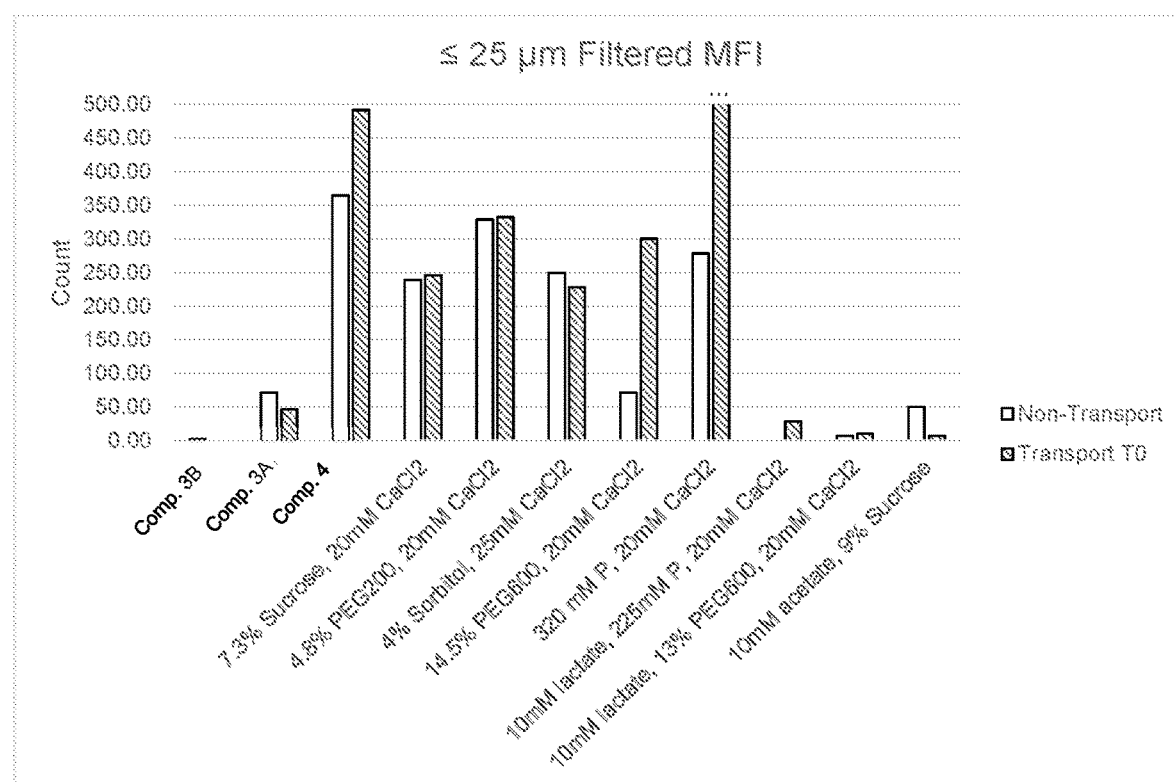
FIG. 36 is a bar graph of stability of adalimumab formulations as determined by MFI. The symbol " . . . " indicates a value above the maximum shown on the y-axis.

Stability also was assessed by measuring HMWS by SE-HPLC after 0 days, after transport, and after storing the transported sample at 40° C. for 2 weeks. The results are shown in FIG. 30. The lower the concentration, the lower the amount of HMWS. This is shown in comparing Comp 3B, Comp 3A and Comp 4 in which as the concentration changes from 170 mg/mL to 100 mg/mL to 50 mg/mL the HMWS is correspondingly reduced. For the other formulations tested, at 170 mg/mL, there are differences in the amount of HMWS after two weeks at 40° C. The lowest amount of HMWS was measured for the acetate formulation with sucrose (12H), followed by the lactate buffered formulation with proline (12F) and finally the formulation with the high amount of PEG 600 (12G). In formulations at 100 mg/mL, the lowest HMWS was found in the self-buffering formulation with sorbitol and calcium chloride (12C). The addition of PEG 200 resulted in more HMWS at 100 mg/mL (12B).

Stability was further assessed by MFI. The results are shown in FIGS. 31-36. High particle counts at 5 μM were measured in the formulation containing proline and calcium chloride after transport stress (12E). In general, particle counts were higher at 100 mg/mL than at 170 mg/mL at the 5 μM particle size. At 100 mg/mL, formulation Comp 3A and the self-buffered formulation with sorbitol had lower particle counts at 5 μM post transport than the other formulations tested at this concentration (compare 12C and Comp 3A to 12A, 12B, 12D and 12E). The particle count trends observed at 5 μM were also observed at the 10 μM particle size. The lowest particle counts at 10 μM were measured at 170 mg/mL. At 100 mg/mL, a low particle count increase post transport was also observed in the self-buffered formulation with sorbitol (12C) and in Comp 3A. Finally, the particle count trends reported for the 5 μM and 10 particle sizes were also observed at 25 μM. The lowest particle counts were again at the 25 size. At 100 mg/mL, the lowest particle counts post transport were measured in formulations Comp 3A, 12A and 12C.

Example 13

Effect of PEG, Proline, and Calcium Chloride on Formulation Stability

Adalimumab biosimilar starting material at 200 mg/mL was diluted to 180 mg/mL and then subjected to dialysis using 3 kD cutoff dialysis tubing in the following buffers: 20 mM calcium chloride, pH adjusted with MSA or MEA; 14.4 mM sodium phosphate with 7.7 mM citrate, 105 mM sodium chloride and 1.2% mannitol, pH adjusted with HCl or NaOH to a final pH of 4.8; 10 mM lactate with 20 mM calcium chloride, pH adjusted with MSA or MEA; and 4.2% mannitol, pH adjusted with MSA or MEA. Stock excipient solutions were then added to achieve the final concentrations as shown in Table 13 and the pH was adjusted to 5.2 if needed. The formulations are provided in Table 13.

TABLE 13

| Ref. | Buffer/pH Adjusting Agent | Excipient(s) | Surfactant | pH | Ab conc. (mg/mL) |
|---|---|---|---|---|---|
| Comp. 5A | —/HCl, NaOH | 4.2% mannitol | 0.1% Polysorbate 80 | 5.2 | 100 |
| Comp. 6A | 14.1 mM sodium phosphate 7.7 mM citrate/ HCl, NaOH | 105 mM NaCl 1.2% mannitol | 0.1% Polysorbate 80 | 5.2 | 100 |
| 13A | —/MSA, MEA | 9% PEG600 20 mM calcium chloride | 0.1% Pluronic F68 | 5.2 | 100 |
| 13B | —/MSA, MEA | 6.9% PEG600 0.6% PEG200 20 mM calcium chloride | 0.1% Pluronic F68 | 5.2 | 100 |
| 13C | —/MSA, MEA | 4.5% PEG600 1.8% PEG200 20 mM calcium chloride | 0.1% Pluronic F68 | 5.2 | 100 |
| 13D | —/MSA, MEA | 1.2% PEG600 3% PEG200 20 mM calcium chloride | 0.1% Pluronic F68 | 5.2 | 100 |
| 13E | —/MSA, MEA | 4% PEG200 20 mM calcium chloride | 0.1% Pluronic F68 | 5.2 | 100 |
| 13F | —/MSA, MEA | 7.3% PEG600 20 mM calcium chloride 60 mM proline | 0.1% Pluronic F68 | 5.2 | 100 |
| 13G | —/MSA, MEA | 5.5% PEG600 20 mM calcium chloride 120 mM proline | 0.1% Pluronic F68 | 5.2 | 100 |
| 13H | —/MSA, MEA | 2.5% PEG600 20 mM calcium chloride 180 mM proline | 0.1% Pluronic F68 | 5.2 | 100 |
| 13I | —/MSA, MEA | 20 mM calcium chloride 240 mM proline | 0.1% Pluronic F68 | 5.2 | 100 |

TABLE 13-continued

| Ref. | Buffer/pH Adjusting Agent | Excipient(s) | Surfactant | pH | Ab conc. (mg/mL) |
|---|---|---|---|---|---|
| 13J | 10 mM lactate/ MSA, MEA | 20 mM calcium chloride 8.4% PEG 600 | 0.1% Pluronic F68 | 5.2 | 100 |
| 13K | 10 mM lactate/ MSA, MEA | 20 mM calcium chloride 4% PEG 600, 1.6% PEG 200 | 0.1% Pluronic F68 | 5.2 | 100 |
| Comp. 5B | —/HCl, NaOH | 4.2% mannitol | 0.1% Polysorbate 80 | 5.2 | 170 |
| Comp. 6B | 14.1 mM sodium phosphate 7.7 mM citrate/ HCl, NaOH | 105 mM NaCl 1.2% mannitol | 0.1% Polysorbate 80 | 5.2 | 170 |
| 13L | 10 mM lactate/ MSA, MEA | 8.4% PEG600 20 mM calcium chloride | 0.1% Pluronic F68 | 5.2 | 170 |
| 13M | 10 mM lactate/ MSA, MEA | 4% PEG600 1.6% PEG200 20 mM calcium chloride | 0.1% Pluronic F68 | 5.2 | 170 |
| 13N | 10 mM lactate/ MSA, MEA | 3.8% PEG200 20 mM calcium chloride | 0.1% Pluronic F68 | 5.2 | 170 |
| 13O | 10 mM lactate/ MSA, MEA | 20 mM calcium chloride 220 mM proline | 0.1% Pluronic F68 | 5.2 | 170 |

Figure 37:
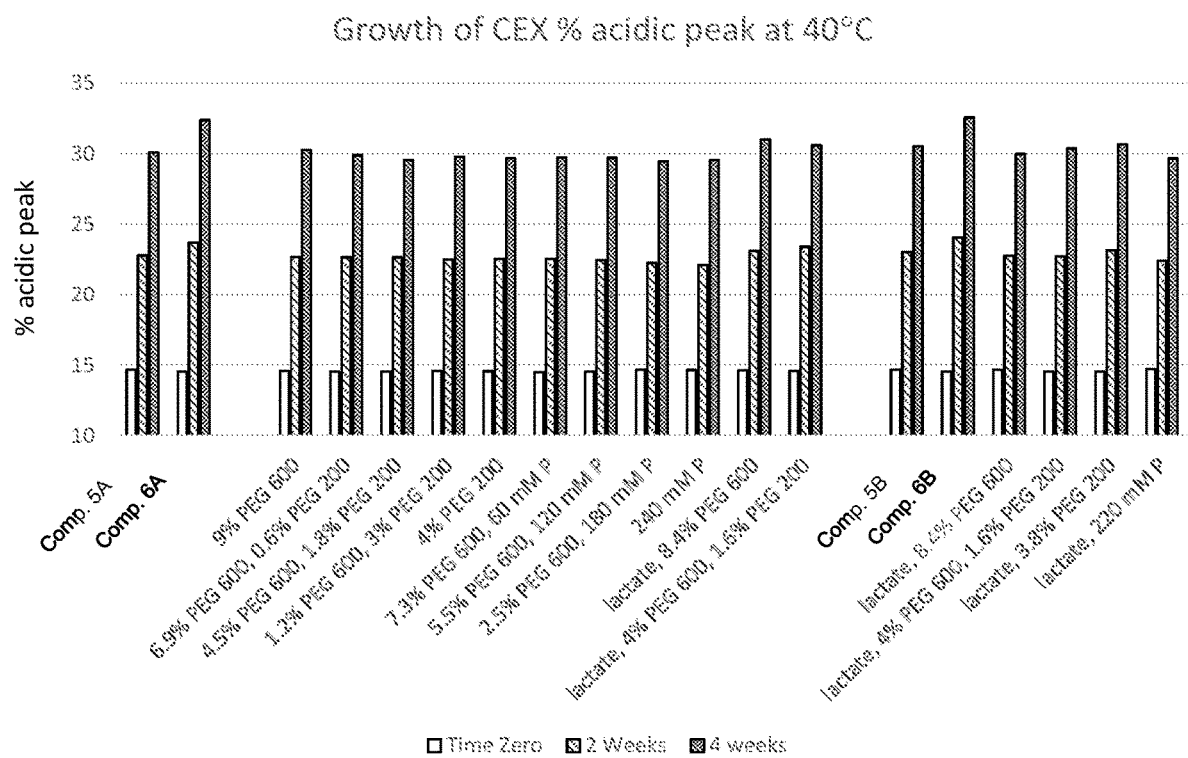
FIG. 37 is a bar graph of stability of adalimumab formulations as determined by CEX-HPLC.
Figure 38:
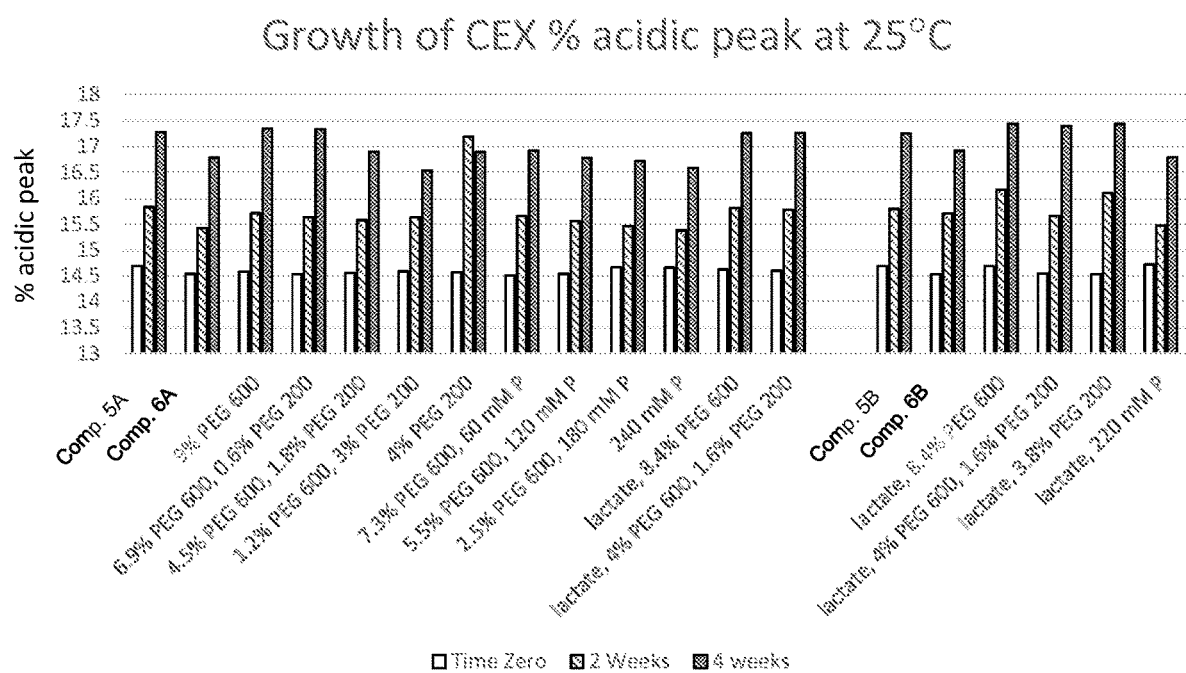
FIG. 38 is a bar graph of stability of adalimumab formulations as determined by CEX-HPLC.

To assess stability, the % acidic peak was measured by CEX-HPLC after 0, 2, and 4 weeks at 40° C. and at 25° C. The results are shown in FIG. 37 and FIG. 38. At 25° C., after 4 weeks, the lowest % acidic peak was found in the formulation containing proline and calcium chloride (13I) and the formulation with PEG 200 and PEG 600 and calcium chloride (13D). Lower growth was also observed in formulations with a mixture of PEG 600, proline and calcium chloride (13H) and in the formulation buffered with sodium phosphate (Comp 6A). In formulations at a concentration of 170 mg/mL, the lowest % acidic peak after storage for 4 weeks at 25° C. was found in the lactate buffer formulation with proline (13O) and in the sodium phosphate buffered formulation (Comp 6B). After 4 weeks at 40° C., meaningful differences between formulations were not as apparent. The highest amount of % acidic peak found after 4 weeks at 40° C. were in the formulations buffered with sodium phosphate at both 100 and 170 mg/mL (Comp 6A, Comp 6B respectively.)

Figure 39:
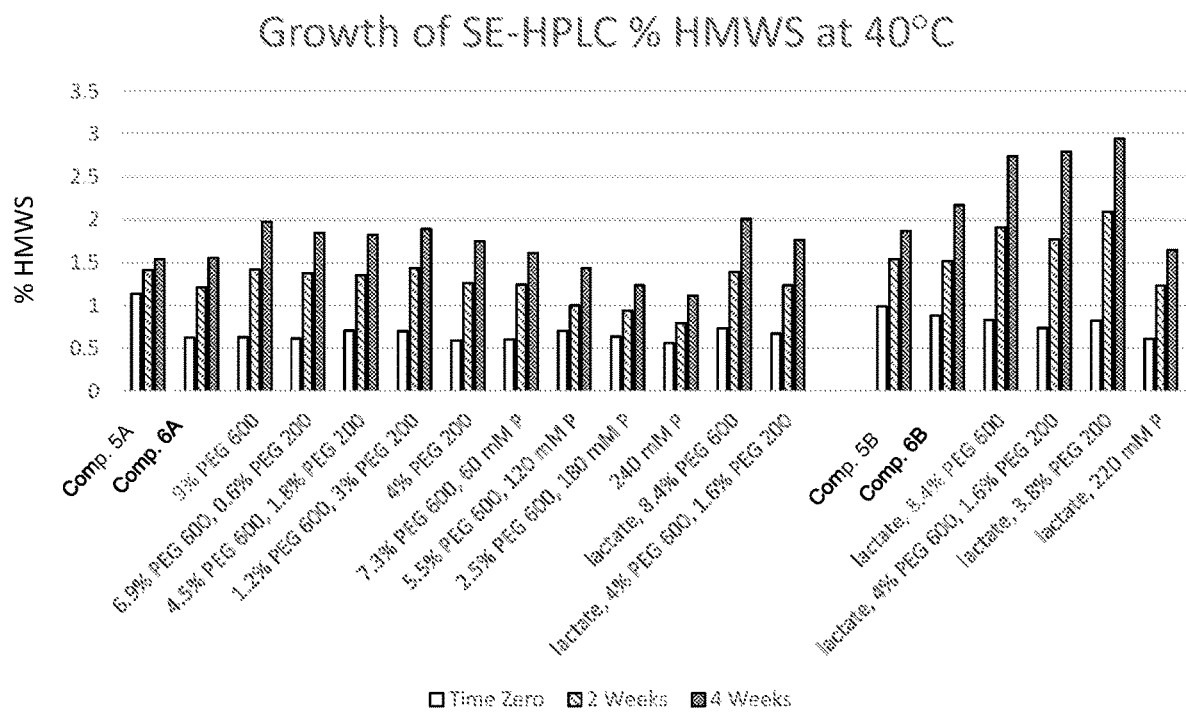
FIG. 39 is a bar graph of stability of adalimumab formulations as determined by SE-HPLC.
Figure 40:
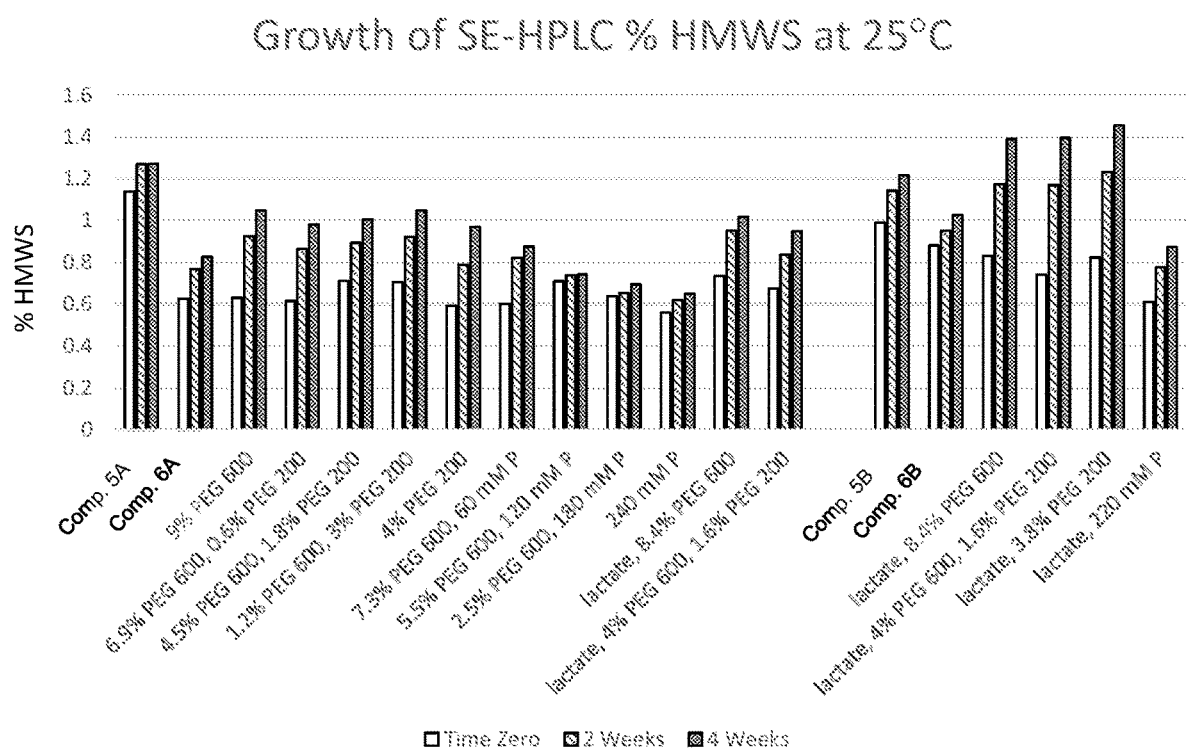
FIG. 40 is a bar graph of stability of adalimumab formulations as determined by SE-HPLC.
Figure 41:
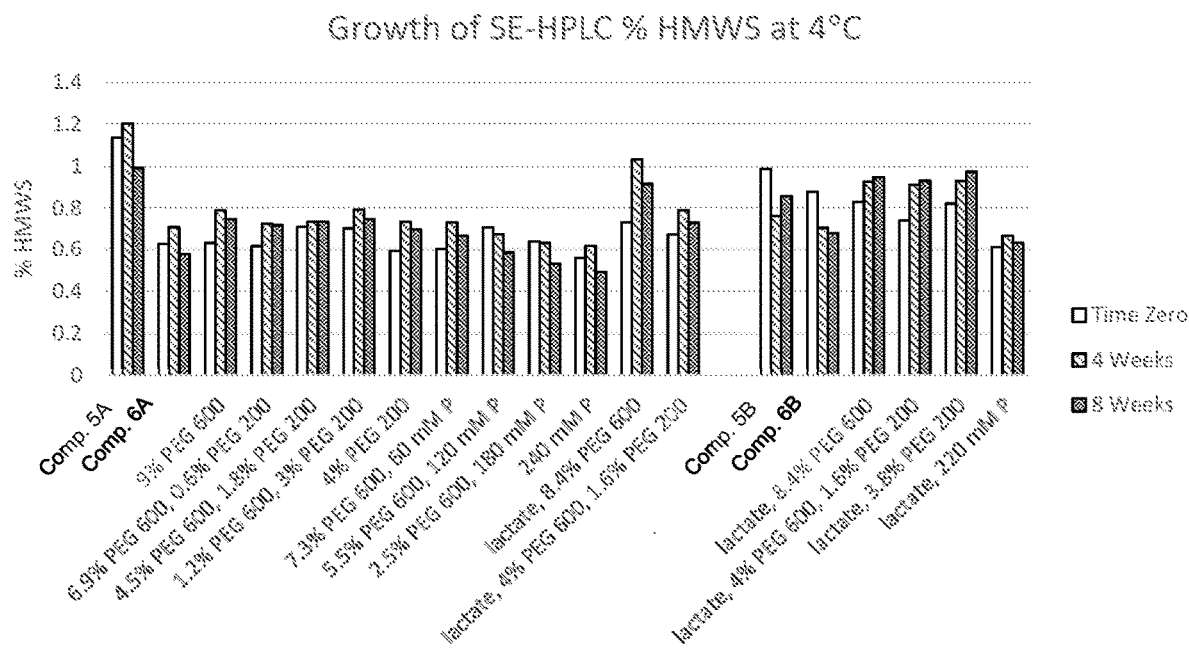
FIG. 41 is a bar graph of stability of adalimumab formulations as determined by SE-HPLC.
Figure 42:
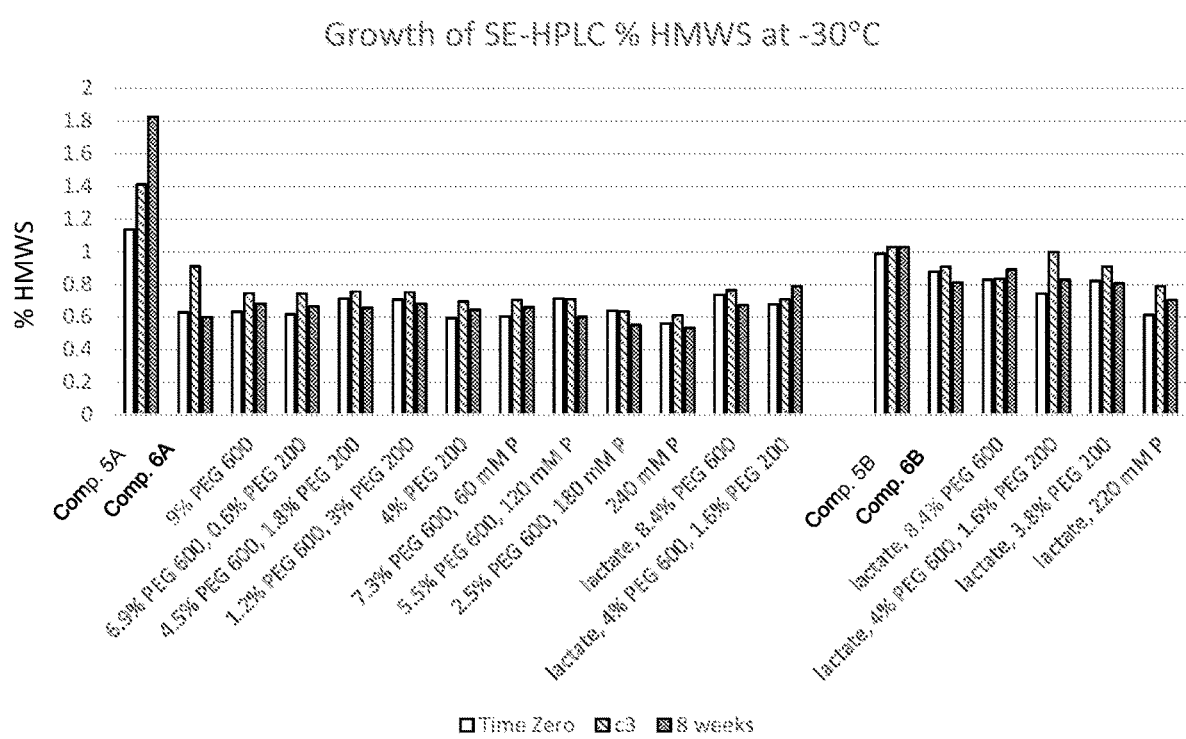
FIG. 42 is a bar graph of stability of adalimumab formulations as determined by SE-HPLC.

Stability was assessed by measuring HMWS by SE-HPLC after 0, 2, and 4 weeks at 40° C. and at 25° C. The results are shown in FIG. 39 and FIG. 40. At 25° C., after 4 weeks, the formulation with proline and calcium chloride had the lowest HMWS (13I). Otherwise, increasing concentrations of PEG 600 and lower proline levels in formulations resulted in higher amounts of HMWS (compare 13I, 13H, 13G and 13F). In formulations at 170 mg/mL stored for 4 weeks at 25° C., the proline formulation with calcium chloride was again superior in having the lowest HMWS (13O). At 40° C., similar trends to those observed at 25° C. were noted. The proline formulations had the lowest amount of HMWS at both 100 mg/mL and 170 mg/mL (13I, 13O). At 4° C., stability was assessed by measuring HMWS by SE-HPLC after 0, 4, and 8 weeks. The results are shown in FIG. 41. Minimal growth of HMWS is observed at 4° C. in most formulations. At time zero, the lowest HMWS in the 100 mg/mL formulation is found in the proline formulation with calcium chloride (13I). Likewise, at 170 mg/mL, HMWS is minimized in the lactate buffer formulation with proline at time zero (13O). Finally, stability was assessed by measuring HMWS by SE-HPLC after 0 weeks, after 3 F/T cycles, and after 8 weeks at −30° C. The results are shown in FIG. 42. In agreement with the results obtained at 4° C., the proline formulation at 100 and 170 mg/mL (13I, 13O) had the lowest amount of HMWS and no meaningful change in HMWS after the freeze thaw cycles. Most formulations did not show meaningful change upon repeated freezing and thawing at −30° C. The lone exception appears to be the Comp 5A formulation, in which HMWS increased upon repeated freezing and thawing and after 8 weeks at −30° C.

Example 14

Effect of PEG, Proline, MEA, MSA and Calcium Chloride on Formulation Stability

Adalimumab biosimilar starting material at 50 mg/mL was prepared using 3.5 kD cutoff dialysis tubing in the following buffers: 5 mM MEA with 5 mM MSA, pH adjusted using MSA or MEA to a final pH of 4.8; 14.4 mM sodium phosphate with 7.7 mM citrate, 105 mM sodium chloride and 1.2% mannitol, pH adjusted with HCl or NaOH to a final pH of 4.8; 4.2% mannitol, pH adjusted with HCl or NaOH to a final pH of 4.8; 10 mM acetate with 9% sucrose, pH adjusted with HCl or NaOH to a final pH of 4.8. Stock excipient solutions were then added to achieve the final concentrations as shown in Table 14 and the pH was adjusted to 5.2 if needed. The formulations are provided in Table 14.

TABLE 14

| Ref. | Buffer | Excipient(s) | pH Adjusting Agent | pH | Ab conc. (mg/mL) |
|---|---|---|---|---|---|
| Comp. 7 | 14.1 mM sodium phosphate 7.7 mM citrate | 105 mM NaCl 1.2% mannitol | HCl, NaOH | 5.2 | 50 |
| Comp. 8 | — | 4.2% mannitol | HCl, NaOH | 5.2 | 50 |
| 14A | 10 mM acetate | 9% sucrose | HCl, NaOH | 5.2 | 50 |
| 14B | — | 10.4% PEG600 | MSA, MEA | 5.2 | 50 |
| 14C | — | 8.5% PEG600 25 mM calcium chloride | MSA, MEA | 5.2 | 50 |
| 14D | — | 6.4% PEG600 50 mM calcium chloride | MSA, MEA | 5.2 | 50 |
| 14E | — | 3.7% PEG600 75 mM calcium chloride | MSA, MEA | 5.2 | 50 |
| 14F | — | 100 mM calcium chloride | MSA, MEA | 5.2 | 50 |
| 14G | — | 300 mM proline | MSA, MEA | 5.2 | 50 |
| 14H | — | 225 mM proline 25 mM calcium chloride | MSA, MEA | 5.2 | 50 |
| 14I | — | 150 mM proline 50 mM calcium chloride | MSA, MEA | 5.2 | 50 |
| 14J | — | 75 mM proline 75 mM calcium chloride | MSA, MEA | 5.2 | 50 |
| 14K | — | 240 mM proline 60 mM MEA 60 mM MSA | MSA, MEA | 5.2 | 50 |
| 14L | — | 180 mM proline 60 mM MEA 60 mM MSA | MSA, MEA | 5.2 | 50 |
| 14M | — | 120 mM proline 90 mM MEA 90 mM MSA | MSA, MEA | 5.2 | 50 |

Figure 43:
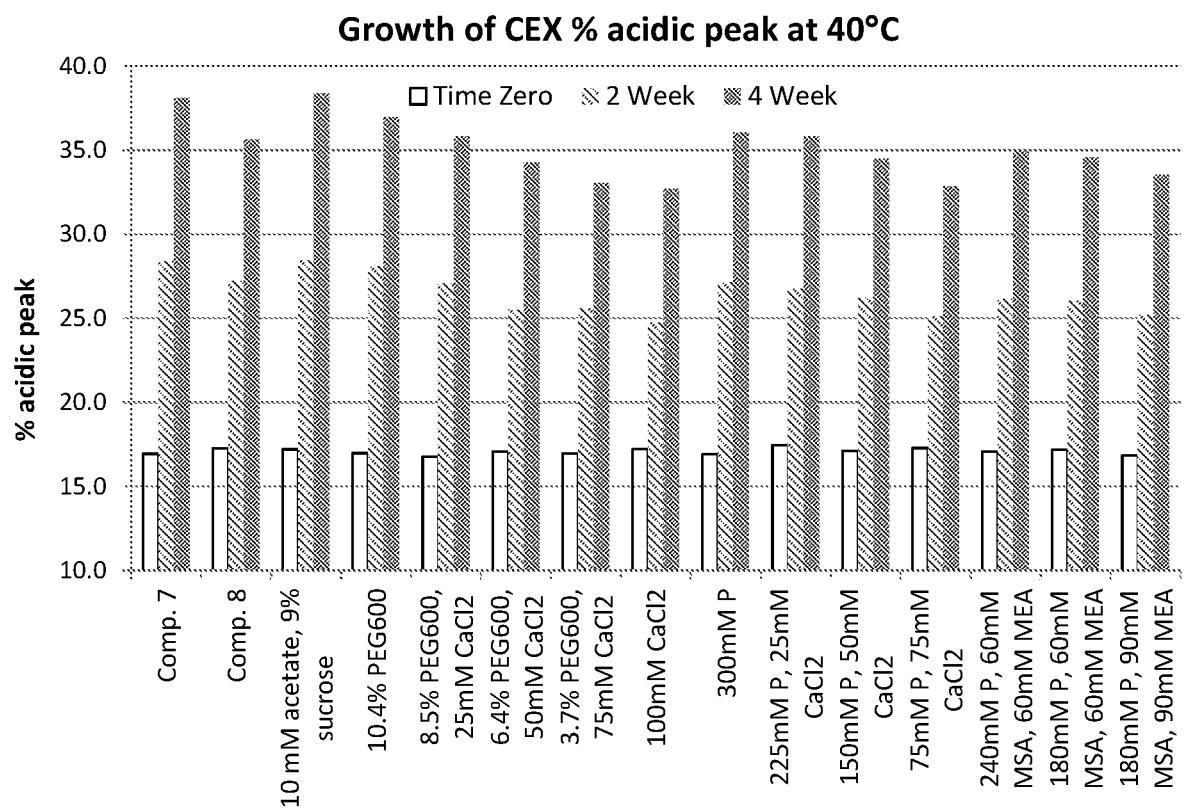
FIG. 43 is a bar graph of stability of adalimumab formulations as determined by CEX-HPLC.
Figure 44:
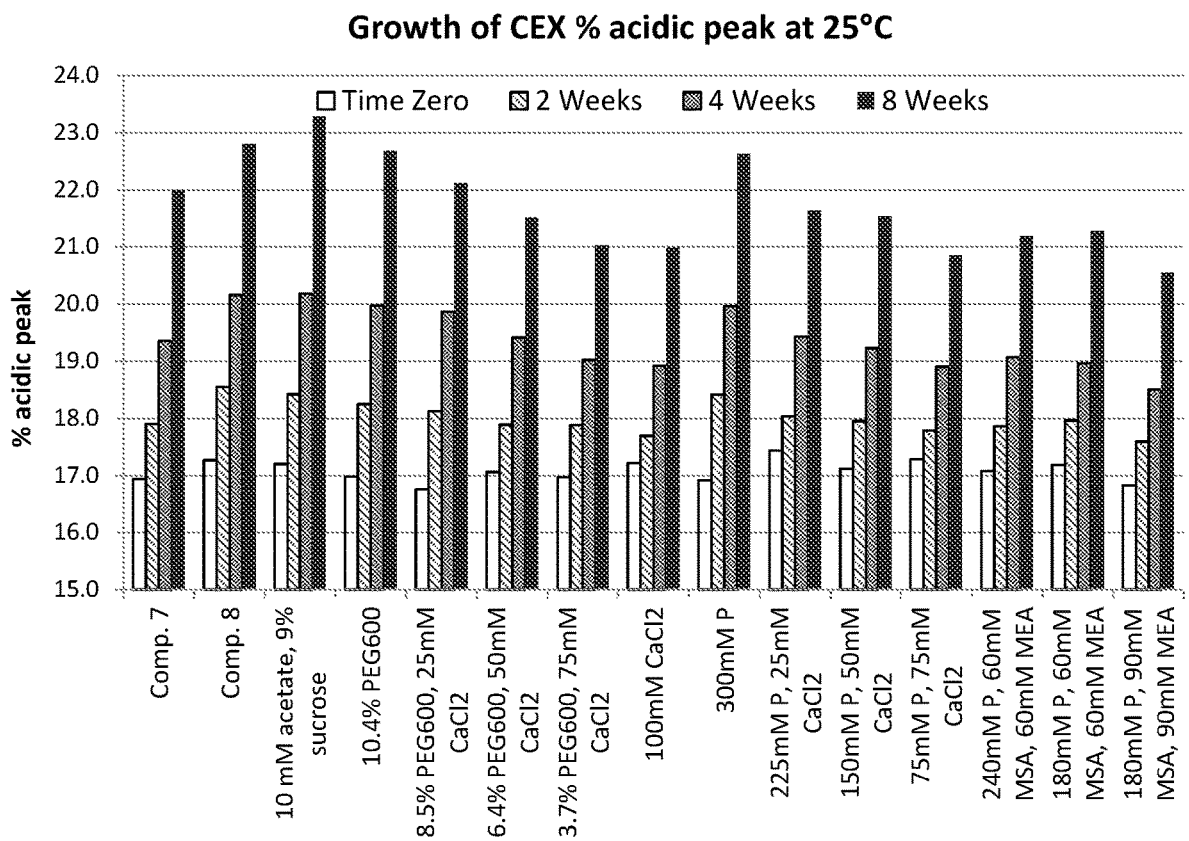
FIG. 44 is a bar graph of stability of adalimumab formulations as determined by CEX-HPLC.
Figure 45:
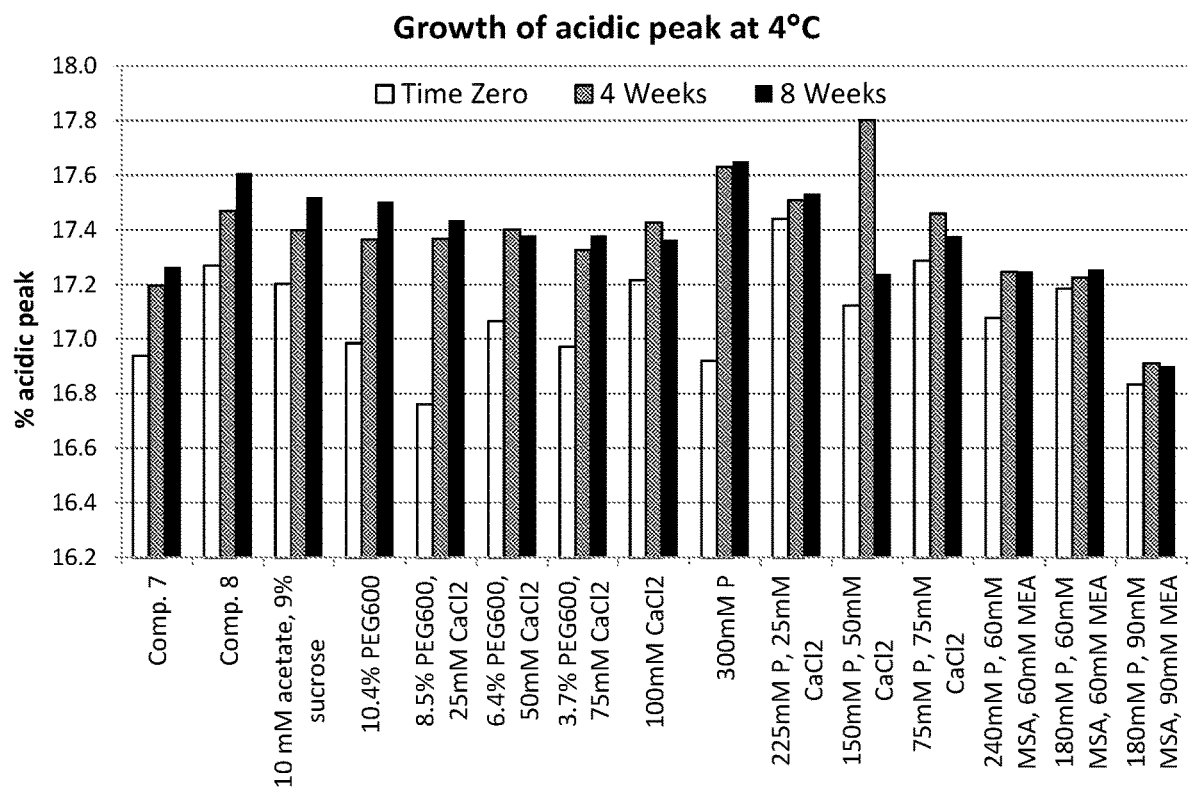
FIG. 45 is a bar graph of stability of adalimumab formulations as determined by CEX-HPLC.
Figure 46:
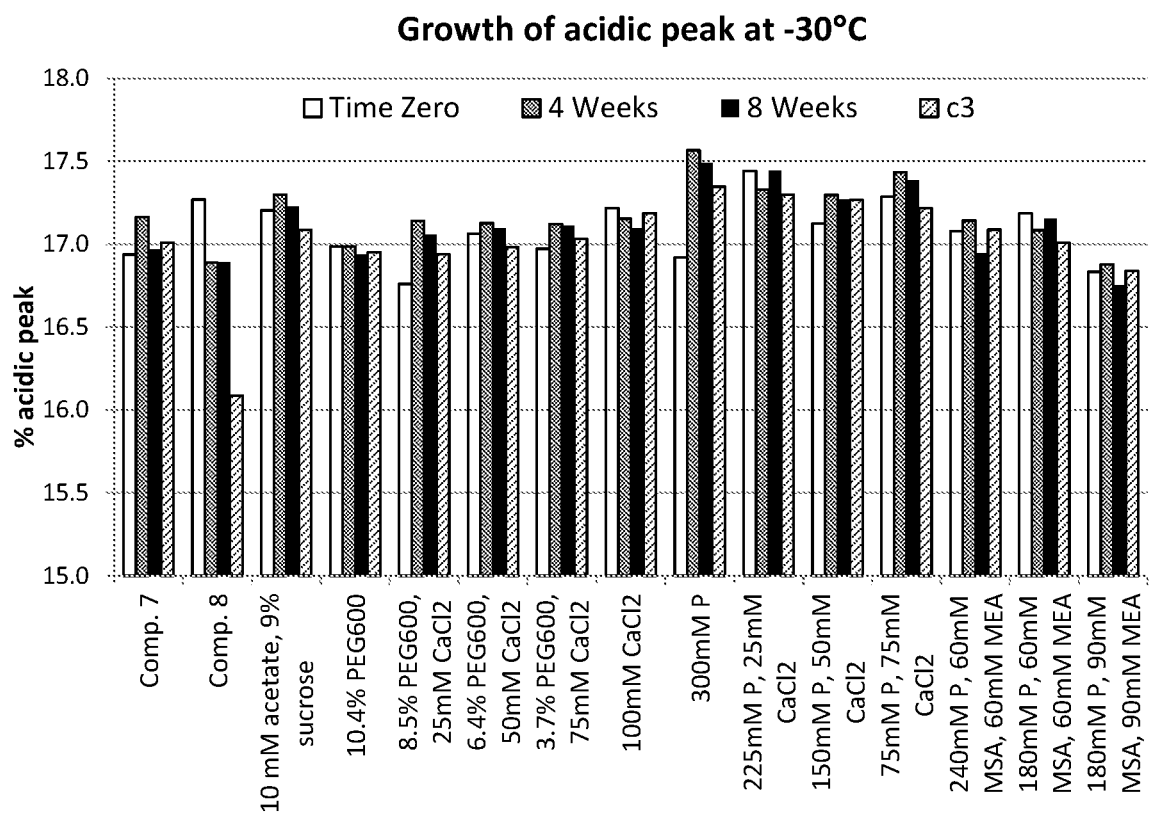
FIG. 46 is a bar graph of stability of adalimumab formulations as determined by CEX-HPLC.

To assess stability, the % acidic peak was measured by CEX-HPLC after 0, 2, and 4 weeks at 40° C. and after 0, 2, 4, and 8 weeks at 25° C. The results are shown in FIG. 43 and FIG. 44. At 25° C., after 8 weeks, lower amounts of HMWS were measured in the formulation with proline and high MEA and MSA (14M) and in the formulations with the higher concentrations of calcium chloride (14E, 14F and 14J). As is shown by comparing formulations 14B, 14C, 14D, 14E and 14F, the level of HMWS increased as the concentration of PEG 600 increased after 8 weeks at 25° C. Similar trends were observed at 40° C. that had been apparent at 25° C. Increasing levels of calcium chloride were beneficial in minimizing the formation of HMWS. PEG 600 was not preferred for stability at 40° C. Low HMWS was observed in the formulation containing proline and high MEA and MSA after 4 weeks at 40° C. Stability was assessed by measuring acidic peak by CEX-HPLC after 0, 4 and 8 weeks at 4° C. The results are shown in FIG. 45. Minor differences were measured in the % acidic peak at time zero and after storage for 8 weeks at 4° C. These differences were not considered meaningful. Stability was assessed by measuring acidic peak by CEX-HPLC after 0 days, after 3 F/T cycles, and after 4 weeks at −30° C. The results are shown in FIG. 46. Consistent with the results obtained at 4° C., differences between formulations were minor and apparent growth of the % acidic peak was not observed after multiple freeze thaws and 8 weeks storage at −30° C.

Figure 47:
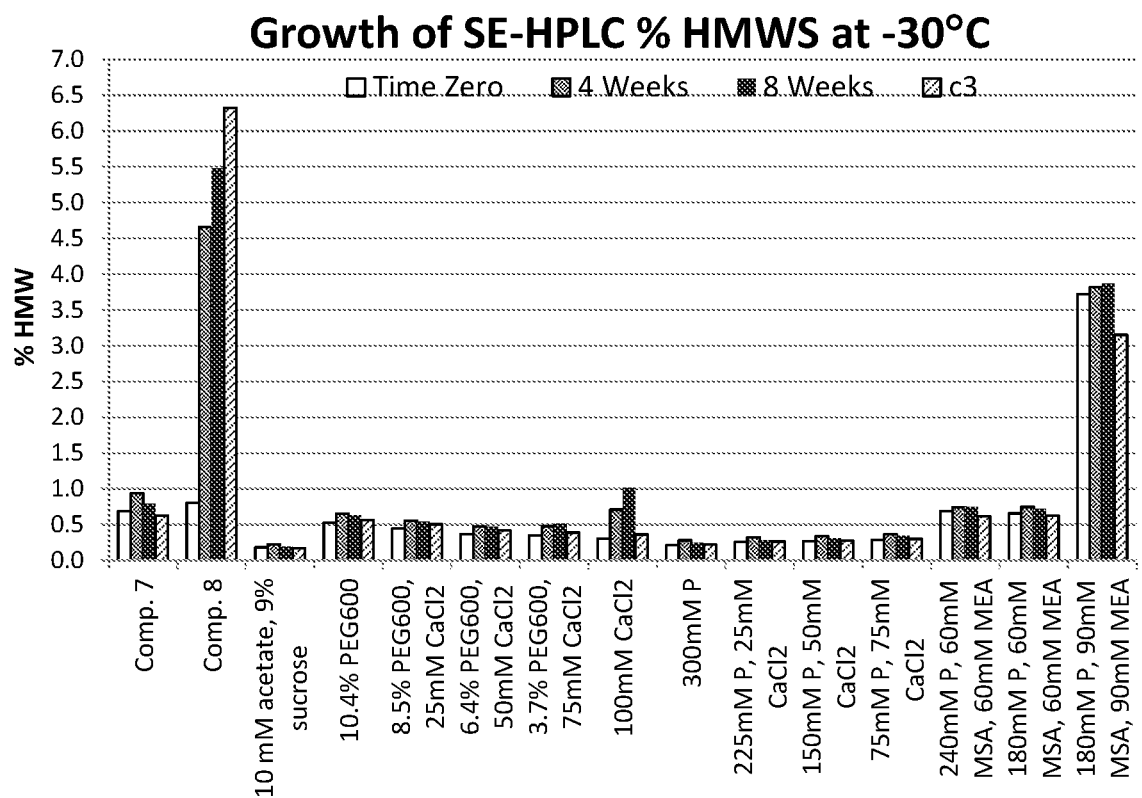
FIG. 47 is a bar graph of stability of adalimumab formulations as determined by SE-HPLC.
Figure 48:
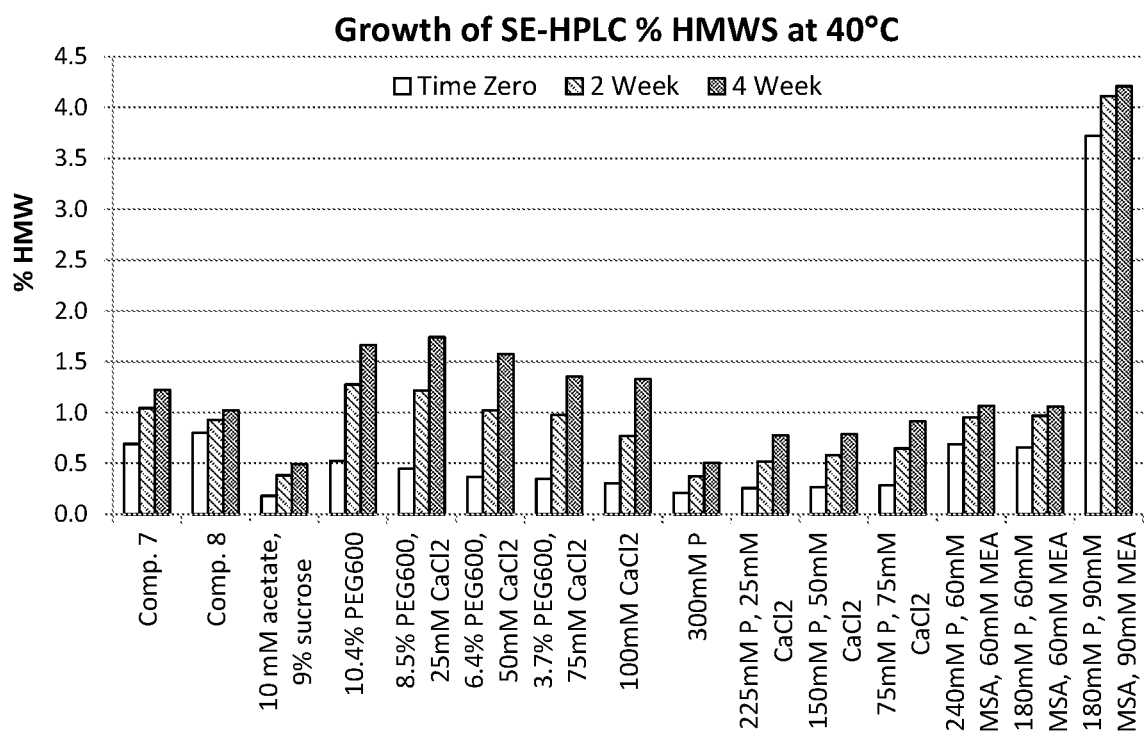
FIG. 48 is a bar graph of stability of adalimumab formulations as determined by SE-HPLC.
Figure 49:
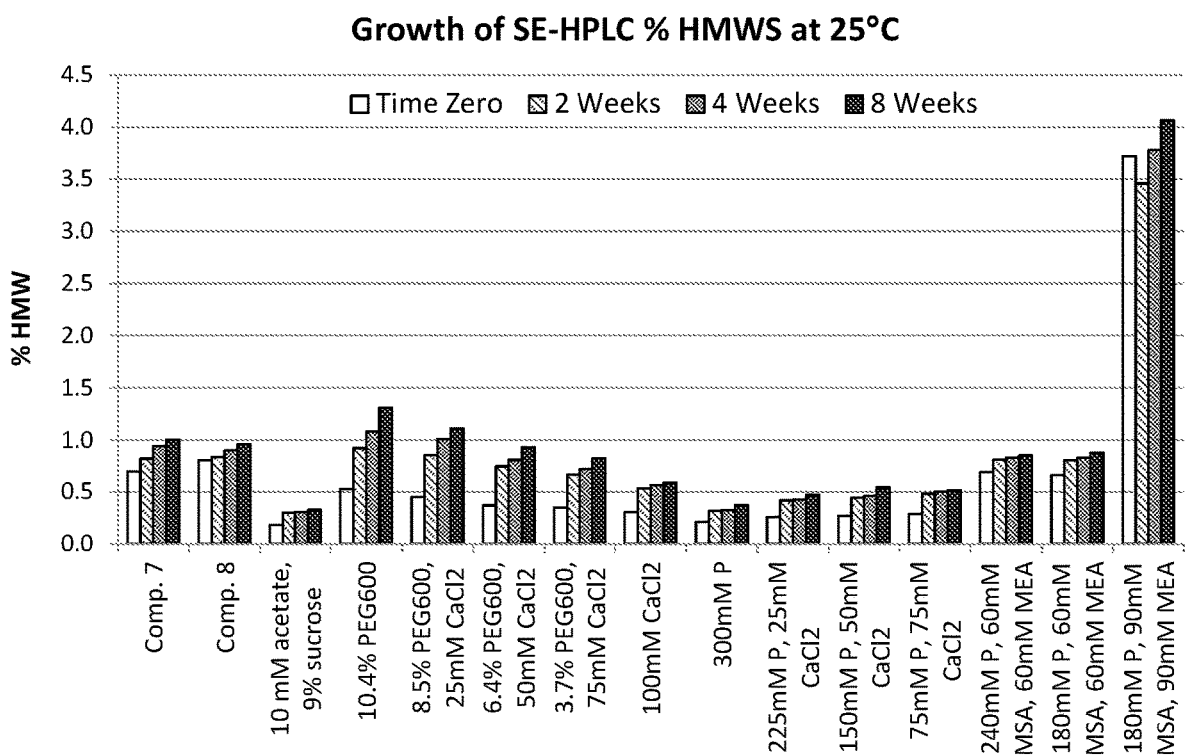
FIG. 49 is a bar graph of stability of adalimumab formulations as determined by SE-HPLC.
Figure 50:
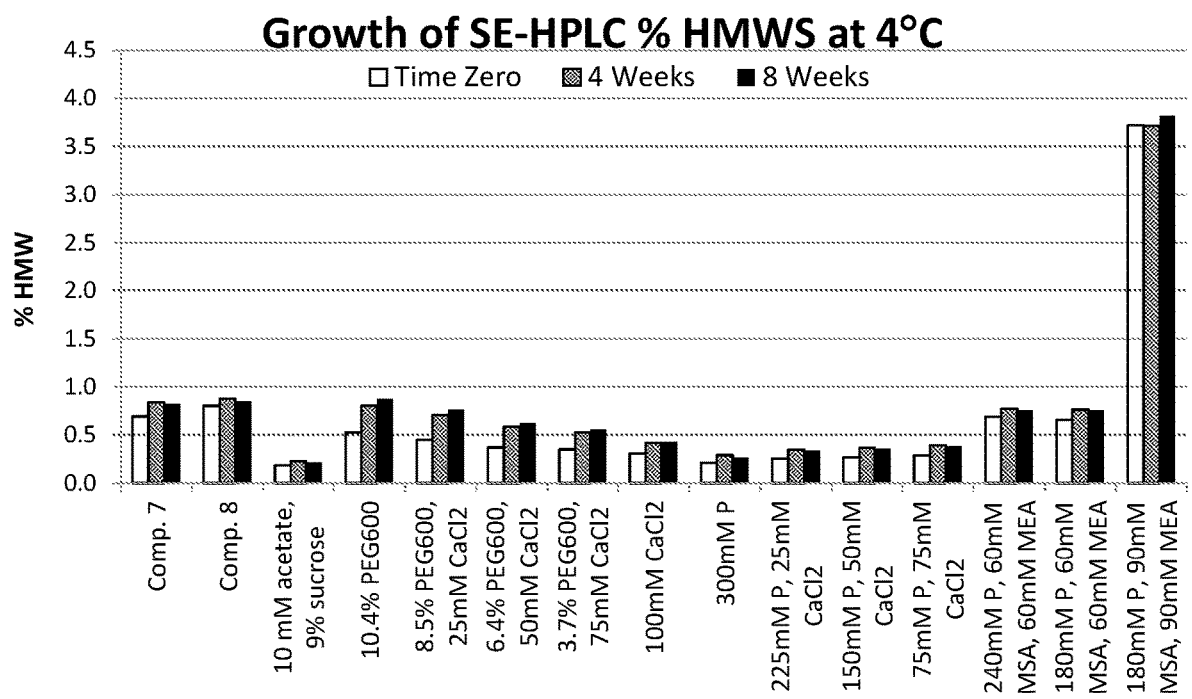
FIG. 50 is a bar graph of stability of adalimumab formulations as determined by SE-HPLC.

Stability also was assessed by measuring HMWS by SE-HPLC after 0 days and after 3 F/T cycles. The results are shown in FIG. 47. For most formulations, multiple freezing and thawing did not result in growth of HMWS, with the exception of formulation Comp 8. Several formulations, although not showing an increase in HMWS after multiple freeze thaw steps, did grow in HMWS after storage at −30° C. following the freeze thaw steps (formulations Comp. 8, self-buffered, and 14M, containing high amounts of MEA and MSA). Stability was assessed by measuring HMWS by SE-HPLC after 0 and 2 weeks at 40° C. and at 25° C. The results are shown in FIG. 48 and FIG. 49. After storage at 40° C. for 4 weeks, HMWS growth appeared to be higher in formulations containing PEG 600 or higher amounts of calcium chloride and in the formulation buffered with sodium phosphate (Comp 7, 14B, 14C, 14D, 14E, 14F). Overall, the highest amount of HMWS at >3% was measured in the formulation with higher MEA and MSA (14M). Low amounts of HMWS were observed in the formulation buffered with acetate and the proline formulation (14A, 14G). Similar trends were observed at 25° C. as were found at 40° C. Low HMWS were apparent in formulations 14A and 14G, with PEG 600 not preferred for stability, along with high levels of MEA and MSA. Finally, stability was also assessed at 4° C. by SE-HPLC after 0, 4 and 8 weeks. The results are shown in FIG. 50. Meaningful growth of HMWS at 4° C. was not observed in most formulations, with the exception of the formulations containing higher amounts of PEG 600 (14B, 14C). As discussed previously, at time zero the highest HMWS was observed in the formulation containing high levels of MEA and MSA.

Example 15

Stability of Self-Buffered, Lactate Buffered, and Acetate Buffered Formulations Three adalimumab formulations were prepared, as shown in Table 15.

TABLE 15

| Ref. | Buffer/pH Adjusting Agent | Excipients | Surfactant | pH | Ab conc. (mg/mL) | Conductivity |
|---|---|---|---|---|---|---|
| 15A | —/HCl, Ca(OH)$_2$ | 4% sorbitol, 30 mM calcium chloride | 0.05% Pluronic F68 | 5.2 | 100 | 4.7 mS/cm |
| 15B | 10 mM Lactate/HCl, Ca(OH)$_2$ | 6% sucrose, 30 mM calcium chloride | 0.006% Pluronic F68 | 5.1 | 100 | 4.78 mS/cm |
| 15C | 10 mM Acetate/HCl, NaOH | 6% sucrose, 45 mM NaCl | 0.1% Polysorbate 80 | 5.2 | 100 | 4.05 mS/cm |

Figure 51:
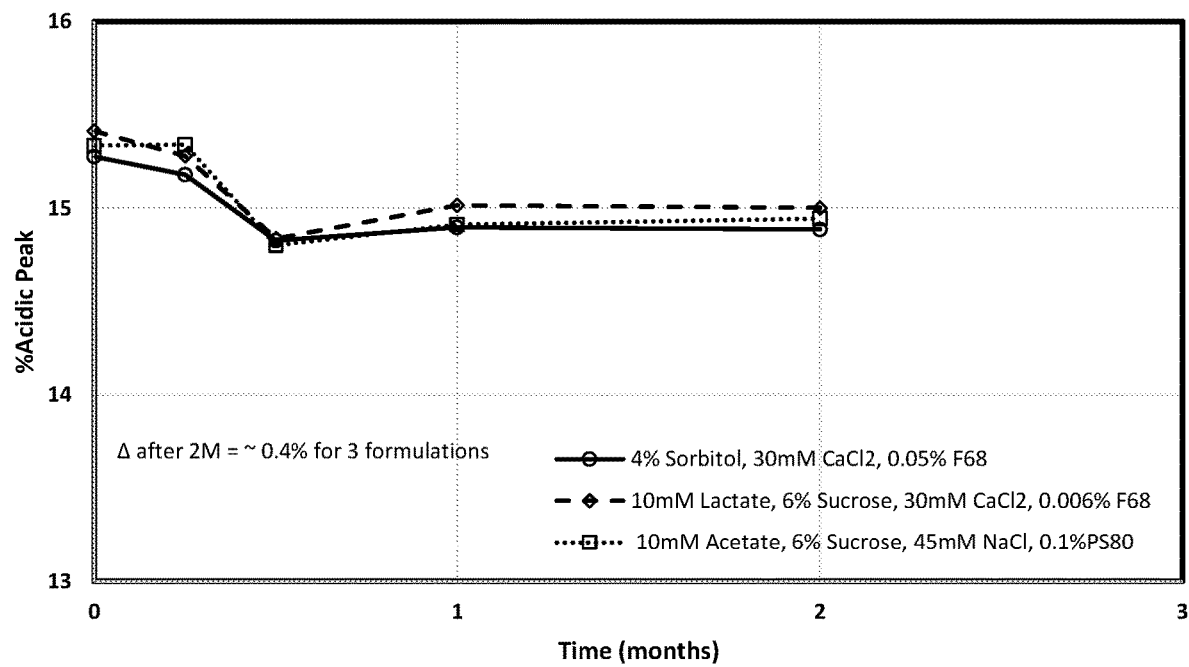
FIG. 51 is a line graph of stability of adalimumab formulations as determined by CEX-HPLC.
Figure 52:
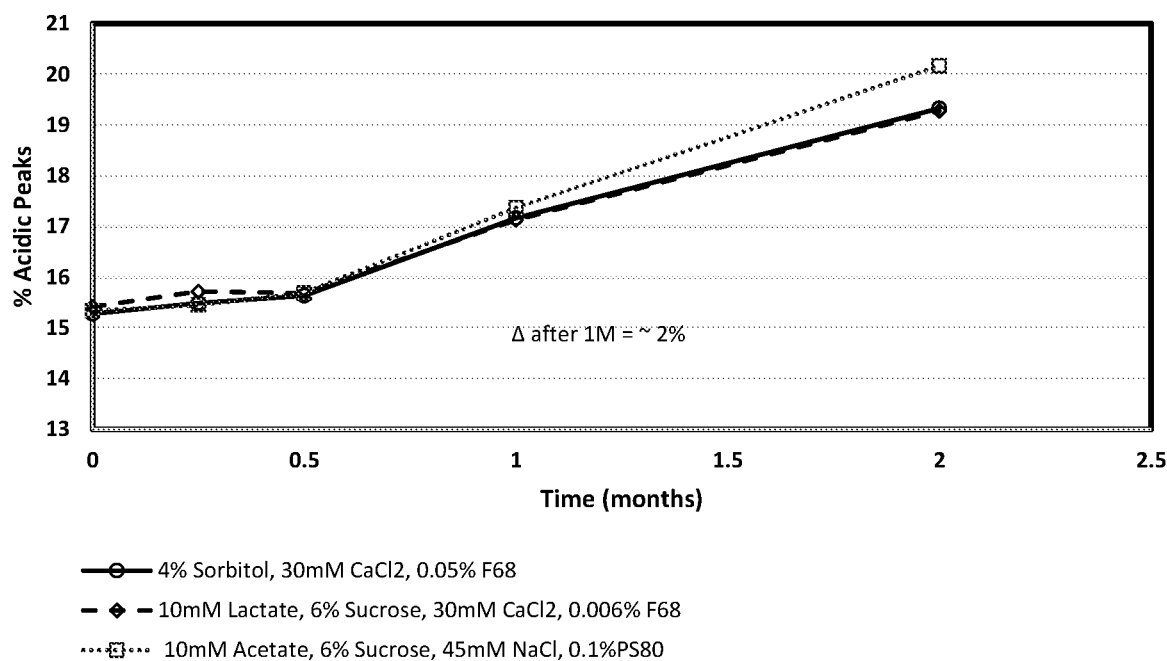
FIG. 52 is a line graph of stability of adalimumab formulations as determined by CEX-HPLC.

To assess stability, the % acidic peak was measured by CEX-HPLC at 0 days, 1 week, 2 weeks, 1 month, and 2 months, at 2-8° C., and at 0 days, 1 week, 2 weeks, 1 month, and 2 months at 25° C. The results are shown in FIG. 51 (2-8° C.) and FIG. 52 (25° C.). All three formulation (formulations 15A-C) exhibited similar stability with respect to acidic species at 2-8° C. At 25° C., formulation 15C (acetate buffer with sodium chloride) had the highest amount of % acidic peak.

Figure 53:
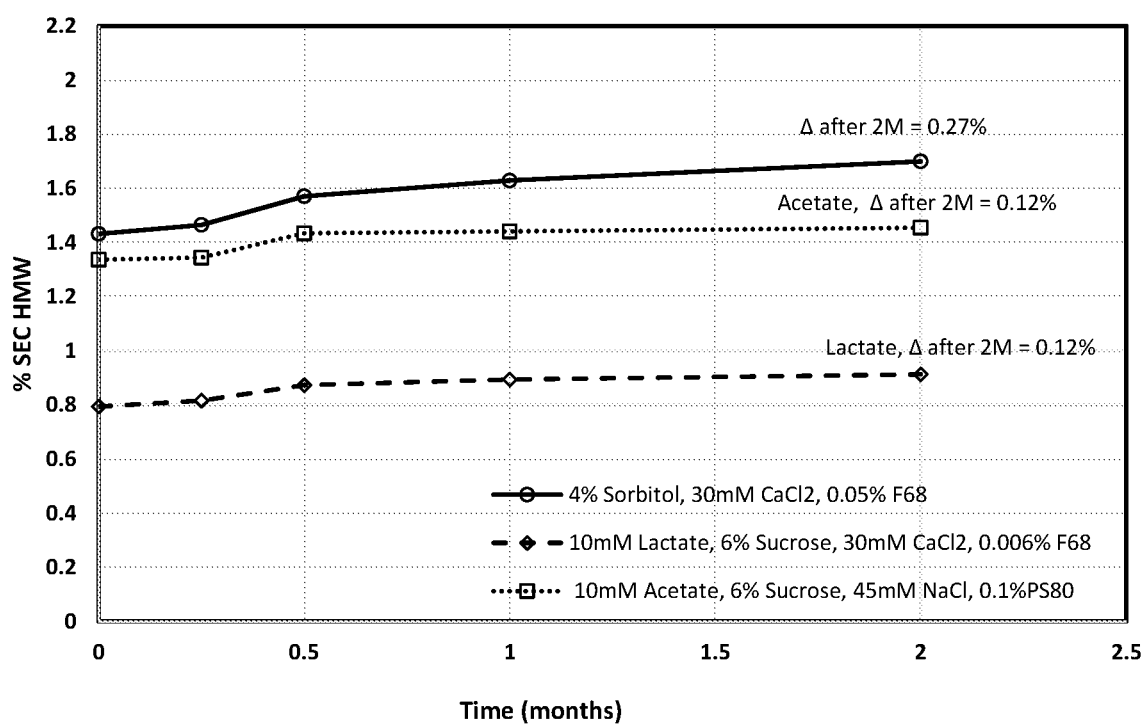
FIG. 53 is a line graph of stability of adalimumab formulations as determined by SE-HPLC.
Figure 54:
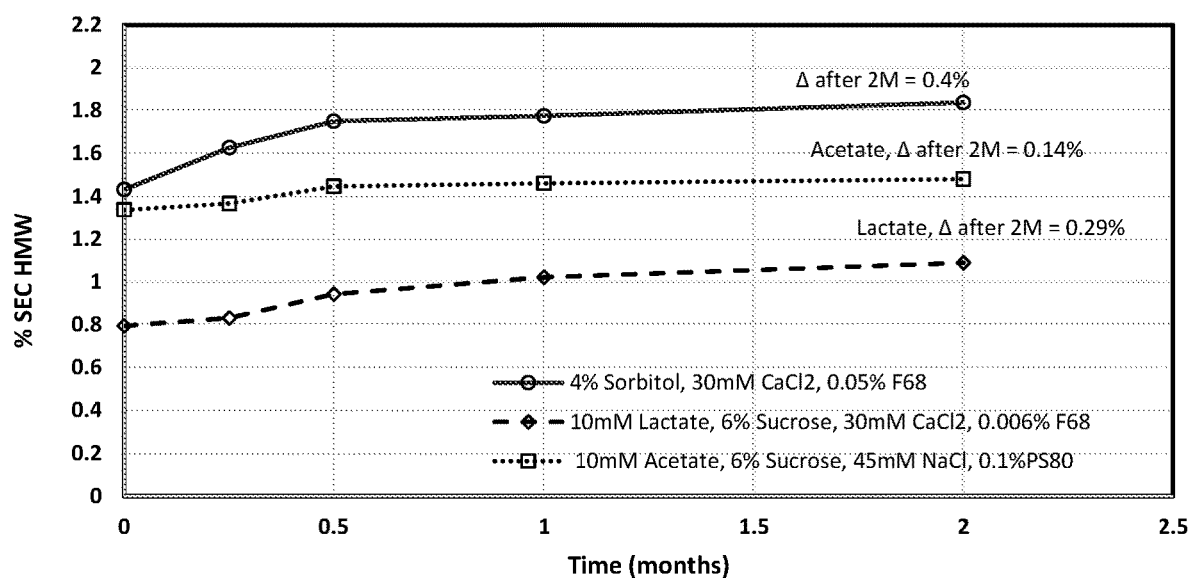
FIG. 54 is a line graph of stability of adalimumab formulations as determined by SE-HPLC.

Stability also was assessed by measuring HMWS by SE-HPLC after 0 days, 1 week, 2 weeks, 1 month, and 2 months at 2-8° C., and after 0 days, 1 week, 2 weeks, 1 month, and 2 months at 25° C. The results are shown in FIGS. 53 (2-8° C.) and 54 (25° C.). At time zero, the highest HMWS was measured in the self-buffered formulation, followed by the acetate buffer formulation with sodium chloride and the lactate buffer formulation with calcium chloride, respectively. This trend was maintained at 4° C. over time, with the lactate buffer formulation having the least amount of HMWS. Likewise, at 25° C., the lactate buffer formulation exhibited the least growth of HMWS. At the 1 and 2 month time point, the rate of degradation also slowed down compared to the earlier time points at 25° C. This trend was observed for all formulations at 25° C. At 4° C., the rate of growth of HMWS were similar for each formulation, with a minor increase observed in all formulations after time zero and up to two weeks, followed by a leveling off of the rate after the two week time point. The lactate buffer formulation also had the lowest amount of HMWS at time zero.

Figure 55:
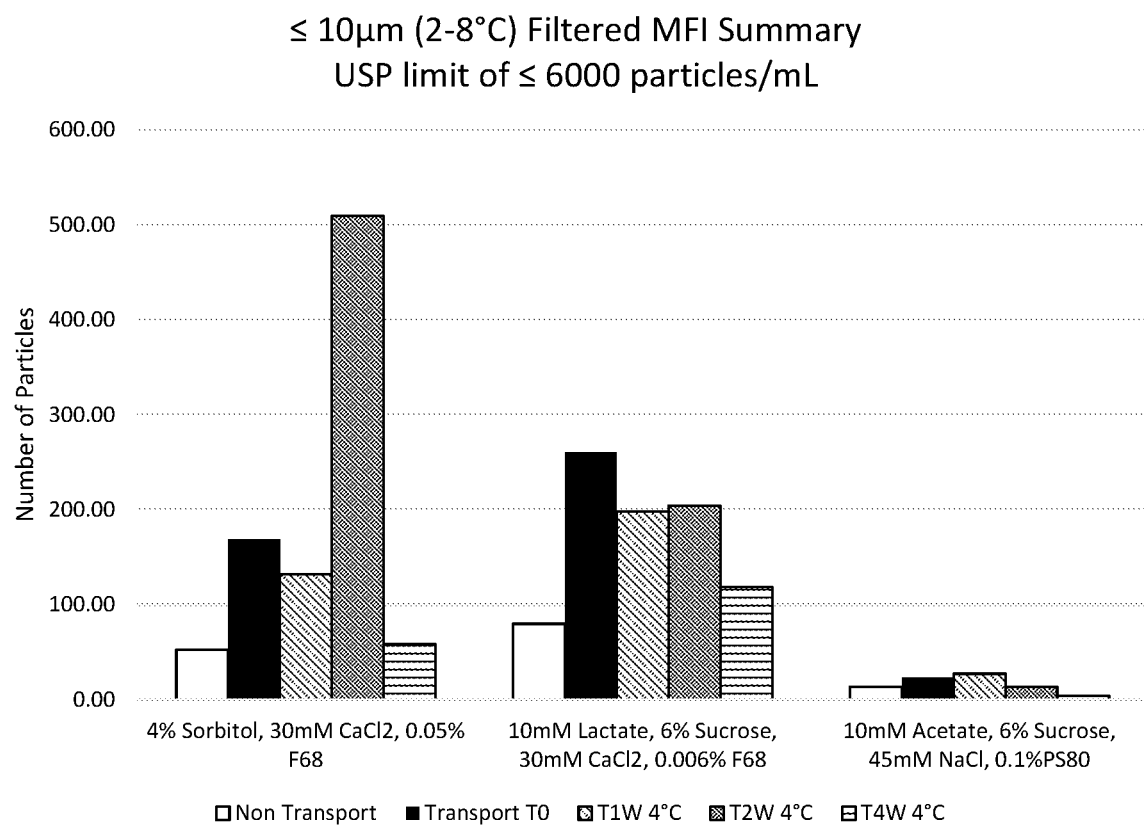
FIG. 55 is a bar graph of stability of adalimumab formulations as determined by MFI.
Figure 56:
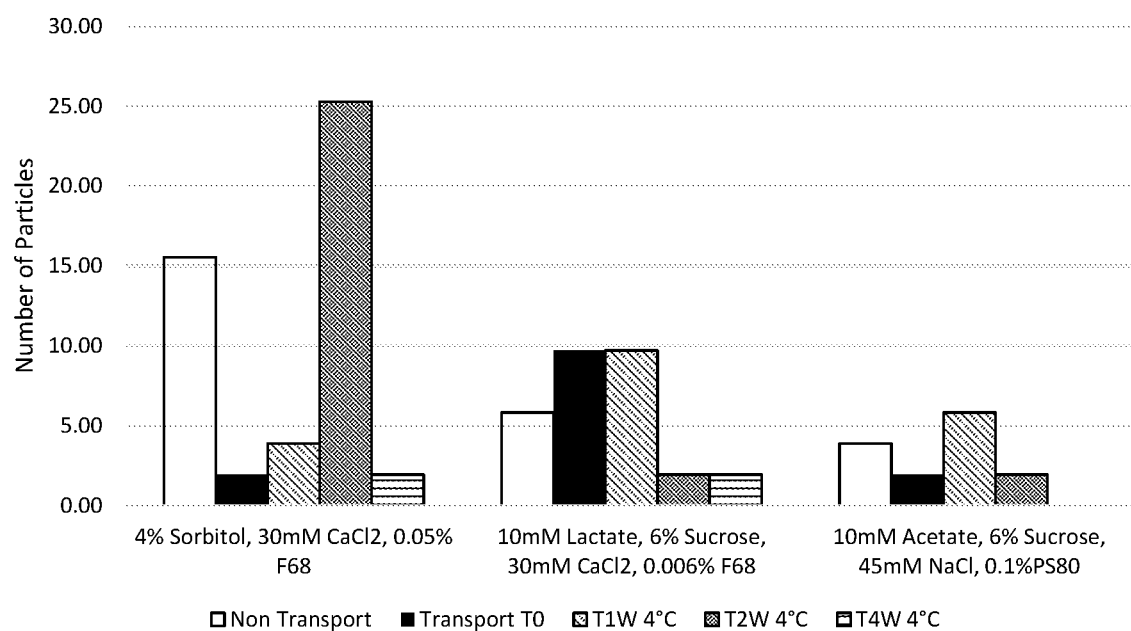
FIG. 56 is a bar graph of stability of adalimumab formulations as determined by MFI.
Figure 57:
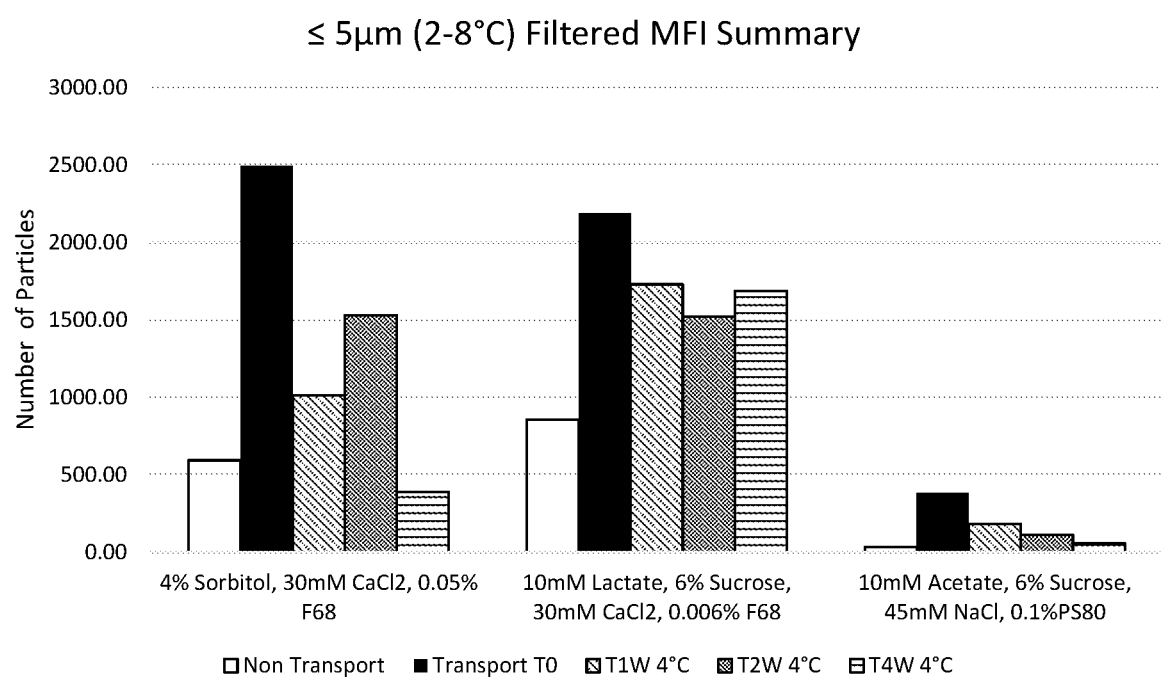
FIG. 57 is a bar graph of stability of adalimumab formulations as determined by MFI.
Figure 58:
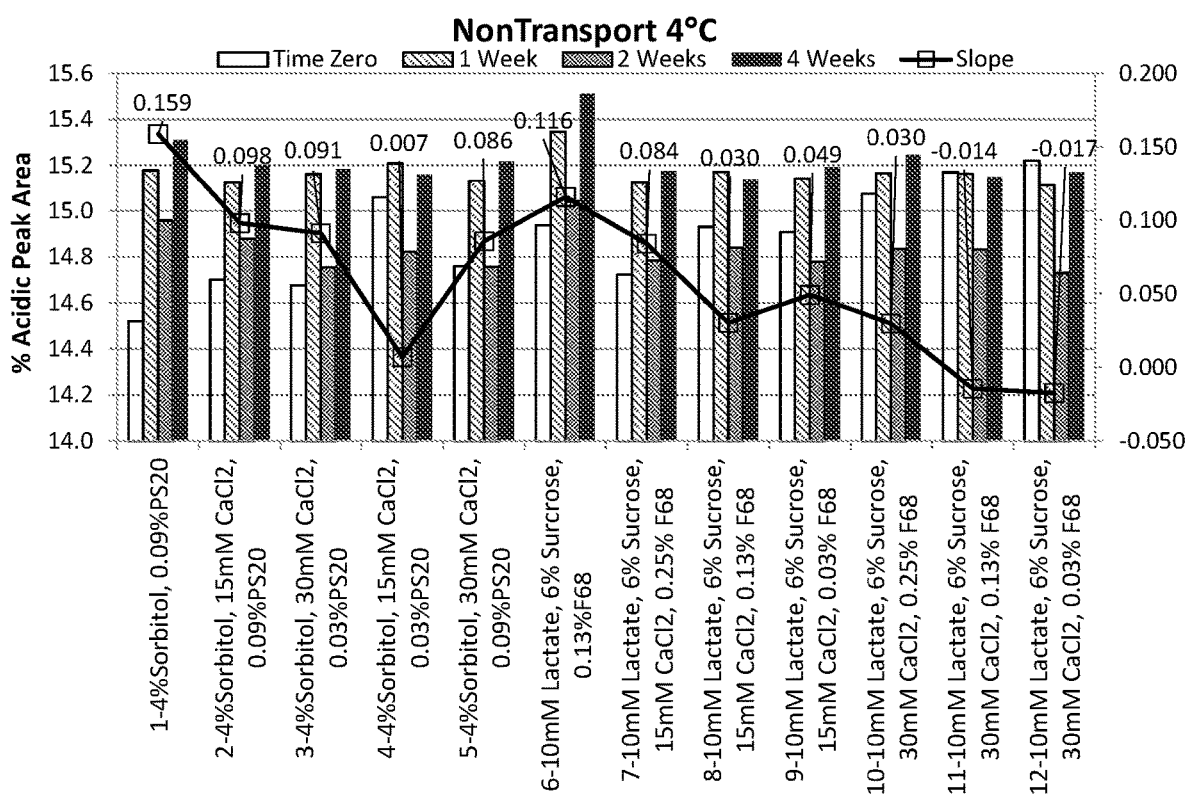
FIG. 58 is a bar graph of stability of adalimumab formulations (non-transport at 4° C.) as determined by CEX-HPLC.
Figure 59:
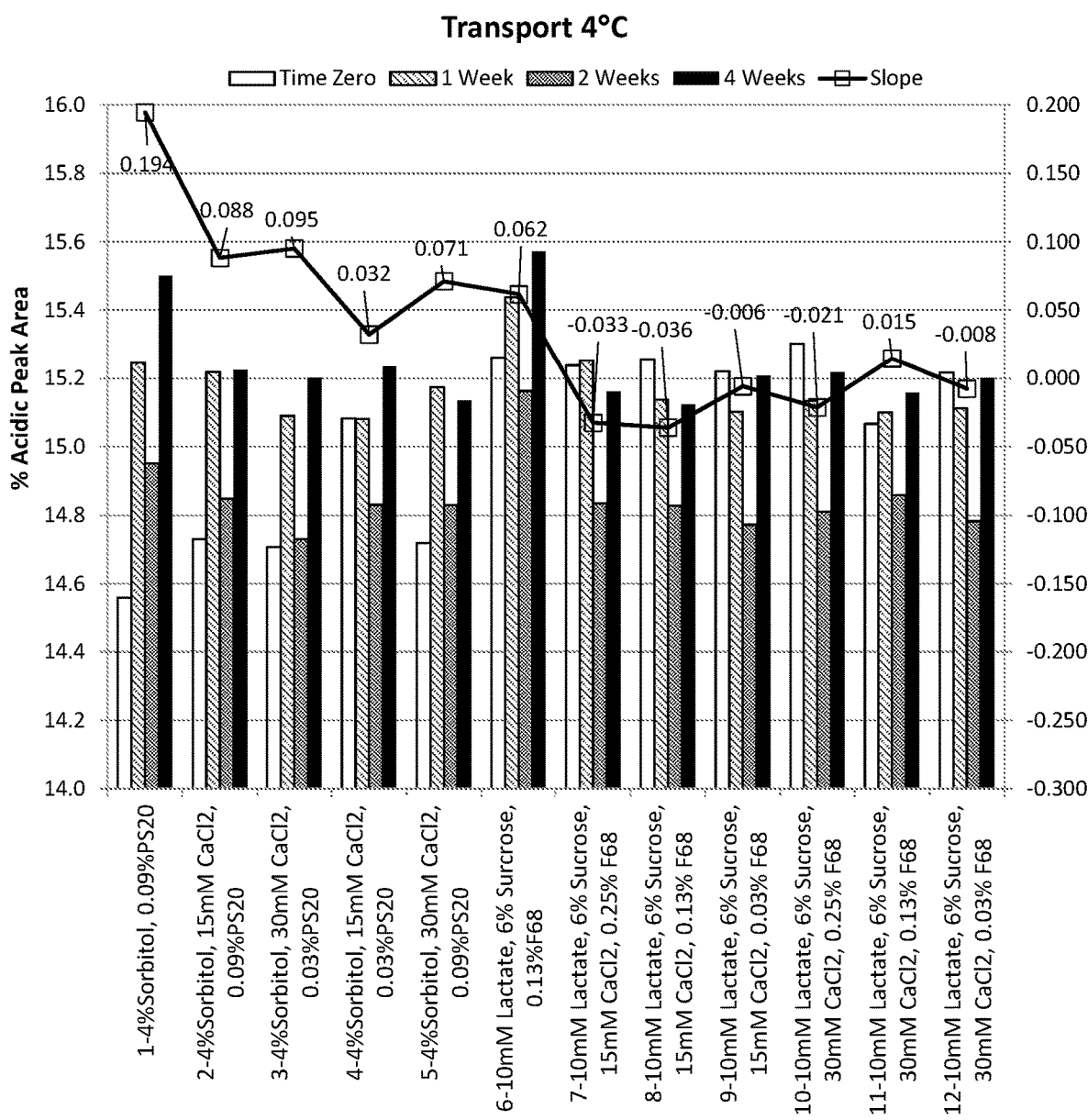
FIG. 59 is a bar graph of stability of adalimumab formulations (transport at 4° C.) as determined by CEX-HPLC.
Figure 60:
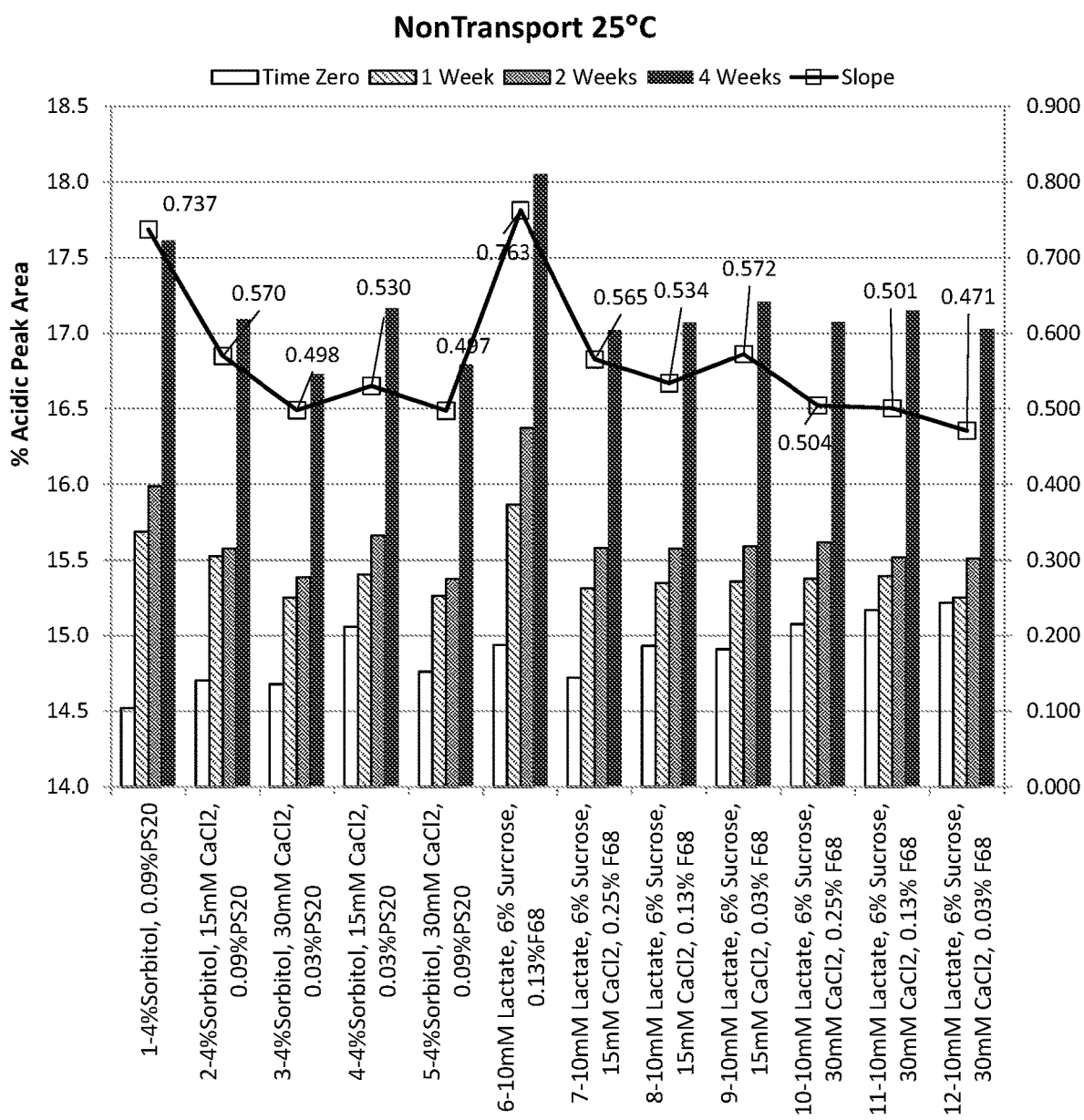
FIG. 60 is a bar graph of stability of adalimumab formulations (non-transport at 25° C.) as determined by CEX-HPLC.
Figure 61:
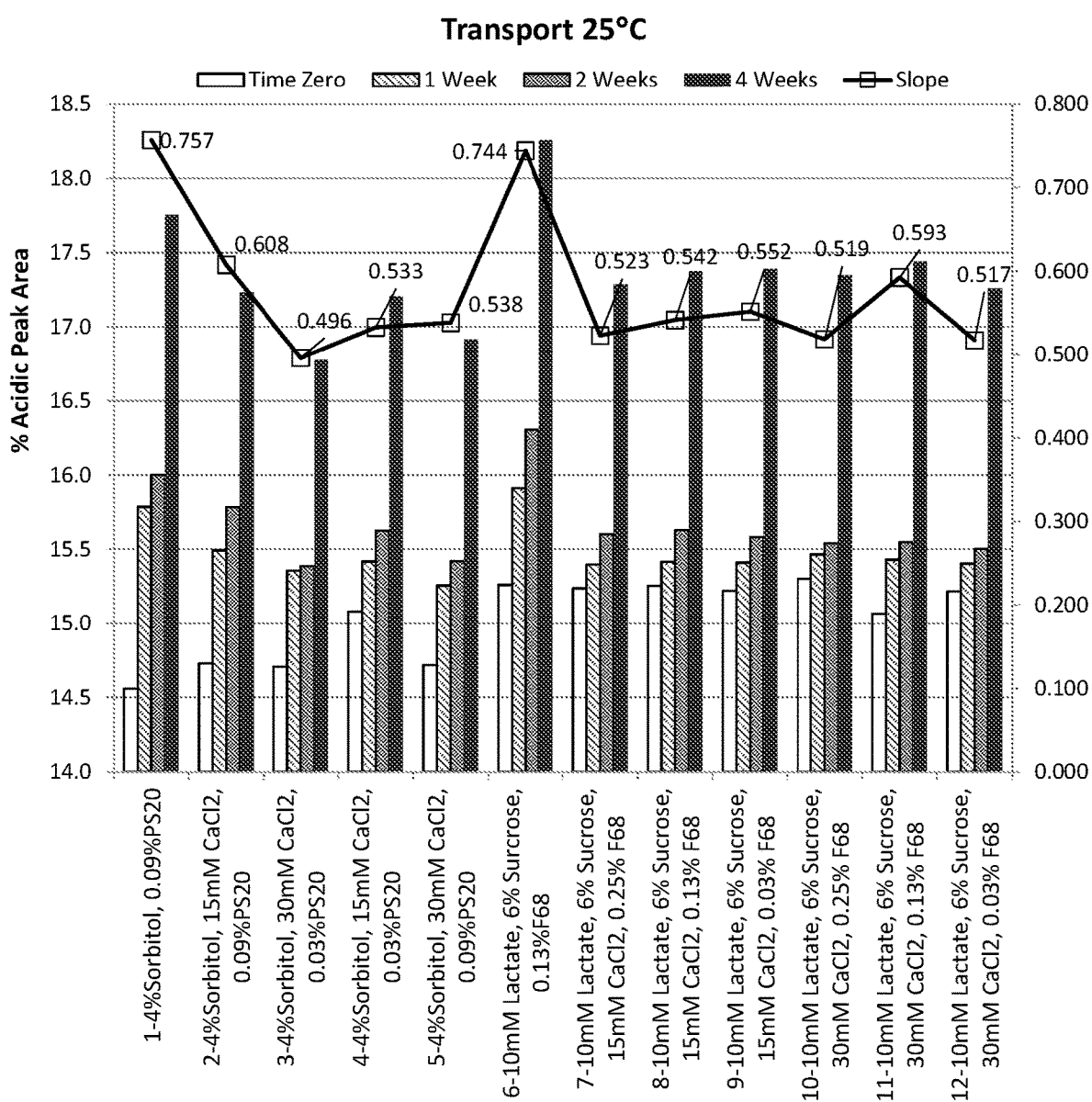
FIG. 61 is a bar graph of stability of adalimumab formulations (transport at 25° C.) as determined by CEX-HPLC.
Figure 62:
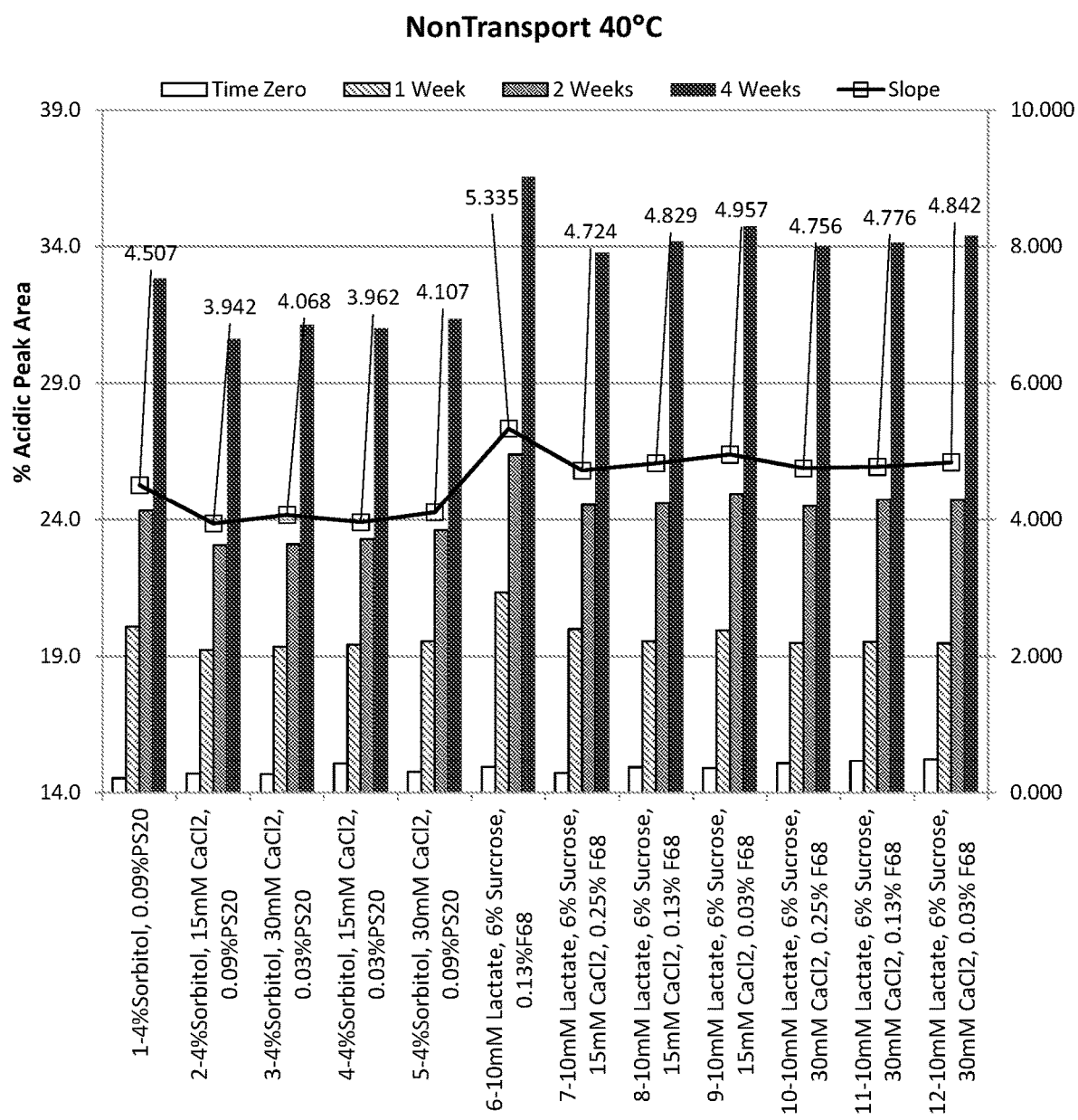
FIG. 62 is a bar graph of stability of adalimumab formulations (non-transport at 40° C.) as determined by CEX-HPLC.
Figure 63:
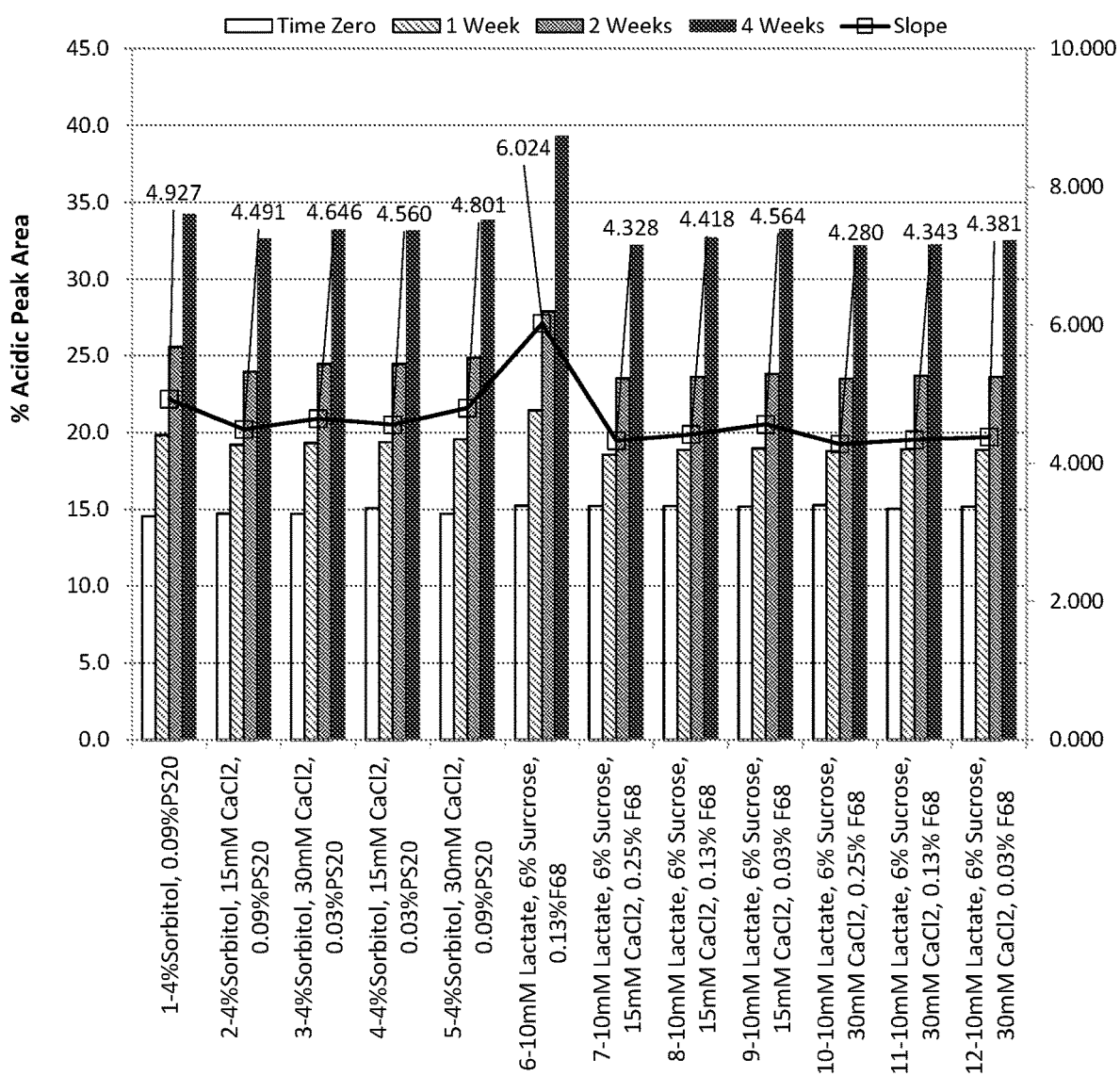
FIG. 63 is a bar graph of stability of adalimumab formulations (transport at 40° C.) as determined by CEX-HPLC.
Figure 64:
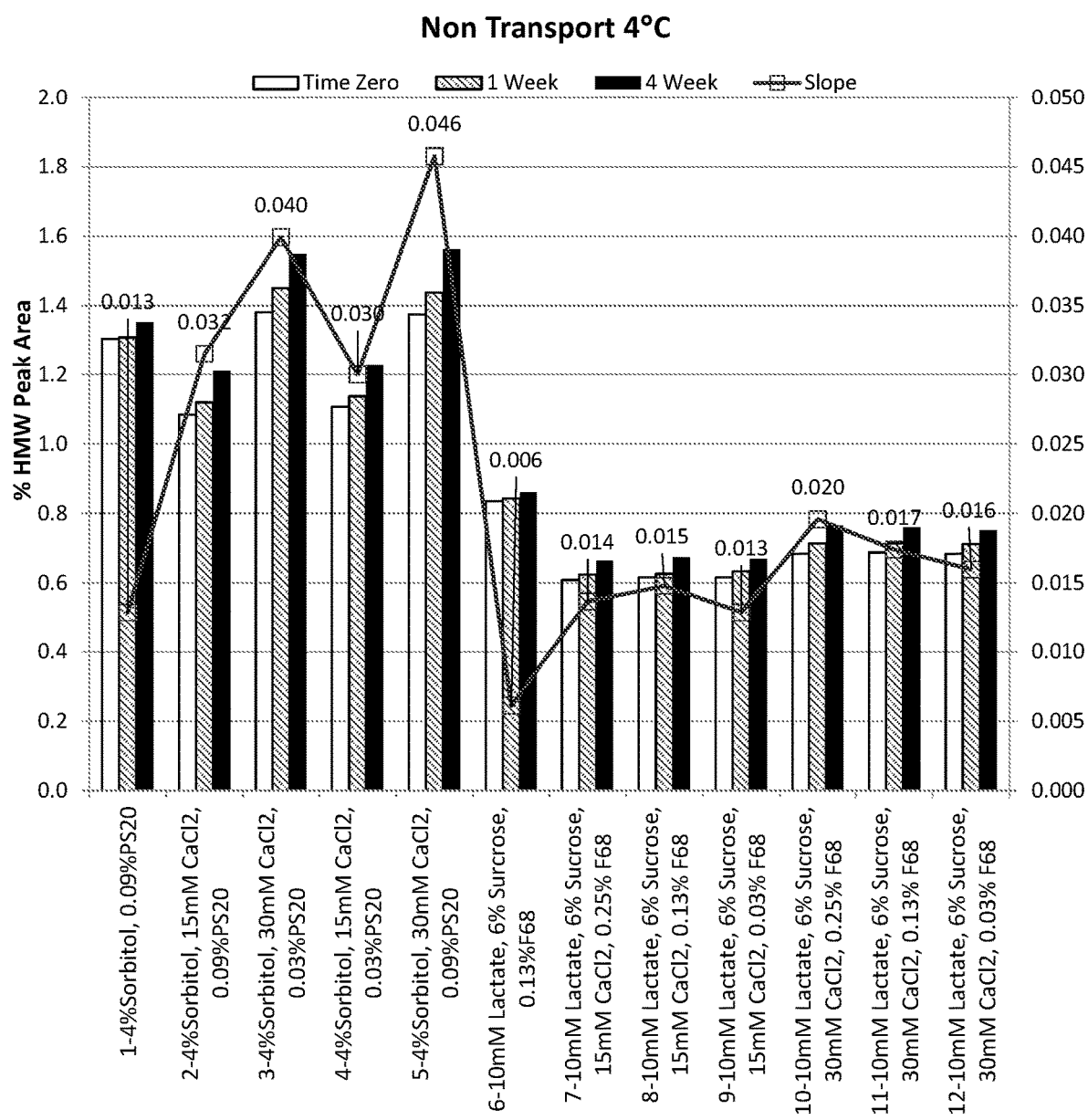
FIG. 64 is a bar graph of stability of adalimumab formulations (non-transport at 4° C.) as determined by SE-HPLC.
Figure 65:
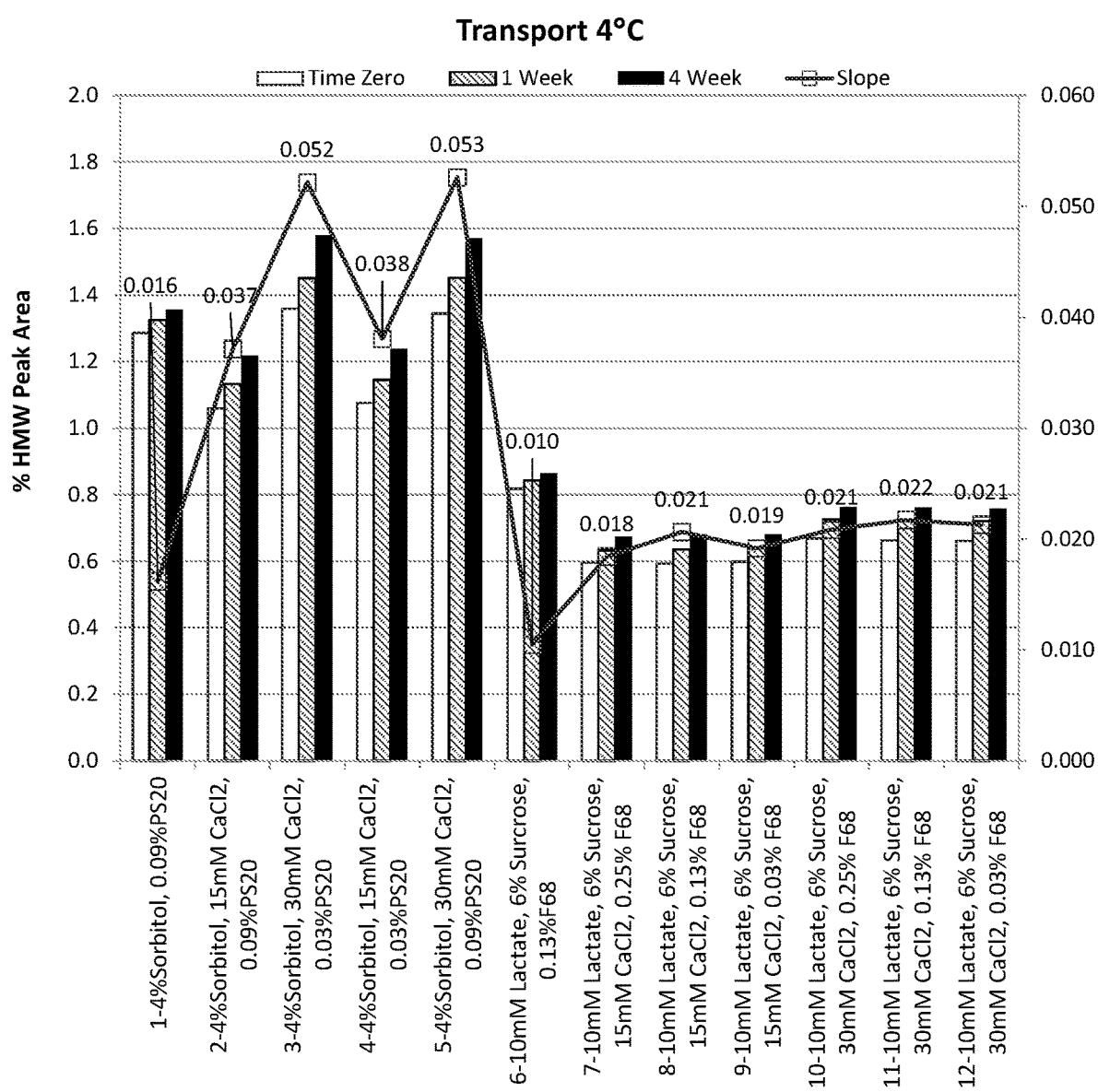
FIG. 65 is a bar graph of stability of adalimumab formulations (transport at 4° C.) as determined by SE-HPLC.
Figure 66:
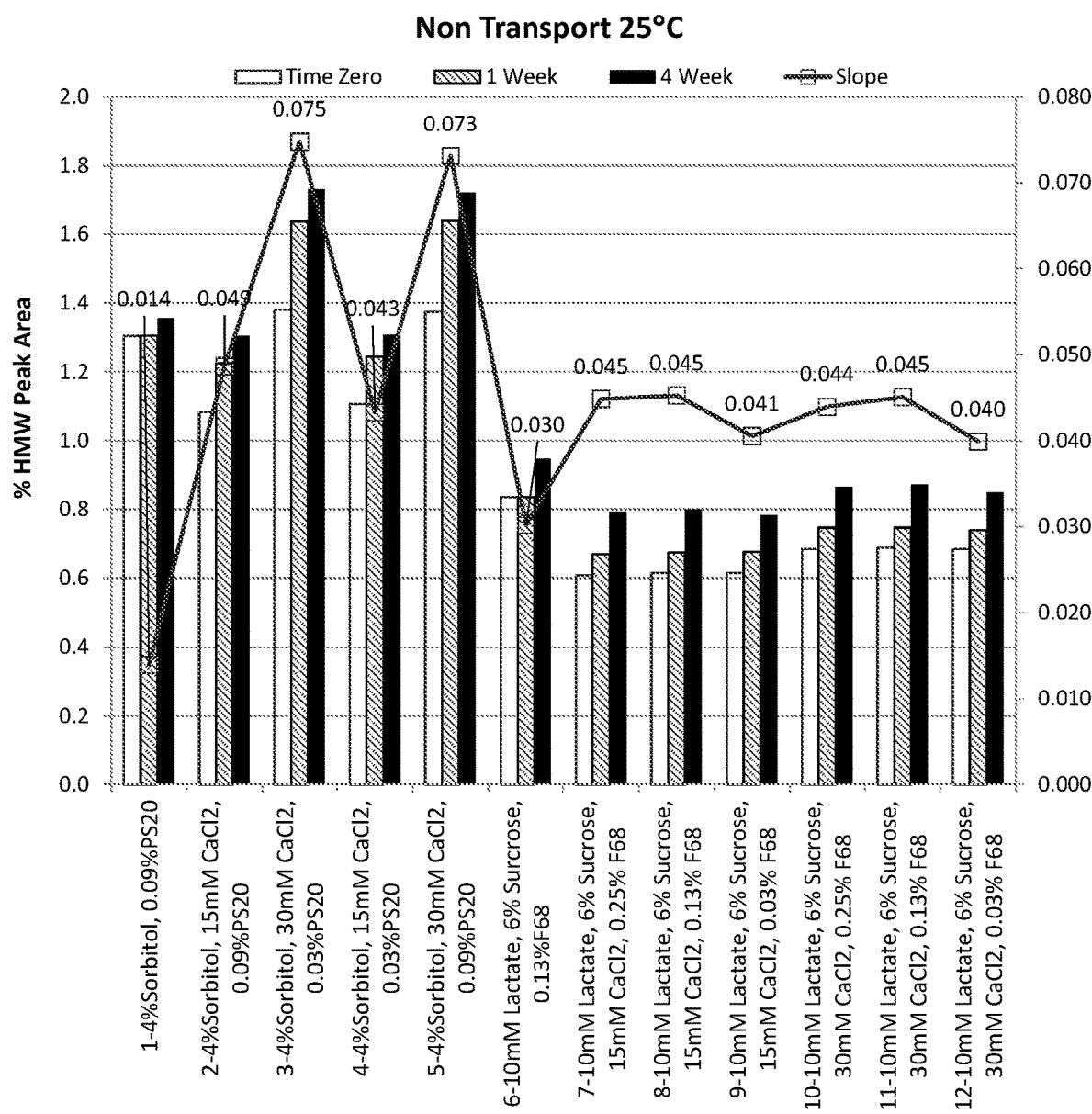
FIG. 66 is a bar graph of stability of adalimumab formulations (non-transport at 25° C.) as determined by SE-HPLC.
Figure 67:
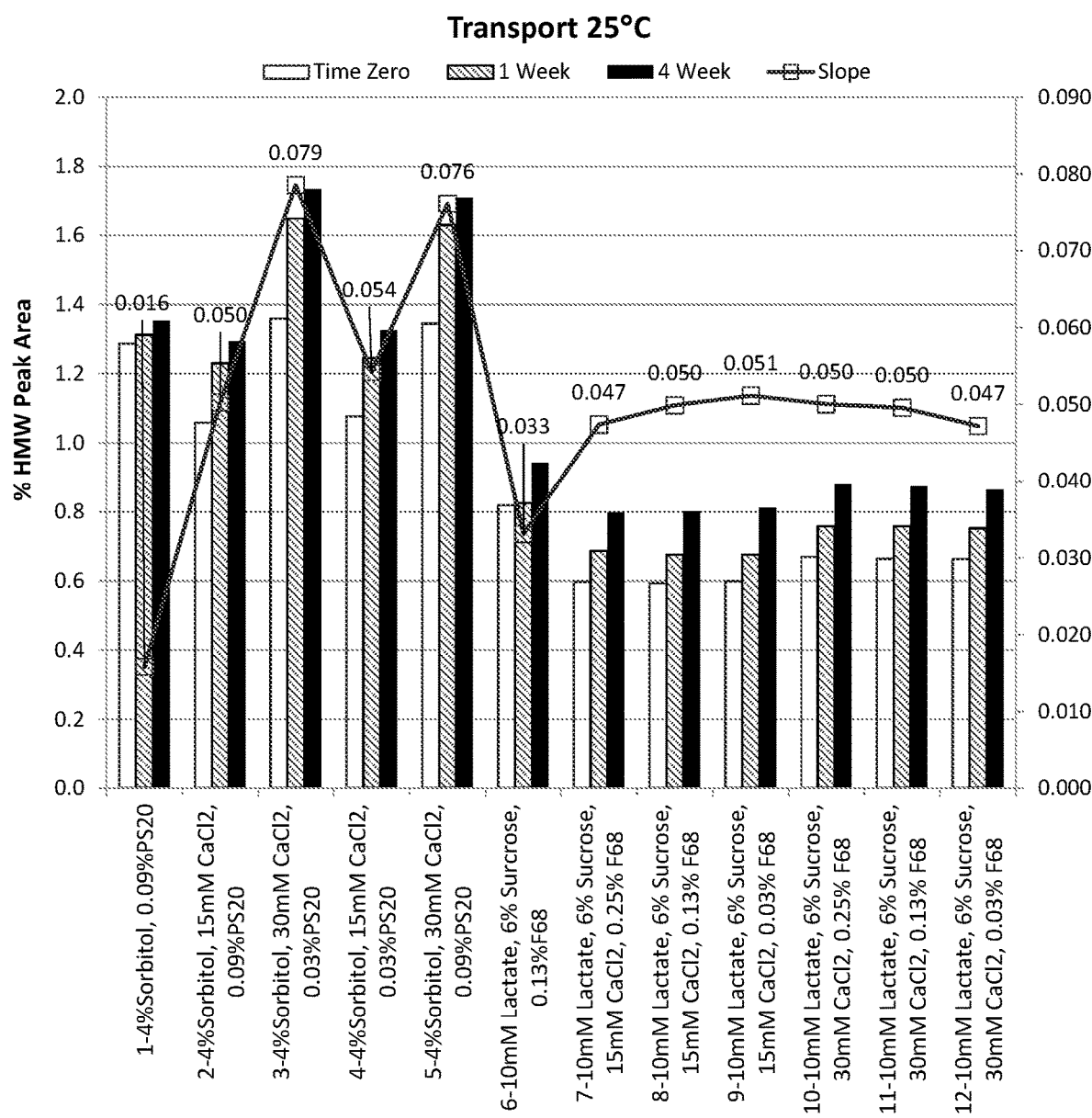
FIG. 67 is a bar graph of stability of adalimumab formulations (transport at 25° C.) as determined by SE-HPLC.
Figure 68:
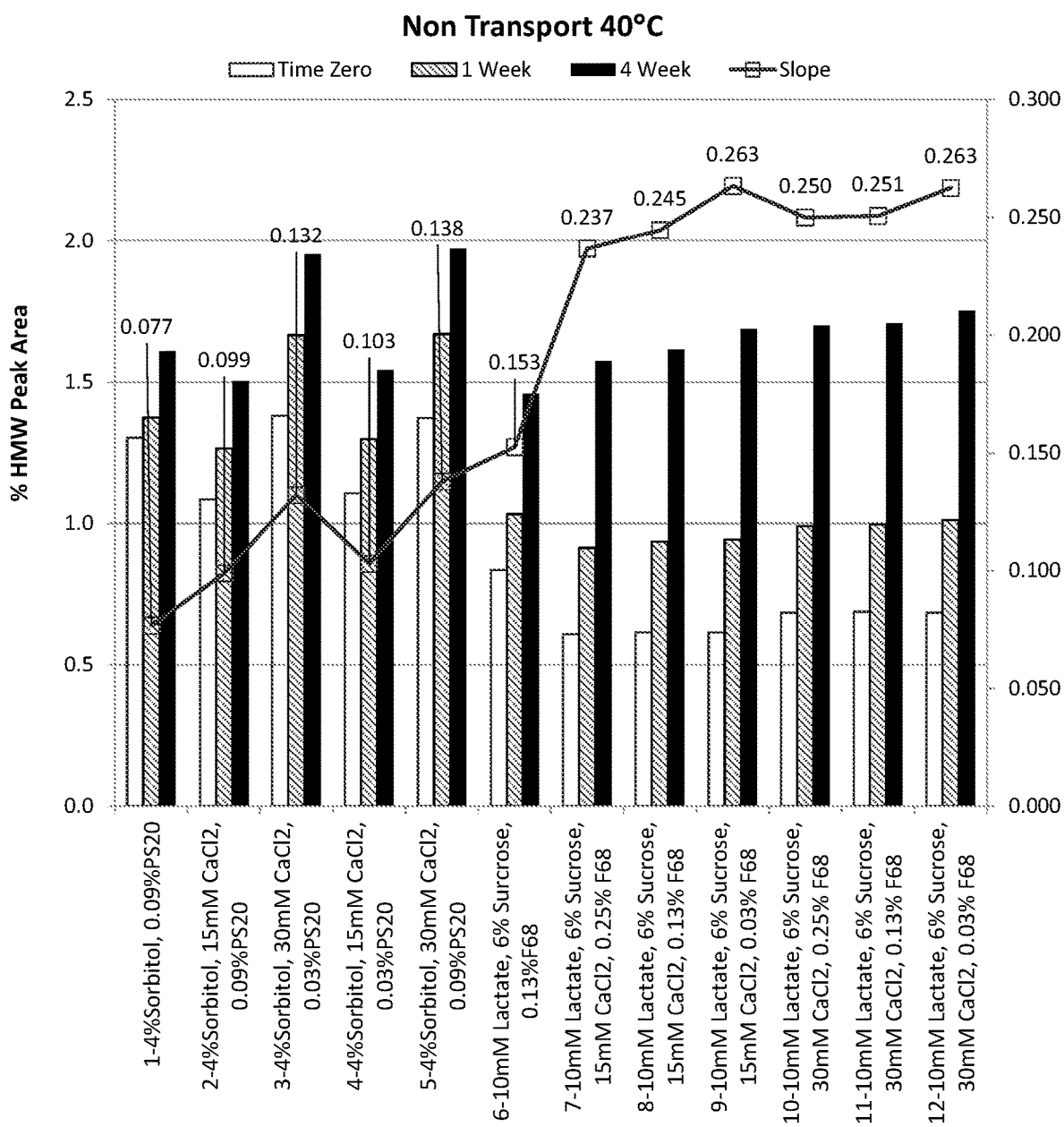
FIG. 68 is a bar graph of stability of adalimumab formulations (non-transport at 40° C.) as determined by SE-HPLC.
Figure 69:
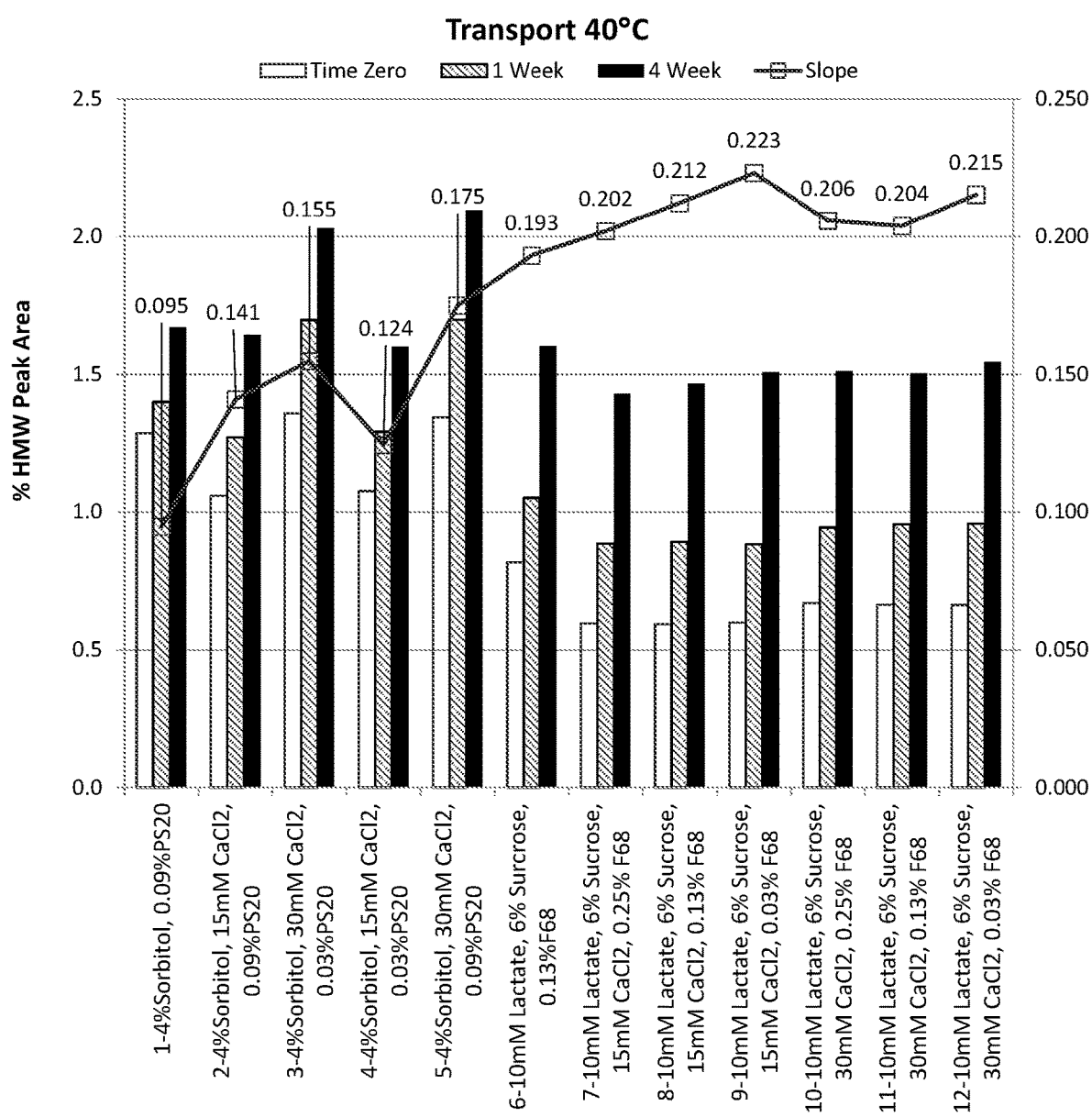
FIG. 69 is a bar graph of stability of adalimumab formulations (transport at 40° C.) as determined by SE-HPLC.

Stability also was assessed by measuring the count of 5 μM, 10 μM, and 25 μM sub-visible particles by MFI in non-transported and transported samples at 2-8° C. for 1, 2, and 4 weeks. The particles exhibited an equivalent circular diameter of at least 5.000 and an aspect ratio of less than 0.700. The results are shown in FIGS. 55-57. All formulations at ≤25 μM had low particle counts. For the 10 μM sub-visible counts, the acetate formulation (formulation 15B) showed the lowest amount of sub-visible particles. For the non-spherical ≤5 μM particle counts, the self-buffered and lactate buffer formulations (formulations 15A and 15C) showed higher particle counts at t=0 (pre-transport) and at later time points compared to the acetate formulation with sodium chloride. In general, for ≤5 μM particle counts, each formulation showed an increase in particles post-transport, followed by a trend of lower particle counts at the 1 week, 2 week and 4 week time points.

Example 16

Effect of Surfactant and Salt on Formulation Stability

Several adalimumab formulations (formulations 16A-16L) were prepared, as shown in Table 16.

TABLE 16

| Ref. | Buffer/pH Adjusting Agent | CaCl$_2$ (mM) | Excipient | Surfactant | pH | Ab conc. (mg/mL) | Conductivity Osmolality Viscosity |
|---|---|---|---|---|---|---|---|
| 16A | —/— | 0 | 4% sorbitol | 0.09% Polysorbate 20 | 5.21 | 97.89 | 0.76 mS/cm<br>241 mOsm<br>2.54 mPa·s |
| 16B | —/60 μL Ca(OH)$_2$ | 15 | 4% sorbitol | 0.09% Polysorbate 20 | 5.09 | 99.37 | 3.01 mS/cm<br>283 mOsm<br>2.59 mPa·s |
| 16C | —/40 μL Ca(OH)$_2$ | 30 | 4% sorbitol | 0.03% Polysorbate 20 | 5.06 | 103.47 | 4.98 mS/cm<br>317 mOsm<br>2.62 mPa·s |
| 16D | —/40 μL Ca(OH) | 15 | 4% sorbitol | 0.03% Polysorbate 20 | 5.1 | 99.99 | 3.07 mS/cm<br>283 mOsm<br>2.46 mPa·s |

TABLE 16-continued

| Ref. | Buffer/pH Adjusting Agent | CaCl$_2$ (mM) | Excipient | Surfactant | pH | Ab conc. (mg/mL) | Conductivity Osmolality Viscosity |
|---|---|---|---|---|---|---|---|
| 16E | —/60 µL Ca(OH)$_2$ | 30 | 4% sorbitol | 0.09% Polysorbate 20 | 5.03 | 103.77 | 4.97 mS/cm 316 mOsm 2.54 mPa · s |
| 16F | 10 mM Lactate/— | 0 | 6% sucrose | 0.10% Pluronic F68 | 5.25 | 97.68 | 0.744 mS/cm 219 mOsm 2.82 mPa · s |
| 16G | 10 mM Lactate/— | 15 | 6% sucrose | — | 5.09 | 111.79 | 2.99 mS/cm 268 mOsm 3.03 mPa · s |
| 16H | 10 mM Lactate/— | 15 | 6% sucrose | 0.08% Pluronic F68 | 5.09 | 106.72 | 2.97 mS/cm 266 mOsm 3.00 mPa · s |
| 16I | 10 mM Lactate/— | 15 | 6% sucrose | 0.02% Pluronic F68 | 5.06 | 109.35 | 2.99 mS/cm 268 mOsm 2.93 mPa · s |
| 16J | 10 mM Lactate/— | 30 | 6% sucrose | 0.2% Pluronic F68 | 5.04 | 101.79 | 4.99 mS/cm 305 mOsm 2.75 mPa · s |
| 16K | 10 mM Lactate/— | 30 | 6% sucrose | 0.08% Pluronic F68 | 5.05 | 102.27 | 5.03 mS/cm 309 mOsm 2.70 mPa · s |
| 16L | 10 mM Lactate/— | 30 | 6% sucrose | 0.03% Pluronic F68 | 5.04 | 104.89 | 5.06 mS/cm 308 mOsm 2.68 mPa · s |

To assess stability, the % acidic peak was measured by CEX-HPLC in non-transported samples and transported samples at 0, 1, and 2 weeks at 4° C., 25° C., and 40° C. The results are shown in FIGS. 58-63. No meaningful differences in the % acidic peak were exhibited at time 0 for all twelve formulations. The lack of meaningful differences between formulations was also apparent after 1 month at 4° C. for both transport stressed and non-transport stressed conditions. At 25° C., and 40° C., as a general trend, formulations without calcium chloride (16A and 16F) had the highest amount of % acidic peak after 1 month. In addition, differences between transported stressed and non-transported stressed formulations were not apparent at 25° C. At 40° C., the non-transported formulations that were self-buffered and containing calcium chloride (16B-16E) had lower rates of growth of % acidic peak compared to the identical formulations that were transport stressed. Otherwise, the presence of calcium chloride appears to reduce the formation of the acidic peak at both 25° C. and at 40° C.

Stability also was assessed by measuring HMWS by SE-HPLC after 0 days, after transport, and after storing the non-transported and transported samples at 4° C., 25° C., or 40° C. for 1, 2, and 4 weeks. The results are shown in FIGS. 64-69. The formulations having the combination of lactate buffer and calcium chloride (e.g., formulations 16G-16L), versus self-buffered and formulations with sorbitol (formulations 16A-E), exhibited the lowest amount of HMWS at time 0. Formulations having lactate buffer exhibited better stability than formulations without lactate buffer at 25° C. Formulations having 15 mM of calcium chloride (formulations 16G-16I) exhibited better stability than formulations having 0 mM or 30 mM of calcium chloride. This trend was more apparent in the self-buffered formulations (16A-16E) in which 15 mM calcium chloride was superior for stability at 25° C. compared to self-buffered formulations with 30 mM calcium chloride. Overall, formulations having the combination of lactate buffer and calcium chloride exhibited surprisingly superior stability at 25° C. After storage for 1 month at 40° C., the growth of HMWS appeared to increase faster in the lactate buffer formulations compared to the self-buffered formulations, however the amount of HMWS formed did not exceed that of the HMWS measured in the self-buffered formulations at this same temperature and time point. In general, formulations having the combination of lactate buffer and 15 mM calcium chloride exhibited the lowest amount of HMWS, in part, because they initially had the lowest amount of HMWS.

Figure 70A:
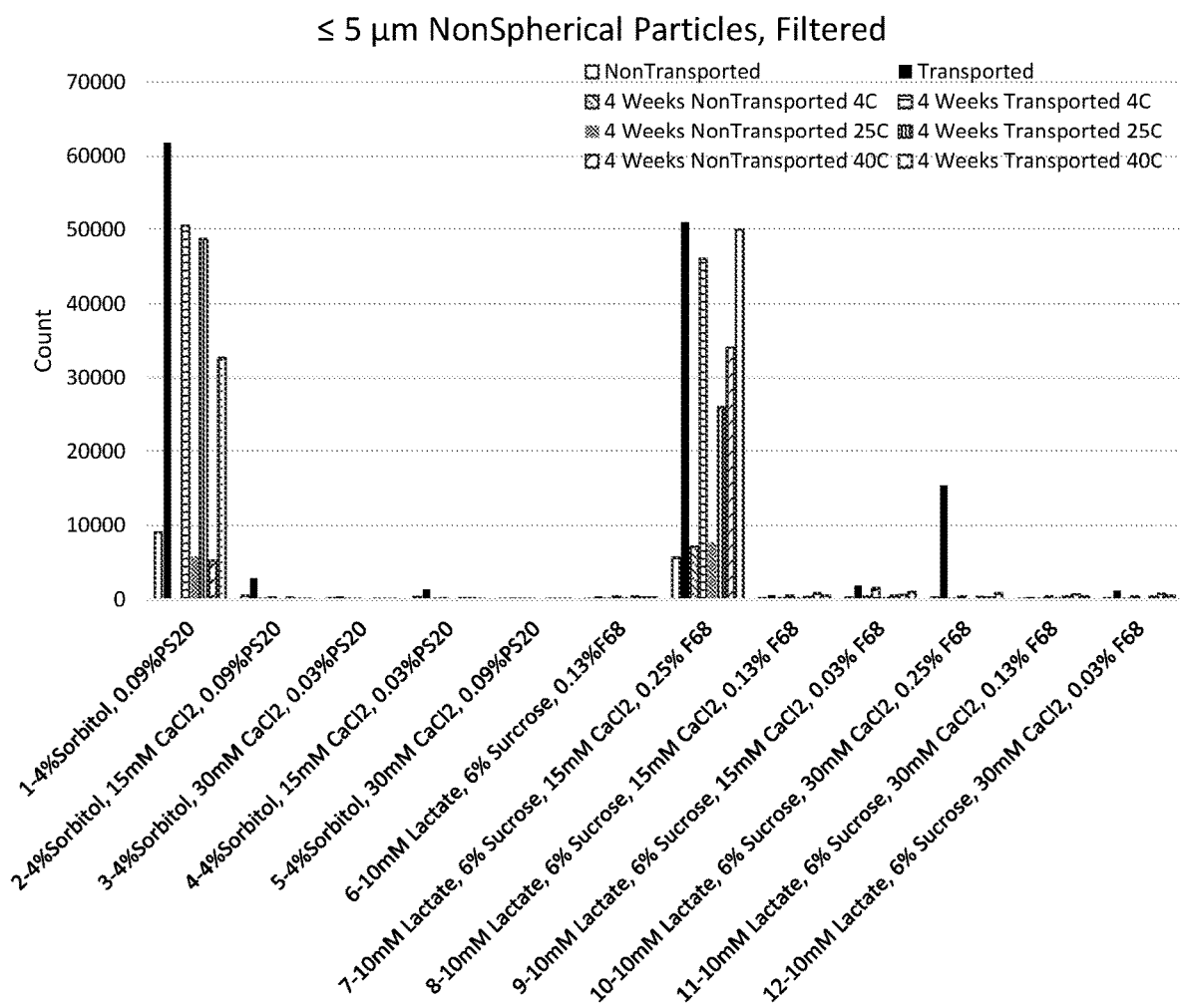
FIGS. 70A-B are a bar graph of stability of adalimumab formulations as determined by MFI.
Figure 70B:
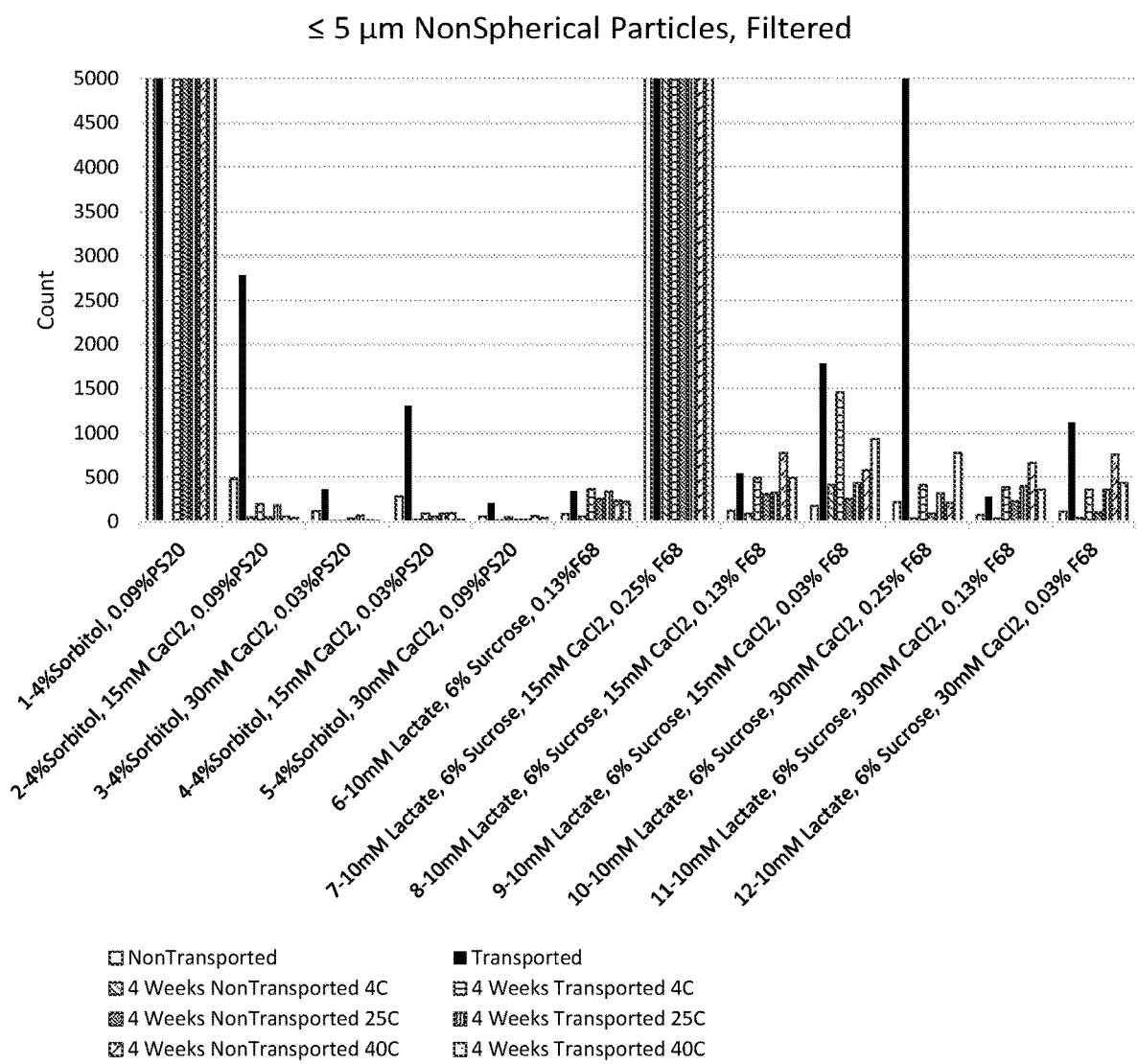
Figure 71A:
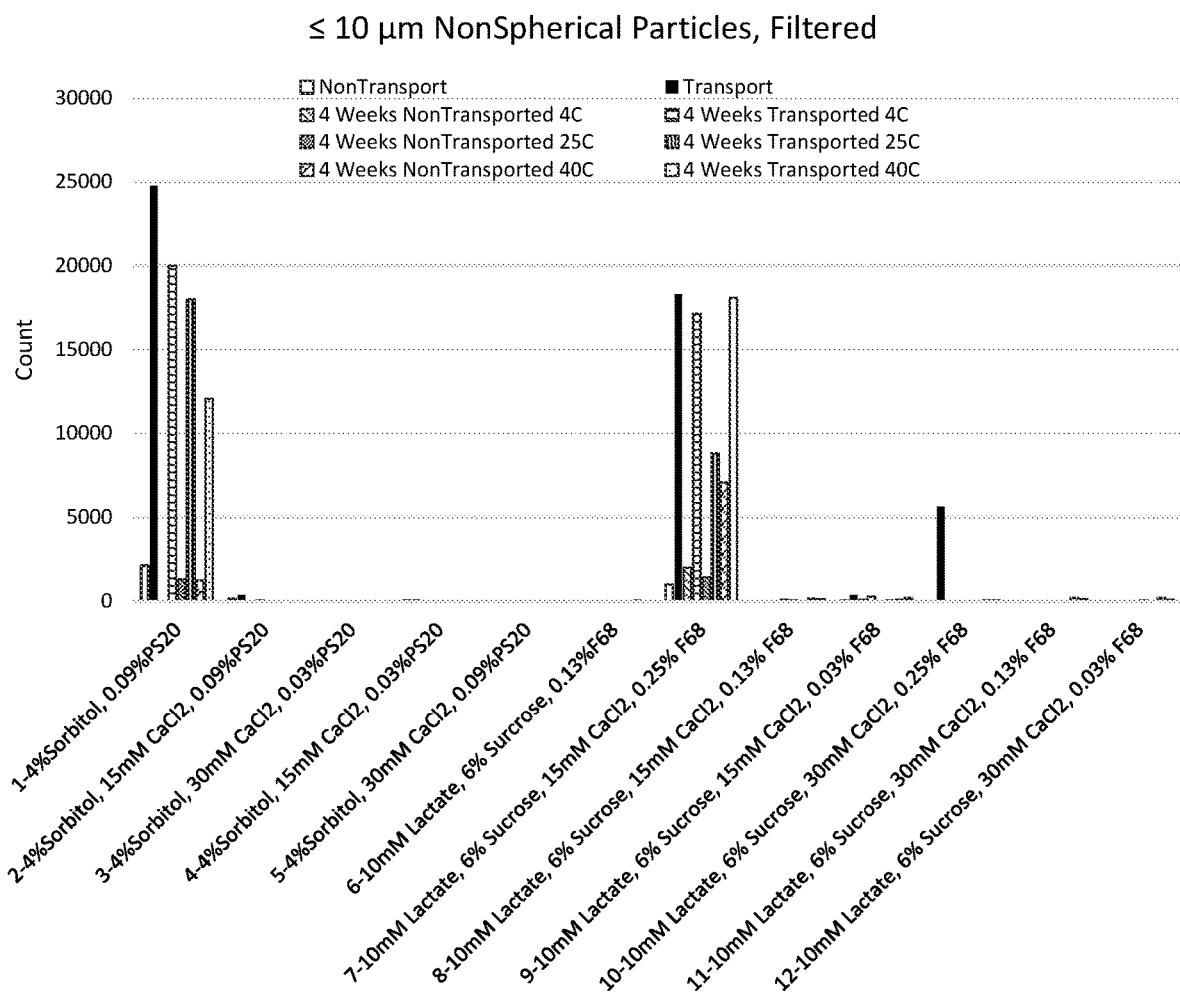
FIGS. 71A-B are a bar graph of stability of adalimumab formulations as determined by MFI.
Figure 71B:
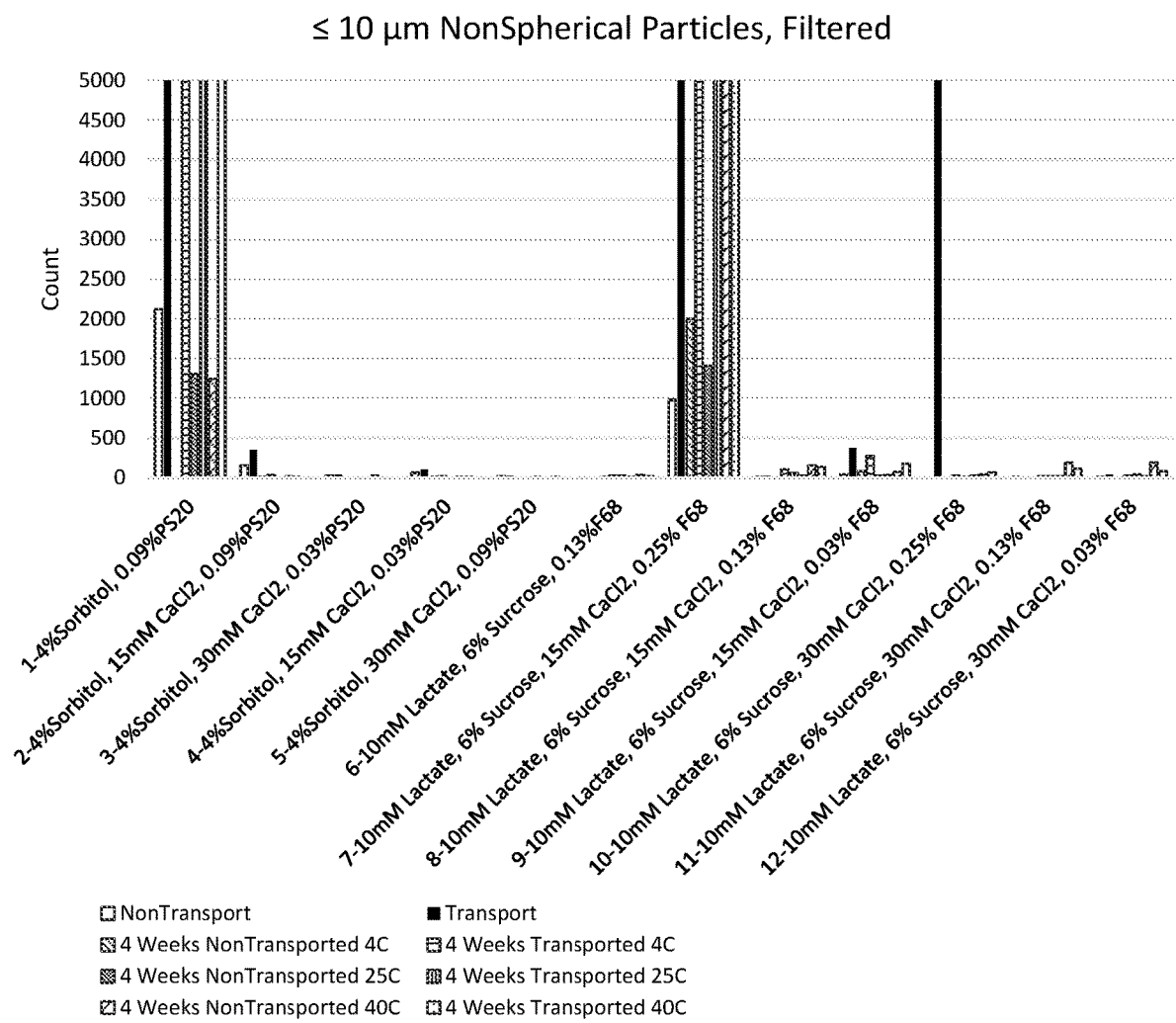
Figure 72A:
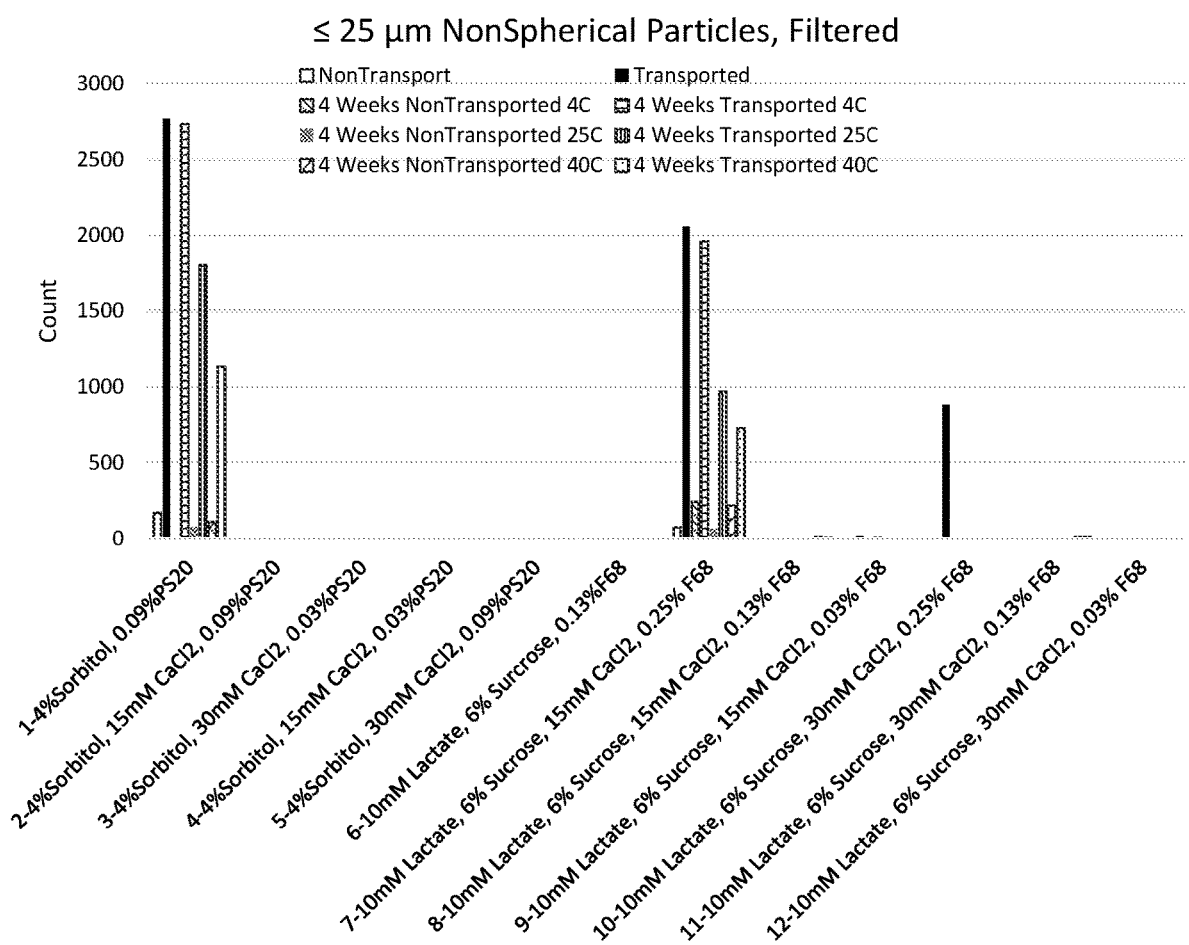
FIGS. 72A-B are a bar graph of stability of adalimumab formulations as determined by determined by MFI.
Figure 72B:
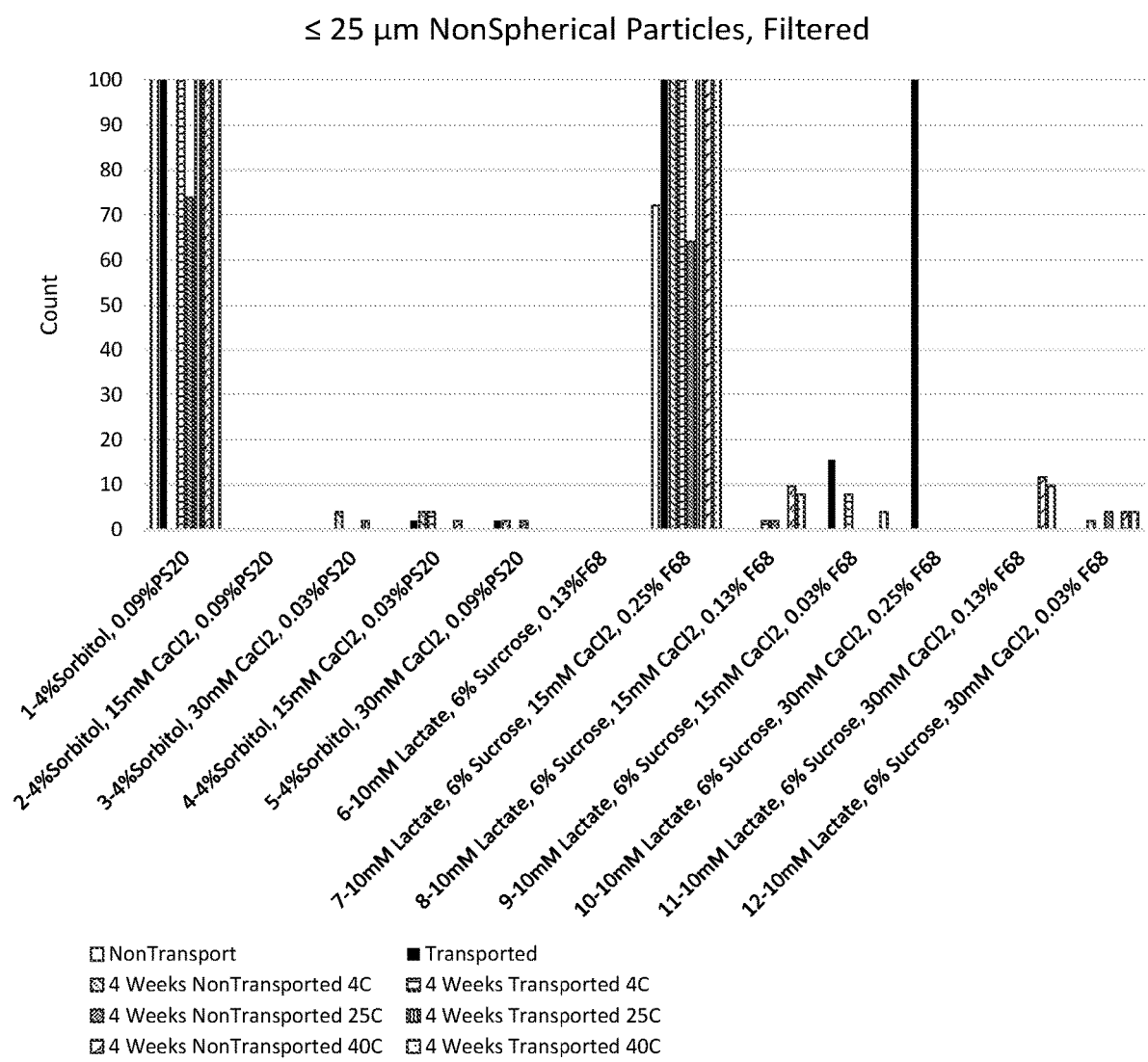
Figure 73:
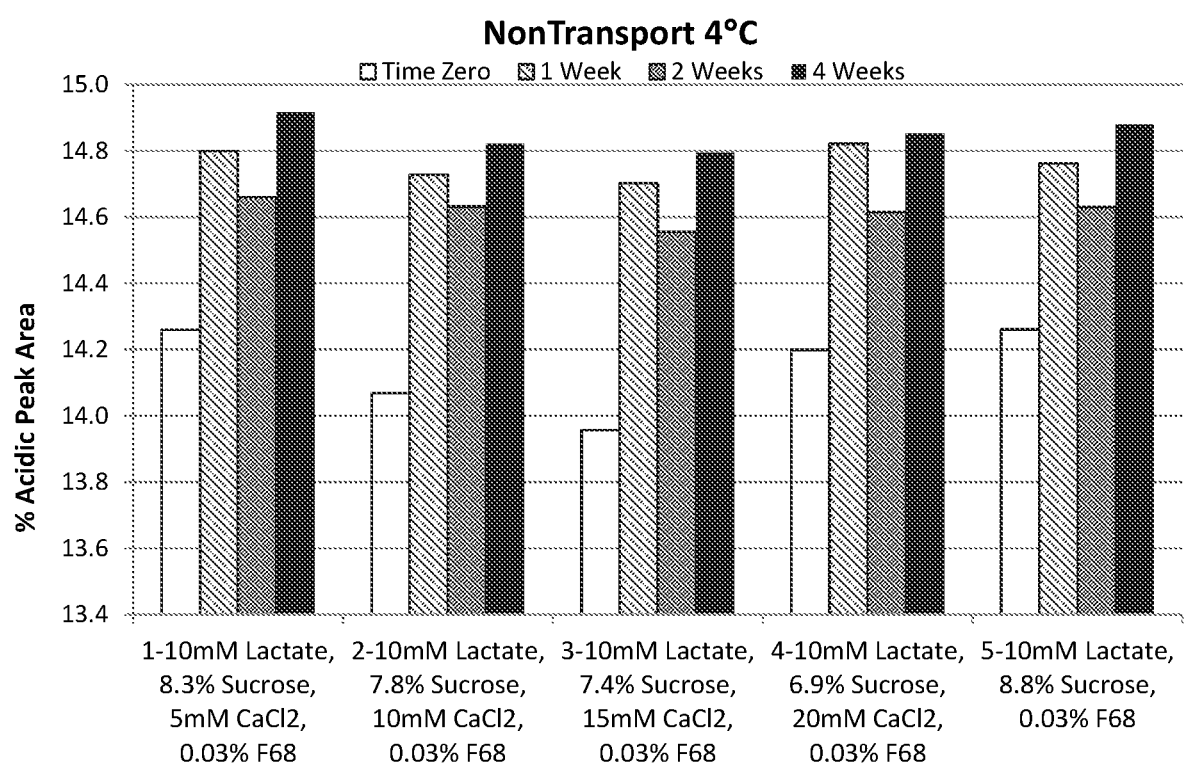
FIG. 73 is a bar graph of stability of adalimumab formulations (non-transport at 4° C.) as determined by CEX-HPLC.
Figure 74:
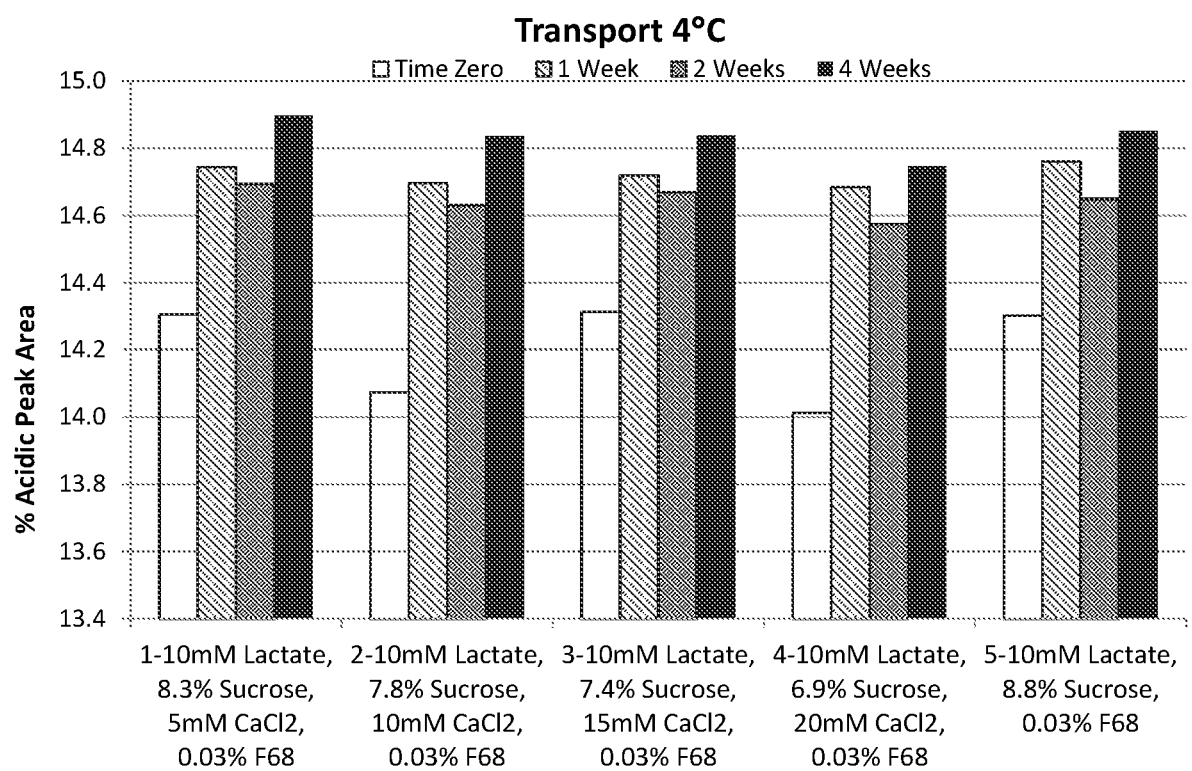
FIG. 74 is a bar graph of stability of adalimumab formulations (transport at 4° C.) as determined by CEX-HPLC.
Figure 75:
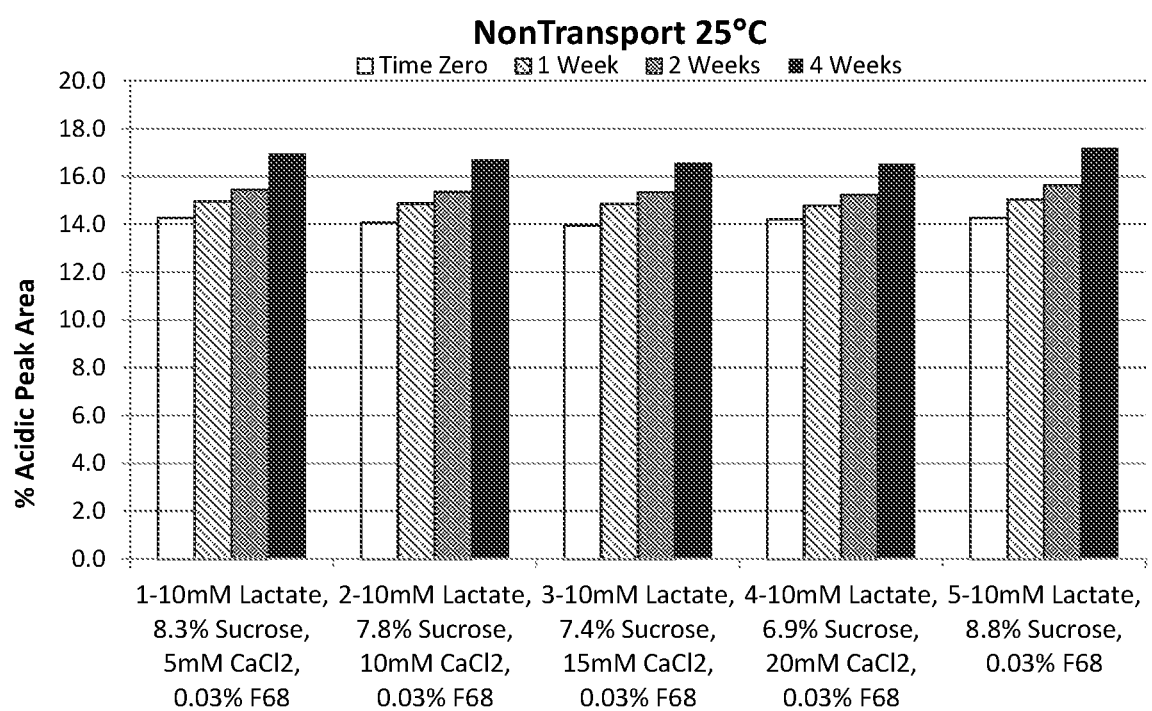
FIG. 75 is a bar graph of stability of adalimumab formulations (non-transport at 25° C.) as determined by CEX-HPLC.
Figure 76:
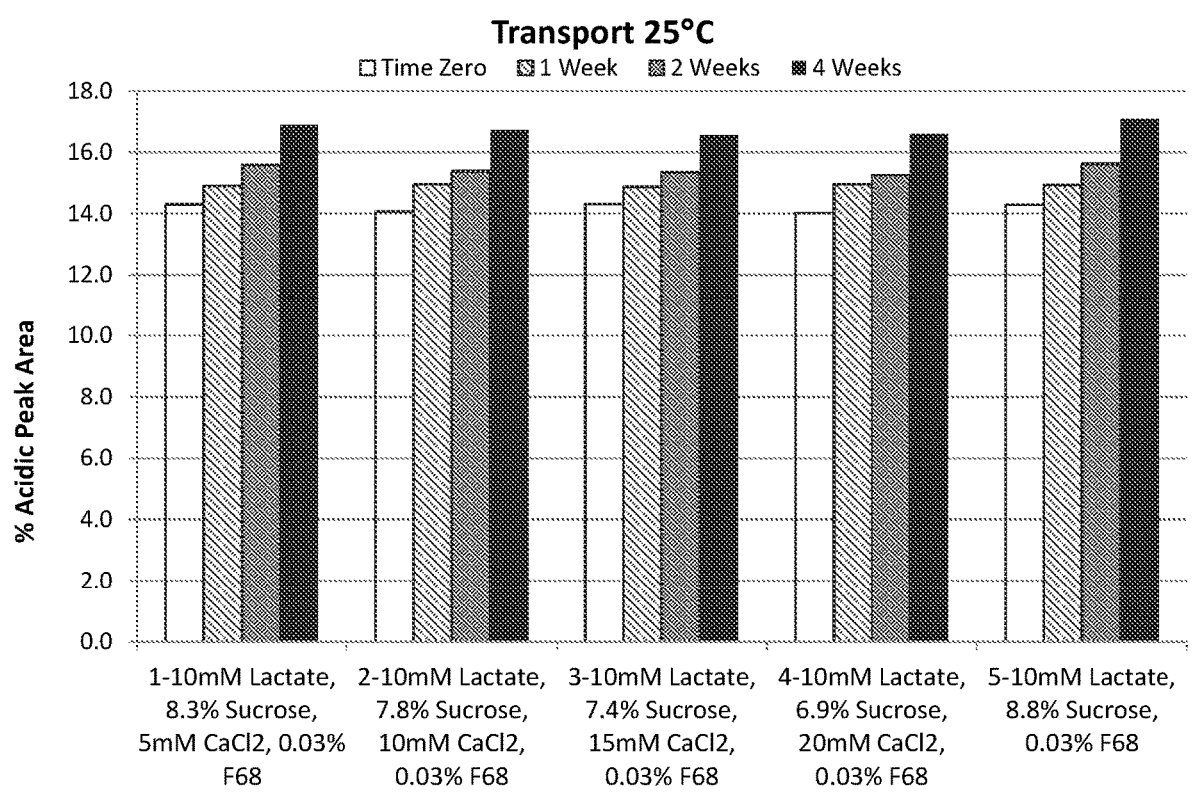
FIG. 76 is a bar graph of stability of adalimumab formulations (transport at 25° C.) as determined by CEX-HPLC.
Figure 77:
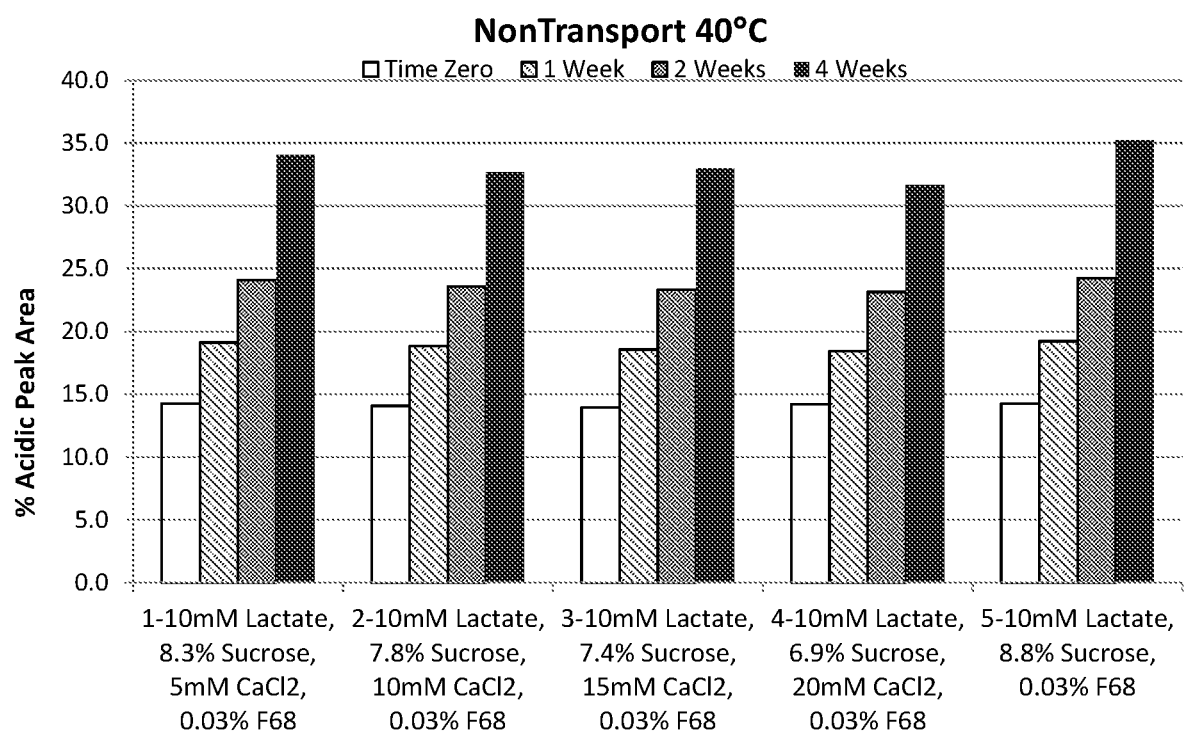
FIG. 77 is a bar graph of stability of adalimumab formulations as (non-transport at 40° C.) determined by CEX-HPLC.
Figure 78:
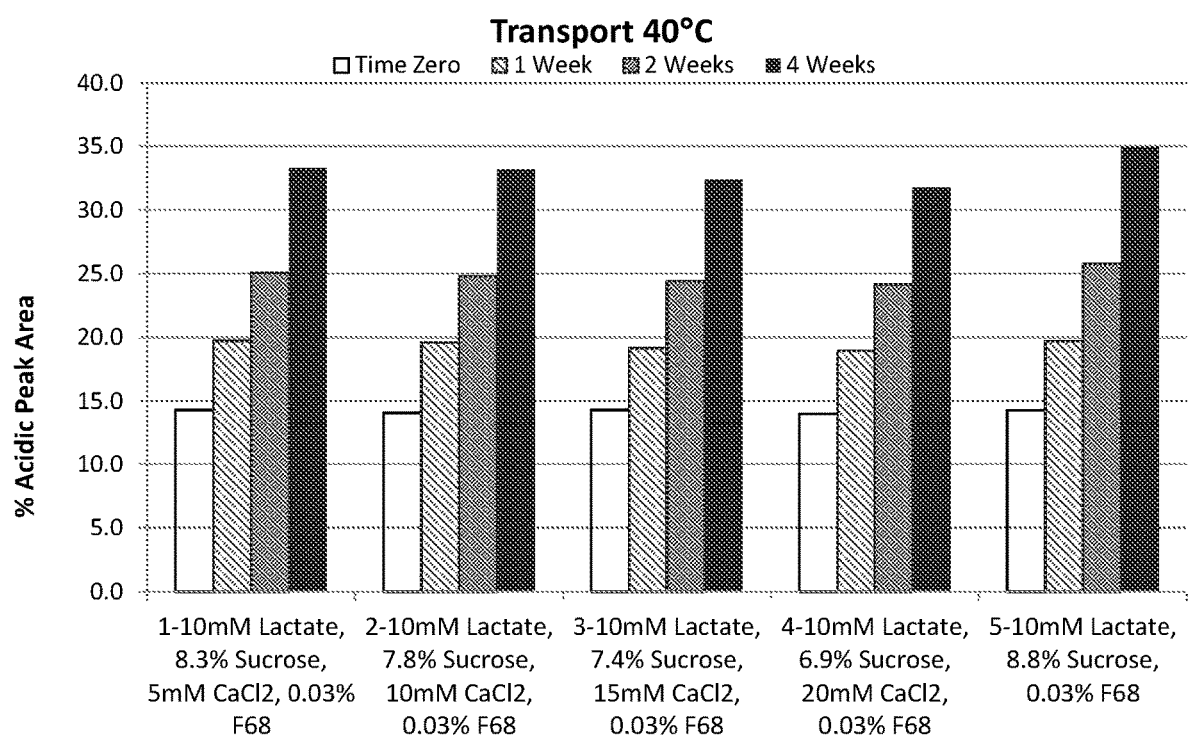
FIG. 78 is a bar graph of stability of adalimumab formulations (transport at 40° C.) as determined by CEX-HPLC.
Figure 79:
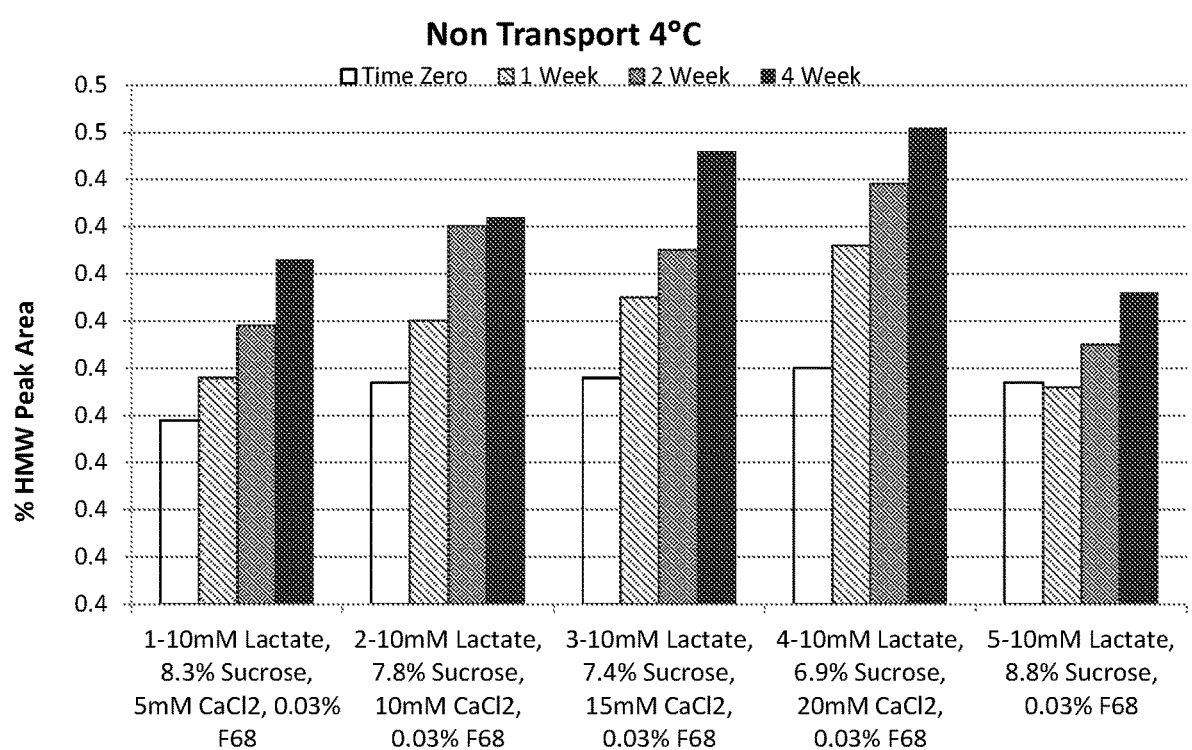
FIG. 79 is a bar graph of stability of adalimumab formulations (non-transport at 4° C.) as determined by SE-HPLC.
Figure 80:
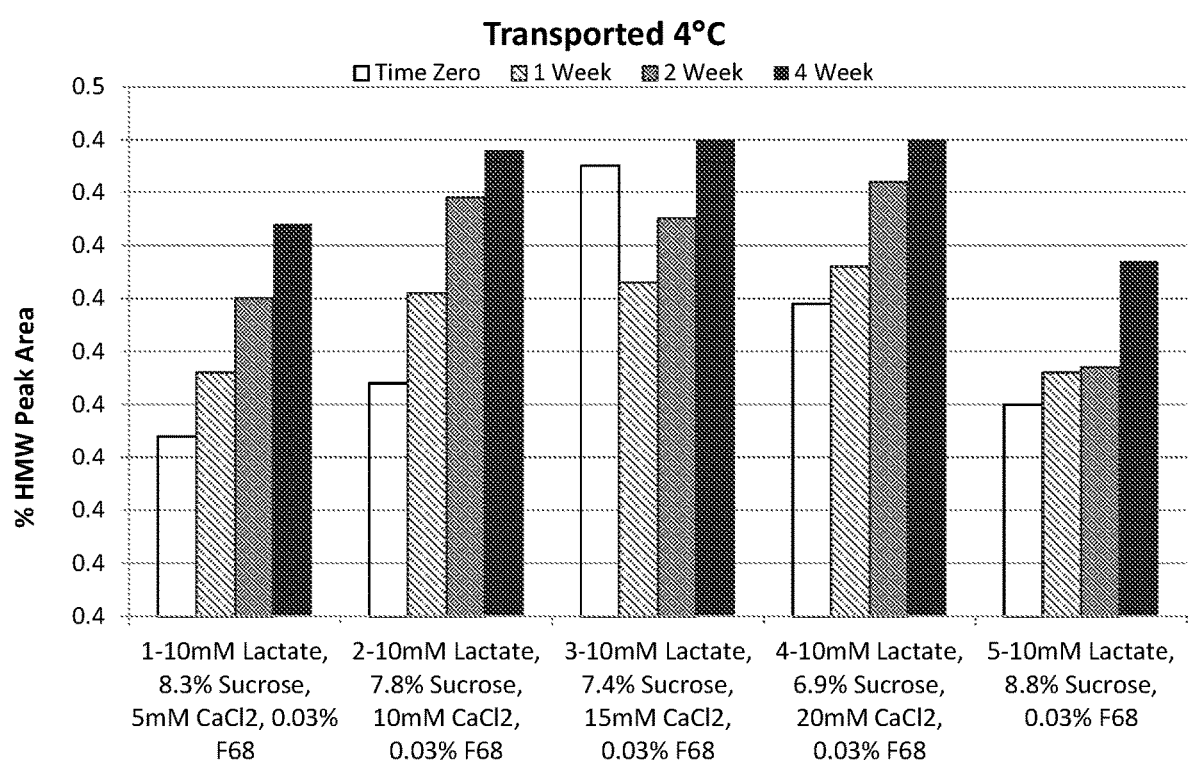
FIG. 80 is a bar graph of stability of adalimumab formulations (transport at 4° C.) as determined by SE-HPLC.
Figure 81:
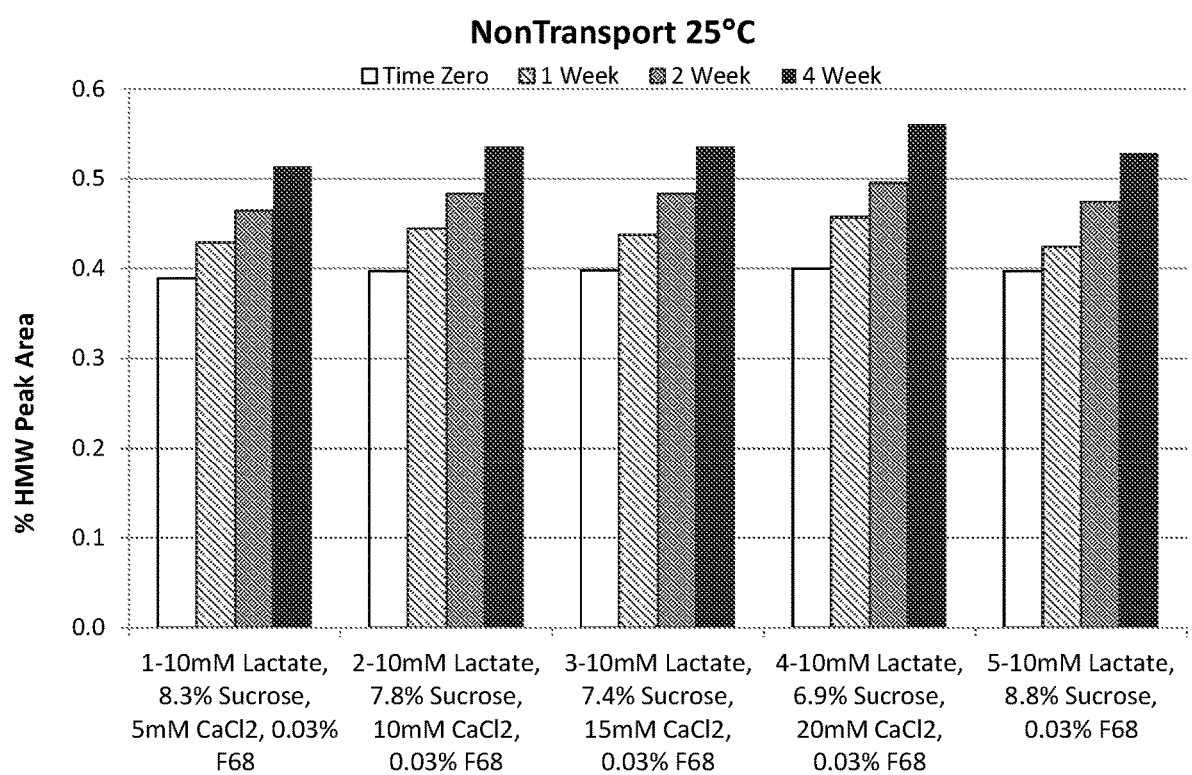
FIG. 81 is a bar graph of stability of adalimumab formulations (non-transport at 25° C.) as determined by SE-HPLC.
Figure 82:
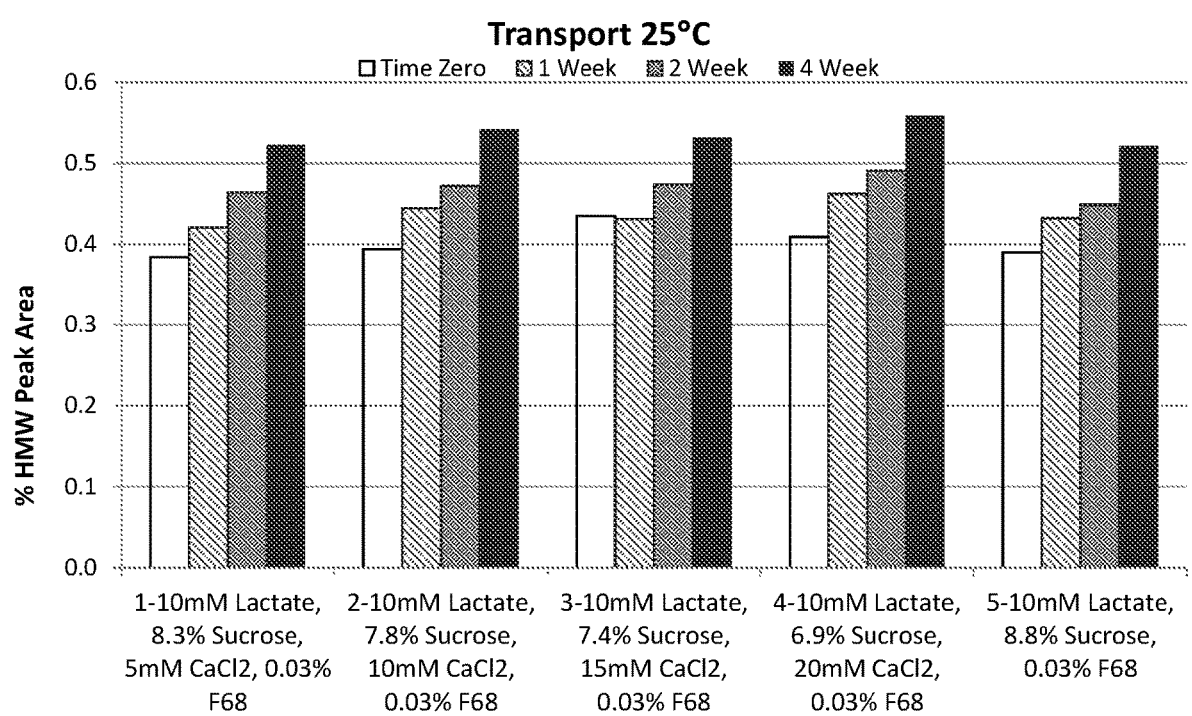
FIG. 82 is a bar graph of stability of adalimumab formulations (transport at 25° C.) as determined by SE-HPLC.
Figure 83:
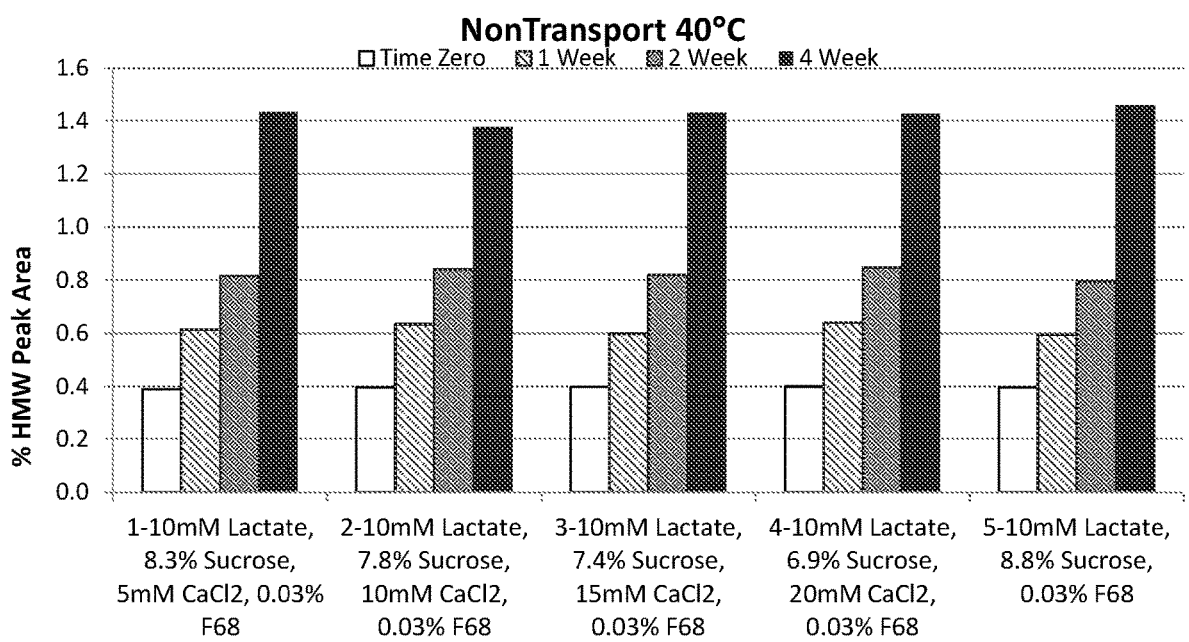
FIG. 83 is a bar graph of stability of adalimumab formulations (non-transport at 40° C.) as determined by SE-HPLC.
Figure 84:
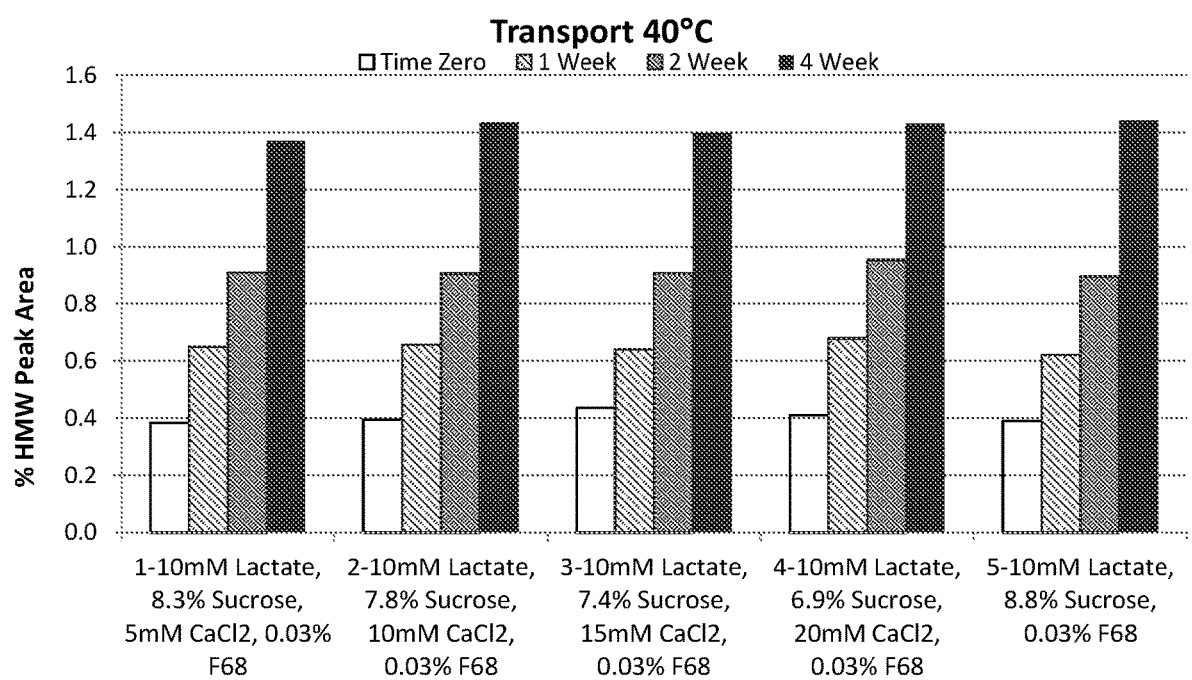
FIG. 84 is a bar graph of stability of adalimumab formulations (transport at 40° C.) as determined by SE-HPLC.

Stability also was assessed by measuring the count of 5 µM, 10 µM, and 25 µM sub-visible particles by MFI in non-transported and transported samples at 4° C., 25° C., or 40° C. for 1, 2, and 4 weeks. The particles exhibited an equivalent circular diameter of at least 5.000 and an aspect ratio of less than 0.700. The results are shown in FIGS. 70-72. For the 5 µM size particles, the lactate buffered formulation with 0.25% Pluronic F68 had the highest number of particles following transport and at later time points. In the self-buffered formulations, the absence of calcium chloride resulted likewise in a high 5 µM particle count initially and over time. These results were not expected, especially with the higher level of Pluronic F68 in the lactate buffer formulation associated with high particle counts. In the lactate buffer formulations in general at 5 µM, 0.13% Pluronic F68 appeared best at minimizing particles in formulations with either 15 mM or 30 mM calcium chloride. FIGS. 70A-B. At the 10 µM particle level, a similar trend to that observed for the 5 µM results was observed. The lactate buffer formulation with 0.13% Pluronic F68 was effective in reducing the number of particles compared to higher Pluronic F68 at 0.25%. FIGS. 71A-B. Finally, at 25 Pluronic F68 at 0.13% minimized particle growth in lactate buffer formulations. Calcium chloride at concentrations of either 15 or 30 mM minimized particle growth in self-buffered formulations in the presence of PS 20. FIGS. 72A-B.

Example 17

Effect of Calcium Chloride Concentration on the Stability of Lactate Buffer Formulations Several adalimumab formulations (formulations 17A-17E) were prepared, as shown in Table 17.

TABLE 17

| Ref. | Buffer/pH Adjusting Agent | CaCl$_2$ (mM) | Excipient | Surfactant | pH | Ab conc. (mg/mL) | Conductivity Osmolality |
|---|---|---|---|---|---|---|---|
| 17A | 10 mM Lactate/ HCl, Ca(OH)$_2$ | 5 | 8.3% sucrose | 0.03% Pluronic F68 | 5.11 | 100 | 1.339 mS/cm 292 mOsm |
| 17B | 10 mM Lactate/ HCl, Ca(OH)$_2$ | 10 | 7.8% sucrose | 0.03% Pluronic F68 | 5.12 | 100 | 2.125 mS/cm 304 mOsm |
| 17C | 10 mM Lactate/ HCl, Ca(OH)$_2$ | 15 | 7.4% sucrose | 0.03% Pluronic F68 | 5.10 | 100 | 2.792 mS/cm 304 mOsM |
| 17D | 10 mM Lactate/ HCl, Ca(OH)$_2$ | 20 | 6.9% sucrose | 0.03% Pluronic F68 | 5.13 | 100 | 3.527 mS/cm 302 mOsM |
| 17E | 10 mM Lactate/ HCl, Ca(OH)$_2$ | — mM | 8.8% sucrose | 0.03% Pluronic F68 | 5.23 | 100 | 0.534 mS/cm 314 mOsM |

To assess stability, the % acidic peak was measured by CEX-HPLC after 0 days, after transport, and after 1 week, 2 weeks and 4 weeks at 4° C., 25° C. and 40° C. The results are shown in FIGS. 73-78. At time zero, the % acidic peak was similar either with or without transport stress, with only minor variability observed. After 1 month at 25° C., the rate of growth was similar in all formulations, with the level of calcium chloride in the range evaluated in this study having minor to no impact, tested in both transport stressed and non-transport stressed samples. In formulations stored at 40° C., a smaller amount of % acidic peak was observed as the level of calcium chloride increased after 1 month's storage. This trend was observed for both the transport and non-transport stressed formulations. Otherwise, transport stress did not appear to result in higher rates of degradation.

Stability also was assessed by measuring HMWS by SE-HPLC after 0 days, after transport, and after storing the non-transported and transported samples at 4° C., 25° C., or 40° C. for 1, 2, and 4 weeks. The results are shown in FIGS. 79-84. At time zero, a very minor increase in HMWS was observed as the calcium chloride level increased. This is most likely not meaningful, considering assay variability. Formulations that were transport stressed did not appear to have higher HMWS than non-transport stressed formulations. After one month at 25° C. and at 40° C., it is difficult to detect a correlation in formulations with a higher amount of HMWS and increasing amounts of calcium chloride. These results suggest that levels of calcium chloride in the range tested do not adversely affect stability with respect to the formation of HMWS.

Figure 85:
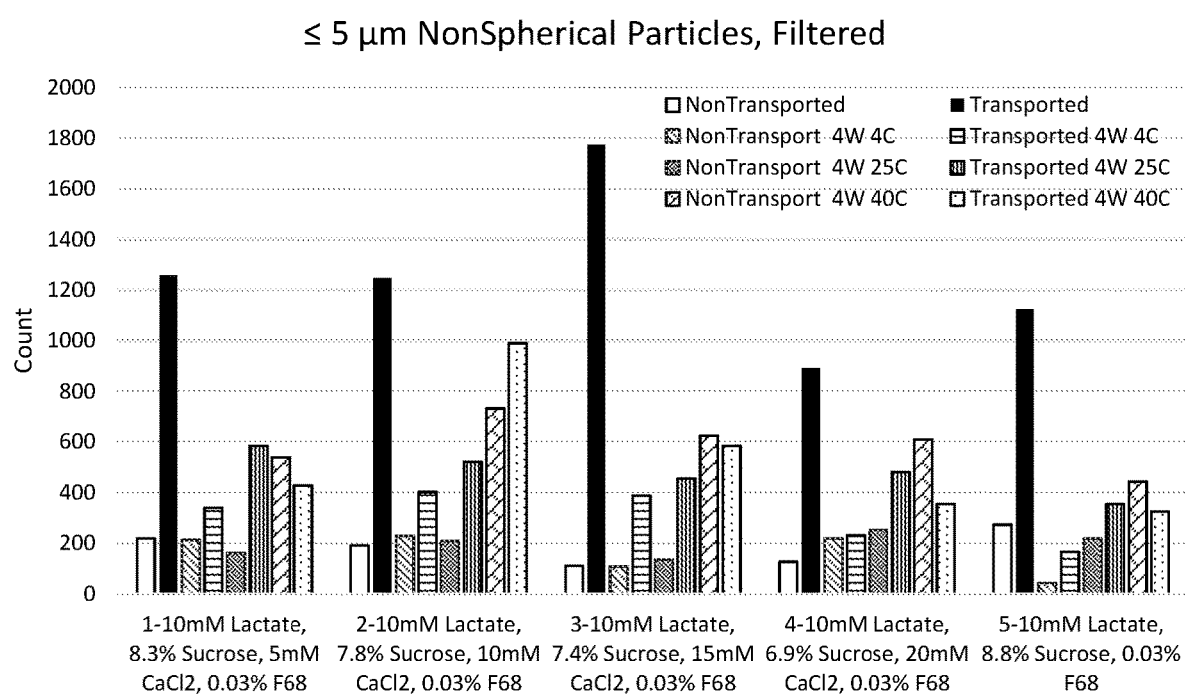
FIG. 85 is a bar graph of stability of adalimumab formulations as determined by MFI.
Figure 86:
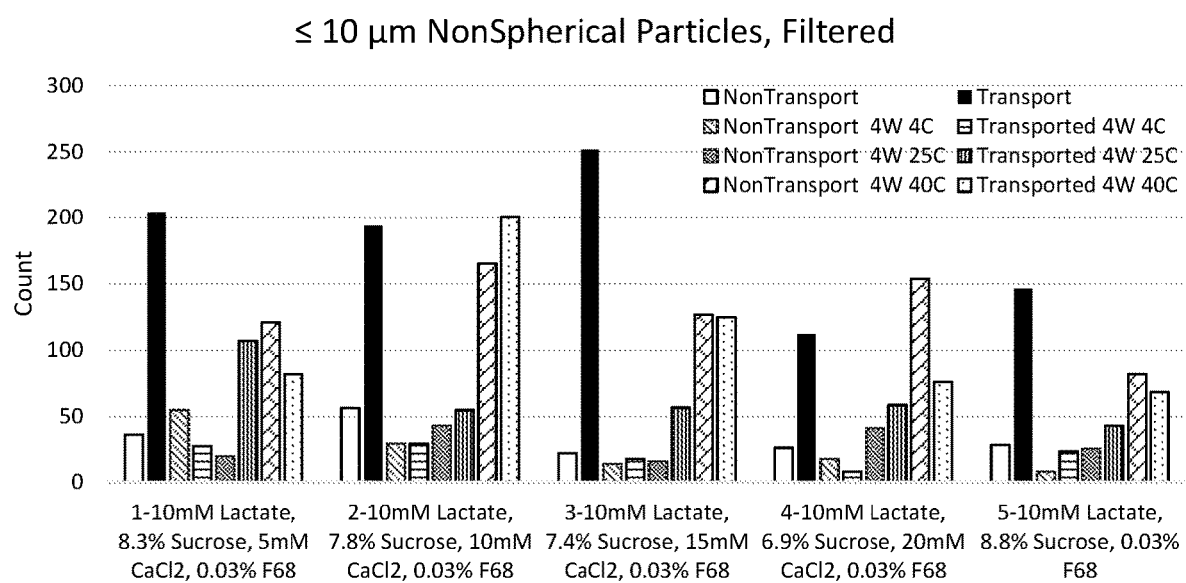
FIG. 86 is a bar graph of stability of adalimumab formulations as determined by MFI.
Figure 87:
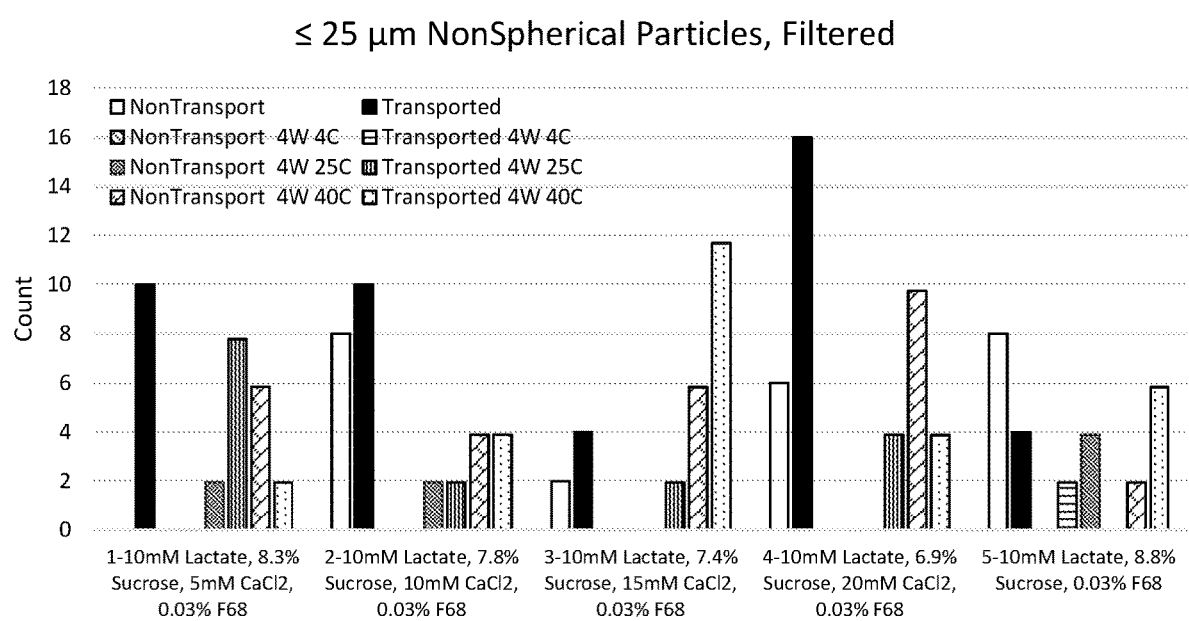
FIG. 87 is a bar graph of stability of adalimumab formulations as determined by MFI.

Stability also was assessed by measuring the count of 5 µM, 10 µM, and 25 µM sub-visible particles by MFI in non-transported and transported samples. The particles exhibited an equivalent circular diameter of at least 5.000 and an aspect ratio of less than 0.700. The results are shown in FIGS. 85-87. In formulations tested for particle counts at ≤5 µm, counts appeared to spike after transport stress, however the particle counts dropped at all time points and temperature conditions thereafter. High temperature exposure (25° C., 40° C.) resulted in only a modest increase in particles. There was a less apparent spike in particles ≤10 µm in most formulations that had been transport stressed, but the counts were also reduced at the 1 month time point at all temperatures tested. A modest particle count increase was also observed in samples stored after 1 month at 25° C. and 40° C. MFI results measured for particles in the range ≤25 µm did not show an apparent trend, as the number of particles was low or not detected.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this disclosure that certain changes and modifications may be made thereto without departing from the spirit or scope of the disclosed embodiments.

What is claimed:

1. A formulation comprising about 180 mg/mL adalimumab, 20 mM glutamate, and 160 mM monoethanolamine (MEA).

\* \* \* \* \*